US012410409B2

(12) United States Patent
Kawaoka et al.

(10) Patent No.: US 12,410,409 B2
(45) Date of Patent: *Sep. 9, 2025

(54) INFLUENZA VIRUSES WITH MUTANT PB2 GENE SEGMENT AS LIVE ATTENUATED VACCINES

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US); Makoto Ozawa, Kagoshima (JP)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 35 days.

This patent is subject to a terminal disclaimer.

(21) Appl. No.: 17/835,830

(22) Filed: Jun. 8, 2022

(65) Prior Publication Data

US 2023/0348864 A1 Nov. 2, 2023

Related U.S. Application Data

(60) Division of application No. 16/694,748, filed on Nov. 25, 2019, now Pat. No. 11,384,339, which is a continuation of application No. 14/699,213, filed on Apr. 29, 2015, now Pat. No. 10,513,692, which is a continuation of application No. 13/594,611, filed on Aug. 24, 2012, now Pat. No. 9,101,653.

(60) Provisional application No. 61/527,935, filed on Aug. 26, 2011.

(51) Int. Cl.
| | |
|---|---|
| *C12N 7/00* | (2006.01) |
| *A61K 35/76* | (2015.01) |
| *A61K 39/09* | (2006.01) |
| *A61K 39/12* | (2006.01) |
| *A61K 39/145* | (2006.01) |
| *G01N 33/569* | (2006.01) |
| *A61K 39/00* | (2006.01) |

(52) U.S. Cl.
CPC ............. *C12N 7/00* (2013.01); *A61K 35/76* (2013.01); *A61K 39/092* (2013.01); *A61K 39/12* (2013.01); *A61K 39/145* (2013.01); *G01N 33/56983* (2013.01); *A61K 2039/5252* (2013.01); *A61K 2039/5254* (2013.01); *A61K 2039/5256* (2013.01); *A61K 2039/543* (2013.01); *A61K 2039/70* (2013.01); *C12N 2760/16121* (2013.01); *C12N 2760/16134* (2013.01); *C12N 2760/16143* (2013.01); *C12N 2760/16151* (2013.01); *C12N 2760/16171* (2013.01); *G01N 2333/11* (2013.01)

(58) Field of Classification Search
None
See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,578,473 | A | 11/1996 | Palese et al. |
| 5,716,821 | A | 2/1998 | Wertz et al. |
| 5,750,394 | A | 5/1998 | Palese et al. |
| 5,786,199 | A | 7/1998 | Palese |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,001,634 | A | 12/1999 | Palese et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,270,958 | B1 | 8/2001 | Olivo et al. |
| 6,271,011 | B1 | 8/2001 | Lee et al. |
| 6,358,733 | B1 | 3/2002 | Motwani et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,843,996 | B1 | 1/2005 | Parkin et al. |
| 6,872,395 | B2 | 3/2005 | Kawaoka |
| 6,890,710 | B1 | 5/2005 | Palese et al. |
| 6,951,752 | B2 | 10/2005 | Reiter et al. |
| 6,951,754 | B2 | 10/2005 | Hoffmann |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

"Japanese Application Serial No. 2003-568038, Notice of Allowance mailed Nov. 30, 2009", 5 pgs.
"Brazilian Application Serial No. PI0307679-2, Response filed Dec. 11, 2019 to Office Action mailed Oct. 3, 2019", w English Claims, 59 pgs.
"European Application Serial No. 16778485.9, Response filed Dec. 19, 2019 to Communication Pursuant to Article 94(3) EPC mailed Aug. 22, 2019", 20 pgs.

(Continued)

*Primary Examiner* — Benjamin P Blumel
(74) *Attorney, Agent, or Firm* — Schwegman Lundberg & Woessner, P.A.

(57) ABSTRACT

The invention provides a recombinant biologically contained influenza virus that is a PB2 knockout virus, e.g., one that is useful to generate a multivalent vaccine, and methods of making and using that virus.

14 Claims, 28 Drawing Sheets

Figure 3A:
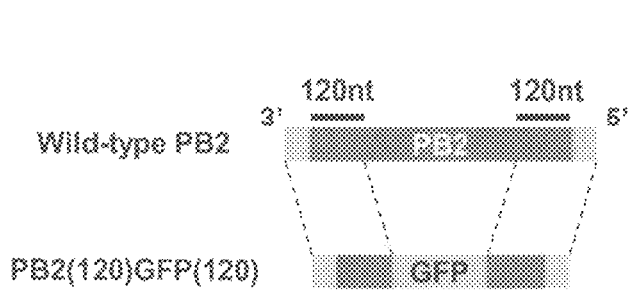

Specification includes a Sequence Listing.

(56) References Cited

U.S. PATENT DOCUMENTS

| | | |
|---|---|---|
| 6,974,695 B2 | 12/2005 | Vogels et al. |
| 7,037,707 B2 | 5/2006 | Webster et al. |
| 7,176,021 B2 | 2/2007 | Kawaoka |
| 7,211,378 B2 | 5/2007 | Kawaoka et al. |
| 7,226,774 B2 | 6/2007 | Kawaoka |
| 7,312,064 B2 | 12/2007 | Hoffmann |
| 7,335,356 B2 | 2/2008 | Hart et al. |
| 7,507,411 B2 | 3/2009 | Zhou et al. |
| 7,566,458 B2 | 7/2009 | Yang et al. |
| 7,585,657 B2 | 9/2009 | Kawaoka |
| 7,588,769 B2 | 9/2009 | Kawaoka |
| 7,601,356 B2 | 10/2009 | Jin et al. |
| 7,670,837 B2 | 3/2010 | Schwartz |
| 7,682,618 B2 | 3/2010 | Bavari et al. |
| 7,723,094 B2 | 5/2010 | Kawaoka et al. |
| 7,833,788 B2 | 11/2010 | Pau et al. |
| 7,883,844 B2 | 2/2011 | Nouchi et al. |
| 7,955,833 B2 | 6/2011 | Reiter et al. |
| 7,959,930 B2 | 6/2011 | De Wit et al. |
| 7,968,101 B2 | 6/2011 | Kawaoka et al. |
| 7,972,843 B2 | 7/2011 | Hoffmann |
| 7,993,924 B2 | 8/2011 | Billeter et al. |
| 8,012,736 B2 | 9/2011 | Hoffman et al. |
| 8,043,856 B2 | 10/2011 | Kawaoka et al. |
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,298,805 B2 | 10/2012 | Kawaoka |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,465,960 B2 | 6/2013 | Kawaoka et al. |
| 8,475,806 B2 | 7/2013 | Kawaoka |
| 8,507,247 B2 | 8/2013 | Kawaoka et al. |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 8,597,661 B2 | 12/2013 | Kawaoka et al. |
| 8,679,819 B2 | 3/2014 | Kawaoka |
| 8,877,209 B2 | 11/2014 | Kawaoka et al. |
| 8,900,595 B2 | 12/2014 | Kawaoka et al. |
| 9,101,653 B2 | 8/2015 | Kawaoka et al. |
| 9,109,013 B2 | 8/2015 | Kawaoka et al. |
| 9,222,118 B2 | 12/2015 | Kawaoka et al. |
| 9,254,318 B2 | 2/2016 | Kawaoka et al. |
| 9,284,533 B2 | 3/2016 | Bilsel et al. |
| 9,474,798 B2 | 10/2016 | Watanabe et al. |
| 9,757,446 B2 | 9/2017 | LeFebvre et al. |
| 9,890,363 B2 | 2/2018 | Kawaoka |
| 9,926,535 B2 | 3/2018 | Kawaoka et al. |
| 9,950,057 B2 | 4/2018 | Kawaoka et al. |
| 10,053,671 B2 | 8/2018 | Kawaoka et al. |
| 10,059,925 B2 | 8/2018 | Kawaoka et al. |
| 10,119,124 B2 | 11/2018 | Watanabe et al. |
| 10,130,697 B2 | 11/2018 | Watanabe |
| 10,172,934 B2 | 1/2019 | Kawaoka et al. |
| 10,246,686 B2 | 4/2019 | Kawaoka et al. |
| 10,358,630 B2 | 7/2019 | Kawaoka et al. |
| 10,494,613 B2 | 12/2019 | Kawaoka et al. |
| 10,513,692 B2 | 12/2019 | Kawaoka et al. |
| 10,633,422 B2 | 4/2020 | Kawaoka et al. |
| 10,808,229 B2 | 10/2020 | Kawaoka et al. |
| 11,007,262 B2 | 5/2021 | Watanabe et al. |
| 11,046,934 B2 | 6/2021 | Kawaoka et al. |
| 11,180,737 B2 | 11/2021 | Kawaoka et al. |
| 11,197,925 B2 | 12/2021 | Kawaoka et al. |
| 11,197,926 B2 | 12/2021 | Kawaoka et al. |
| 11,241,492 B2 | 2/2022 | Kawaoka et al. |
| 11,384,339 B2 | 7/2022 | Kawaoka et al. |
| 11,389,523 B2 | 7/2022 | Kawaoka et al. |
| 11,390,649 B2 | 7/2022 | Kawaoka et al. |
| 11,739,303 B2 | 8/2023 | Kawaoka et al. |
| 11,807,872 B2 | 11/2023 | Kawaoka et al. |
| 11,851,648 B2 | 12/2023 | Kawaoka et al. |
| 12,258,557 B2 | 3/2025 | Kawaoka et al. |
| 2002/0010143 A1 | 1/2002 | Barbosa et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2003/0215794 A1 | 11/2003 | Kawaoka et al. |
| 2004/0002061 A1 | 1/2004 | Kawaoka |
| 2004/0029251 A1 | 2/2004 | Hoffman et al. |
| 2004/0057967 A1 | 3/2004 | Bavari et al. |
| 2004/0063141 A1 | 4/2004 | Lok |
| 2004/0077086 A1 | 4/2004 | Reiter et al. |
| 2004/0132164 A1 | 7/2004 | Doyle et al. |
| 2004/0142322 A1 | 7/2004 | Malcolm et al. |
| 2004/0219170 A1 | 11/2004 | Kawaoka |
| 2004/0241139 A1 | 12/2004 | Hobom et al. |
| 2004/0242518 A1 | 12/2004 | Chen et al. |
| 2005/0003349 A1 | 1/2005 | Kawaoka |
| 2005/0037487 A1 | 2/2005 | Kawaoka et al. |
| 2005/0095583 A1 | 5/2005 | Pekosz et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266023 A1 | 12/2005 | Bavari et al. |
| 2005/0266026 A1 | 12/2005 | Hoffmann et al. |
| 2006/0057116 A1 | 3/2006 | Kawaoka et al. |
| 2006/0088909 A1 | 4/2006 | Compans |
| 2006/0099609 A1 | 5/2006 | Bavari et al. |
| 2006/0134138 A1 | 6/2006 | Kawaoka et al. |
| 2006/0166321 A1 | 7/2006 | Kawaoka et al. |
| 2006/0188977 A1 | 8/2006 | Schwartz et al. |
| 2006/0216702 A1 | 9/2006 | Compans et al. |
| 2006/0240515 A1 | 10/2006 | Dimitrov et al. |
| 2006/0246092 A1 | 11/2006 | Neirynck et al. |
| 2007/0141699 A1 | 6/2007 | Kawaoka |
| 2007/0231348 A1 | 10/2007 | Kawaoka et al. |
| 2008/0009031 A1 | 1/2008 | Kawaoka |
| 2008/0187557 A1 | 8/2008 | Sambhara |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0292658 A1 | 11/2008 | De Wit et al. |
| 2008/0293040 A1 | 11/2008 | Kawaoka et al. |
| 2008/0311148 A1 | 12/2008 | Hoffmann |
| 2008/0311149 A1 | 12/2008 | Hoffmann |
| 2009/0017444 A1 | 1/2009 | Kawaoka et al. |
| 2009/0047728 A1 | 2/2009 | Kawaoka et al. |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2009/0311669 A1 | 12/2009 | Kawaoka |
| 2009/0324640 A1 | 12/2009 | Kawaoka et al. |
| 2010/0080825 A1 | 4/2010 | Kawaoka et al. |
| 2010/0112000 A1 | 5/2010 | Schwartz |
| 2010/0183671 A1 | 7/2010 | Gregersen et al. |
| 2010/0247572 A1 | 9/2010 | Kawaoka |
| 2010/0267116 A1 | 10/2010 | Kawaoka et al. |
| 2011/0020374 A1 | 1/2011 | Frazer |
| 2011/0027314 A1 | 2/2011 | Broeker |
| 2011/0045022 A1 | 2/2011 | Tsai |
| 2011/0081373 A1 | 4/2011 | Kawaoka et al. |
| 2011/0110978 A1 | 5/2011 | Kawaoka et al. |
| 2011/0159031 A1 | 6/2011 | Falkner et al. |
| 2011/0236417 A1 | 9/2011 | Watanabe et al. |
| 2011/0263554 A1 | 10/2011 | Kawaoka et al. |
| 2011/0300604 A1 | 12/2011 | Kawaoka et al. |
| 2012/0020997 A1 | 1/2012 | Hoffman et al. |

(56) References Cited

U.S. PATENT DOCUMENTS

| | | |
|---|---|---|
| 2012/0034600 A1 | 2/2012 | Gregersen |
| 2012/0058124 A1 | 3/2012 | Kurosawa et al. |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2012/0251568 A1 | 10/2012 | Garcia-Sastre et al. |
| 2013/0095135 A1 | 4/2013 | Collignon et al. |
| 2013/0183741 A1 | 7/2013 | Park et al. |
| 2013/0230552 A1 | 9/2013 | Kawaoka et al. |
| 2013/0243744 A1 | 9/2013 | Betenbaugh |
| 2013/0316434 A1 | 11/2013 | Reiter et al. |
| 2014/0227310 A1 | 8/2014 | Li et al. |
| 2015/0017205 A1 | 1/2015 | Kawaoka et al. |
| 2015/0166967 A1 | 6/2015 | Kawaoka et al. |
| 2015/0307851 A1 | 10/2015 | Kawaoka et al. |
| 2015/0368621 A1 | 12/2015 | Kawaoka et al. |
| 2016/0024193 A1 | 1/2016 | Ayalon et al. |
| 2016/0024479 A1 | 1/2016 | Kawaoka et al. |
| 2016/0115518 A1 | 4/2016 | Kawaoka et al. |
| 2016/0208223 A1 | 7/2016 | Kawaoka et al. |
| 2016/0215040 A1 | 7/2016 | Kyratsous et al. |
| 2016/0355790 A1 | 12/2016 | Kawaoka et al. |
| 2017/0058265 A1 | 3/2017 | Kawaoka et al. |
| 2017/0067029 A1 | 3/2017 | Kawaoka et al. |
| 2017/0096645 A1 | 4/2017 | Watanabe et al. |
| 2017/0097334 A1 | 4/2017 | Kawaoka et al. |
| 2017/0121391 A1 | 5/2017 | Kawaoka et al. |
| 2017/0258888 A1 | 9/2017 | Kawaoka |
| 2017/0298120 A1 | 10/2017 | Sasisekharan |
| 2017/0354730 A1 | 12/2017 | Kawaoka et al. |
| 2018/0245054 A1 | 8/2018 | Kawaoka et al. |
| 2018/0273588 A1 | 9/2018 | Kawaoka et al. |
| 2018/0340152 A1 | 11/2018 | Kawaoka et al. |
| 2019/0032023 A1 | 1/2019 | Kawaoka et al. |
| 2019/0048324 A1 | 2/2019 | Kawaoka et al. |
| 2019/0117759 A1 | 4/2019 | Wantanabe et al. |
| 2019/0167781 A1 | 6/2019 | Kawaoka et al. |
| 2020/0188506 A1 | 6/2020 | Kawaoka et al. |
| 2020/0237899 A1 | 7/2020 | Kawaoka et al. |
| 2020/0263142 A1 | 8/2020 | Kawaoka et al. |
| 2020/0263143 A1 | 8/2020 | Kawaoka et al. |
| 2020/0291384 A1 | 9/2020 | Kawaoka et al. |
| 2021/0061862 A1 | 3/2021 | Kawaoka et al. |
| 2021/0102178 A1 | 4/2021 | Kawaoka et al. |
| 2021/0121545 A1 | 4/2021 | Knoll et al. |
| 2021/0228708 A1 | 7/2021 | Smith et al. |
| 2021/0246432 A1 | 8/2021 | Kawaoka et al. |
| 2021/0252130 A1 | 8/2021 | Watanabe et al. |
| 2021/0290754 A1 | 9/2021 | Kawaoka et al. |
| 2021/0299249 A1 | 9/2021 | Kawaoka et al. |
| 2022/0025339 A1 | 1/2022 | Kawaoka et al. |
| 2022/0202926 A1 | 6/2022 | Kawaoka et al. |
| 2022/0202927 A1 | 6/2022 | Kawaoka et al. |
| 2022/0241396 A1 | 8/2022 | Kawaoka et al. |
| 2023/0321217 A1 | 10/2023 | Kawaoka et al. |
| 2023/0346911 A1 | 11/2023 | Kawaoka et al. |
| 2024/0010995 A1 | 1/2024 | Kawaoka et al. |
| 2024/0076632 A1 | 3/2024 | Kawaoka et al. |
| 2024/0238403 A1 | 7/2024 | Kawaoka et al. |
| 2024/0318167 A1 | 9/2024 | Kawaoka et al. |

FOREIGN PATENT DOCUMENTS

| | | |
|---|---|---|
| AU | 2014290203 B2 | 12/2020 |
| AU | 2017221444 B2 | 11/2021 |
| BR | PI0410702 B1 | 4/2022 |
| CA | 2379012 A1 | 1/2001 |
| CA | 2816242 C | 1/2019 |
| CN | 1826407 A | 8/2006 |
| CN | 101472941 A | 7/2009 |
| CN | 1826407 B | 9/2013 |
| CN | 105296356 A | 2/2016 |
| CN | 103540614 B | 2/2018 |
| CN | 109477074 A | 3/2019 |
| CN | 113874496 A | 12/2021 |
| CN | 114929269 A | 8/2022 |
| EP | 0687471 A1 | 12/1995 |
| EP | 0700991 A1 | 3/1996 |
| EP | 0702085 A1 | 3/1996 |
| EP | 0704533 A1 | 4/1996 |
| EP | 1201760 A1 | 5/2002 |
| EP | 2010557 B1 | 2/2014 |
| EP | 1572910 B1 | 12/2015 |
| EP | 1631663 B1 | 8/2016 |
| EP | 2747778 B1 | 12/2017 |
| EP | 3009507 B1 | 6/2020 |
| EP | 2493912 B1 | 7/2020 |
| EP | 3022296 B1 | 12/2022 |
| IL | 171831 A | 5/2015 |
| JP | 07-203958 | 8/1995 |
| JP | 2002536992 A | 11/2002 |
| JP | 2003528570 A | 9/2003 |
| JP | 2004500842 A | 1/2004 |
| JP | 2004531232 A | 10/2004 |
| JP | 2005523698 A | 8/2005 |
| JP | 2005245302 A | 9/2005 |
| JP | 2005535288 A | 11/2005 |
| JP | 2006525815 A | 11/2006 |
| JP | 2007518395 A | 7/2007 |
| JP | 2007525175 A | 9/2007 |
| JP | 2007529997 A | 11/2007 |
| JP | 2008520248 A | 6/2008 |
| JP | 2009511084 A | 3/2009 |
| JP | 2009523252 A | 6/2009 |
| JP | 2009553352 A | 9/2009 |
| JP | 2010530248 A | 9/2010 |
| JP | 2011530295 A | 12/2011 |
| JP | 4927290 | 5/2012 |
| JP | 4927290 B2 | 5/2012 |
| JP | 2013507990 A | 3/2013 |
| JP | 2013511280 A | 4/2013 |
| JP | 2014131516 A | 7/2014 |
| JP | 2014039551 A | 3/2015 |
| JP | 2016500007 A | 1/2016 |
| JP | 2016521553 A | 7/2016 |
| JP | 2016144463 A | 8/2016 |
| JP | 2016524915 A | 8/2016 |
| JP | 2016169225 A | 9/2016 |
| JP | 2017527557 A | 9/2017 |
| JP | 2017197555 A | 11/2017 |
| JP | 2018064493 A | 4/2018 |
| JP | 6352974 B2 | 6/2018 |
| JP | 6375329 B2 | 7/2018 |
| JP | 2019510481 A | 4/2019 |
| JP | 2020010711 A | 1/2020 |
| JP | 2020114250 | 7/2020 |
| JP | 2021500891 A | 1/2021 |
| JP | 2021036878 A | 3/2021 |
| JP | 2021184761 A | 12/2021 |
| JP | 2021533157 A | 12/2021 |
| JP | 2021536228 A | 12/2021 |
| JP | 2022066209 A | 4/2022 |
| JP | 2022522112 A | 4/2022 |
| JP | 2022527235 A | 6/2022 |
| JP | 2022172369 A | 11/2022 |
| JP | 2022551805 A | 12/2022 |
| KR | 101113432 B1 | 2/2012 |
| MX | 285206 | 3/2011 |
| NO | 341506 | 11/2017 |
| WO | WO-9610631 A1 | 4/1996 |
| WO | WO-9610632 A1 | 4/1996 |
| WO | WO-9640955 A1 | 12/1996 |
| WO | WO-9737000 A1 | 10/1997 |
| WO | WO-9802530 A1 | 1/1998 |
| WO | WO-9848834 A1 | 11/1998 |
| WO | WO-9853078 A1 | 11/1998 |
| WO | WO-9928445 A1 | 6/1999 |
| WO | WO-0053786 A1 | 9/2000 |
| WO | WO-0060050 A2 | 10/2000 |
| WO | WO-2000060050 A2 | 10/2000 |
| WO | WO-0060050 A3 | 1/2001 |
| WO | WO-2001004333 A1 | 1/2001 |
| WO | WO-2001025462 A1 | 4/2001 |
| WO | WO-0179273 A2 | 10/2001 |

(56) References Cited

FOREIGN PATENT DOCUMENTS

| | | |
|---|---|---|
| WO | WO-2001079273 A2 | 10/2001 |
| WO | WO-0183794 A2 | 11/2001 |
| WO | WO-2001083794 A2 | 11/2001 |
| WO | WO-0210143 A1 | 1/2002 |
| WO | WO-02064757 A2 | 8/2002 |
| WO | WO-02074795 A2 | 9/2002 |
| WO | WO-03068923 A2 | 8/2003 |
| WO | WO-2003068923 A2 | 8/2003 |
| WO | WO-03076462 A1 | 9/2003 |
| WO | WO-2003080846 A1 | 10/2003 |
| WO | WO-03091401 A2 | 11/2003 |
| WO | WO-2003091401 A2 | 11/2003 |
| WO | WO-2004142322 A1 | 7/2004 |
| WO | WO-2004094466 A2 | 11/2004 |
| WO | WO-04112831 A2 | 12/2004 |
| WO | WO-2004112831 A2 | 12/2004 |
| WO | WO2004112831 A3 | 12/2004 |
| WO | WO-05028658 A2 | 3/2005 |
| WO | WO-05028658 A3 | 3/2005 |
| WO | WO-2005028658 A2 | 3/2005 |
| WO | Wo-2005062820 A2 | 7/2005 |
| WO | WO-2006051069 A2 | 5/2006 |
| WO | WO-2007044024 A2 | 4/2007 |
| WO | WO-2007044024 A3 | 4/2007 |
| WO | WO-2007126810 A2 | 11/2007 |
| WO | WO-2007126810 A3 | 11/2007 |
| WO | WO-2007146057 A2 | 12/2007 |
| WO | WO-2007146057 A3 | 12/2007 |
| WO | WO-08156681 A3 | 12/2008 |
| WO | WO-2008147496 A2 | 12/2008 |
| WO | WO-2008147496 A3 | 12/2008 |
| WO | WO-2008156681 A2 | 12/2008 |
| WO | WO-2008156778 A2 | 12/2008 |
| WO | WO-2008156778 A3 | 12/2008 |
| WO | WO-2008157583 A1 | 12/2008 |
| WO | WO-09008921 A3 | 1/2009 |
| WO | WO-09008921 A9 | 1/2009 |
| WO | WO-2009007244 A2 | 1/2009 |
| WO | WO-2009008921 A2 | 1/2009 |
| WO | WO-2009014919 A2 | 1/2009 |
| WO | WO-2008156778 A9 | 2/2009 |
| WO | WO-09128867 A2 | 10/2009 |
| WO | WO-2009152181 A1 | 12/2009 |
| WO | WO-2009128867 A3 | 3/2010 |
| WO | WO-2010053573 A2 | 5/2010 |
| WO | WO-2010053573 A3 | 7/2010 |
| WO | WO-2011014645 A1 | 2/2011 |
| WO | WO-2011056591 A1 | 5/2011 |
| WO | WO-2011087839 A1 | 7/2011 |
| WO | WO-2011126370 A1 | 10/2011 |
| WO | WO-2011130627 A2 | 10/2011 |
| WO | WO-2012045882 A2 | 4/2012 |
| WO | WO-2012177924 A2 | 12/2012 |
| WO | WO-2013032942 A1 | 3/2013 |
| WO | WO-2013032942 A9 | 3/2013 |
| WO | WO-2013034069 A1 | 3/2013 |
| WO | WO-2013087945 A2 | 6/2013 |
| WO | WO-2013148302 A1 | 10/2013 |
| WO | WO-2014195920 A2 | 12/2014 |
| WO | WO-2015009743 A1 | 1/2015 |
| WO | WO-2015031166 A1 | 3/2015 |
| WO | WO-2015134488 A1 | 9/2015 |
| WO | WO-2015142671 A2 | 9/2015 |
| WO | WO-2015196150 A2 | 12/2015 |
| WO | WO-2015196150 A3 | 12/2015 |
| WO | WO-2016144933 A1 | 9/2016 |
| WO | WO-2016207853 A2 | 12/2016 |
| WO | WO-2017007839 A1 | 1/2017 |
| WO | WO-2017040203 A1 | 3/2017 |
| WO | WO-2017136575 A1 | 8/2017 |
| WO | WO-2017143236 A1 | 8/2017 |
| WO | WO-2019084310 A1 | 5/2019 |
| WO | WO-2019241579 A1 | 12/2019 |
| WO | WO-2020033527 A2 | 2/2020 |
| WO | WO-2020041311 A1 | 2/2020 |
| WO | 2020061443 | 3/2020 |
| WO | WO-2020/033527 A3 | 3/2020 |
| WO | WO-2020163804 A1 | 8/2020 |
| WO | WO-2020167432 A2 | 8/2020 |
| WO | WO-2020223699 A1 | 11/2020 |
| WO | WO-2020167432 A3 | 12/2020 |
| WO | WO-2020264141 A1 | 12/2020 |
| WO | WO-2021041624 A2 | 3/2021 |
| WO | WO-2021041624 A3 | 5/2021 |
| WO | WO-2021150874 A1 | 7/2021 |
| WO | WO-2021195410 A1 | 9/2021 |
| WO | WO-2021242597 A1 | 12/2021 |
| WO | 2022245888 | 11/2022 |
| WO | 2023125889 | 7/2023 |
| WO | 2023164556 | 8/2023 |
| WO | WO-2024015510 A1 | 1/2024 |
| WO | WO-2024197167 A1 | 9/2024 |

OTHER PUBLICATIONS

"Japanese Application Serial No. 2018-510751, Examiners Decision of Final Refusal mailed Dec. 17, 2019", w English Translation, 10 pgs.

"Japanese Application Serial No. 2018-510751, Response filed Apr. 17, 2020 to Examiners Decision of Final Refusal mailed Dec. 17, 2019", w English Claims, 7 pgs.

"European Application Serial No. 16778485.9, Communication Pursuant to Article 94(3) EPC mailed May 25, 2020", 5 pgs.

"European Application Serial No. 16778485.9, Response filed Oct. 5, 2020 to Communication Pursuant to Article 94(3) EPC mailed May 25, 2020", 14 pgs.

"Japanese Application Serial No. 2020-073952, Notification of Reasons for Refusal mailed May 20, 2021", w o English Translation, 2 pgs.

Result 1, NCBI Blast nucleotide search of Seq ID No. 3, database "nr"; Result 4, NCBI Blast nucleotide search of Seq ID No. 4, database "nr", (Jul. 22, 2006), 11 pgs.

Result 2, NCBI Blast nucleotide search of Seq ID No. 5, database "nr"; Result 4, NCBI Blast nucleotide search of Seq ID No. 6, database "nr", (Jul. 22, 2006), 6 pgs.

Results 1, NCBI Blast nucleotide search of Seq ID No. 7, database "nr"; Result 1, NCBI Blast nucleotide search of Seq ID No. 8, database "nr", (Jul. 23, 2006), 8 pgs.

Result 17, NCBI Blast nucleotide search of Seq ID No. 2, database "nr", (Jul. 18, 2006), 3 pgs.

Result 7, NCBI Blast nucleotide search of Seq ID: 1, database "nr", (Jul. 18, 2006), 3 pgs.

FLUMISTTM Package Insert Template, [Online]. Retrieved from the Internet: http://www.fda.gov/downloads/BiologicsBioodVaccines!Vaccines/ApprovedProducts/UCM294307.pdf, (Mar. 1, 2012), 26 pgs.

"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 10/855,975 Response filed Aug. 28, 2007 to Final Office Action mailed Jun. 28, 2007", 16 pgs.

"Final O.A Jun. 28, 2007", 5 pgs.

"Application Serial No. 04809419.7, Office Action Mailed Sep. 9, 2009", 3 pgs.

"U.S. Appl. No. 09/834,095, Advisory Action mailed Jan. 8, 2004", 3 pgs.

"U.S. Appl. No. 09/834,095, Final Office Action mailed Aug. 26, 2003", 12 pgs.

"U.S. Appl. No. 09/834,095, Non-Final Office Action mailed Nov. 4, 2002", 12 pgs.

"U.S. Appl. No. 09/834,095, Notice of Allowance mailed Sep. 27, 2004", 13 pgs.

"U.S. Appl. No. 09/834,095, Office Action mailed Apr. 20, 2004", 11 pgs.

(56) References Cited

OTHER PUBLICATIONS

"U.S. Appl. No. 09/834,095, Response filed Feb. 4, 2003 to Office Action mailed Nov. 4, 2002", 14 pgs.
"U.S. Appl. No. 09/834,095, Response filed Jun. 12, 2003 to Restriction Requirement mailed Apr. 22, 2003", 2 pgs.
"U.S. Appl. No. 09/834,095, Response filed Jun. 18, 2004 to Office Action mailed Apr. 20, 2004", 11 pgs.
"U.S. Appl. No. 09/834,095, Response filed Aug. 1, 2002 to Restriction Requirement mailed Jul. 1, 2002", 3 pgs.
"U.S. Appl. No. 09/834,095, Response filed Nov. 26, 2003 to Final Office Action mailed Aug. 26, 2003", 10 pgs.
"U.S. Appl. No. 09/834,095, Restriction Requirement mailed Apr. 22, 2003", 5 pgs.
"U.S. Appl. No. 09/834,095, Restriction Requirement mailed Jul. 1, 2002", 9 pgs.
"U.S. Appl. No. 09/834,095, Supplemental Amendment filed Aug. 4, 2004", 7 pgs.
"U.S. Appl. No. 10/353,856, Final Office Action mailed Jun. 1, 2006", 10 pgs.
"U.S. Appl. No. 10/353,856, Non-Final Office Action mailed Sep. 30, 2005", 9 pgs.
"U.S. Appl. No. 10/353,856, Non-Final Office Action mailed Dec. 16, 2004", 11 pgs.
"U.S. Appl. No. 10/353,856, Notice of Allowance mailed Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment mailed Mar. 8, 2007", 2 pgs.
"U.S. Appl. No. 10/353,856, Response filed Feb. 28, 2006 to Non-Final Office Action mailed Sep. 30, 2005", 10 pgs.
"U.S. Appl. No. 10/353,856, Response filed Apr. 7, 2005 to Non-Final Office Action mailed Dec. 16, 2004", 10 pgs.
"U.S. Appl. No. 10/353,856, Response filed Aug. 17, 2006 to Final Office Action mailed Jun. 1, 2006", 11 pgs.
"U.S. Appl. No. 10/353,856, Response filed Oct. 8, 2004 to Restriction Requirement mailed Sep. 10, 2004", 2 pgs.
"U.S. Appl. No. 10/353,856, Restriction Requirement mailed Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/827,995, Final Office Action mailed Nov. 15, 2006", 10 pgs.
"U.S. Appl. No. 10/827,995, Non-Final Office Action mailed Jun. 2, 2006", 15 pgs.
"U.S. Appl. No. 10/827,995, Non-Final Office Action mailed Oct. 25, 2007", 7 pgs.
"U.S. Appl. No. 10/827,995, Notice of Allowance mailed Feb. 17, 2009", 9 pgs.
"U.S. Appl. No. 10/827,995, Notice of Allowance mailed Jul. 2, 2008", 9 pgs.
"U.S. Appl. No. 10/827,995, Notice of Allowance mailed Oct. 17, 2008", 7 pgs.
"U.S. Appl. No. 10/827,995, Notice of Non-Compliant Amendment Jul. 25, 2007", 4 pgs.
"U.S. Appl. No. 10/827,995, Proposed Examiner's Amendment mailed Jun. 5, 2008", 6 ogs.
"U.S. Appl. No. 10/827,995, Response filed Mar. 3, 2008 to Office Action mailed Oct. 25, 2007", 10 pgs.
"U.S. Appl. No. 10/827,995, Response filed May 14, 2007 Final Office Action mailed Nov. 15, 2006", 16 pgs.
"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action mailed Jun. 2, 2006", 15 pgs.
"U.S. Appl. No. 10/855,875 , Response filed May 17, 2012 to Non Final Office Action mailed Mar. 15, 2012", 15 pgs.
"U.S. Appl. No. 10/855,875, Final Office Action mailed Mar. 11, 2008", FOAR, 20 Pgs.
"U.S. Appl. No. 10/855,875, Final Office Action mailed Aug. 2, 2006", 34 pgs.
"U.S. Appl. No. 10/855,875, Final Office Action mailed Dec. 10, 2010", 15 pgs.
"U.S. Appl. No. 10/855,875, Non Final Office Action mailed Mar. 15, 2012", 15 pgs.
"U.S. Appl. No. 10/855,875, Non-Final Office Action mailed Feb. 19, 2010", 7 pgs.
"U.S. Appl. No. 10/855,875, Non-Final Office Action mailed May 3, 2007", 13 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action mailed Aug. 2, 2007", 14 pgs.
"U.S. Appl. No. 10/855,875, Response filed Mar. 18, 2011 to Final Office Action mailed Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Dec. 7, 2009 to Non Final Office Action mailed Aug. 7, 2009", 15 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.
"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,975, Advisory Action mailed Sep. 6, 2006", 3 pgs.
"U.S. Appl. No. 10/855,975, Advisory Action mailed Sep. 13, 2007", 3 pgs.
"U.S. Appl. No. 10/855,975, Advisory Action mailed Dec. 24, 2008", 4 pgs.
"U.S. Appl. No. 10/855,975, Final Office Action mailed May 17, 2006", 7 pgs.
"U.S. Appl. No. 10/855,975, Final Office Action mailed Jun. 28, 2007", 7 pgs.
"U.S. Appl. No. 10/855,975, Final Office Action mailed Aug. 7, 2008", 5 pgs.
"U.S. Appl. No. 10/855,975, Non-Final Office Action mailed Jan. 4, 2008", 10 pgs.
"U.S. Appl. No. 10/855,975, Non-Final Office Action mailed Jan. 19, 2007", 7 pgs.
"U.S. Appl. No. 10/855,975, Non-Final Office Action mailed May 29, 2009", 5 pgs.
"U.S. Appl. No. 10/855,975, Non-Final Office Action mailed Nov. 30, 2005", 11 pgs.
"U.S. Appl. No. 10/855,975, Notice of Allowance mailed Dec. 16, 2009", 19 pgs.
"U.S. Appl. No. 10/855,975, Response filed Jan. 29, 2009 to Advisory Action mailed Dec. 24, 2008", 15 pgs.
"U.S. Appl. No. 10/855,975, Response filed Feb. 28, 2006 to Non-Final Office Action mailed Nov. 30, 2005", 15 pgs.
"U.S. Appl. No. 10/855,975, Response filed Apr. 3, 2008 to Non Final Office Action mailed Jan. 4, 2008", 16 pgs.
"U.S. Appl. No. 10/855,975, Response filed Apr. 19, 2007 to Non-Final Office Action mailed Jan. 19, 2007", 16 pgs.

(56) References Cited

OTHER PUBLICATIONS

"U.S. Appl. No. 10/855,975, Response filed Aug. 13, 2009 to Non Final Office Action mailed May 29, 2009", 19 pgs.
"U.S. Appl. No. 10/855,975, Response filed Aug. 17, 2006 to Final Office Action mailed May 17, 2006", 13 pgs.
"U.S. Appl. No. 10/855,975, Response filed Aug. 28, 2007 to Final Office Action mailed Jun. 28, 2007", 15 pgs.
"U.S. Appl. No. 10/855,975, Response filed Sep. 28, 2005 to Restriction Requirement mailed Jul. 12, 2005", 3 pgs.
"U.S. Appl. No. 10/855,975, Response filed Dec. 11, 2008 to Final Office Action mailed Aug. 7, 2008", 14 pgs.
"U.S. Appl. No. 10/855,975, Restriction Requirement mailed Jul. 12, 2005", 8 pgs.
"U.S. Appl. No. 10/855,875, Response filed Nov. 2, 2007 to Office Action mailed May 3, 2007", 16 pgs.
"U.S. Appl. No. 11/043,768 Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Jun. 23, 2009 to Non-Final Office Action mailed Feb. 23, 2009", 9 pgs.
"U.S. Appl. No. 11/043,768, Response filed Sep. 13, 2007 to Restriction Requirement mailed Mar. 13, 2007", 10 pgs.
"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,786, Final Office Action mailed Feb. 3, 2011", 10 pgs.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006", 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.

"U.S. Appl. No. 11/654,863 Final Office Action mailed Jul. 17, 2017", 11 pgs.
"U.S. Appl. No. 11/654,863 Restriction Requirement mailed Sep. 3, 2010", 5 pgs.
"U.S. Appl. No. 11/654,863, Appeal Brief filed Apr. 30, 2014", 22 pgs.
"U.S. Appl. No. 11/654,863, Appeal Decision mailed Aug. 3, 2016", 11 pgs.
"U.S. Appl. No. 11/654,863, Decision on Pre-Appeal Brief Request mailed Dec. 5, 2013", 2 pgs.
"U.S. Appl. No. 11/654,863, Declaration of Dr. Heinz Feldmann dated Jan. 9, 2018", 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief mailed Jun. 18, 2014", 10 pgs.
"U.S. Appl. No. 11/654,863, Final Office Action mailed Jul. 11, 2013", 9 pgs.
"U.S. Appl. No. 11/654,863, Final Office Action mailed Sep. 12, 2018", 12 pgs.
"U.S. Appl. No. 11/654,863, Final Office Action mailed Oct. 25, 2011", 9 pgs.
"U.S. Appl. No. 11/654,863, Non Final Office Action mailed Feb. 11, 2013", 10 pgs.
"U.S. Appl. No. 11/654,863, Non Final Office Action mailed Mar. 29, 2018", 12 pgs.
"U.S. Appl. No. 11/654,863, Non Final Office Action mailed Jun. 27, 2011", 9 pgs.
"U.S. Appl. No. 11/654,863, Non Final Office Action mailed Dec. 2, 2010", 8 pgs.
"U.S. Appl. No. 11/654,863, Non Final Office Action mailed Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action mailed Jul. 17, 2017", 9 pgs.
"U.S. Appl. No. 11/654,863, Response filed Apr. 18, 2012 to Final Office Action mailed Oct. 25, 2011", 8 pgs.
"U.S. Appl. No. 11/654,863, Response filed Jun. 2, 2011 to Non Final Office Action mailed Dec. 2, 2010", 6 pgs.
"U.S. Appl. No. 11/654,863, Response filed Jun. 7, 2013 to Non Final Office Action mailed Feb. 11, 2013", 10 pgs.
"U.S. Appl. No. 11/654,863, Response filed Jun. 21, 2017 to Non Final Office Action mailed Dec. 21, 2016", 11 pgs.
"U.S. Appl. No. 11/654,863, Response filed Jul. 9, 2018 to Non Final Office Action mailed Mar. 29, 2018", 10 pgs.
"U.S. Appl. No. 11/654,863, Response filed Sep. 28, 2010 to Restriction Requirement mailed Sep. 3, 2010", 6 pgs.
"U.S. Appl. No. 11/654,863, Response filed Oct. 6, 2011 to Non Final Office Action mailed Jun. 27, 2011", 9 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non Final Office Action mailed Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.

(56) References Cited

OTHER PUBLICATIONS

"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Respons filed Jun. 22, 2010 to Non Final Office Action mailed Feb. 22, 2010", 33 pgs.
"U.S. Appl. No. 11/729,557, Response filed Apr. 27, 2011 to Final Office Action mailed Feb. 2, 2011", 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557, Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Response filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 11/810,956, Final Office Action mailed Mar. 22, 2010", 8 pgs.
"U.S. Appl. No. 11/810,956, Non-Final Office Action mailed Aug. 11, 2009", 9 pgs.
"U.S. Appl. No. 11/810,956, Response filed Jan. 11, 2010 to Non Final Office Action mailed Aug. 11, 2009", 8 pgs.
"U.S. Appl. No. 11/810,956, Response filed Apr. 23, 2009 to Restriction Requirement mailed Mar. 23, 2009", 6 pgs.
"U.S. Appl. No. 11/810,956, Restriction Requirement mailed Mar. 23, 2009", 6 pgs.
"U.S. Appl. No. 12/058,389, Advisory Action mailed Jan. 2, 2013", 2 pgs.
"U.S. Appl. No. 12/058,389, Final Office Action mailed Jan. 22, 2010", 8 pgs.
"U.S. Appl. No. 12/058,389, Final Office Action mailed Nov. 14, 2012", 7 pgs.
"U.S. Appl. No. 12/058,389, Non Final Office Action mailed Aug. 10, 2012", 5 pgs.
"U.S. Appl. No. 12/058,389, Non Final Office Action mailed Dec. 8, 2011", 8 pgs.
"U.S. Appl. No. 12/058,389, Non-Final Office Action mailed Apr. 13, 2009", 12 pgs.
"U.S. Appl. No. 12/058,389, Notice of Allowability mailed Mar. 22, 2013", 8 pgs.
"U.S. Appl. No. 12/058,389, Notice of Allowance mailed Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action mailed Aug. 10, 2012", 7 pgs.
"U.S. Appl. No. 12/058,389, Response filed Feb. 6, 2009 to Restriction Requirement mailed Dec. 3, 2008", 7 pgs.
"U.S. Appl. No. 12/058,389, Response filed Apr. 10, 2012 to Non Final Office Action mailed Dec. 8, 2011", 7 pgs.
"U.S. Appl. No. 12/058,389, Response filed Jun. 16, 2010 to Final Office Action mailed Jan. 22, 2010", 6 pgs.
"U.S. Appl. No. 12/058,389, Response filed Oct. 13, 2009 to Non Final Office Action mailed Apr. 13, 2009", 9 pgs.
"U.S. Appl. No. 12/058,389, Response filed Dec. 18, 2012 to Non Final Office Action mailed Nov. 14, 2012", 7 pgs.
"U.S. Appl. No. 12/058,389, Restriction Requirement mailed Dec. 3, 2008", 7 pgs.

"U.S. Appl. No. 12/139,183, Non Final Office Action mailed Jan. 6, 2011", 12 pgs.
"U.S. Appl. No. 12/139,183, Non-Final Office Action mailed Jan. 4, 2010", 6 pgs.
"U.S. Appl. No. 12/139,183, Non-Final Office Action mailed Jul. 13, 2010", 15 pgs.
"U.S. Appl. No. 12/139,183, Notice of Allowance mailed Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action mailed Jan. 6, 2011", 21 pgs.
"U.S. Appl. No. 12/139,183, Response filed Apr. 12, 2010 to Non Final Office Action mailed Jan. 4, 2010", 17 pgs.
"U.S. Appl. No. 12/139,183, Response filed Aug. 18, 2009 to Restriction Requirement mailed Jul. 24, 2009", 16 pgs.
"U.S. Appl. No. 12/139,183, Response filed Sep. 21, 2010 to Non Final Office Action mailed Jul. 13, 2010", 21 pgs.
"U.S. Appl. No. 12/139,183, Restriction Requirement mailed Jul. 24, 2009", 12 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.
"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action mailed Jun. 12, 2014", 28 pgs.
"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Oct. 14, 2014 to Non Final Office Action mailed Jun. 12, 2014", 16 pgs.
"U.S. Appl. No. 12/214,414, Response filed Dec. 21, 2011 to Advisory Action mailed Oct. 21, 2011", 10 pgs.
"U.S. Appl. No. 12/245,296, Final Office Action mailed Jul. 11, 2013", 15 pgs.
"U.S. Appl. No. 12/245,296, Final Office Action mailed Dec. 17, 2010", 16 pgs.
"U.S. Appl. No. 12/245,296, Non Final Office Action mailed Mar. 25, 2013", 14 pgs.
"U.S. Appl. No. 12/245,296, Non-Final Office Action mailed Jun. 1, 2010", 13 pgs.
"U.S. Appl. No. 12/245,296, Notice of Allowance mailed Aug. 1, 2014", 10 pgs.
"U.S. Appl. No. 12/245,296, Preliminary Amendment mailed Jan. 28, 2009", 14 pgs.

(56) References Cited

OTHER PUBLICATIONS

"U.S. Appl. No. 12/245,296, Response filed Jan. 8, 2013 to Final Office Action mailed Jul. 11, 2013", 10 pgs.
"U.S. Appl. No. 12/245,296, Response filed Apr. 8, 2010 to Restriction Requirement mailed Mar. 9, 2010", 6 pgs.
"U.S. Appl. No. 12/245,296, Response filed May 17, 2011 to Final Office Action mailed Dec. 17, 2010", 10 pgs.
"U.S. Appl. No. 12/245,296, Response filed Jun. 7, 2013 to Non Final Office Action mailed Mar. 25, 2013", 9 pgs.
"U.S. Appl. No. 12/245,296, Response filed Oct. 1, 2010 to Non Final Office Action mailed Jun. 1, 2010", 12 pgs.
"U.S. Appl. No. 12/245,296, Restriction Requirement mailed Mar. 9, 2010", 6 pgs.
"U.S. Appl. No. 12/467,492, Restriction Requirement mailed Nov. 22, 2010", 6 pgs.
"U.S. Appl. No. 12/854,578 , Response filed Oct. 1, 2012 to Non Final Office Action mailed Jun. 29, 2012", 10 pgs.
"U.S. Appl. No. 12/854,578, Final Office Action mailed Nov. 29, 2012", 8 pgs.
"U.S. Appl. No. 12/854,578, Non Final Office Action mailed Jun. 29, 2012", 8 pgs.
"U.S. Appl. No. 12/854,578, Notice of Allowance mailed Apr. 10, 2013", 6 pgs.
"U.S. Appl. No. 12/854,578, PTO Response to 312 Amendment mailed Jul. 18, 2013", 2 pgs.
"U.S. Appl. No. 12/854,578, Response filed Feb. 28, 2013 to Final Office Action mailed Nov. 29, 2012", 8 pgs.
"U.S. Appl. No. 12/854,578, Restriction Requirement mailed Apr. 6, 2012", 6 pgs.
"U.S. Appl. No. 12/912,411, Advisory Action mailed Feb. 5, 2014", 3 pgs.
"U.S. Appl. No. 12/912,411, Examiner Interview Summary mailed Feb. 11, 2014", 2 pgs.
"U.S. Appl. No. 12/912,411, Final Office Action mailed Jan. 14, 2015", 10 pgs.
"U.S. Appl. No. 12/912,411, Final Office Action mailed Oct. 25, 2013", 11 pgs.
"U.S. Appl. No. 12/912,411, Non Final Office Action mailed Jun. 7, 2013", 8 pgs.
"U.S. Appl. No. 12/912,411, Non Final Office Action mailed Sep. 24, 2014", 11 pgs.
"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Jan. 27, 2014 to Final Office Action mailed Oct. 25, 2013", 11 pgs.
"U.S. Appl. No. 12/912,411, Response filed Feb. 18, 2013 to Restriction Requirement mailed Oct. 17, 2012", 9 pgs.
"U.S. Appl. No. 12/912,411, Response filed Feb. 25, 2014 to Final Office Action mailed Oct. 25, 2013", 11 pgs.
"U.S. Appl. No. 12/912,411, Response filed Mar. 16, 2015 to Final Office Action mailed Jan. 14, 2015", 9 pgs.
"U.S. Appl. No. 12/912,411, Response filed Oct. 7, 2013 to Non Final Office Action mailed Jun. 7, 2013", 10 pgs.
"U.S. Appl. No. 12/912,411, Response filed Dec. 31, 2014 to Non Final Office Action mailed Sep. 24, 2014", 12 pgs.
"U.S. Appl. No. 12/912,411, Restriction Requirement mailed Oct. 17, 2012", 9 pgs.
"U.S. Appl. No. 13/070,110 Response filed Feb. 14, 2017 to Final Office Action mailed Sep. 14, 2016", 8 pgs.
"U.S. Appl. No. 13/070,110, Advisory Action mailed Mar. 3, 2017", 5 pgs.
"U.S. Appl. No. 13/070,110, Examiner Interview Summary mailed Jan. 16, 2018", 3 pgs.
"U.S. Appl. No. 13/070,110, Final Office Action mailed Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Jul. 21, 2017", 14 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.
"U.S. Appl. No. 13/070,110, Non Final Office Action mailed Dec. 21, 2012", 7 pgs.
"U.S. Appl. No. 13/070,110, Notice of Allowance mailed Mar. 26, 2018", 6 pgs.
"U.S. Appl. No. 13/070,110, Notice of Allowance mailed Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication mailed Aug. 15, 2018", 2 pgs.
"U.S. Appl. No. 13/070,110, Response filed Jan. 22, 2018 to Non Final Office Action mailed Jul. 21, 2017", 10 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Jun. 20, 2017 to Advisory Action mailed Mar. 3, 2017", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action mailed Apr. 3, 2015", 11 pgs.
"U.S. Appl. No. 13/070,110, Response filed Nov. 12, 2013 to Final Office Action mailed Jun. 12, 2013", 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 13/113,244, Final Office Action mailed Feb. 27, 2014", 8 pgs.
"U.S. Appl. No. 13/113,244, Non Final Office Action mailed Jul. 5, 2013", 6 pgs.
"U.S. Appl. No. 13/113,244, Non Final Office Action mailed Oct. 1, 2012", 7 pgs.
"U.S. Appl. No. 13/113,244, Notice of Allowance mailed Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement mailed Oct. 31, 2011", 10 pgs.
"U.S. Appl. No. 13/113,244, Response filed Feb. 20, 2013 to Non Final Office Action mailed Oct. 1, 2012", 12 pgs.
"U.S. Appl. No. 13/113,244, Response filed Jun. 13, 2014 to Final Office Action mailed Feb. 27, 2014", 6 pgs.
"U.S. Appl. No. 13/113,244, Response filed Oct. 31, 2013 to Non Final Office Action mailed Jul. 5, 2013", 12 pgs.
"U.S. Appl. No. 13/113,244, Restriction Requirement mailed Oct. 31, 2011", 8 pgs.
"U.S. Appl. No. 13/127,951, Advisory Action mailed Jul. 16, 2014", 3 pgs.
"U.S. Appl. No. 13/127,951, Final Office Action mailed Apr. 9, 2014", 23 pgs.
"U.S. Appl. No. 13/127,951, Non Final Office Action mailed Sep. 26, 2013", 18 pgs.
"U.S. Appl. No. 13/127,951, Notice of Allowance mailed Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication mailed Oct. 23, 2015", 2 pgs.
"U.S. Appl. No. 13/127,951, Response filed Mar. 18, 2014 to Non Final Office Action mailed Sep. 26, 2013", 14 pgs.
"U.S. Appl. No. 13/127,951, Response filed Jul. 7, 2014 to Final Office Action mailed Apr. 9, 2014", 10 pgs.

(56) References Cited

OTHER PUBLICATIONS

"U.S. Appl. No. 13/127,951, Response filed Aug. 30, 2013 to Restriction Requirement mailed Apr. 30, 2013", Aug. 30, 2013.
"U.S. Appl. No. 13/127,951, Response filed Oct. 9, 2014 to Advisory Action mailed Jul. 16, 2014", 10 pgs.
"U.S. Appl. No. 13/127,951, Restriction Requirement mailed Apr. 30, 2013", 15 pgs.
"U.S. Appl. No. 14/332,121, Non Final Office Action mailed May 16, 2016", 9 pgs.
"U.S. Appl. No. 14/332,121, Notice of Allowance mailed Feb. 15, 2017", 10 pgs.
"U.S. Appl. No. 14/332,121, Notice of Allowance mailed Jun. 15, 2017", 8 pgs.
"U.S. Appl. No. 14/332,121, Notice of Allowance mailed Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement mailed Jul. 30, 2015", 9 pgs.
"U.S. Appl. No. 14/332,121, Response filed Sep. 7, 2017 to Notice of Allowability mailed Jun. 15, 2017", 8 pgs.
"U.S. Appl. No. 14/332,121, Response filed Oct. 11, 2016 to Non Final Office Action mailed May 16, 2016", 9 pgs.
"U.S. Appl. No. 14/332,121, Restriction Requirement mailed Jul. 30, 2015", 9 pgs.
"U.S. Appl. No. 14/332,121, Supplemental Amendment filed Jan. 23, 2017", 10 pgs.
"U.S. Appl. No. 14/528,997, Advisory Action mailed Aug. 9, 2017", 3 pgs.
"U.S. Appl. No. 14/528,997, Final Office Action mailed Feb. 10, 2017", 9 pgs.
"U.S. Appl. No. 14/528,997, Non Final Office Action mailed Jun. 16, 2016", 12 pgs.
"U.S. Appl. No. 14/528,997, Non Final Office Action mailed Jun. 29, 2018", 7 pgs.
"U.S. Appl. No. 14/528,997, Notice of Allowance mailed Mar. 8, 2019", 7 pgs.
"U.S. Appl. No. 14/528,997, PTO Response to Rule 312 Communication mailed Jun. 19, 2019", 2 pgs.
"U.S. Appl. No. 14/528,997, Response filed Mar. 16, 2016 to Restriction Requirement mailed Sep. 16, 2015", 11 pgs.
"U.S. Appl. No. 14/528,997, Response filed Jul. 27, 2017 to Final Office Action mailed Feb. 10, 2017", 11 pgs.
"U.S. Appl. No. 14/528,997, Response filed Oct. 10, 2016 to Non Final Office Action mailed Jun. 16, 2016", 12 pgs.
"U.S. Appl. No. 14/528,997, Response filed Nov. 16, 2018 to Non Final Office Action mailed Jun. 29, 2018", 11 pgs.
"U.S. Appl. No. 14/528,997, Restriction Requirement mailed Sep. 16, 2015", 8 pgs.
"U.S. Appl. No. 14/745,236, Advisory Action mailed Nov. 15, 2017", 2 pgs.
"U.S. Appl. No. 14/745,236, Final Office Action mailed Aug. 25, 2017", 16 pgs.
"U.S. Appl. No. 14/745,236, Non Final Office Action mailed Feb. 2, 2017", 14 pgs.
"U.S. Appl. No. 14/745,236, Notice of Allowability mailed Jul. 5, 2018", 4 pgs.
"U.S. Appl. No. 14/745,236, Notice of Allowance mailed Feb. 5, 2018", 9 pgs.
"U.S. Appl. No. 14/745,236, PTO Response to Rule 312 Communication mailed Jul. 10, 2018", 2 pgs.
"U.S. Appl. No. 14/745,236, Response filed May 2, 2017 to Non Final Office Action mailed Feb. 2, 2017", 10 pgs.
"U.S. Appl. No. 14/745,236, Response filed Nov. 6, 2017 to Final Office Action mailed Aug. 25, 2017", 12 pgs.
"U.S. Appl. No. 14/745,236, Response filed Dec. 14, 2017 to Final Office Action mailed Aug. 25, 2017", 12 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 14/816,807, Non Final Office Action mailed Oct. 3, 2017", 7 pgs.
"U.S. Appl. No. 14/816,807, Notice of Allowance mailed Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication mailed Jul. 6, 2018", 2 pgs.
"U.S. Appl. No. 14/816,807, Response filed Jan. 3, 2018 to Non Final Office Action mailed Oct. 3, 2017", 8 pgs.
"U.S. Appl. No. 14/816,807, Response filed May 1, 2017 to Restriction Requirement mailed Nov. 1, 2016", 9 pgs.
"U.S. Appl. No. 14/816,807, Restriction Requirement mailed Nov. 1, 2016", 8 pgs.
"U.S. Appl. No. 14/919,431, Preliminary Amendment filed Jan. 4, 2016", 8 pgs.
"U.S. Appl. No. 15/000,851, Non Final Office Action mailed Jan. 26, 2017", 15 pgs.
"U.S. Appl. No. 15/000,851, Notice of Allowance mailed Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action mailed Jan. 26, 2017", 16 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"U.S. Appl. No. 15/170,556, Final Office Action mailed Jul. 30, 2019", 6 pgs.
"U.S. Appl. No. 15/170,556, Non Final Office Action mailed Feb. 8, 2019", 11 pgs.
"U.S. Appl. No. 15/170,556, Non Final Office Action mailed Jul. 27, 2018", 10 pgs.
"U.S. Appl. No. 15/170,556, Notice of Allowability mailed Jan. 29, 2020", 4 pgs.
"U.S. Appl. No. 15/170,556, Notice of Allowance mailed Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement mailed Feb. 16, 2018", 8 pgs.
"U.S. Appl. No. 15/170,556, Response filed Oct. 29, 2018 to Non Final Office Action mailed Jul. 27, 2018", 9 pgs.
"U.S. Appl. No. 15/170,556, Response filed Nov. 18, 2019 to Final Office Action mailed Jul. 30, 2019", 8 pgs.
"U.S. Appl. No. 15/170,556, Response filed Apr. 15, 2019 to Non Final Office Action mailed Feb. 8, 2019", 9 pgs.
"U.S. Appl. No. 15/170,556, Restriction Requirement mailed Feb. 16, 2018", 7 pgs.
"U.S. Appl. No. 15/170,556. PTO Response to Rule 312 Communication mailed Apr. 3, 2020", 2 pgs.
"U.S. Appl. No. 15/203,581, Examiners Interview Summary mailed Sep. 11, 2017", 1 pg.
"U.S. Appl. No. 15/203,581, Notice of Allowance mailed Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication mailed Dec. 27, 2017", 2 pgs.
"U.S. Appl. No. 15/203,581, Response filed Aug. 15, 2017 to Restriction Requirement mailed Jun. 16, 2017", 8 pgs.
"U.S. Appl. No. 15/203,581, Restriction Requirement mailed Jun. 16, 2017", 8 pgs.
"U.S. Appl. No. 15/204,381, Advisory Action mailed Feb. 7, 2019", 3 pgs.
"U.S. Appl. No. 15/204,381, Advisory Action mailed Aug. 25, 2020", 3 pgs.

(56) References Cited

OTHER PUBLICATIONS

"U.S. Appl. No. 15/204,381, Final Office Action mailed Feb. 27, 2020", 21 pgs.
"U.S. Appl. No. 15/204,381, Final Office Action mailed Jul. 9, 2021", 14 pgs.
"U.S. Appl. No. 15/204,381, Final Office Action mailed Sep. 21, 2018", 10 pgs.
"U.S. Appl. No. 15/204,381, Non Final Office Action mailed Feb. 23, 2018", 10 pgs.
"U.S. Appl. No. 15/204,381, Non Final Office Action mailed Jun. 13, 2019", 23 pgs.
"U.S. Appl. No. 15/204,381, Non Final Office Action mailed Oct. 6, 2020", 15 pgs.
"U.S. Appl. No. 15/204,381, Preliminary Amendment filed Oct. 25, 2016", 74 pgs.
"U.S. Appl. No. 15/204,381, Response filed Jan. 2, 2019 to Final Office Action mailed Sep. 21, 2018", 6 pgs.
"U.S. Appl. No. 15/204,381, Response filed Jan. 19, 2018 to Restriction Requirement mailed Oct. 13, 2017", 6 pgs.
"U.S. Appl. No. 15/204,381, Response filed Apr. 6, 2021 to Non Final Office Action mailed Oct. 6, 2020", 12 pgs.
"U.S. Appl. No. 15/204,381, Response filed May 30, 2018 to Non Final Office Action mailed Feb. 23, 2018", 9 pgs.
"U.S. Appl. No. 15/204,381, Response filed Jul. 27, 2020 to Final Office Action mailed Feb. 27, 2020", 11 pgs.
"U.S. Appl. No. 15/204,381, Response filed Aug. 27, 2020 to Advisory Action mailed Aug. 25, 2020", 2 pgs.
"U.S. Appl. No. 15/204,381, Response Filed Nov. 14, 2019 to Non Final Office Action mailed Jun. 13, 2019", 9 pgs.
"U.S. Appl. No. 15/204,381, Response Filed Mar. 21, 2019 to Advisory Action mailed Feb. 7, 2019", 7 pgs.
"U.S. Appl. No. 15/204,381, Restriction Requirement mailed Oct. 13, 2017", 10 pgs.
"U.S. Appl. No. 15/227,147, Preliminary Amendment filed Oct. 10, 2016", 7 pgs.
"U.S. Appl. No. 15/227,147, Restriction Requirement mailed Jan. 19, 2017", 14 pgs.
"U.S. Appl. No. 15/292,595, Non Final Office Action mailed Sep. 25, 2017", 13 pgs.
"U.S. Appl. No. 15/292,595, Notice of Allowance mailed Feb. 28, 2018", 9 pgs.
"U.S. Appl. No. 15/292,595, Notice of Allowance mailed Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action mailed Sep. 25, 2017", 9 pgs.
"U.S. Appl. No. 15/436,245, Corrected Notice of Allowability mailed Nov. 10, 2021", 2 pgs.
"U.S. Appl. No. 15/436,245, Final Office Action mailed Mar. 24, 2021", 9 pgs.
"U.S. Appl. No. 15/436,245, Final Office Action mailed Nov. 18, 2019", 9 pgs.
"U.S. Appl. No. 15/436,245, Non Final Office Action mailed Apr. 19, 2019", 9 pgs.
"U.S. Appl. No. 15/436,245, Non Final Office Action mailed Sep. 4, 2020", 9 pgs.
"U.S. Appl. No. 15/436,245, Notice of Allowance mailed Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication mailed Oct. 27, 2021", 2 pgs.
"U.S. Appl. No. 15/436,245, Response filed Apr. 27, 2020 to Final Office Action mailed Nov. 18, 2019", 10 pgs.
"U.S. Appl. No. 15/436,245, Response filed Jun. 24, 2021 to Final Office Action mailed Mar. 24, 2021", 11 pgs.
"U.S. Appl. No. 15/436,245, Response filed Dec. 4, 2020 to Non Final Office Action mailed Sep. 4, 2020", 12 pgs.
"U.S. Appl. No. 15/436,245, Response filed Jul. 29, 2019 to Non-Final Office Action mailed Apr. 19, 2019", 11 pgs.
"U.S. Appl. No. 15/436,245, Restriction Requirement mailed Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action mailed Feb. 6, 2018", 8 pgs.
"U.S. Appl. No. 15/593,039, Notice of Allowance mailed Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication mailed Oct. 9, 2018", 2 pgs.
"U.S. Appl. No. 15/593,039, Response filed Apr. 30, 2018 to Non Final Office Action mailed Feb. 4, 2018", 8 pgs.
"U.S. Appl. No. 15/593,039, Response filed Dec. 18, 2017 to Restriction Requirement mailed Oct. 18, 2017", 8 pgs.
"U.S. Appl. No. 15/593,039, Restriction Requirement mailed Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance mailed Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement mailed Jan. 3, 2019", 6 pgs.
"U.S. Appl. No. 15/915,486 Supplemental Preliminary Amendment Filed Mar. 12, 2019", 5 pgs.
"U.S. Appl. No. 15/915,486, Advisory Action mailed Jun. 28, 2021", 7 pgs.
"U.S. Appl. No. 15/915,486, Advisory Action mailed Jul. 13, 2020", 3 pgs.
"U.S. Appl. No. 15/915,486, Final Office Action mailed Jan. 11, 2022", 9 pgs.
"U.S. Appl. No. 15/915,486, Final Office Action mailed Jan. 27, 2020", 8 pgs.
"U.S. Appl. No. 15/915,486, Final Office Action mailed Feb. 1, 2021", 8 pgs.
"U.S. Appl. No. 15/915,486, Non Final Office Action mailed Sep. 2, 2021", 8 pgs.
"U.S. Appl. No. 15/915,486, Non Final Office Action mailed Sep. 15, 2020", 10 pgs.
"U.S. Appl. No. 15/915,486, Non Final Office Action mailed Oct. 24, 2019", 10 pgs.
"U.S. Appl. No. 15/915,486, Response filed Jan. 3, 2020 to Non Final Office Action mailed Oct. 24, 2019", 8 pgs.
"U.S. Appl. No. 15/915,486, Response filed Jun. 1, 2021 to Final Office Action mailed Feb. 1, 2021", 10 pgs.
"U.S. Appl. No. 15/915,486, Response filed Jun. 23, 2020 to Final Office Action mailed Jan. 27, 2020", 7 pgs.
"U.S. Appl. No. 15/915,486, Response filed Jul. 27, 2021 to Advisory Action mailed Jun. 28, 2021", 10 pgs.
"U.S. Appl. No. 15/915,486, Response filed Nov. 30, 2021 to Non Final Office Action mailed Sep. 2, 2021", 6 pgs.
"U.S. Appl. No. 15/915,486, Response filed Dec. 21, 2020 to Non Final Office Action mailed Sep. 15, 2020", 7 pgs.
"U.S. Appl. No. 15/915,486, Restriction Requirement mailed Aug. 5, 2019", 9 pgs.
"U.S. Appl. No. 15/966,092, Interview Summary mailed Mar. 2, 2021", 2 pgs.
"U.S. Appl. No. 15/966,092, Non Final Office Action mailed Jun. 26, 2020", 22 pgs.
"U.S. Appl. No. 15/966,092, Notice of Allowance mailed Feb. 11, 2021", 5 pgs.
"U.S. Appl. No. 15/966,092, Response filed Oct. 26, 2020 to Non Final Office Action mailed Jun. 26, 2020", 9 pgs.
"U.S. Appl. No. 16/046,250, Non Final Office Action mailed Mar. 6, 2020", 10 pgs.

(56) References Cited

OTHER PUBLICATIONS

"U.S. Appl. No. 16/046,250, Notice of Allowance mailed Jun. 15, 2020", 9 pgs.
"U.S. Appl. No. 16/046,250, Response filed Jun. 3, 2020 to Non Final Office Action mailed Mar. 6, 2020", 10 pgs.
"U.S. Appl. No. 16/046,250, Response filed Oct. 25, 2019 to Restriction Requirement mailed Jul. 25, 2019", 9 pgs.
"U.S. Appl. No. 16/046,250, Restriction Requirement mailed Jul. 25, 2019", 7 pgs.
"U.S. Appl. No. 16/170,321, Advisory Action mailed Feb. 23, 2021", 3 pgs.
"U.S. Appl. No. 16/170,321, Corrected Notice of Allowability mailed Sep. 29, 2021", 2 pgs.
"U.S. Appl. No. 16/170,321, Final Office Action mailed Dec. 14, 2020", 13 pgs.
"U.S. Appl. No. 16/170,321, Non Final Office Action mailed Apr. 13, 2020", 13 pgs.
"U.S. Appl. No. 16/170,321, Notice of Allowance mailed Aug. 4, 2021", 10 pgs.
"U.S. Appl. No. 16/170,321, PTO Response to Rule 312 Communication mailed Sep. 1, 2021", 2 pgs.
"U.S. Appl. No. 16/170,321, Response filed Jan. 24, 2020 to Restriction Requirement mailed Nov. 27, 2019", 9 pgs.
"U.S. Appl. No. 16/170,321, Response filed Jan. 26, 2021 to Final Office Action mailed Dec. 14, 2020", 9 pgs.
"U.S. Appl. No. 16/170,321, Response filed Mar. 9, 2021 to Advisory Action mailed Feb. 23, 2021", 9 pgs.
"U.S. Appl. No. 16/170,321, Response filed Sep. 11, 2020 to Non Final Office Action mailed Apr. 13, 2020", 9 pgs.
"U.S. Appl. No. 16/170,321, Restriction Requirement mailed Nov. 27, 2019", 10 pgs.
"U.S. Appl. No. 16/173,605 Preliminary Amendment Filed Nov. 18, 2019", 5 pgs.
"U.S. Appl. No. 16/173,605, Final Office Action mailed Jul. 27, 2020", 7 pgs.
"U.S. Appl. No. 16/173,605, Non Final Office Action mailed Mar. 13, 2020", 10 pgs.
"U.S. Appl. No. 16/173,605, Notice of Allowance mailed Jan. 13, 2021", 6 pgs.
"U.S. Appl. No. 16/173,605, Response filed Jul. 13, 2020 to Non Final Office Action mailed Mar. 13, 2020", 13 pgs.
"U.S. Appl. No. 16/173,605, Response filed Dec. 21, 2020 to Final Office Action mailed Jul. 27, 2020", 7 pgs.
"U.S. Appl. No. 16/545,761, Final Office Action mailed Oct. 20, 2021", 10 pgs.
"U.S. Appl. No. 16/545,761, Non Final Office Action mailed Feb. 11, 2021", 12 pgs.
"U.S. Appl. No. 16/545,761, Notice of Allowance mailed Mar. 9, 2022", 6 pgs.
"U.S. Appl. No. 16/545,761, Preliminary Amendment filed Feb. 7, 2020", 9 pgs.
"U.S. Appl. No. 16/545,761, PTO Response to Rule 312 Communication mailed May 13, 2022", 2 pgs.
"U.S. Appl. No. 16/545,761, Response filed Feb. 16, 2022 to Final Office Action mailed Oct. 20, 2021", 10 pgs.
"U.S. Appl. No. 16/545,761, Response filed Jun. 30, 2021 to Non Final Office Action mailed Feb. 11, 2021", 13 pgs.
"U.S. Appl. No. 16/749,910, Notice of Allowance mailed Sep. 22, 2021", 10 pgs.
"U.S. Appl. No. 16/749,910, Response filed Jun. 17, 2021 to Restriction Requirement mailed Apr. 19, 2021", 11 pgs.
"U.S. Appl. No. 16/749,910, Restriction Requirement mailed Apr. 19, 2021", 9 pgs.
"U.S. Appl. No. 16/785,449, Final Office Action mailed Mar. 18, 2022", 12 pgs.
"U.S. Appl. No. 16/785,449, Non Final Office Action mailed Jul. 21, 2021", 9 pgs.
"U.S. Appl. No. 16/785,449, Non Final Office Action mailed Sep. 22, 2022", 13 pgs.
"U.S. Appl. No. 16/785,449, Response filed Jan. 20, 2023 to Non Final Office Action mailed Sep. 22, 2022", 8 pgs.
"U.S. Appl. No. 16/785,449, Response filed Jun. 27, 2022 to Final Office Action mailed Mar. 18, 2022", 7 pgs.
"U.S. Appl. No. 16/785,449, Response filed Jul. 2, 2021 to Restriction Requirement mailed Jun. 21, 2021", 6 pgs.
"U.S. Appl. No. 16/785,449, Response filed Dec. 17, 2021 to Non Final Office Action mailed Jul. 21, 2021", 8 pgs.
"U.S. Appl. No. 16/785,449, Restriction Requirement mailed Jun. 21, 2021", 8 pgs.
"U.S. Appl. No. 16/785,449, Final Office Action mailed Mar. 22, 2023", 16 pgs.
"U.S. Appl. No. 16/865,194, Notice of Allowance mailed Mar. 3, 2022", 9 pgs.
"U.S. Appl. No. 16/865,194, Response filed Dec. 20, 2021 to Restriction Requirement mailed Oct. 20, 2021", 11 pgs.
"U.S. Appl. No. 16/865,194, Restriction Requirement mailed Oct. 20, 2021", 7 pgs.
"U.S. Appl. No. 17/004,583, 312 Amendment filed Mar. 16, 2023", 7 pgs.
"U.S. Appl. No. 17/004,583, Advisory Action mailed Aug. 30, 2022", 2 pgs.
"U.S. Appl. No. 17/004,583, Final Office Action mailed Jun. 9, 2022", 6 pgs.
"U.S. Appl. No. 17/004,583, Non Final Office Action mailed Feb. 24, 2022", 5 pgs.
"U.S. Appl. No. 17/004,583, Non Final Office Action mailed Sep. 29, 2022", 8 pgs.
"U.S. Appl. No. 17/004,583, Notice of Allowability mailed Feb. 10, 2023", 4 pgs.
"U.S. Appl. No. 17/004,583, Notice of Allowance mailed Feb. 1, 2023", 10 pgs.
"U.S. Appl. No. 17/004,583, Preliminary Amendment filed Dec. 21, 2020", 6 pgs.
"U.S. Appl. No. 17/004,583, PTO Response to Rule 312 Communication mailed Feb. 23, 2023", 4 pgs.
"U.S. Appl. No. 17/004,583, PTO Response to Rule 312 Communication mailed Apr. 6, 2023", 3 pgs.
"U.S. Appl. No. 17/004,583, Response filed Jan. 31, 2022 to Restriction Requirement mailed Nov. 24, 2021", 7 pgs.
"U.S. Appl. No. 17/004,583, Response filed May 24, 2022 to Non Final Office Action mailed Feb. 24, 2022", 9 pgs.
"U.S. Appl. No. 17/004,583, Response filed Aug. 9, 2022 to Final Office Action mailed Jun. 9, 2022", 9 pgs.
"U.S. Appl. No. 17/004,583, Response filed Sep. 8, 2022 to Advisory Action mailed Aug. 30, 2022", 15 pgs.
"U.S. Appl. No. 17/004,583, Response filed Dec. 29, 2022 to Non Final Office Action mailed Sep. 29, 2022", 8 pgs.
"U.S. Appl. No. 17/004,583, Restriction Requirement mailed Nov. 24, 2021", 10 pgs.
"U.S. Appl. No. 17/004,583, Supplemental Amendment filed Mar. 28, 2023", 6 pgs.
"U.S. Appl. No. 17/155,625, Advisory Action mailed Jan. 20, 2023", 3 pgs.
"U.S. Appl. No. 17/155,625, Final Office Action mailed Sep. 28, 2022", 18 pgs.
"U.S. Appl. No. 17/155,625, Non Final Office Action mailed May 26, 2022", 10 pgs.
"U.S. Appl. No. 17/155,625, Notice of Allowance mailed Apr. 12, 2023", 11 pgs.
"U.S. Appl. No. 17/155,625, Response filed Feb. 28, 2023 to Advisory Action mailed Jan. 20, 2023", 8 pgs.
"U.S. Appl. No. 17/155,625, Response filed May 2, 2022 to Restriction Requirement mailed Mar. 3, 2022", 7 pgs.
"U.S. Appl. No. 17/155,625, Response filed Aug. 29, 2022 to Non Final Office Action mailed May 26, 2022", 8 pgs.
"U.S. Appl. No. 17/155,625, Response filed Dec. 28, 2022 to Final Office Action mailed Sep. 28, 2022", 8 pgs.
"U.S. Appl. No. 17/155,625, Restriction Requirement mailed Mar. 3, 2022", 9 pgs.
"U.S. Appl. No. 17/212,836, Non Final Office Action mailed Feb. 16, 2023", 12 pgs.

(56) References Cited

OTHER PUBLICATIONS

"U.S. Appl. No. 17/212,836, Response filed Oct. 19, 2022 to Restriction Requirement mailed Aug. 19, 2022", 6 pgs.
"U.S. Appl. No. 17/212,836, Restriction Requirement mailed Aug. 19, 2022", 7 pgs.
"U.S. Appl. No. 17/229,001, Preliminary Amendment filed Apr. 26, 2021", 7 pgs.
"U.S. Appl. No. 17/352,845, Non Final Office Action mailed Dec. 16, 2022", 15 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2004249133, First Examiner's Report mailed May 5, 2008", 4 pgs.
"Australian Application Serial No. 2004274860, Office Action mailed May 21, 2008", 2 pgs.
"Australian Application Serial No. 2014290203, First Examination Report mailed Oct. 10, 2019", 4 pgs.
"Australian Application Serial No. 2014290203, Response filed Mar. 13, 2020 to First Examination Report mailed Oct. 10, 2019", 16 pgs.
"Australian Application Serial No. 2014290203, Response filed Jun. 24, 2020 to Subsequent Examiners Report mailed Mar. 23, 2020", 16 pgs.
"Australian Application Serial No. 2014290203, Response filed Sep. 29, 2020 to Subsequent Examiners Report mailed Jul. 21, 2020", 25 pgs.
"Australian Application Serial No. 2014290203, Response filed Dec. 9, 2020 to Subsequent Examiners Report mailed Oct. 6, 2020", 14 pgs.
"Australian Application Serial No. 2014290203, Subsequent Examiners Report mailed Mar. 23, 2020", 6 pgs.
"Australian Application Serial No. 2014290203, Subsequent Examiners Report mailed Jul. 21, 2020", 5 pgs.
"Australian Application Serial No. 2014290203, Subsequent Examiners Report mailed Oct. 6, 2020", 4 pgs.
"Australian Application Serial No. 2017221444, First Examination Report mailed Jul. 8, 2020", 6 pgs.
"Australian Application Serial No. 2017221444, Fourth Examiners Report mailed Jun. 29, 2021", 3 pgs.
"Australian Application Serial No. 2017221444, Response filed Jan. 25, 2021 to Subsequent Examiners Report mailed Nov. 27, 2020", 18 pgs.
"Australian Application Serial No. 2017221444, Response filed Jun. 2, 2021 to Subsequent Examiners Report mailed Feb. 24, 2021", 20 pgs.
"Australian Application Serial No. 2017221444, Response filed Jul. 6, 2021 to Fourth Examiners Report mailed Jun. 29, 2021", 7 pgs.
"Australian Application Serial No. 2017221444, Response filed Nov. 13, 2020 to First Examination Report mailed Jul. 8, 2020", 13 pgs.
"Australian Application Serial No. 2017221444, Subsequent Examiners Report mailed Feb. 24, 2021", 4 pgs.
"Australian Application Serial No. 2017221444, Subsequent Examiners Report mailed Nov. 27, 2020", 4 pgs.
"Australian Application Serial No. 2021201844, First Examination Report filed Sep. 29, 2022", 3 pgs.
"Australian Application Serial No. 2021201844, Voluntary Amendment filed Dec. 6, 2021", 17 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.
"Brazil Application Serial No. PI 0410702-0, Office Action mailed Oct. 6, 2020", (w/ English Translation), 9 pgs.
"Brazil Application Serial No. PI 0410702-0, Response filed Dec. 14, 2020 to Office Action mailed Oct. 6, 2020", (w/ English Translation of Claims), 42 pgs.
"Brazilian Application Serial No. PI 0410702-0, Office Action mailed Nov. 1, 2019", (w/ English Translation), 6 pgs.
"Brazilian Application Serial No. PI 0410702-0, Response filed Feb. 6, 2020 to Office Action mailed Nov. 1, 2019", (w/ English Translation of Claims), 92 pgs.
"Brazilian Application Serial No. PI0410702-0, Office Action mailed Apr. 1, 2020", (w/ English Summary), 6 pgs.
"Brazilian Application Serial No. PI0410702-0, Response filed Aug. 28, 2020 to Office Action mailed Apr. 1, 2020", (w/ English Translation of Claims), 86 pgs.
"Canadian Application Serial No. 2,406,180, Office Action mailed Sep. 9, 2008", 5 pgs.
"Canadian Application Serial No. 2,406,180, Response filed Jan. 26, 2009 to Official Action mailed Sep. 9, 2008", 22 pgs.
"Canadian Application Serial No. 2,525,953, Non Final Office Action mailed Mar. 30, 2022", 4 pgs.
"Canadian Application Serial No. 2,525,953, Office Action mailed Jan. 29, 2020", 4 pgs.
"Canadian Application Serial No. 2,525,953, Office Action mailed Apr. 28, 2021", 7 pgs.
"Canadian Application Serial No. 2,525,953, Office Action mailed Oct. 3, 2017", 4 pgs.
"Canadian Application Serial No. 2,525,953, Office Action mailed Nov. 2, 2018", 6 pgs.
"Canadian Application Serial No. 2,525,953, Response filed Apr. 3, 2018 to Office Action mailed Oct. 3, 2017", 46 pgs.
"Canadian Application Serial No. 2,525,953, Response filed May 2, 2019 to Office Action mailed Nov. 2, 2018", 31 pgs.
"Canadian Application Serial No. 2,525,953, Response filed May 25, 2020 to Office Action mailed Jan. 29, 2020", 35 pgs.
"Canadian Application Serial No. 2,525,953, Response filed Aug. 26, 2021 to Office Action mailed Apr. 28, 2021", 16 pgs.
"Canadian Application Serial No. 3,014,435, Office Action mailed Oct. 26, 2021", 4 pgs.
"Canadian Application Serial No. 3,014,435, Office Action mailed Nov. 6, 2020", 5 pgs.
"Canadian Application Serial No. 3,014,435, Office Action mailed Nov. 13, 2019", 4 pgs.
"Canadian Application Serial No. 3,014,435, Response filed Feb. 25, 2022 to Office Action mailed Oct. 26, 2021", 15 pgs.
"Canadian Application Serial No. 3,014,435, Response filed Mar. 5, 2021 to Office Action mailed Nov. 6, 2020", 20 pgs.
"Canadian Application Serial No. 3,014,435, Response filed Mar. 13, 2020 to Office Action mailed Nov. 13, 2019", 18 pgs.
"Chinese Application Serial No. 202080048487.4, Voluntary Amendment filed Dec. 5, 2022", w/ English Claims, 33 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480021259.9, First Offiice Action issued on Aug. 24, 2007", (w/ English Translation), 9 pgs.
"Chinese Application Serial No. 200480021259.9, Response filed Mar. 7, 2008 to Office Action issued on Aug. 24, 2007", (w/ English Translation of Claims), 13 pgs.
"Chinese Application Serial No. 200480022014, First Office Action mailed Aug. 24, 2007", w/English Translation, 6 pgs.
"Chinese Application Serial No. 201780024821.0, Office Action mailed Jun. 15, 2022", (w/ English Translation), 6 pgs.
"Chinese Application Serial No. 201780024821.0, Office Action mailed Nov. 30, 2021", (w/ English Translation), 21 pgs.
"Chinese Application Serial No. 201780024821.0, Response filed Apr. 12, 2022 to Office Action mailed Nov. 30, 2021", (w/ English Translation of Claims), 17 pgs.
"Chinese Application Serial No. 201780024821.0, Response filed Aug. 30, 2022 to Office Action mailed Jun. 15, 2022", w/ English Claims, 18 pgs.

(56) References Cited

OTHER PUBLICATIONS

"Chinese Application Serial No. 201780024821.0, Response to Examiner Telephone Interview filed Sep. 26, 2022", w/ English Claims, 10 pgs.
"Chinese Application Serial No. 202080048487.4, Notification to Make Rectification mailed Jan. 18, 2022", w/o English Translation, 1 pg.
"Chinese Application Serial No. 202080048487.4, Notification to Make Rectification mailed May 26, 2022", w/o English translation, 1 pg.
"Confirmed Cases of Avian Influenza A(H5N1)", World Health Organization, (Jan. 28, 2004), 1 pg.
"Declaration of Anne Koch Ballard dated Oct. 6, 2011", 1 pg.
"Eurasian Application Serial No. 200501890, Office Action mailed Mar. 23, 2007", (w English Translation), 2 pgs.
"Eurasian Application Serial No. 200501890, Office Action mailed Sep. 4, 2008", (English Translation), 1 pg.
"Eurasian Application Serial No. 200501890, Office Action mailed Dec. 17, 2007", (w/ English Translation), 6 pgs.
"Eurasian Application Serial No. 200501890, Response filed Mar. 26, 2008 to Office Action mailed Dec. 17, 2007", (w/ English Translation of Claims), 15 pgs.
"Eurasian Application Serial No. 200501890, Response filed Jun. 14, 2007 to Office Action mailed Mar. 23, 2007", (w/ English Translation of Claims), 11 pgs.
"Eurasian Application Serial No. 200501890, Response filed Dec. 17, 2008 to Office Action mailed Sep. 4, 2008", (w/ English Translation of Claims), 14 pgs.
"Eurasian Application Serial No. 200701097, Office Action mailed Sep. 4, 2008", OAR-MISC, 2 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial 17709236.8 , Response filed Apr. 26, 2019 to Communication Pursuant to Rules 161(1) and 162 EPC mailed Oct. 19, 2018", 9 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action mailed Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Jan. 21, 2008 to Communication dated Aug. 10, 2007", 11 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04776133.3, Communication mailed Mar. 30, 2006", 3 pgs.
"European Application Serial No. 04776133.3, Response filed Jan. 25, 2007 to Communication mailed Mar. 30, 2006", 20 pgs.
"European Application Serial No. 04809419.7, Communication mailed Apr. 3, 2007", 3 pgs.
"European Application Serial No. 04809419.7, Response filed Oct. 19, 2007 to (Communication mailed Apr. 3, 2007", 20 pgs.
"European Application Serial No. 10777154.5, Communication Pursuant to Article 94(3) EPC mailed Apr. 4, 2018", 7 pgs.
"European Application Serial No. 10777154.5, Communication Pursuant to Article 94(3) EPC mailed Jun. 11, 2019", 3 pgs.
"European Application Serial No. 10777154.5, Communication Pursuant to Article 94(3) EPC mailed Oct. 12, 2017", 7 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Feb. 21, 2018 to Communication Pursuant to Article 94(3) EPC mailed Oct. 12, 2017", 12 pgs.
"European Application Serial No. 10777154.5, Response filed Jul. 29, 2019 to Communication Pursuant to Article 94(3) EPC mailed Jun. 11, 2019", 57 pgs.
"European Application Serial No. 10777154.5, Response filed Sep. 7, 2018 to Communication Pursuant to Article 94(3) EPC mailed Apr. 4, 2018", 18 pgs.
"European Application Serial No. 10777154.5, Summons to Attend Oral Proceedings mailed Jan. 7, 2019", 5 pgs.
"European Application Serial No. 14745060.5, Communication Pursuant to Article 94(3) EPC mailed Feb. 6, 2018", 5 pgs.
"European Application Serial No. 14745060.5, Communication Pursuant to Article 94(3) EPC mailed Mar. 12, 2020", 4 pgs.
"European Application Serial No. 14745060.5, Communication Pursuant to Article 94(3) EPC mailed Jul. 18, 2019", 5 pgs.
"European Application Serial No. 14745060.5, Communication Pursuant to Article 94(3) EPC mailed Sep. 15, 2021", 4 pgs.
"European Application Serial No. 14745060.5, Communication Pursuant to Article 94(3) EPC mailed Sep. 18, 2018", 4 pgs.
"European Application Serial No. 14745060.5, Communication Pursuant to Article 94(3) EPC mailed Nov. 9, 2020", 4 pgs.
"European Application Serial No. 14745060.5, Response filed Jan. 5, 2022 to Communication Pursuant to Article 94(3) EPC mailed Sep. 15, 2021", 78 pgs.
"European Application Serial No. 14745060.5, Response filed Jan. 28, 2020 to Communication Pursuant to Article 94(3) EPC mailed Jul. 18, 2019", 9 pgs.
"European Application Serial No. 14745060.5, Response filed Mar. 27, 2019 to Communication Pursuant to Article 94(3) EPC mailed Sep. 18, 2018", 13 pgs.
"European Application Serial No. 14745060.5, Response filed May 12, 2021 to Communication Pursuant to Article 94(3) EPC mailed Nov. 9, 2020", 12 pgs.
"European Application Serial No. 14745060.5, Response filed Jun. 15, 2018 to Communication Pursuant to Article 94(3) EPC mailed Feb. 6, 2018", 14 pgs.
"European Application Serial No. 14745060.5, Response filed Jul. 17, 2020 to Communication Pursuant to Article 94(3) EPC mailed Mar. 12, 2020", 52 pgs.
"European Application Serial No. 16778485.9, Communication Pursuant to Article 94(3) EPC mailed Feb. 18, 2022", 4 pgs.
"European Application Serial No. 16778485.9, Response filed Aug. 9, 2022 to Communication Pursuant to Article 94(3) EPC mailed Feb. 18, 2022", 14 pgs.
"European Application Serial No. 17709236.8, Communication Pursuant to Article 94(3) EPC mailed Jun. 8, 2022", 6 pgs.
"European Application Serial No. 17709236.8, Communication Pursuant to Article 94(3) EPC mailed Jul. 6, 2021", 10 pgs.
"European Application Serial No. 17709236.8, Response filed Jan. 17, 2022 to Communication Pursuant to Article 94(3) EPC mailed Jul. 6, 2021", 13 pgs.
"European Application Serial No. 17709236.8, Response filed Oct. 11, 2022 to Communication Pursuant to Article 94(3) EPC mailed Jun. 8, 2022", 65 pgs.
"European Application Serial No. 18800815.5, Response to Communication pursuant to Rules 161(1) and 162 EPC filed Dec. 15, 2020", 14 pgs.
"European Application Serial No. 19778696.5, Response to Communication persuant to Rules 161 and 162 filed Oct. 15, 2021", 39 pgs.
"European Application Serial No. 20714015.3, Response to Communication persuant to Rules 161 and 162 filed Apr. 7, 2022", 10 pgs.

(56) References Cited

OTHER PUBLICATIONS

"European Application Serial No. 20731609.2, Response to Communication persuant to Rules 161 and 162 filed Mar. 16, 2022", 17 pgs.
"European Application Serial No. 20768781.5, Response to Communication pursuant to Rules 161 and 162 filed Oct. 17, 2022", 17 pgs.
"Gen Bank Accession AFP82914", matrix protein 1 [Influenza A virus (A/reassortant/IVR-148(Brisbane/59/2007 × Texas/1/1977) (H1N1))], (2012), 2 pgs.
"Gen Bank Accession JX414012", Influenza A virus (A/reassortant/IVR-148(Brisbane/59/2007 × Texas/1/1977)(H1 N1) segment 7 matrix protein 2 (M2) and matrix protein 1 (M1) genes, complete cds, (2012), 2 pgs.
"Gen Bank Accessions QHU79173", surface glycoprotein [Severe acute respiratory syndrome coronavirus 2], (Mar. 17, 2020), 3 pgs.
"GFP antibody (ab6556) datasheet", (r) abcam. [online], [retrieved on Dec. 5, 2004]. Retrieved from the Internet: <URL: http://www.abcam.com/index.html?datasheet=6556>, (2004), 5 pgs.
"https://www.abcam.com/gfp-antibody-ab6556", [online]. [accessed on Dec. 5, 2004]. Retrieved from the Internet: http://www.abcam.com/index.html?datasheet=6556, (Dec. 5, 2004), 5 pgs.
"Indian Application Serial No. 02082/KOLNP/2005, Examination Report mailed Mar. 17, 2008" 1 pg.
"Indian Application Serial No. 02082/KOLNP/2005, Examination Report mailed Dec. 28, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 10, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 2272/KOLNP/2005, First Examination Report mailed Mar. 17, 2008", 10 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009" 1 pg.
"Indian Application Serial No. 2388/KOLNP/2005, First Examination Report mailed Mar. 28, 2007", 10 pgs.
"Influenza B/Ann Arbor/1/66 (cold-adapted) nonstructural protein (seg 8) RNA, complete cds", GenBank Accession M20224, (Aug. 2, 1993), 2 pgs.
"Influenza B/lee/40, neuraminidase & nb (seg 6) rna", Database EM_VI E.B.I. Hinxton U.K., (Jun. 13, 1985), 10 pgs.
"International Application No. PCT/US2004/016680, International Search Report", (Feb. 2, 2005), 7 pgs.
"International Application Serial No. PCT/US2021/033365, International Search Report mailed Sep. 24, 2021", 6 pgs.
"International Application Serial No. PCT/US2021/033365, Written Opinion mailed Sep. 24, 2021", 6 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report mailed Oct. 15, 2002", 13 pgs.
"International Application Serial No. PCT/US01/11963, International Search Report mailed May 7, 2002", 5 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US2004/012050, International Search Report mailed Feb. 2, 2005", 8 pgs.
"International Application Serial No. PCT/US2004/012050, International Search Report mailed Feb. 2, 2005", 8 pgs.
"International Application Serial No. PCT/US2004/012050, Written Opinion mailed Feb. 2, 2005", 12 pgs.
"International Application Serial No. PCT/US2004/016649, International Preliminary Report on Patentability mailed Dec. 15, 2005", 7 pgs.
"International Application Serial No. PCT/US2004/016649, International Search Report mailed Apr. 18, 2005", 6 pgs.
"International Application Serial No. PCT/US2004/016680, International Preliminary Report on Patentability mailed Dec. 15, 2005", 11 pgs.
"International Application Serial No. PCT/US2005/041991, International Search Report mailed Jun. 4, 2007", 5 pgs.
"International Application Serial No. PCT/US2005/041991, Written Opinion mailed Jun. 4, 2007", 6 pgs.
"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.
"International Application Serial No. PCT/US2007/013407, International Search Report mailed Oct. 24, 2008", 10 pgs.
"International Application Serial No. PCT/US2007/013407, Written Opinion mailed Oct. 24, 2008", 14 pgs.
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"International Application Serial No. PCT/US2008/007417, International Search Report mailed Jan. 30, 2009", 20 pgs.
"International Application Serial No. PCT/US2008/007417, Written Opinion mailed Jan. 30, 2009", 10 pgs.
"International Application Serial No. PCT/US2008/007582, International Search Report and Written Opinion mailed Feb. 18, 2009", 16 pgs.
"International Application Serial No. PCT/US2016/041172, International Preliminary Report on Patentability mailed Jan. 18, 2018", 10 pgs.
"International Application Serial No. PCT/US2017/018443, International Preliminary Report on Patentability mailed Aug. 30, 2018", 11 pgs.
"International Application Serial No. PCT/US2017/018443, International Search Report mailed May 22, 2017", 9 pgs.
"International Application Serial No. PCT/US2017/018443, Written Opinion mailed May 22, 2017", 9 pgs.
"International Application Serial No. PCT/US2018/057576, International Preliminary Report on Patentability mailed May 7, 2020", 12 pgs.
"International Application Serial No. PCT/US2018/057576, International Search Report mailed Mar. 25, 2019", 7 pgs.
"International Application Serial No. PCT/US2018/057576, Invitation to Pay Additional Fees and Partial Search Report mailed Jan. 31, 2019", 16 pgs.
"International Application Serial No. PCT/US2018/057576, Written Opinion mailed Mar. 25, 2019", 10 pgs.
"International Application Serial No. PCT/US2019/037084, International Preliminary Report on Patentability mailed Dec. 24, 2020", 12 pgs.
"International Application Serial No. PCT/US2019/037084, International Search Report mailed Nov. 14, 2019", 10 pgs.
"International Application Serial No. PCT/US2019/037084, Invitation to Pay Add'l Fees and Partial Search Report mailed Sep. 24, 2019", 10 pgs.
"International Application Serial No. PCT/US2019/037084, Written Opinion mailed Nov. 14, 2019", 10 pgs.
"International Application Serial No. PCT/US2019/045476, International Preliminary Report on Patentability mailed Feb. 18, 2021", 13 pgs.
"International Application Serial No. PCT/US2019/045476, International Search Report mailed Feb. 11, 2020", 8 pgs.

(56) References Cited

OTHER PUBLICATIONS

"International Application Serial No. PCT/US2019/045476, Invitation to Pay Additional Fees mailed Dec. 17, 2019", 14 pgs.
"International Application Serial No. PCT/US2019/045476, Written Opinion mailed Feb. 11, 2020", 13 pgs.
"International Application Serial No. PCT/US2019/047263, International Preliminary Report on Patentability mailed Mar. 4, 2021", 8 pgs.
"International Application Serial No. PCT/US2019/047263, International Search Report mailed Dec. 20, 2019", 5 pgs.
"International Application Serial No. PCT/US2019/047263, Written Opinion mailed Dec. 20, 2019", 6 pgs.
"International Application Serial No. PCT/US2020/014659, International Preliminary Report on Patentability mailed Aug. 5, 2021", 12 pgs.
"International Application Serial No. PCT/US2020/014659, International Search Report mailed Nov. 6, 2020", 7 pgs.
"International Application Serial No. PCT/US2020/014659, Invitation to Pay Additional Fees mailed Sep. 16, 2020", 11 pgs.
"International Application Serial No. PCT/US2020/014659, Written Opinion mailed Nov. 6, 2020", 10 pgs.
"International Application Serial No. PCT/US2020/017342, International Preliminary Report on Patentability mailed Aug. 19, 2021", 8 pgs.
"International Application Serial No. PCT/US2020/017342, International Search Report mailed Jun. 26, 2020", 6 pgs.
"International Application Serial No. PCT/US2020/017342, Written Opinion mailed Jun. 26, 2020", 6 pgs.
"International Application Serial No. PCT/US2020/031176, International Preliminary Report on Patentability mailed Nov. 11, 2021", 9 pgs.
"International Application Serial No. PCT/US2020/031176, International Search Report mailed Jul. 22, 2020", 6 pgs.
"International Application Serial No. PCT/US2020/031176, Written Opinion mailed Jul. 22, 2020", 7 pgs.
"International Application Serial No. PCT/US2020/048130, International Preliminary Report on Patentability mailed Mar. 10, 2022", 11 pgs.
"International Application Serial No. PCT/US2020/048130, International Search Report mailed Apr. 20, 2021", 9 pgs.
"International Application Serial No. PCT/US2020/048130, Invitation to Pay Additional Fees mailed Jan. 13, 2021", 7 pgs.
"International Application Serial No. PCT/US2020/048130, Written Opinion mailed Apr. 20, 2021", 9 pgs.
"International Application Serial No. PCT/US2021/014586, International Preliminary Report on Patentability mailed Aug. 4, 2022", 10 pgs.
"International Application Serial No. PCT/US2021/014586, International Search Report mailed May 20, 2021", 7 pgs.
"International Application Serial No. PCT/US2021/014586, Written Opinion mailed May 20, 2021", 8 pgs.
"International Application Serial No. PCT/US2021/024200, International Preliminary Report on Patentability mailed Oct. 6, 2022", 8 pgs.
"International Application Serial No. PCT/US2021/024200, International Search Report mailed Jul. 16, 2021", 6 pgs.
"International Application Serial No. PCT/US2021/024200, Written Opinion mailed Jul. 16, 2021", 6 pgs.
"International Application Serial No. PCT/US2021/033365, International Preliminary Report on Patentability mailed Dec. 8, 2022", 8 pgs.
"Israel Application Serial No. 183026, Office Action mailed Feb. 9, 2009", w/English Translation, 2 pgs.
"Israel Application Serial No. 238584, Office Action mailed Jul. 24, 2017", w/English Translation, 2 pgs.
"Israel Application Serial No. 238584, Response filed Nov. 21, 2017 to Office Action mailed Jul. 24, 2017", W/English Translation, 2 pgs.
"Israeli Application Serial No. 171831, Notification of Defects mailed Nov. 10, 2008", w/English Translation, 10 pgs.
"Israeli Application Serial No. 171372, Office Action mailed Nov. 6, 2008", (Translation), 12 pgs.
"Israeli Application Serial No. 238584, Notification of Defects in Patent Application mailed Jul. 21, 2019", (w/ English Translation), 5 pgs.
"Israeli Application Serial No. 238584, Office Action mailed Aug. 23, 2018", (w/ English Translation), 6 pgs.
"Israeli Application Serial No. 238584, Response filed Nov. 21, 2017 to Office Action mailed Jul. 24, 2017", (Translation), 2 pgs.
"Israeli Application Serial No. 238584, Response filed Nov. 21, 2019 to Notification of Defects in Patent Application mailed Jul. 21, 2019", (w/ English Translation of Claims), 6 pgs.
"Israeli Application Serial No. 238584, Response Filed Dec. 10, 2018 to Office Action mailed Aug. 23, 2018", (w/ English Translation of Claims), 10 pgs.
"Japanese Application Serial No. 2022-144599, Voluntary Amendment filed Nov. 9, 2022", w/ English Claims, 14 pgs.
"Japanese Application Serial No. 2022-544779, Voluntary Amendment filed Sep. 9, 2022", w/ English Claims, 8 pgs.
"Japanese Application Serial No. 2016-053990, Office Action mailed Jun. 6, 2017", (w/ English Translation), 4 pgs.
"Japanese Application Serial No. 2016-053990, Response filed Dec. 6, 2017 to Office Action mailed Jun. 6, 2017", (w/ English Translation of Amended Claims), 14 pgs.
"Japanese Application Serial No. 2016-110879, Office Action mailed May 30, 2017", (w/ English Translation), 7 pgs.
"Japanese Application Serial No. 2016-110879, Response filed Nov. 30, 2017 to Office Action mailed May 30, 2017", (w/ English Translation of Claims), 25 pgs.
"Japanese Application Serial No. 2016-527046, Examiners Decision of Final Refusal mailed May 21, 2019", (w/ English Translation), 20 pgs.
"Japanese Application Serial No. 2016-527046, Reasons For Rejection mailed Aug. 14, 2018", (w/ English Translation), 14 pgs.
"Japanese Application Serial No. 2016-527046, Response Filed Dec. 4, 2018 to Reasons For Rejection mailed Aug. 14, 2018", (w/ English Translation of Amended Claims), 18 pgs.
"Japanese Application Serial No. 2018-543688, Notification of Reasons for Rejection mailed Oct. 29, 2019", w/ English Translation, 14 pgs.
"Japanese Application Serial No. 2018-543688, Office Action mailed Jun. 30, 2020", w/ English translation, 11 pgs.
"Japanese Application Serial No. 2018-543688, Response filed Apr. 28, 2020 to Notification of Reasons for Rejection mailed Oct. 29, 2019", w/ English Claims, 12 pgs.
"Japanese Application Serial No. 2019-171818, Examiners Decision of Final Refusal mailed Oct. 5, 2021", (w/ English Translation), 15 pgs.
"Japanese Application Serial No. 2019-171818, Notification of Reasons for Rejection mailed Nov. 10, 2020", (w/ English Translation), 11 pgs.
"Japanese Application Serial No. 2019-171818, Preliminary Examination Report mailed May 10, 2022", (w/ English Translation), 2 pgs.
"Japanese Application Serial No. 2019-171818, Response filed Feb. 4, 2022 to Examiners Decision of Final Refusal mailed Oct. 5, 2021", (w/ English Translation of Claims), 21 pgs.
"Japanese Application Serial No. 2019-171818, Response filed May 10, 2021 to Notification of Reasons for Rejection mailed Nov. 10, 2020", (w/ English Translation of Claims), 12 pgs.
"Japanese Application Serial No. 2019-171818, Response filed Dec. 2, 2022 to Preliminary Examination Report mailed May 10, 2022", w/ English Claims, 44 pgs.
"Japanese Application Serial No. 2019-171818, Trial Brief filed Mar. 30, 2022", (w/ English Translation), 14 pgs.
"Japanese Application Serial No. 2020-073952, Examiners Decision of Final Refusal mailed Aug. 4, 2022", w/ English translation, 3 pgs.
"Japanese Application Serial No. 2020-073952, Final Notification of Reasons for Refusal mailed Jan. 25, 2022", w/ English Translation, 11 pgs.

(56) References Cited

OTHER PUBLICATIONS

"Japanese Application Serial No. 2020-073952, Response filed Apr. 20, 2022 to Final Notification of Reasons for Refusal mailed Jan. 25, 2022", w/ English Claims, 40 pgs.
"Japanese Application Serial No. 2020-073952, Response filed Sep. 9, 2021 to Notification of Reasons for Refusal mailed May 20, 2021", w/ English Claims, 27 pgs.
"Japanese Application Serial No. 2020-073952, Response filed Dec. 2, 2022 to Examiners Decision of Final Refusal mailed Aug. 4, 2022", w/ English Claims, 36 pgs.
"Japanese Application Serial No. 2020-182549, Examiners Decision of Final Refusal mailed Jun. 7, 2022", (w/ English Translation), 11 pgs.
"Japanese Application Serial No. 2020-182549, Notification of Reasons for Refusal mailed Nov. 30, 2021", (w/ English Translation), 10 pgs.
"Japanese Application Serial No. 2020-182549, Response filed Feb. 28, 2022 to Notification of Reasons for Refusal mailed Nov. 30, 2021", (w/ English Translation of Claims), 52 pgs.
"Japanese Application Serial No. 2020-182549, Response filed Oct. 6, 2022 to Examiners Decision of Final Refusal mailed Jun. 7, 2022", w/ English Claims, 21 pgs.
"Japanese Application Serial No. 2020-523276, Examiners Decision of Final Refusal mailed May 10, 2022", w/ English Translation, 13 pgs.
"Japanese Application Serial No. 2020-523276, Notification of Reasons for Refusal mailed Jul. 27, 2021", w/ English Translation, 12 pgs.
"Japanese Application Serial No. 2020-523276, Response filed Jan. 12, 2022 to Notification of Reasons for Refusal mailed Jul. 27, 2021", w/ English Claims, 27 pgs.
"Japanese Application Serial No. 2021-146743, Notification of Reasons for Rejection mailed Aug. 17, 2022", w/ English Translation, 3 pgs.
"Japanese Application Serial No. 2021-506434, Notification of Reasons for Refusal mailed May 10, 2022", w/ English translation, 10 pgs.
"Japanese Application Serial No. 2021-506434, Response filed Feb. 18, 2022 to Office Action mailed Dec. 21, 2021", 135 pgs.
"Japanese Application Serial No. 2021-506434, Response filed Nov. 7, 2022 to Notification of Reasons for Refusal mailed May 10, 2022", w/ English Claims, 13 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal mailed Dec. 13, 2022", w/ English Translation, 14 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ English Translation), 9 pgs.
"Korean Application Serial No. 10-2005-7020077, Response filed Aug. 28, 2007 to Notice of Preliminary Rejection mailed Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action mailed Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.
"Mexican Application Serial No. PA/a/2005/012712, Official Action mailed Mar. 5, 2009", (English Translation), 2 pgs.
"Neuraminidase [Influenza A virus (A/Aichi/2/1968 (H3N2))]", GenBank: BAD16642.1, NCBI, [online]. Retrieved from the Internet: <URL: http://www.ncbi.nlm.nih.gov/protein/46401580>, (2008), 3 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 12, 2008", 1 pg.
"New Zealand Application Serial No. 543446, Response mailed Mar. 20, 2008 to Examination Report mailed Feb. 29, 2008", 2 pgs.
"New Zealand Application Serial No. 543587, Examination Report mailed Mar. 1, 2007", 1 pg.
"New Zealand Application Serial No. 543587, Examination Report mailed Jul. 7, 2006", 2 pgs.
"New Zealand Application Serial No. 543587, Response filed Aug. 7, 2007 to Examination Reports mailed Jul. 7, 2006 and Mar. 1, 2007", 24 pgs.
"New Zealand Application Serial No. 543587, Second Examination Report mailed Feb. 25, 2008", 2 pgs.
"New Zealand Application Serial No. 555245, First Examination Report mailed Aug. 26, 2008", 2 pgs.
"Norway Application Serial No. 20056074, Response filed Jul. 25, 2017 to Office Action mailed Apr. 25, 2017", (w/ English Translation of Amended Claims), 111 pgs.
"PCT Application Serial No. PCT/US2005/041991, International Preliminary Report on Patentability / Written Opinion mailed Jul. 19, 2007", 8 pgs.
"Polymerase PA [Influenza A virus (A/swine/Yangzhou/1/2008(H9N2))]", GenBank: ADK98493.1, [Online]. Retrieved from the Internet: <URL: https://www.ncbi.nlm.nih.gov/protein/ADK98493.1/>, 2 pgs.
"RecName: Full=Non-structural protein 1; Short=NS1; AltName: Full=NS1 B", GenPept Accesion P08013, NS1 of Influenza B strain B/Yamagata/1/73, (Dec. 9, 2015), 2 pgs.
"RNA World", http://faculty.uca.edu/~benw/biol4415/lecture10a/tsld003.htm, (Observed Feb. 25, 2003), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion mailed Jun. 19, 2007", 5 pgs.
"Singaporean Application Serial No. 200506858-0, Examination Report mailed Feb. 9, 2007", 4 pgs.
"Singaporean Application Serial No. 200506858-0, Response filed Dec. 22, 2006 to Written Opinion mailed Jul. 26, 2006", 18 pgs.
"Singaporean Application Serial No. 200506858-0, Written Opinion mailed Jul. 26, 2006", 8 pgs.

(56) References Cited

OTHER PUBLICATIONS

"Singaporean Application Serial No. 200507468-7, Examination Report mailed Mar. 19, 2008", 5 pgs.
"Singaporean Application Serial No. 200507468-7, Invitation to Respond to Written Opinion mailed Jun. 12, 2007", 6 pgs.
"Singaporean Application Serial No. 200507468-7, Response filed Nov. 7, 2007 to Invitation to Respond to Written Opinion mailed Jun. 12, 2007", 9 pgs.
"ST3GAL6 Gene ID: 478535", ncbi, nlm, [Online]. Retrieved from the Internet: <URL: https://www.ncbi.nlm.nih.gov/gene/47853> Sep. 14, 2022, (Aug. 17, 2022), 14 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainian Application Serial No. 200512619, Office Action mailed Feb. 27, 2009", (w/ English Translation), 21 pgs.
Albo, C., et al., "The 5' Ends of Thogoto Virus (Orthomyxoviridae) mRNAS Are Homogeneous in both Length and Sequence", Journal of Virology, 70(12), (1996), 9013-9017.
Author Unknown, "New Approaches to Influenza Vaccine", Medscape—Infections in Medicine, http://www.medscape.com/viewarticle/417404_3, (Observed Feb. 26, 2003), 4 pgs.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an integral component of the membrane of influenza B virus.", J Gen Virol., 77 ( Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4 1425-1427, (2010), 3 pgs.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Boyer, J. C., et al., "Infectious transcripts and cDNA clones of RNA viruses", Virology, 198(2), (Feb. 1994), 415-426.
Bradfute, S. B., "The Early Clinical Development of Ebola Virus Treatments", Exp. Opin. Invest. Drugs 26(1):, (2017), 5 pgs.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brands, R., et al., "Influvac: A Safe Madin Darby Canine Kidney (MDCK) Cell Culture-Based Influenza Vaccine", Dev. Biol. Stand., 98, (1999), 93-100.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.

Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al., "Immunodominance of Antigenic Site B in the Hemagglutinin of the Current H3N2 In?uenza Virus in Humans and Mice", Journal of Virology, 92(20): e01100-18, (Oct. 2018), 1-13.
Brown, TA, "Studying DNA", Genomes—NCBI Bookshelf, Brown TA. Genomes. 2nd edition. Oxford: Wiley-Liss; 2002, (2002), 26 pgs.
Bruhl, P., et al., "Humoral and Cell-Mediated Immunity to Vero Cell-Derived Influenza Vaccine", Vaccine, 19, (2001), 1149-1158.
Buchholz, U. J., et al., "Generation of Bovine Respiratory Syncytial Virus (BRSV) From CDNA: BRSV NS2 is Not Essential for Virus Replication in Tissue Culture, and the Human RSV Leader Region Acts as a Functional BRSV Genome Promoter", Journal of Virology, 73(1), (1999), 251-259.
Bukreyev, A., et al., "Recovery of infectious respiratory syncytial virus expressing an additional, foreign gene", Journal of Virology, 70(10), (Oct. 1996), 6634-6641.
Bullido, R., et al., "Influenza A Virus Nep (NS2 protein) Downregulates RNA Synthesis of Model Template RNAs", Journal of Virology, 75(10), (May 2001), 4912-4917.
Bullido, R., et al., "Influenza A virus NEP(NS2 protein) downregulates RNA synthesis of model template RNAs", Journal of Virology, vol. 75 4912-4917, (May 2001), 6 pgs.
Cao, S., et al., "Characterization of the Nucleocytoplasmic Shuttle of the Matrix Protein of Influenza B Virus", Journal of Virology., 88(13), (Jul. 2014), 7464-7473.
Cardona, C. J., "Avian Influenza", http://www.vetmed.ucdavis.edu/vetex/INF-PO_AvianInfluenzaFS.html, ((Observed Feb. 22, 2003), 3 pgs.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Chen, H. et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chiba, Shiho, et al., "Multivalent nanoparticle-based vaccines protect hamsters against SARS-CoV-2 after a single immunization", Communications Biology, 4: 597, (2021), 1-9.
Cho, Alice, et al., "Implications of Broadly Neutralizing Antibodies in the Development of a Universal Influenza Vaccine", Current Opinion In Virology, vol. 17 110-115, (Apr. 1, 2016), 6 pgs.
Chothia, Cyrus, et al., "Canonical Structures for the Hypervariable Regions of Immunoglobulins.", J Mol Biol., 196(4), (1987), 901-917.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.
Chung, C, et al., "Glycoengineering of Chinese Hamster Ovary Cells for Improving Biotherapeutics Efficacies", A dissertation submitted to Johns Hopkins University in conformity with the requirements for the degree of Doctor of Philosophy, Retrieved from the Internet: <https://jscholarship.library.jhu.edu/handle/177>, (2016), 137 pgs.
Claas, E C. J., et al., "Human Influenza A H5N1 Virus Related to a Highly Pathogenic Avian Influenza Virus", The Lancet, 351, (1998), 472-477.
Clarke, D. K., et al., "Rescue of Mumps Virus From cDNA", Journal of Virology, 74(10), (2000), 4831-4838.
Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).
Collins, P. L., et al., "Chapter 41—Parainfluenza Viruses", In: Fields Virology, edited by Fields, B. N., et al. (3rd Edition, 1996, Lippincott-Raven Publishers, Philadelphia, PA, 1205-1241.

(56) References Cited

OTHER PUBLICATIONS

Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad, Sci. USA, 92, (1995), 11563-11567.

Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.

Conzelmann, K.-K., "Genetic Engineering of Animal RNA Viruses", Trends in Microbiology, 4(10), (1996), 386-393.

Conzelmann, K.-K., "Genetic manipulation of non-segmented negative-strand RNA viruses", Journal of General Virology, 77(Pt. 3), (Mar. 1996), 381-389.

Conzelmann, K.-K., "Nonsegmented Negative-Strand RNA Viruses: Genetics and Manipulation of Viral Genomes", Annu. Rev. Genet., 32, (1998), 123-162.

Conzelmann, K.-K., "Rescue of Synthetic Genomic RNA Analogs of Rabies Virus by Plasmid-Encoded Proteins", Journal of Virology, 68(2), (1994), 713-719.

Cunningham, Brian C, et al., "High-Resolution Epitope Mapping of hGH-Receptor Interactions by Alanine-Scanning Mutagenesis", Science 244:4908, (1989), 6 pgs.

Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.

De, B. P., et al., "Requirements and Functions of Vesicular Stomatitis Virus L and NS Proteins in the Transcription Process in Vitro", Biochemical and Biophysical Research Communications, 126(1), (1985), 40-49.

De, B. P., et al., "Rescue of synthetic analogs of genome RNA of human parainfluenza virus type 3", Virology, 196(1), (Sep. 1993), 344-348.

De, B. P., et al., "Reverse Genetics of Negative Strand RNA Viruses", Indian Journal of Biochemistry & Biophysics, 31, (1994), 367-375.

De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.

De La Luna, S., et al., "Influenza Virus NS1 Protein Enhances the Rate of Translation Initiation of Viral mRNAs", Journal of Virology, 69(4), (1995), 2427-2435.

Dimock, K., et al., "Rescue of Synthetic Analogs of Genomic RNA and Replicative-Intermediate RNA of Human Parainfluenza Virus Type 3", Journal of Virology, 67(5), (1993), 2772-2778.

Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.

Du, Q., "Ribozyme Enzymology", http://academic.brooklyn.cuny.edu/chem/zhuang/QD/toppage1.htm, (Observed Feb. 25, 2003), 8 pgs.

Duff, K. C., et al., "The secondary structure of influenza A M2 transmembrane domain", FEBS Letters, 311 (3), (Oct. 1992), pp. 256-258.

Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.

Dumoulin, Mireille, et al., "Single-domain antibody fragments with high conformational stability", Protein Science, 11, (2002), 500-515.

Dunn, E. F., et al., "Transcription of a recombinant bunyavirus RNA template by transiently expressed bunyavirus proteins", Virology, 211(1), (1995), 133-143.

Durbin, A. P., et al., "Recovery of infectious human parainfluenza virus type 3 from cDNA", Virology, 235(2), (Sep. 1, 1997), 323-332.

Dyall, J., et al., ""Identification of inhibitors of Ebola virus with a subgenomic replication system"", Antiviral Research, 70(1), 19th International Conference on Antiviral Research, San Juan, PR (May 7-11, 20006), (May 2006), p. A39.

Elhefnawi, M, et al., "Identification of novel conserved functional motifs across most Influenza A viral strains", Virology Journal, 8:44, (2011), 10 pages.

Elliott, R. M., "Emerging Viruses: The Bunyaviridae", Molecular Medicine, 3(9), (1997), 572-577.

Elliott, R. M., et al., "Rescue of Infectious Bunyavirus Entirely From Cloned cDNA", 10th International Conference on Negative Strand Virus, (Abstract No. 96), (1997), 1 pg.

Elliott, R. M., et al., "Some Highlights of Virus Research in 1990", Journal of General Virology, 72(Part 8), (1991), 1761-1779.

Emerson, S. U., et al., "Both NS and L Proteins Are Required for In Vitro RNA Synthesis by Vesicular Stomatitis Virus", Journal of Virology, 15(6), (1975), 1348-1356.

Enami, K., et al., "Influenza virus NS1 protein stimulates translation of the M1 protein", Journal of Virology, 68 1432-1437, (1994), 6 pgs.

Enami, M., "An Influenza Virus Containing Nine Different RNA Segments", Virology, 185(1), (1991), 291-298.

Enami, M., et al., "High-Efficiency Formation of Influenza Virus Transfectants", Journal of Virology, 65(5), (1991), 2711-2713.

Enami, M., et al., "Introduction of Site-Specific Mutations Into the Genome of Influenza Virus", Proc. Natl. Acad. Sci. USA, 87, (1990), 3802-3805.

Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.

Fahey, J. L., et al., "Status of Immune-Based Therapies in HIV Infection and Aids", Clinical and Experimental Immunology, 88(1), (1992), 1-5.

Fischer, W. B, et al., "Viral ion channels: structure and function.", Biochim Biophys Acta., 1561(1), (Mar. 19, 2002), 27-45.

Fodor, E., et al., "Rescue of Influenza A Virus from Recombinant DNA", Journal of Virology, 73(11), XP002151487; ISSN:0022-538X, (Nov. 1999), 9679-9682.

Fortes, P., et al., "Influenza Virus NS1 Protein Inhibits Pre-mRNA Splicing and Blocks mRNA Nucleocytoplasmic Transport", The EMBO Journal, 13(3), (1994), 704-712.

Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.

Friers, et al., "Soluble recombinant influenza vaccines", Phil. Trans. R. Soc. Lond. B (2001). vol. 356 1961-1963, (2001), 4 pgs.

Garay, R. P, et al., "Cancer relapse under chemotherapy: why TLR2/4 receptor agonists can help", Eur J Pharmacol., 563(1-3), (Jun. 1, 2007), 1-17.

Garcia-Sastre, A., et al., "Genetic Manipulation of Negative-Strand RNA Virus Genomes", Annu. Rev. Microbiol., 47, (1993), 765-790.

Garcia-Sastre, A., et al., "The cytoplasmic tail of the neuraminidase protein of influenza A virus does not play an important role in the packaging of this protein into viral envelopes", Virus Research, 37(1), (1995), 37-47.

Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.

Garrett, L., "Deadly Ebola, Avian Influenza Re-Emerging", Newsday.com, (Feb. 20, 2003), 3 pgs.

Gerdil, C., "The Annual Production Cycle for Influenza Vaccine", Vaccine, 21 1776-1779, (2003), 4 pgs.

Giddings, A M, et al., "The matrix protein of HIV-1 is not sufficient for assembly and release of virus-like particles", Virology, 248(1), (1998), 108-16.

(56) References Cited

OTHER PUBLICATIONS

Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.

Gomez-Puertas, P., et al., "Influenza Virus Matrix Protein Is The Major Driving Force in Virus Budding", Journal of Virology, 74 11538-11547, (Dec. 1, 2000), 10 pgs.

Gorman, O T, et al., "Evolution of influenza A virus PB2 genes: implications for evolution of the ribonucleoprotein complex and origin of human influenza A virus", J. Virol., 64(10), (Oct. 1990), 4893-4902.

Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.

Govorkova, E A, et al., "Replication of Influenza A Viruses in a Green Monkey Kidney Continuous Cell Line (Vero)", J. Infect. Dis. 172(1), (1995), 250-253.

Grambas, S., et al., "Influence of amantadine resistance mutations on the pH regulatory function of the M2 protein of influenza A viruses", Virology, 191(2), (Dec. 1992), 541-549.
Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.
Groseth, A., et al., "RNA Polymerase I-Driven Minigenome System for Ebola Viruses", Journal of Virology, 79(7), (2005), 4425-4433.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Hagen, M., et al., "Recombinant Influenza Virus Polymerase: Requirement of both 5' and 3' Viral Ends for Endonuclease Activity", Journal of Virology, 68(3), (1994), 1509-1515.
Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.
Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.
Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.
Halstead, Scott B,. et al., "Dengue Antibody-Dependent Enhancement: Knowns and Unknowns", Microbiology Spectrum, 2(6), (2014), 1-18.
Harding, Alfred T, et al., "Rationally Designed Influenza Virus Vaccines That Are Antigenically Stable during Growth in Egg", MBIO, vol. 8, No. 3, eO0669-17, (Jul. 5, 2017), 1-16.
Harmsen, M. M., et al., "Properties, production, and applications of camelid single-domain antibody fragments", Appl Microbiol Biotechnol,77, (2007), 13-22.
Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatada, E., et al., "Binding of Influenza A Virus NS1 Protein to dsRNA in vitro", Journal of General Virology, 73, (1992), 3325-3329.
Hatakeyama, S., et al., "Dissection and identification of regions required to form pseudoparticles by the interaction between the nucleocapsid (N) and membrane (M) proteins of SARS coronavirus", Virology, 380(1), (2008), 99-108.
Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.
Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
He, X., et al., "Generation of SARS-CoV-2 reporter replicon for high-throughput antiviral screening and testing", Proc. Natl. Acad. Sci. USA, 118(15): e2025866118, (2021), 8 pgs.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Ho, Y., et al., "Assembly of human severe acute respiratory syndrome coronavirus-like particles", Biochem Biophys Res Commun, 318(4), (2004), 833-838.
Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.
Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.
Hoffman, E., et al., "Ambisense Approach for the Generation of Influenza A Virus: vRNA and mRNA Synthesis from One Template", Virology 267(2) 310-317, (Feb. 15, 2006), 8 pgs.
Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.
Hoffmann, E., et al., "A Dna transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, Erich, et al., "A DNA transfection system for generation of influenza A virus from eight plasmids", Proceedings of the National Academy of Sciences, vol. 97, No. 11, (2000), 6108-6113.
Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.
Holsinger, L. J., et al., "Influenza A Virus M2 Ion Channel Protein: a Structure-Function Analysis", Journal of Virology, 68 (3), (1994), pp. 1551-1563.
Honda, A., et al., "RNA Polymerase of Influenza Virus: Role of NP in RNA Chain Elongation", The Journal of Biochemistry, 104(6), (1988), 1021-1026.
Horimoto, "Designing Vaccines for Pandemic Influenza", Current Topics Microbiol Immunol 333, (2009), 165-176.

(56) References Cited

OTHER PUBLICATIONS

Horimoto, T., et al., "Enhanced growth of seed viruses for H5N1 influenza vaccines", Virology, 366(1), (Sep. 15, 2007), 23-27.

Horimoto, T., et al., "Generation of Influenza A Viruses with Chimeric (Type A/B) Hemagglutinins", Journal of Virology, 77(14) 8031-8038, (2003), 11 pgs.
Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.
Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.
Huang, T. S, et al., "Determinaton of Influenza Virus Proteins Required for Genome Replication", Jounal of Virology, vol. 64 5669-5673, (1990), 5 pgs.
Huang, T.-S., et al., "Determination of Influenza Virus Proteins Required for Genome Replication", Journal of Virology, 64(11), (1990), 5669-5673.
Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.
Huddleston, J. A., et al., "The Sequence of the Nucleoprotein Gene of Human Influenza A Virus, Strain A/NT/60/68", Nucleic Acids Research, 10(3), (1982), 1029-1038.
Huisman, W., et al., "Vaccine-induced enhancement of viral infections", Vaccine, 27(4), (2009), 505-512.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Jackson, D., et al., "A reverse genetics approach for recovery of recombinant influenza B viruses entirely from cDNA.", J Virol., 76(22), (Nov. 2002), 11744-7.
Jahrling, P. B., et al., "Ebola Hemorrhagic Fever: Evaluation of Passive Immunotherapy in Nonhuman Primates", J. Infect. Dis. 196, (2007), 4 pgs.
Jasenosky, Luke D, et al., "Ebola Virus VP40-Induced Particle Formation and Association with the Lipid Bilayer", Journal of Virology, 75 (110, (Jun. 2001), 5205-5214.
Jiang, H, et al., "Influenza virus genome C4 promoter/origin attenuates its transcription and replication activity by the low polymerase recognition activity", Virology, 408(2), (2010), 190-196.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Jin, H., et al., "Influenza virus hemagglutinin and neuraminidase cytoplasmic tails control particle shape", The EMBO Journal, 16(6), (1997), 1236-1247.
Jin, H., et al., "The influenza virus hemagglutinin cytoplasmic tail is not essential for virus assembly or infectivity", The EMBOL Journal, 13(22), (1994), 5504-5515.
Johnson, David A, et al., "TLR4 Agonists as Vaccine Adjuvants", Vaccine Adjuvants and Delivery Systems, (2007), 131-156.
Ju, X., et al., "A novel cell culture system modeling the SARS-CoV-2 life cycle", PloS Pathogens, 17(3): e1009439, (2021), 23 pgs.
Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaoka, Y., "Mutant Cells With Altered Sialic Acid", U.S. Appl. No. 11/644,179, filed Dec. 22, 2006, 51 pgs.
Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.
Kijima, H., et al., "Therapeutic Application of Ribozymes", Pharmac. Ther., 68(2), (1995), 247-267.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H., et al., "Cold adaptation generates mutations associated with the growth of influenza B vaccine viruses", Vaccine, 33(43), (2015), 5786-5793.
Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.
Kimura, N., et al., "An In Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.
Kistner, O., et al., "Development of a mammalian cell (Vero) derived candidate influenza virus vaccine", Vaccine, 16(9-10), (May-Jun. 1998), 960-8.
Kistner, O., et al., "Development of a Vero Cell-Derived Influenza Whole Virus Vaccine", Dev. Biol. Stand., 98, (1999), 101-110.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Kon, Theone C, et al., "Influenza Vaccine Manufacturing: Effect of Inactivation, Splitting and Site of Manufacturing. Comparison of Influenza Vaccine Production Processes", PLoS One, 11(3), e0150700, (Mar. 9, 2016), 19 pgs.
Konarska, M. M., et al., "Structure of RNAs Replicated by the DNA-Dependent T7 RNA Polymerase", Cell, 63(2), (1990), 609-618.
Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.
Kovesdi, I., et al., "Adenoviral Vectors for Gene Transfer", Current Opinion in Biotechnology, 8(5), (Oct. 1997), 583-589.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990), 9 pgs.
Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.
Kumar, P. K. R., et al., "Artificial Evolution and Natural Ribozymes", The FASEB Journal, 9, (1995), 1183-1195.

(56) References Cited

OTHER PUBLICATIONS

Kunik, Vered, et al., "Paratome: an online tool for systematic identification of antigen-binding regions in antibodies based on sequence or structure", Nucleic Acids Research, vol. 40, Issue W1, (2012), W521-W524.
Kunkel, T. A., "Rapid and Efficient Site-Specific Mutagenesis Without Phenotypic Selection", Proc. Natl. Acad. Sci. USA, 82, (1985), 488-492.
Kuwahara, Tomoko, et al., "Characterization of cell-derived and egg-passaged influenza A/Saitama/103/2014 (H3N2) strain", The 65th Annual Meeting of the Japanese Society of Virology, (2017), 1 pg.
Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71(3), (2018), 234-238.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Lawson, N. D., "Recombinant Vesicular Stomatitis Viruses From DNA", Proc. Natl. Acad. Sci. USA, 92(10), (1995), 4477-4481.
Laxman, B., "Noninvasive Real-Time Imaging of Apoptosis", PNAS, 99(26), (2002), 16551-16555.
Lazarovits, Janette, et al., "Endocytosis of Chimeric Influenza Virus Hemagulutinin Proteins That Lack a Cytoplasmic Recognition Feature for Coated Pits", The Journal of Cell Biology, vol. 134, No. 2, (1996), 339-348.
Le, T., "CaSpeR5, a family of *Drosophila* transgenesis and shuttle vectors with improved multiple cloning sites", Biotechniques, 42(2), (Feb. 2007), 164-166.
Leahy, M. B., et al., "An Endonuclease Switching Mechanism in the Virion RNA and cRNA Promoters of Thogoto Orthomyxovirus", Journal of Virology, 72(3), (1998), 2305-2309.
Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.
Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, Dong-Hun, et al., "Progress and hurdles in development of influenza virus-like particle vaccines for veterinary use", Korean Vaccine Society, (2014), 133-139.
Lee, Jeffrey E., et al., "Complex of a Protective Antibody with Its Ebola Virus GP Peptide Epitope: Unusual Features of a V?x Light Chain", J. Mol. Biol., 375, (2007), 202-216.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6NI avian influenza viruses isolated in Taiwan between 1972 and 2005", Avian Diseases, 50(4), (Dec. 2006), 561-571.
Lefranc, Marie-Paule, et al., "IMGT unique numbering for immunoglobulin and T cell receptor variable domains and Ig superfamily V-like domains", Developmental & Comparative Immunology, 27, (2003), 55-77.
Lembo, A, et al., "Administration of a synthetic TLR4 agonist protects mice from pneumonic tularemia.", J Immunol., 180(11), 7574-81.
Levis, R., et al., "Deletion Mapping of Sindbis Virus DI RNAs Derived From cDNAs Defines the Sequences Essential for Replication and Packaging", Cell, 44, (1986), 137-145.
Li, et al., "Selection of antigenically advanced variants of seasonal influenza viruses", Nature Microbiology, 1 (6), (2016), 1-10.
Li, Junwei, et al., "Engineering Influenza Viral Vectors", Bioengineered, vol. 4, No. 1, (Jan. 1, 2013), 9-14.
Li, K. S., et al., "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Li, S., et al., "Electroporation of Influenza Virus Ribonucleoprotein Complexes for Rescue of the Nucleoprotein and Matrix Genes", Virus Research, 37(2), (1995), 153-161.
Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.
Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.
Liu, Y., et al., "A live-attenuated SARS-CoV-2 vaccine candidate with accessory protein deletions", bioRxiv [online]. [retrieved Jun. 10, 2022]. Retrieved from the Internet: <URL: https://www.biorxiv.org/content/10.1101/2022.02.14.480460v1.full.pdf>, (2022), 44 pgs.
Liu, Z, et al., "Fine mapping of the antigen-antibody interaction of scFv215 A recombinant antibody inhibiting RNA polymerase II from *Drosophila melanogaster*", J. Mol. Recog. 12:103-111, (1999), 9 pgs.
Longnecker, R., et al., "VWV- and SH3-domain interactions with Epstein-Barr virus MP2A", Exp Cell Res., 257(2), (Jun. 15, 2000), Abstract Only.
Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Mansky, L. M, "Retrovirus mutation rates and their role in genetic variation", J Gen Virol., 79 (Pt 6), (Jun. 1998), 1337-45.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.

(56) References Cited

OTHER PUBLICATIONS

Martorelli Di, Genova B., et al., "Intestinal delta-6-desaturase activity determines host range for Toxoplasma sexual reproduction", PLoS Biology, vol. 17, No. 8, E3000364, (Aug. 20, 2019), XP055619380, (Aug. 20, 2019), 1-19.
Matrosovich, M, et al., "Overexpression of the [alpha]-2,6-sialyltransferase in MDCK cells increases influenza virus sensitivity to neuraminidase inhibitors", Journal of Virology, the American Society for Microbiology, US, vol. 77, No. 15, (Aug. 1, 2003), 8418-8425.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21) 12364-12373, (2014), 10 pgs.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McCullers, et al., "Multiple Genotypes of Influenza B Virus Circulated between 1979 and 2003,", Journal of Virology, vol. (78), No. (23) 12817-12828, (2004), 13 pgs.
McCullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.
McKee, Dwight L, et al., "Candidate drugs against SARS-CoV-2 and COVID-19", Pharmacological Research, Academic Press, London, GB, vol. 157, (Apr. 29, 2020), 9 pgs.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
McSharry, J. J, et al., "Phenotypic Drug Susceptibility Assay for Influenza Virus Neuraminidase Inhibitors", Cinical and Diagnostic Laboratory Immunology vol. (11), No. (2),, (2004), 10 pgs.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of biologically active influenza virus core proteins using a vaccinia virus-T7 RNA polymerase expression system", Journal of General Virology, 75 2109-2114, (1994), 6 pgs.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Mittler, E., et al., "Role of the transmembrane domain of marburg virus surface protein GP in assembly of the viral envelope.", J Virol., 81(8), (Apr. 2007), 3942-8.
Miyoshi, H., et al., "Development of Self-Inactivating Lentivirus Vector", Journal of Virology, 72(10), (1998), 8150-8157.
Monto, A. S, et al., "Detection of influenza viruses resistant to neuraminidase inhibitors in global surveillance during the first 3 years of their use", Antimicrobal Agents and Chemotherapy, 50(7) 2395-2402, (2006), 8 pgs.
Monto, Arnold S, et al., "Comparative efficacy of inactivated and live attenuated influenza vaccines.", N Engl J Med., 361(13) 1260-7, (Sep. 24, 2009), 8 pgs.
Morita, S., et al., "Plat-E: an efficient and stable system for transient packaging of retroviruses", Gene Therapy, 7(12), (2000), 1063-1066.
Moss, B., et al., "New Mammalian Expression Vectors", Nature, 348, (1990), 91-92.
Moyer, S. A., et al., "Assembly and Transcription of Synthetic Vesicular Stomatitis Virus Nucleocapsids", Journal of Virology, 65(5), (1991), 2170-2178.
Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.
Muhlberger, E., et al., "Three of the four nucleocapsid proteins of Marburg virus,NP, VP35, and L, are sufficient to mediate replication and transcription of Marburg virus-specific monocistronic minigenomes", Journal of Virology, 72(11) 8756-8764. (1998), 11 pgs.
Muhlberger, Elke, "Filovirus replication and transcription", Future Virol., 2:205, (2007), 16 pgs.
Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Murphy, Brian R, et al., "Virulence of Avian Influenza A Viruses for Squirrel Monkeys", Infection and Immunity 37 (3), (Sep. 1982), 1119-1126.
Muyldermans, S, "Nanobodies: Natural single-domain antibodies", Ann. Rev. Biochem. 82, (2013), 1 pg.
Naim, H. Y., et al., "Basis for Selective Incorporation of Glycoproteins into the Influenza Virus Envelope", Journal of Virology, 67(8), (1993), 4831-4841.
Naito, S., et al., "Function and Structure of RNA Polymerase From Vesicular Stomatitis Virus", The Journal of Biological Chemistry, 251(14), (1976), 4307-4314.
Nara, et al., "How Can Vaccines Against Influenza and Other Viral Diseases Be Made More Effective?", PLoS Biology, 8 (12), (2010), e1000571.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "A Decade After the Generation of a Negative-Sense RNA Virus From Cloned cDNA-What Have We Learned?", Journal of General Virology, 83(11), (Nov. 2002), 2635-2662.
Neumann, G., et al., "An Improved Reverse Genetics System for Influenza A Virus Generation and Its Implications for Vaccine Production", Proc. Natl. Acad. Sci. USA, 102(46) 16825-16829, (2005), 5 pgs.
Neumann, G., et al., "An improved reverse genetics system for influenza A virus generation and its implications for vaccine production", Proc. Natl. Acad. Sci. USA. 102(46), (2005), 16825-16829.
Neumann, G., et al., "Emergence and pandemic potential of swine-origin H1N1 influenza virus", Nature (London), 459(7249), (Jun. 2009), 931-939.

(56) References Cited

OTHER PUBLICATIONS

Neumann, G., et al., "Generation of influenza A virus from cloned cDNAs—historical perspective and outlook for the new millenium.", Rev Med Virol., 12(1), XP002314285, (Jan.-Feb. 2002), 13-30.

Neumann, G., et al., "Genetic Engineering of Influenza and Other Negative-Strand RNA Viruses Containing Segmented Genomes", Advances in Virus Research, 53, (1999), 265-300.

Neumann, G., et al., "Nuclear Import and Export of Influenza Virus Nucleoprotein", Journal of Virology, 71(12), (1997), 9690-9700.

Neumann, G., et al., "RNA Polymerase I-Mediated Expression of Influenza Viral RNA Molecules", Virology, 202(1), (1994), 477-479.

Neumann, G., et al., "Synthesis of Influenza Virus: New impetus from an old enzyme, RNA polymerase I", Virus Research 82(1-2), (Jan. 30, 2002), 153-158.

Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.

Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.

Niwa, H., et al., "Efficient Selection for High-Expression Transfectants With a Novel Eukaryotic Factor", Gene, 108(2), (1991), 193-199.

Noda, Takeshi, et al., "Three-dimensional analysis of ribonucleoprotein complexes in influenza A virus", Nature Communications, 3, (2012), 1-6.

Odagiri, T., et al., "Nucleotide Sequence of the PA Gene of Influenza A/WSN/33 (H1N1)", Nucleic Acids Research, 18 (3), Department of Virology, (Jan. 9, 1990). 1 pg.

Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.

Onishi, M., et al., "Applications of retrovirus-mediated expression cloning", Experimental Hematology, 24(2), (1996), 324-329.

Orkin, S. H, et al., "Report and Recommendations of the Panel to Assess the NIH Investment in Research on Gene Therapy", http://www.nih.gov/news/panelrep.html, (Dec. 7, 1995), 37 pgs.

Ozaki, "Generation of High-Yielding Influenza A Viruses in African Green Monkey Kidney (Vero) Cells by Reverse Genetics", J Virol 78(4), (2004), 1851-1857.

Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.

Ozawa, M., et al., "An adenovirus vector-mediated reverse genetics system for Influenza A virus generation", Journal of Virology, The American society For Microbiology, US vol. 81 (17), XP002471230, ISSN: 0022-538X, (Jun. 27, 2007), 9556-9559.

Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.

Palese, P., et al., "47. Orthomyxoviridae: The Viruses and Their Replication", In: Fields Virology (5th Edition), (2007), 90 pgs.

Palese, P., "Negative-Strand RNA Viruses: Genetic Engineering and Applications", Proc. Natl. Acad. Sci. USA, 93(21), (1996), 11354-11358.

Park, Eun K., et al., "The M2 Ectodomain is important for its incorporation into influenza A virions", J. of Virology, vol. 72, No. 3, XP002196797, (Mar. 1998), 2449-2455.

Park, K. H., et al., "Rescue of a Foreign Gene by Sendai Virus", Proc. Natl. Acad. Sci. USA, 88, (1991), 5537-5541.

Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.

Peiris, J. S. M., et al., "Re-Emergence of Fatal Human Influenza A Subtype H5N1 Disease", The Lancet, 363 617-619, (2004), 3 pgs.

Pekosz, A., "Commentary—Reverse Genetics of Negative-Strand RNA Viruses: Closing the Circle", Proc. Natl. Acad. Sci. USA, 96, (1999), 8804-8806.

Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

Pelet, T., et al., "High throughput screening assay for negative single stranded RNA virus polymerase inhibitors", Journal of Virological Methods, 128 29-36, (2005), 8 pgs.

Percy, N., et al., "Expression of a Foreign Protein by Influenza A Virus", Journal of Virology, 68(7), (1994), 4486-4492.

Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.

Perez, D. R., et al., "The Matrix 1 Protein of Influenza A Virus Inhibits the Transcriptase Activity of a Model Influenza Reporter Genome in Vivo", Virology, 249(1), (1998), 52-61.

Perez, Jasmine T., et al., "Unit 15G.4—Insertion of a GFP Reporter Gene in Influenza Virus", Curr Protoc Microbiol., (2013), 20 pgs.

Peterson, B. C., et al., "Homologous sequences other than insertion elements can serve as recombination sites in plasmid drug resistance gene amplification", Journal of Bacteriology, Oct. 1983 156(1) 177-185, (1983), 5 pgs.

Piller, S C., et al., "Vpr protein of human immunodeficiency virus type 1 forms cation-selective channels in planar lipid bilayers", PNAS, 93, (1996), 111-1115.

Ping, J., et al., "Development of high-yield influenza B virus vaccine viruses", Proc. Natl. Acad. Sci. USA, 113(51), (Dec. 5, 2016), E8296-E8305.

Ping, Jihui, et al., "Development of high-yield influenza A virus vaccine viruses", Nature Communications, [online]. Retrieved from the Internet: <http://www.nature.eom/article-assets/npg/ncomms/2015/150902/ncomms9148/extref/ncomms9148-sl.pdf>, (Sep. 2, 2015), 50 pgs.

Pinto, L. H., et al., "Influenza Virus M2 Protein Has Ion Channel Activity", Cell, 69, (May 1992), pp. 517-528.

Pittman, Kelly J., et al., "Z-DNA Binding Protein Mediates Host Control of Toxoplasma gondii Infection", Infection and Immunity, 84(10), (Oct. 2016), 3063-3070.

Plant, E P, et al., "Mutations to A/PuertoRico/8/34 PB1 gene improves seasonal reassortant influenza A virus growth kinetics", Vaccine, 31(1), (Dec. 1, 2012), 207-212.

Pleschka, S., et al., "A Plasmid-Based Reverse Genetics System for Influenza A Virus", Journal of Virology, 70(6), (1996), 4188-4192.

Pley, H. W., et al., "Three-Dimensional Structure of a Hammerhead Ribozyme", Nature, 372, (1994), 68-74.

Popova, Lyubov, et al., "Immunodominance of Antigenic Site B over Site of Hemagglutinin of Recent H3N2 Influenza Viruses", PLoS One, vol. 7 No. 7, (Jul. 25, 2012), e41895.

Potter, C. W., "Chapter 1—Chronicle of Influenza Pandemics", In: Textbook of Influenza, Nicholson, K. G., et al., Editors, (Blackwell Scientific Publication), (1998), 3-18.

Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.

Preston, Andrew, "Choosing a Cloning Vector", Methods in Molecular Biology, vol. 235, *E. coli* Plasmid Vectors 19-27, Edited by: N. Casali and A. Preston, (2003), 9 pgs.

Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.

(56) References Cited

OTHER PUBLICATIONS

Puzelli, S., et al., "Changes in the Hemagglutinins and Neuraminidase of Human Influenza B Viruses Isolated in Italy During the Feb. 2001, Mar. 2002, and Apr. 2003 Seasons", Journal of Medical Virology, 74(4) 629-640, (2004), 12 pgs.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981), 4 pgs.
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Ramanunninair, Manojkumar, et al., "Molecular Signature of High Yield (Growth) Influenza A Virus Reassortants Prepared as Candidate Vaccine Seeds", PLoS One, 8(6): e65955, (2013), 1-16.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Ricardo-Lax, I., et al., "Replication and single-cycle delivery of SARS-CoV-2 replicons", Science, 374(6571), (2021), 1099-1106 (9 pgs).
Roberts, A., et al., "Minireview—Recovery of Negative-Strand RNA Viruses From Plasmid DNAs: A Positive Approach Revitalizes a Negative Field", Virology, 247(1), (1998), 1-6.
Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 (Pt 4) 799-802, (Apr. 1984), 4 pgs.
Ruigrok, R W, et al., "Structural Characterization and Membrane Binding Properties of the Matrix Protein VP40 of Ebola Virus", Journal of Molecular Biology, 300(1), (2000), 103-112.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.
Sansom, M. S., et al., "Influenza virus M2 Protein: a molecular modelling study of the ion channel", Protein Engineering, 6 (1), (1993), pp. 65-74.
Saphire, E. O., et al., "Feverish Quest for Ebola Immunotherapy: Straight or Cocktail", Trends Microbial, 24(9), (Sep. 2016), 684-686.
Satterlee, B., "Production of H5N1 avian influenza virus vaccine by plasmid-based reverse genetics technology", Basic Biotechnology eJournal, vol. 4, pp. 93-98, (2008), 93-98 Pgs.
Saunders, Kevin O., et al., “Neutralizing antibody vaccine for pandemic and pre-emergent coronaviruses”, Nature, 594, (2021), 553-559 (27 pgs.).
Schares, G., et al., “Oocysts of Neospora caninum, Hammondia heydorni, Toxoplasma gondii and Hammondia hammondi in faeces collected from dogs in Germany”, International Journal of Parasitology, vol. 35, No. 14, (Dec. 1, 2005), XP027737007, (Dec. 1, 2005), 1525-1537.
Schickli, J. H, et al., “Plasmid-only Rescue of Influenza A Virus Vaccine Candidates”, Philosophical Transactions of the Royal Society of London. Series B, Biological Sciences, 356(1416), (Dec. 29, 2001), 1965-1973.
Schlesinger, S., “RNA Viruses as Vectors for the Expression of Heterologous Proteins”, Molecular Biotechnology, 3(2), (1995), 155-165.
Schmidt, Kristina Maria, et al., “Marburg Virus Reverse Genetics Systems”, Viruses 2016, 8, 178; doi: 10.3390 / v8060178, www.mdpi.com/journal/viruses, (2016), 17 pgs.
Schnell, M. J., “Infectious Rabies Viruses From Cloned cDNA”, The EMBO Journal, 13(18), (1994), 4195-4203.
Schnell, Matthias J, et al., “Requirement for a non-specific glycoprotein cytoplasmic domain sequence to drive efficient budding of vesicular stomatitis virus”, EMBO Journal, 17 (5), (1998), 1289-1296.
Schotsaert, M, et al., “Universal M2 ectodomain-based influenza A vaccines: preclinical and clinical developments”, Expert Rev Vaccines. Apr. 2009;8(4):, 499-508.
Seong, B. L., et al., “A New Method for Reconstituting Influenza Polymerase and RNA in Vitro: A Study of the Promoter Elements for cRNA and vRNA Synthesis in Vitro and Viral Rescue in Vivo”, Virology, 186(1), (1992), 247-260.
Sheridan, Cormac, et al., “Innovators target vaccines for variants and shortages in global South”, Nature Biotechnology, 39(4), (Apr. 2021), 393-396.
Shi, Pei-Yong, “Infectious cDNA Clone of the Epidemic West Nile Virus from New York City”, Journal of Virology 5847-5856, (Jun. 2002), 10 pgs.
Shimojima, M., et al., “Tyro3 family-mediated cell entry of Ebola and Marburg viruses”, J Virol., 80(20), (Oct. 2006), 10109-16.
Shortridge, K. F., et al., “Characterization of Avian H5N1 Influenza Viruses From Poultry in Hong Kong”, Virology, 252 331-342, (1998), 12 pgs.
Sidhu, M. S., et al., “Rescue of Synthetic Measles Virus Minireplicons: Measles Genomic Termini Direct Efficient Expression and Propagation of a Reporter Gene”, Virology, 208, (1995), 800-807.
Silvas, J. A., et al., “Contribution of SARS-CoV-2 Accessory Proteins to Viral Pathogenicity in K18 Human ACE2 Transgenic Mice”, J Virol, 95(17): e00402-21, (Sep. 2021), 1-14.
Siu, Y. L., et al., “The M, E, and N Structural Proteins of the Severe Acute Respiratory Syndrome Coronavirus Are Required for Efficient Assembly, Trafficking, and Release of Virus-Like Particles”, J Virol., 82(22), (2008), 11318-11330.
Skehel, J. J., et al., “On the Mechanism of Inhibition of Influenza Virus Replication by Amantadine Hydrochloride”, The Journal of General Virology, 38 (1), (1977), pp. 97-110.
Smatti, Maria K., et al., “Viral-Induced Enhanced Disease Illness”, Front Microbiol, vol. 9: Article 2991, (Dec. 2018), 1-19.
Smeenk, et al., “Mutations in the Hemagglutinin and Matrix Genes of a Virulent Influenza Virus Variant, A/FM/1/47-MA, Control Different Stages in Pathogenesis”, Virus Research 44, (1996), 79-95.
Smura, T, “Surface glycoprotein [Severe acute respiratory syndrome coronavirus 2]”, Gen Bank Accessions QH062107, (Feb. 11, 2020), 2 pgs.
Stroud, Chad K., et al., “Disruption of FADS2 gene in mice impairs male reproduction and causes dermal and intestinal ulceration”, Journal of Lipid Research, vol. 50, (2009), 1870-1880.
Subbarao, E. K., et al., “Rescue of an InfluenzaA Virus Wild-Type PB2 Gene and a Mutant Derivative Bearing a Site-Specific Temperature-Sensitive and Attenuating Mutation”, Journal of Virology, 67(12), (1993), 7223-7228.
Subbarao, E. K., et al., “Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen”, Journal of Virology, 69(10), (1995), 5969-5977.
Subbarao, K., et al., “Characterization of an Avian Influenza A (H5N1) Virus Isolated From a Child With a Fatal Respiratory Illness”, Science, 279, (1998), 393-396.
Subbarao, K., et al., “Evaluation of a Genetically Modified Reassortant H5N1 Influenza A Virus Vaccine Candidate Generated by Plasmid-based Reverse Genetics”, Virology, vol. 305(1), (Jan. 5, 2003), 192-200.

(56) References Cited

OTHER PUBLICATIONS

Sugawara, K., et al., "Development of Vero Cell-Derived Inactivated Japanese Encephalities Vaccine", Biologicals, 30 303-314, (2002), 12 pgs.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sun, Weina, et al., "Development of Influenza B Universal Vaccine Candidates Usingthe "Mosaic" Hemagglutinin Approach", American Society For Microbiology, Journal of Virology, Vaccines and Antiviral Agents, vol. 93, Issue 12, (Jun. 2019), 17 pgs.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Takada, A., et al., "Downregulation of beta1 integrins by Ebola virus glycoprotein: implication for virus entry", Virology, 278(1), (Dec. 2000), Abstract Only.
Takada, Ayato, et al., "A system for functional analysis of Ebola? virus?glycoprotein", Proc. Natl. Acad. Sci. USA, 94(26), (1997), 14764-14769.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Infectivity-Enhancing Antibodies to Ebola Virus Glycoprotein" Journal of Virology, 75(5), (2001), 2324-2330.
Takada, Ayato, et al., "Protective efficacy of neutralizing antibodies against Ebola virus infection", Vaccine, 25(6), (2007), 993-999.
Takada, Ayato, et al., "The pathogenesis of Ebola hemorrhagic fever", Trends in Microbiology, 9(10), (2001), 506-511.
Takada, Kosuke, et al., "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273.
Takeda, M., et al., "Influenza a virus M2 ion channel activity is essential for efficient replication in tissue culture.", J Virol., 76(3), (Feb. 2002), 1391-9.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.
Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Tetsutani, K., et al., "Adjuvants in Influenza Vaccines", Vaccine 2012, vol. 30, (2012), 4 pgs.
Thao, Tran Thi Nhu, et al., "Rapid reconstruction of SARS-CoV-2 using a synthetic genomics platform", Nature, vol. 582 561-565, (2020), 24 pgs.
Theriault, S., "The role of reverse genetics systems in determining filovirus pathogenicity", Archives of Virology, Supplementum. 157-177, (2005), 22 pgs.
Thompson, W. W., et al., "Mortality Associated With Influenza and Respiratory Syncytial Virus in the United States", JAMA, 289(2) 179-186, (2003), 8 pgs.
Tobler, K, et al., "Effect of cytoplasmic tail truncations on the activity of the M(2) ion channel of influenza A virus", J Virol., 73(12), (Dec. 1999), 9695-9701.
Towner, J S, et al., "Generation of eGFP express ing recombinant Zaire ebolavirus for analysis of early pathogenesis events and high-throughput antiviral drug screening", Virology, Academic Press ,Orlando, US , vol. 332, No. 1 20-27, XP004715289 ISSN: 0042-6822 the whole document, (Feb. 5, 2005), 8 pgs.
Treanor, J. J, et al., "The B allele of the NS gene of avian influenza viruses, but not the A allele, attenuates a human influenza a virus for squirrel monkeys", Virology, 171(1), (1989), 1-9.
Vaishnava, Shipra, et al., "The Antibacterial Lectin Regllly Promotes the Spatial Segregation of Microbiota and Host in the Intestine", Science, 334 255-258, (2011), 4 pgs.
Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.nlm.nih.gov/pmc/articles/PMC7181998/pdf/main.pdf>, (Apr. 24, 2020), 17 pgs.
Varner, Chad, "Developing Synthetic Multivalent Cellular Effectors", Thesis, School of Chemical and Biomolecular Engineering, Georgia Institute of Technology, (Aug. 2017), 88 pgs.
Verma, I. M, et al., "Gene Therapy—Promises, Problems and Prospects", Nature, 389, 1997), 239-242.
Via, L. E, et al., "Isolation of restriction fragments from large plasmids recovered from bacteria with multiple plasmids", Biotechniques, 11(4), (Oct. 1991), Abstract Only.
Vincke, C, et al., "Introduction to heavy chain antibodies and derived nanobodies", Meth. Mol. Biol. 911, (2012), 13 pgs.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
Waap, Helga, et al., "In vitro isolation and seroprevalence ofin stray cats and pigeons in Lisbon, Portugal", Veterinary Parasitology, vol. 187, No. 3 XP028492469 542-547, (Jan. 17, 2012), 6 pgs.
Wagner, R., et al., "Interdependence of hemagglutinin glycosylation and neuraminidase as regulators of influenza virus growth: a study by reverse genetics", Journal of Virology, 74(14), (Jul. 2000), 6316-6323.
Wan, Yushun, et al., "Molecular mechanism for Antibody-Dependent Enhancement of Coronavirus EntrM", Journal of Virology, 94(5): e02015-19, (2019), 1-15.
Wang, et al., "Glycoengineering of CHO Cells to Improve Product Quality", Methods in Molecular Biology book series (MIMB, vol. 1603) 25-44, (May 11, 2017), 256 pgs.

(56) References Cited

OTHER PUBLICATIONS

Wang, B., et al., "Construction of Non-infectious SARS-CoV-2 Replicons and Their Application in Drug Evaluation", Virologica Sinica, 36, (2021), 890-900.

Wang, C., et al., "Ion Channel Activity of Influenza A Virus M2 Protein: Characterization of the Amantadine Block", Journal of Virology, 67 (9), (Sep. 1993), pp. 5585-5594.

Wang, Sheng-Fan, et al., "Antibody-dependent SARS coronavirus infection is mediated by antibodies against spike proteins", Biochem Biophys Res Commun, 451 208-214, (2014), 8 pgs.

Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.

Wang, Wenlig, et al., "Robust Immunity and Heterologous Protection against Influenza in Mice Elicited by a Novel Recombinant NP-M2e Fusion Protein Expressed in E. coli", PLoS One 7(12): e52488, (Dec. 2012), 1-13.

Wanitchang, Asawin, et al., "Characterization of influenza A virus pseudotyped with the spike protein of porcine epidemic diarrhea virus", Archives of Virology, 163(12), (2018), 3255-3264.

Ward, C. D., et al., "Direct Measurement of the Poliovirus RNA Polymerase Error Frequency In Vitro", Journal of Virology, 62(2), (1988), 558-562.

Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.

Warfield, et al., "", PNAS, vol. 100(26), (2003), pp. 5889-15894.

Watanabe, S., et al., "Ebola virus (EBOV) VP24 inhibits transcription and replication of the EBOV genome", J Infect Dis., 196(Suppl 2), (Nov. 15, 2007), S284-90.

Watanabe, S., et al., "Production of Novel Ebola Virus-Like Particles from cDNAs: an Alternative to Ebola Virus Generation by Reverse Genetics", Journal of Virology, 78(2), (Jan. 2004), 999-1005.

Watanabe, T., et al., "Influenza A virus can undergo multiple cycles of replication without M2 ion channel activity", J Virol., 75(12), (Jun. 2001), 5656-62.

Watanabe, T., et al., "Influenza A Virus with Defective M2 Ion Channel Activity as a Live Vaccine", Virology, 299(2), (Aug. 1, 2002), 266-270.

Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.

Watanabe, Tokiko, et al., "Exploitation of Nucleic Acid Packaging Signals To Generate a Novel In?uenza Virus-Based Vector Stably Expressing Two Foreign Genes", Journal of Virology, 77(19), (Oct. 2003), 10575-10583.

Watanabe, Tokiko, et al., "Influenza A Virus Can Undergo Multiple Cycles of Replication without M2 Ion Channel Activity", Journal of Virology 75(12), (2001), 5656-5662.

Weber, F., et al., "Conserved vRNA end sequences of Thogotoorthomyxovirus suggest a new panhandle structure", Archives of Virology, 142(5), (1997), 1029-1033.

Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.

Webster, R G, et al., "Evolution and molecular epidemiology of H9N2 influenza A viruses from quail in southern China", XP002744257, retrieved from EBI accession No. UNIPR0T:A3R6C9 Database accession No. A3R6C9 the whole document, (Apr. 3, 2007), 1 pg.

Wvei, Hung-Ju, et al., "Fabrication of influenza virus-like particles using M2 fusion proteins for imaging single viruses and designing vaccines", Vaccine, 29, (2011), 7163-7172.

Wei, Kai, et al., "Influenza A Virus Acquires Enhanced Pathogenicity and Transmissibility after Serial Passages in Swine", Journal of Virology, 88(20), (Oct. 2014), 11981-11994.

Wentworth, D E, et al., "The NIAID Influenza Genome Sequencing Project", XP002744258, retrieved from EBI accession No. UNIPROT:U3S198 Database accession No. U3S198 the whole document, (Dec. 11, 2013), 1 pg.

Whelan, S. P. J., et al., "Efficient Recovery of Infectious Vesicular Stomatitis Virus Entirely from cDNA Clones", Proc. Natl. Acad. Sci. USA, 92, (1995), 8388-8392.

Wiedmer, T., et al., "Identification of three new members of the phospholipid scramblase gene family", Biochim Biophys Acta, 1467(1), (Jul. 31, 2000), Abstract Only.

Williams, Mark A., et al., "Effect of Mutations and Deletions in a Bicistronic mRNA on the Synthesis of Influenza B Virus NB and NA Glycoproteins", Journal of Virology, 63(1), (1989), 28-35.

Wills, J. W., et al., "An Assembly Domain of the Rous Sarcoma Virus Gag Protein Required Late in Budding", Journal of Virology, 68(10), (1994), 6605-6618.

Wilson, et al., "Vaccine Potential of Ebola Virus VP24, VP30, VP35 and VP40 Proteins", Virology 286, (2001), 384-90.

Wilson, Julie A, et al., "Epitopes Involved in Antibody-Mediated Protection from Ebola Virus", Science, 287(5458), (Mar. 2000), 1664-1666.

Winkler, K, et al., "Changing the antigen binding specificity by single point mutations of an anti-p24 (HIV-1) antibody", J. Immunol. 165 4505-4514, (2000), 11 pgs.

Wood, J. M., et al., "From Lethal Virus to Life-Saving Vaccine: Developing Inactivated Vaccines for Pandemic Influenza", Nature Reviews Microbiology, 2(10), (2004), 842-847.

Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.

Xiang, J, et al., "Modification in framework region I results in a decreased affinity of chimeric anti-Tag72 antibody", Mol. Immunol. 28(½), (1991), 141-148.

Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10.3390/v15010095, (2023), 23.

Xu, Ruodan, et al., "Construction of SARS-CoV-2 Virus-Like Particles by Mammalian Expression System", Frontiers in Bioengineering and Technology, 8:862, (2020), 1-6.

Yamamoto, K., et al., "Orientation Dependence in Homologous Recombination", Genetics May 1996; 143(1): 27-36, (1996), 27-36.

Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.

Yasuda, J., "Growth Control of Influenza A Virus by M1 Protein: Analysis of Transfectant Viruses Carrying the Chimeric M Gene", Journal of Virology, 68(12), (1994), 8141-8146.

Yen, H L, et al., "Neuraminidase Inhibitor-Resistant Recombinant A/Vietnam/1203/04 (K5N1) Influenza Viruses Retain Their Replication Efficiency and Pathogenicity In Vitro and In Vivo", Journal Of Virology., vol. 81, No. 22, (Nov. 15, 2007), 12418-12426.

Yip, Ming S., et al., "Antibody-dependent infection of human macrophages by severe acute respiratory syndrome coronavirus", Virology Journal, 11: 82, (2014), 11 pgs.

Yu, Q., et al., "Functional cDNA Clones of the Human Respiratory Syncytial (RS) Virus N, P. and L Proteins Support Replication of RS Virus Genomic RNA Analogs and Define Minimal trans-Acting Requirements for RNA Replication", Journal of Virology, 69(4), (1995), 2412-2419.

Yusoff, K., et al., "Nucleotide Sequence Analysis of the L Gene of Newcastle Disease Virus: Homologies With Sendal and Vesicular Stomatitis Viruses", Nucleic Acids Research, 15(10), (1987), 3961-3976.

Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

(56) References Cited

OTHER PUBLICATIONS

Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.

Zeitlin, L., et al., "Antibody Therapeutics for Ebola Virus Disease", Curr. Opin. Viral. 17:, (2016), 11 pgs.

Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zhang, Q.-Y., et al., "SARS-CoV-2 replicon for high-throughput antiviral screening", J Gen Virol,. 102(5), (2021), 1-4.

Zhang, Y., et al., "A bacterial artificial chromosome (BAC)-vectored noninfectious replicon of SARS-CoV-2", Antiviral Research, vol. 185, 104974, (Jan. 2021), 1-9.

Zobel, A., et al., "RNA Polymerase I Catalysed Transcription of Insert Viral cDNA", Nucleic Acids Research, 21(16), (1993), 3607-3614.

"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.

"U.S. Appl. No. 10/081,170, Advisory Action mailed Sep. 27, 2004", 3 pgs.

"U.S. Appl. No. 10/081,170, Final Office Action mailed Apr. 12, 2006", 7 pgs.

"U.S. Appl. No. 10/081,170, Final Office Action mailed Jul. 13, 2004", 8 pgs.

"U.S. Appl. No. 10/081,170, Non Final Office Action mailed Jan. 15, 2004", 9 pgs.

"U.S. Appl. No. 10/081,170, Non Final Office Action mailed Feb. 8, 2005", 9 pgs.

"U.S. Appl. No. 10/081,170, Non Final Office Action mailed Aug. 24, 2005", 9 pgs.

"U.S. Appl. No. 10/081,170, Notice of Allowance mailed Sep. 18, 2006", 8 pgs.

"U.S. Appl. No. 10/081,170, Preliminary Amendment filed May 20, 2003", 2 pgs.

"U.S. Appl. No. 10/081,170, Preliminary Amendment filed Jun. 6, 2002", 1 pg.

"U.S. Appl. No. 10/081,170, Response filed Jan. 24, 2006 to Non Final Office Action mailed Aug. 24, 2005", 11 pgs.

"U.S. Appl. No. 10/081,170, Response filed Apr. 12, 2004 to Non Final Office Action mailed Jan. 15, 2004", 12 pgs.

"U.S. Appl. No. 10/081,170, Response filed Jun. 8, 2005 to Non Final Office Action mailed Feb. 8, 2005", 11 pgs.

"U.S. Appl. No. 10/081,170, Response filed Aug. 17, 2006 to Final Office Action mailed Apr. 12, 2006", 9 pgs.

"U.S. Appl. No. 10/081,170, Response filed Sep. 13, 2004 to Final Office Action mailed Jul. 13, 2004", 10 pgs.

"U.S. Appl. No. 10/081,170, Response filed Oct. 10, 2003 to Restriction Requirement mailed Sep. 10, 2003", 3 pgs.

"U.S. Appl. No. 10/081,170, Restriction Requirement mailed Sep. 10, 2003", 4 pgs.

"U.S. Appl. No. 11/509,249, Final Office Action mailed Jun. 12, 2008", 5 pgs.

"U.S. Appl. No. 11/509,249, Non Final Office Action with Restriction Requirement mailed Aug. 24, 2007", 8 pgs.

"U.S. Appl. No. 11/509,249, Notice of Allowance mailed Apr. 9, 2009", 7 pgs.

"U.S. Appl. No. 11/509,249, Notice of Allowance mailed Nov. 17, 2008", 4 pgs.

"U.S. Appl. No. 11/509,249, Response filed Feb. 20, 2008 to Non Final Office Action mailed Aug. 24, 2007", 11 pgs.

"U.S. Appl. No. 11/509,249, Response filed Oct. 6, 2008 to Office Action mailed Jun. 12, 2008", 11 pgs.

"U.S. Appl. No. 11/644,179 , Response filed Oct. 21, 2013 to Final Office Action mailed May 21, 2013", 8 pgs.

"U.S. Appl. No. 11/644,179, Final Office Action mailed May 21, 2013", 11 pgs.

"U.S. Appl. No. 11/644,179, Final Office Action mailed Jul. 2, 2010", 8 pgs.

"U.S. Appl. No. 11/644,179, Non Final Office Action mailed Nov. 29, 2012", 19 pgs.

"U.S. Appl. No. 11/644,179, Non Final Office Action mailed Dec. 8, 2009", 7 pgs.

"U.S. Appl. No. 11/644,179, Notice of Allowance mailed Nov. 1, 2013", 11 pgs.

"U.S. Appl. No. 11/644,179, Preliminary Amendment filed Dec. 22, 2006", 5 pgs.

"U.S. Appl. No. 11/644,179, Response filed Jan. 30, 2008 to Restriction Requirement mailed Oct. 30, 2007", 5 pgs.

"U.S. Appl. No. 11/644,179, Response filed Apr. 8, 2010 to Non Final Office Action mailed Dec. 8, 2009", 8 pgs.

"U.S. Appl. No. 11/644,179, Response filed Aug. 17, 2010 to Final Office Action mailed Jul. 2, 2010", 8 pgs.

"U.S. Appl. No. 11/644,179, Restriction Requirement mailed Oct. 30, 2007", 7 pgs.

"U.S. Appl. No. 11/644,179, Supplemental Preliminary Amendment filed Feb. 6, 2008", 6 pgs.

"U.S. Appl. No. 11/644,179. Response filed Feb. 20, 2013 to Non Final Office Action mailed Nov. 29, 2012", 10 pgs.

"U.S. Appl. No. 12/113,690, Final Office Action mailed Apr. 15, 2011", 10 pgs.

"U.S. Appl. No. 12/113,690, Non-Final Office Action mailed Nov. 10, 2010", 11 pgs.

"U.S. Appl. No. 12/113,690, Notice of Allowability mailed Aug. 19, 2013", 9 pgs.

"U.S. Appl. No. 12/113,690, Notice of Allowance mailed Jul. 18, 2013", 14 pgs.

"U.S. Appl. No. 12/113,690, Preliminary Amendment filed Jul. 31, 2008", 14 pgs.

"U.S. Appl. No. 12/113,690, Response filed Jun. 23, 2011 to Final Office Action mailed Apr. 15, 2011", 17 pgs.

"U.S. Appl. No. 12/113,690, Response filed Aug. 5, 2010 to Restriction Requirement mailed Apr. 6, 2010", 14 pgs.

"U.S. Appl. No. 12/113,690, Response filed Dec. 22, 2010 to Non Final Office Action mailed Nov. 10, 2010", 19 pgs.

"U.S. Appl. No. 12/113,690, Restriction Requirement mailed Apr. 6, 2010", 10 pgs.

"U.S. Appl. No. 12/470,287 , Response filed Jan. 23, 2012 to Non Final Office Action mailed Jul. 22, 2011", 13 pgs.

"U.S. Appl. No. 12/470,287 , Response filed May 31, 2012 to Final Office Action mailed Apr. 3, 2012", 14 pgs.

"U.S. Appl. No. 12/470,287, Corrected Notice of Allowability mailed Sep. 11, 2012", 2 pgs.

"U.S. Appl. No. 12/470,287, Final Office Action mailed Apr. 3, 2012", 7 pgs.

"U.S. Appl. No. 12/470,287, Non Final Office Action mailed Jul. 22, 2011", 9 pgs.

"U.S. Appl. No. 12/470,287, Notice of Allowance mailed Jun. 19, 2012", 5 pgs.

"U.S. Appl. No. 12/470,287, Response filed Apr. 28, 2011 to Restriction Requirement mailed Dec. 29, 2010", 8 pgs.

"U.S. Appl. No. 12/470,287, Restriction Requirement mailed Dec. 29, 2010", 6 pgs.

"U.S. Appl. No. 13/594,611, Final Office Action mailed Aug. 15, 2014", 7 pgs.

"U.S. Appl. No. 13/594,611, Non Final Office Action mailed Apr. 24, 2014", 9 pgs.

(56) References Cited

OTHER PUBLICATIONS

"U.S. Appl. No. 13/594,611, Notice of Allowance mailed Jan. 13, 2015", 7 pgs.
"U.S. Appl. No. 13/594,611, PTO Response to Rule 312 Communication mailed Apr. 16, 2015", 2 pgs.
"U.S. Appl. No. 13/594,611, Response filed Feb. 25, 2014 to Restriction Requirement mailed Jan. 27, 2014", 8 pgs.
"U.S. Appl. No. 13/594,611, Response filed Jul. 7, 2014 to Non Final Office Action mailed Apr. 24, 2014", 9 pgs.
"U.S. Appl. No. 13/594,611, Response filed Dec. 15, 2014 to Final Office Action mailed Aug. 15, 2014", 10 pgs.
"U.S. Appl. No. 13/594,611, Restriction Requirement mailed Jan. 27, 2014", 8 pgs.
"U.S. Appl. No. 14/699,213, Advisory Action mailed Mar. 7, 2018", 3 pgs.
"U.S. Appl. No. 14/699,213, Final Office Action mailed Dec. 1, 2017", 11 pgs.
"U.S. Appl. No. 14/699,213, Non Final Office Action mailed Jun. 2, 2017", 12 pgs.
"U.S. Appl. No. 14/699,213, Non-Final Office Action mailed Jan. 11, 2019", 10 pgs.
"U.S. Appl. No. 14/699,213, Notice of Allowance mailed Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication mailed Nov. 19, 2019", 2 pgs.
"U.S. Appl. No. 14/699,213, Response filed Feb. 15, 2017 to Restriction Requirement mailed Aug. 15, 2016", 9 pgs.
"U.S. Appl. No. 14/699,213, Response filed Feb. 27, 2018 to Final Office Action mailed Dec. 1, 2017", 34 pgs.
"U.S. Appl. No. 14/699,213, Response filed Aug. 22, 2017 to Non Final Office Action mailed Jun. 2, 2017", 12 pgs.
"U.S. Appl. No. 14/699,213, Response filed Apr. 11, 2019 to Non-Final Office Action mailed Jan. 11, 2019", 13 pgs.
"U.S. Appl. No. 14/699,213, Restriction Requirement mailed Aug. 15, 2016", 10 pgs.
"U.S. Appl. No. 15/247,006 Response filed Jun. 4, 2019 to Final Office Action mailed Feb. 4, 2019", 7 pgs.
"U.S. Appl. No. 15/247,006, Examiner Interview Summary mailed Nov. 27, 2017", 4 pgs.
"U.S. Appl. No. 15/247,006, Final Office Action mailed Feb. 4, 2019", 8 pgs.
"U.S. Appl. No. 15/247,006, Non Final Office Action mailed Apr. 20, 2018", 7 pgs.
"U.S. Appl. No. 15/247,006, Non Final Office Action mailed Sep. 8, 2017", 8 pgs.
"U.S. Appl. No. 15/247,006, Notice of Allowance mailed Jun. 24, 2019", 7 pgs.
"U.S. Appl. No. 15/247,006, Notice of Allowance mailed Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement mailed Mar. 17, 2017", 12 pgs.
"U.S. Appl. No. 15/247,006, Response filed Oct. 22, 2018 to Non Final Office Action mailed Apr. 20, 2018", 14 pgs.
"U.S. Appl. No. 15/247,006, Response filed Dec. 7, 2017 to Non Final Office Action mailed Sep. 8, 2017", 13 pgs.
"U.S. Appl. No. 15/247,006, Restriction Requirement mailed Mar. 17, 2017", 9 pgs.
"U.S. Appl. No. 16/547,262, Non Final Office Action mailed Mar. 31, 2021", 13 pgs.
"U.S. Appl. No. 16/547,262, Notice of Allowance mailed Jul. 22, 2021", 7 pgs.
"U.S. Appl. No. 16/547,262, Response filed Jun. 30, 2021 to Non Final Office Action mailed Mar. 31, 2021", 12 pgs.
"U.S. Appl. No. 16/547,262, Response filed Dec. 17, 2020 to Restriction Requirement mailed Jul. 17, 2020", 12 pgs.
"U.S. Appl. No. 16/547,262, Restriction Requirement mailed Jul. 17, 2020", 6 pgs.
"U.S. Appl. No. 16/694,748, Non Final Office Action mailed Nov. 9, 2021", 6 pgs.
"U.S. Appl. No. 16/694,748, Notice of Allowance mailed Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action mailed Nov. 9, 2021", 7 pgs.
"U.S. Appl. No. 16/694,748, Response filed Jul. 27, 2021 to Restriction Requirement mailed Jan. 27, 2021", 8 pgs.
"U.S. Appl. No. 16/694,748, Restriction Requirement mailed Jan. 27, 2021", 9 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Australian Application Serial No. 2008203186, First Examiner Report mailed Jan. 28, 2011", 2 pgs.
"Australian Application Serial No. 2008203186, Office Action Received mailed Sep. 16, 2010", 1 page.
"Australian Application Serial No. 2008203186, Response filed Mar. 28, 2011 to First Examiner Report mailed Jan. 28, 2011", 51 pgs.
"Australian Application Serial No. 2008203186, Response filed Aug. 29, 2011 to Official Action dated Apr. 13, 2011", 20 pgs.
"Australian Application Serial No. 2008203186, Subsequent Examiner Report mailed Apr. 13, 2011", 2 pgs.
"Brazil Application Serial No. PI0307679-2, Office Action mailed May 16, 2017", 2 pgs.
"Brazil Application Serial No. PI0307679-2, Response filed Jul. 13, 2017 to Office Action mailed May 16, 2017", 9 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI0307679-2, Final Office Action mailed Jul. 7, 2020", w/o English Translation, 6 pgs.
"Brazilian Application Serial No. PI0307679-2, Office Action mailed May 13, 2019", (w/ English Translation), 17 pgs.
"Brazilian Application Serial No. PI0307679-2, Office Action mailed Oct. 3, 2019", (w/ English Translation), 6 pgs.
"Brazilian Application Serial No. PI0307679-2, Office Action mailed Dec. 20, 2016", 2 pgs.
"Brazilian Application Serial No. PI0307679-2, Response filed Feb. 1, 2017 to Office Action mailed Dec. 20, 2016", 6 pgs.
"Brazilian Application Serial No. PI0307679-2, Response filed Aug. 16, 2019 to Office Action mailed May 13, 2019", (w/ English Translation of Claims), 29 pgs.
"Canadian Application Serial No. 11/509,249, Response filed May 16, 2011 to Office Acttion mailed Nov. 18, 2010", 15 pgs.
"Canadian Application Serial No. 2,492,097, Office Action mailed Jan. 10, 2012", 4 pgs.
"Canadian Application Serial No. 2,492,097, Office Action mailed Apr. 24, 2008", 3 pgs.
"Canadian Application Serial No. 2,492,097, Office Action mailed Jul. 31, 2009", 3 pgs.
"Canadian Application Serial No. 2,492,097, Response filed Jan. 29, 2010 to Office Action mailed Jul. 31, 2009", 13 pgs.
"Canadian Application Serial No. 2,492,097, Response filed May 2, 2012 to Office Action mailed Jan. 10, 2012", 12 pgs.
"Canadian Application Serial No. 2,492,097, Response filed Oct. 23, 2008 to Office Action mailed Apr. 24, 2008", 14 pgs.
"Canadian Application Serial No. 2,816,242, Office Action mailed Jun. 16, 2014", 3 pgs.
"Canadian Application Serial No. 2,816,242, Office Action mailed Jul. 12, 2017", 4 pgs.
"Canadian Application Serial No. 2,816,242, Office Action mailed Sep. 16, 2016", 4 pgs.
"Canadian Application Serial No. 2,816,242, Office Action mailed Oct. 5, 2015", 6 pgs.

(56) References Cited

OTHER PUBLICATIONS

"Canadian Application Serial No. 2,816,242, Response filed Jan. 3, 2018 to Office Action mailed Jul. 12, 2017", 13 pgs.
"Canadian Application Serial No. 2,816,242, Response filed Mar. 10, 2017 to Office Action mailed Sep. 16, 2016", 18 pgs.
"Canadian Application Serial No. 2,816,242, Response filed Apr. 5, 2016 to Office Action mailed Oct. 5, 2015", 13 pgs.
"Canadian Application Serial No. 2,816,242, Response filed Dec. 16, 2014 to Office Action mailed Jun. 16, 2014", 9 pgs.
"Canadian Application Serial No. 2492097, Office Action mailed Nov. 18, 2010", 4 pgs.
"Chinese Application Serial No. 03808356.6, Office Action mailed Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Reexamination Notice mailed Nov. 26, 2012", (w/ English Translation), 9 pgs.
"Chinese Application Serial No. 03808356.6, Response filed Mar. 11, 2013 to Office Action mailed Nov. 26, 2012", (w/ English Translation of Amended Claims), 9 pgs.
"Chinese Application Serial No. 03808356.6, Response filed Mar. 16, 2009 to Office Action mailed Sep. 5, 2008", (w/ English Translation of Claims), 8 pgs.
"Chinese Application Serial No. 03808356.6, Response filed Oct. 14, 2011 to Office Action mailed Jul. 1, 2011", (w/ English Translation of Amended Claims), 25 pgs.
"Chinese Application Serial No. 201310400039.8, Notice of Reexamination mailed Aug. 26, 2016", (w/ English Translation), 7 pgs.
"Chinese Application Serial No. 201310400039.8, Office Action mailed Feb. 12, 2015", (w/ English Translation), 10 pgs.
"Chinese Application Serial No. 201310400039.8, Office Action mailed Feb. 15, 2016", (w/ English Translation), 12 pgs.
"Chinese Application Serial No. 201310400039.8, Office Action mailed Apr. 1, 2017", (English Translation), 10 pgs.
"Chinese Application Serial No. 201310400039.8, Office Action mailed Aug. 7, 2015", (w/ English Translation), 10 pgs.
"Chinese Application Serial No. 201310400039.8, Office Action mailed Aug. 21, 2014", (w/ English Translation), 13 pgs.
"Chinese Application Serial No. 201310400039.8, Office Action Response mailed Jun. 16, 2017", W / English Claims, 8 pgs.
"Chinese Application Serial No. 201310400039.8, Response filed Jan. 4, 2015 to Office Action mailed Aug. 21, 2014", (w/ English Translation of Claims), 10 pgs.
"Chinese Application Serial No. 201310400039.8, Response filed Apr. 27, 2015 to Office Action mailed Feb. 12, 2015", (w/ English Translation of Claims), 16 pgs.
"Chinese Application Serial No. 201310400039.8, Response filed Jun. 1, 2016 to Office Action mailed Feb. 15, 2016", (w/ English Translation of Claims), 9 pgs.
"Chinese Application Serial No. 201310400039.8, Response filed Oct. 10, 2016 to Notice of Reexamination mailed Aug. 26, 2016", (w/ English Translation of Claims), 12 pgs.
"Chinese Application Serial No. 201310400039.8, Response filed Oct. 20, 2015 to Office Action mailed Aug. 7, 2015", (w/ English Translation of Claims), 11 pgs.
"Chinese Application Serial No. 201310400039.8, Response filed Aug. 14, 2017 to Office Action Response mailed Jun. 16, 2017", W/ English Claims.
"Chinese Application Serial No. 201310400039.8, Response filed Aug. 7, 2017 to Office Action Response mailed Jun. 16, 2017", W/ English Claims, 10 pgs.
"European Application Serial No. 03716017.3, Office Action mailed Aug. 23, 2012", 4 pgs.
"European Application Serial No. 02724994.5, Office Action mailed Mar. 27, 2009", 2 pgs.
"European Application Serial No. 03716017.3, Communication and Supplementary European Search Report mailed Jan. 2, 2008", 8 pgs.
"European Application Serial No. 03716017.3, Communication mailed May 23, 2006", 3 pgs.
"European Application Serial No. 03716017.3, Communication mailed Jul. 26, 2006", 2 pgs.
"European Application Serial No. 03716017.3, Communication mailed Oct. 20, 2008", 7 pgs.
"European Application Serial No. 03716017.3, Further Written Submissions filed Mar. 19, 2015", 45 pgs.
"European Application Serial No. 03716017.3, Office Action mailed Jul. 27, 2010", 4 pgs.
"European Application Serial No. 03716017.3, Response filed Feb. 4, 2011 to Office Action mailed Jul. 27, 2010", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) mailed Aug. 23, 2012", 19 pgs.
"European Application Serial No. 03716017.3, Response filed Mar. 24, 2015 to Office Action mailed Nov. 3, 2014", 38 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"European Application Serial No. 03716017.3, Response filed Sep. 28, 2015", 15 pgs.
"European Application Serial No. 03716017.3, Result of Consultation mailed Mar. 17, 2015", 5 pgs.
"European Application Serial No. 03716017.3, Summons to Attend Oral proceedings mailed Nov. 3, 2014", 5 pgs.
"European Application Serial No. 12761841.1, Communication pursuant to Article 94(3) EPC mailed Dec. 23, 2016", 6 pgs.
"European Application Serial No. 12761841.1, Response filed Feb. 23, 2017 to Communication pursuant to Article 94(3) EPC mailed Dec. 23, 2016", 9 pgs.
"European Application Serial No. 12761841.1, Voluntary Amendment filed Dec. 1, 2014", 5 pgs.
"European Application Serial No. 15197386.4, Communication Pursuant to Article 94(3) EPC mailed Feb. 21, 2018", 5 pgs.
"European Application Serial No. 15197386.4, Communication Pursuant to Article 94(3) EPC mailed Apr. 21, 2017", 5 pgs.
"European Application Serial No. 15197386.4, Communication Pursuant to Article 94(3) EPC mailed Jun. 19, 2019", 4 pgs.
"European Application Serial No. 15197386.4, extended European Search Report mailed Feb. 26, 2016", 11 pgs.
"European Application Serial No. 15197386.4, Response filed Jul. 3, 2018 to Communication Pursuant to Article 94(3) EPC mailed Feb. 21, 2018", 7 pgs.
"European Application Serial No. 15197386.4, Response filed Aug. 27, 2019 to Communication Pursuant to Article 94(3) EPC mailed Jun. 19, 2019", 61 pgs.
"European Application Serial No. 15197386.4, Response filed Oct. 20, 2016 to Extended European Search Report mailed Feb. 26, 2016", 4 pgs.
"European Application Serial No. 15197386.4, Response filed Oct. 31, 2017 to Communication Pursuant to Article 94(3) EPC mailed Apr. 21, 2017", 5 pgs.
"European Application Serial No. 16778485.9, Communication Pursuant to Article 94(3) EPC mailed Aug. 22, 2019", 5 pgs.
"European Application Serial No. 16778485.9, Office Action mailed Apr. 30, 2018", 3 pgs.
"European Application Serial No. 16778485.9, Response filed Nov. 8, 2018 to Office Action mailed Apr. 30, 2018", 18 pgs.
"Influenza virus A/CHR/ 157/83 genomic RNA for haemagglutinin", 2 pgs.
"International Application Serial No. PCT/US02/05455, International Preliminary Examination Report dated Aug. 17, 2004", 4 pgs.
"International Application Serial No. PCT/US02/05455, International Search Report mailed Mar. 25, 2003", 3 pgs.
"International Application Serial No. PCT/US03/04233, International Search Report mailed Dec. 16, 2005", 7 pgs.
"International Application Serial No. PCT/US2003/004233, International Search Report mailed Dec. 16, 2005", 5 pgs.
"International Application Serial No. PCT/US2008/005641, International Preliminary Report on Patentability dated Nov. 10, 2009", 9 pgs.

(56) References Cited

OTHER PUBLICATIONS

"International Application Serial No. PCT/US2008/005641, International Search Report mailed Feb. 4, 2009", 6 pgs.
"International Application Serial No. PCT/US2008/005641, Written Opinion mailed Feb. 4, 2009", 8 pgs.
"International Application Serial No. PCT/US2012/052368, International Preliminary Report on Patentability mailed Mar. 13, 2014", 8 pgs.
"International Application Serial No. PCT/US2012/052368, International Search Report mailed Dec. 3, 2012", 4 pgs.
"International Application Serial No. PCT/US2012/052368, Written Opinion mailed Dec. 3, 2012", 6 pgs.
"International Application Serial No. PCT/US2016/048691, International Preliminary Report on Patentability mailed Mar. 15, 2018", 7 pgs.
"International Application Serial No. PCT/US2016/048691, International Search Report mailed Nov. 22, 2016", 7 pgs.
"International Application Serial No. PCT/US2016/048691, Written Opinion mailed Nov. 22, 2016", 6 pgs.
"Israel Application Serial No. 163,546, First Examination Report mailed Jul. 28, 2008", (English Translation), 2 pgs.
"Israel Application Serial No. 163,546, Office Action mailed Nov. 12, 2009", (English Translation), 1 pg.
"Israel Application Serial No. 163,546, Office Action mailed Dec. 26, 2007", (English Translation), 1 pg.
"Israel Application Serial No. 163,546, Response filed May 9, 2008 to Office Action mailed Dec. 26, 2007", (English Translation of Amendments), 2 pgs.
"Israel Application Serial No. 163,546, Response filed Jun. 8, 2010 to Office Action mailed Nov. 12, 2009", (English Translation of Claims), 3 pgs.
"Israel Application Serial No. 163,546, Response filed Aug. 16,2009 to Substantive Examination Report mailed Feb. 23, 2009", (English Translation of Claims), 4 pgs.
"Israel Application Serial No. 163,546, Response filed Oct. 20, 2010 to Office Action dated Jun. 8, 2010", (w/ Rnglish Translation of Claims), 8 pgs.
"Israel Application Serial No. 163,546, Response filed Nov. 27, 2008 to First Examination Report mailed Jul. 28, 2008", (w English Translation of Claims), 13 pgs.
"Israel Application Serial No. 163546, Office Action mailed Jun. 8, 2010", (w/ English Translation), 2 pgs.
"Israeli Application Serial No. 163,546, First Examination Report mailed Jul. 28, 2008", (English Translation), 2 pgs.
"Israeli Application Serial No. 163,546, Substantive Examination Report mailed Feb. 23, 2009", (English Translation), 3 pgs.
"Israeli Application Serial No. 211324, Office Action mailed Sep. 18, 2014", (English Translation), 5 pgs.
"Israeli Application Serial No. 211324, Office Action mailed Oct. 18, 2015", (w/ English Translation), 4 pgs.
"Israeli Application Serial No. 211324, Response filed Feb. 16, 2016 to Office Action mailed Oct. 18, 2015", (English Translation of Claims), 4 pgs.
"Israeli Application Serial No. 211324, Response filed Mar. 31, 2015 to Office Action mailed Sep. 8, 2014", (w/ English Translation), 21 pgs.
"Japanese Application Serial No. 2003-315106, Amended Claims filed Oct. 15, 2009 in Response to Office Action mailed Jun. 24, 2009", (English Translation), 6 pgs.
"Japanese Application Serial No. 2003-315106, Notice of Allowance mailed Jan. 5, 2010", (w/ English Translation), 5 pgs.
"Japanese Application Serial No. 2003-315106, Office Action mailed Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Office Action mailed May 15, 2009", (w/ English Translation), 7 pgs.
"Japanese Application Serial No. 2003-568038, Office Action mailed Jul. 10, 2008", (w/ English Translation), 11 pgs.
"Japanese Application Serial No. 2003-568038, Office Action mailed Jul. 21, 2005", 3 pgs.
"Japanese Application Serial No. 2003-568038, Request for Examination filed Aug. 19, 2005 in Response to Official Action mailed Jul. 21, 2005", (w/ Partial English Translation of Specification), 8 pgs.
"Japanese Application Serial No. 2003-568038, Response filed Sep. 14, 2009 to Office Action mailed May 15, 2009", (w/ English Translation of Amended Claims), 10 pgs.
"Japanese Application Serial No. 2003-568038, Response filed Dec. 10, 2008 to Office Action mailed Jul. 10, 2008", (w/ English Translation of Amended Claims), 15 pgs.
"Japanese Application Serial No. 2008-315106, Office Action mailed Jun. 24, 2009", (w/ English Translation), 10 pgs.
"Japanese Application Serial No. 2008-315106, Response filed Oct. 15, 2009 to Office Action mailed Jun. 24, 2009", 103 pgs.
"Japanese Application Serial No. 2008-315106, Response filed Oct. 15, 2009 to Office Action mailed Jun. 24, 2009", (w/ English Translation of Amended Claims), 103 pgs.
"Japanese Application Serial No. 2008-315106, Response filed Dec. 3, 2009 to Office Action mailed Jun. 24, 2009", (w/ English Translation of Claims), 9 pgs.
"Japanese Application Serial No. 2009-238781, Office Action mailed Oct. 11, 2011", (w/ English Translation), 3 pgs.
"Japanese Application Serial No. 2014-527339, Examiners Decision of Final Refusal mailed Feb. 7, 2017", (w/ English Translation), 5 pgs.
"Japanese Application Serial No. 2014-527339, Office Action mailed May 31, 2016", (w/ English Translation), 10 pgs.
"Japanese Application Serial No. 2014-527339, Response filed Sep. 16, 2016 to Office Action mailed May 31, 2016", (w/ English Translation of Amended Claims), 33 pgs.
"Japanese Application Serial No. 2017-111526, Office Action mailed May 14, 2019", (w/ English Translation), 6 pgs.
"Japanese Application Serial No. 2017-111526, Office Action mailed Jun. 26, 2018", (w/ English Translation), 5 pgs.
"Japanese Application Serial No. 2017-111526, Response Filed Dec. 21, 2018 to Office Action mailed Jun. 26, 2018", (w/ English Translation of Amended Claims), 7 pgs.
"Japanese Application Serial No. 2018-510751, Notification of Reasons for Refusal mailed Mar. 13, 2019", (w/ English Translation), 14 pgs.
"Japanese Application Serial No. 2018-510751, Response filed Aug. 9, 2019 to Notification of Reasons for Refusal mailed Mar. 13, 2019", (w/ English Translation of Claims), 24 pgs.
"Korean Application Serial No. 10-2004-7012647, Office Action mailed Feb. 26, 2010", (w/ English Translation), 7 pgs.
"Korean Application Serial No. 10-2004-7012647, Response filed Jun. 10, 2010 to Office Action mailed Feb. 26, 2010", (w/ English Translation of Claims), 17 pgs.
"Korean Application Serial No. 10-2010-7011520, Office Action mailed Jul. 20, 2010", (w/ English Translation), 6 pgs.
"Korean Application Serial No. 10-2010-7011520, Response filed Oct. 20, 2010 to Office Actiion mailed Jul. 20, 2010", (w/ English Translation of Amended Claims), 30 pgs.
"Korean Application Serial No. 10-2010-7011520, Amended Claims filed May 24, 2011 in Response to Office Action mailed Feb. 24, 2011", (English Translation of Amended Claims), 22 pgs.
"Korean Application Serial No. 10-2010-7011520, Office Action mailed Feb. 24, 2011", (w/ English Translation), 5 pgs.
"Mexican Application Serial No. PA/a/2004/007914, Notice of Allowance mailed Jul. 30, 2008", 2 pgs.
"Mexican Application Serial No. PA/a/2004/007914, Office Action mailed Feb. 14, 2008", (w/ English Translation), 3 pgs.
"Mexican Application Serial No. PA/a/2004/007914, Office Action mailed Feb. 22, 2008", (English Translation), 3 pgs.
"Mexican Application Serial No. PA/a/2004/007914, Response filed Jun. 11, 2008 to Office Action mailed Feb. 22, 2008", (w/ English Translation of Claims), 68 pgs.
"Nucleotide sequences of influenza virus segments 1 and 3 reveal mosaic structure of a small viral RNA segment", Database Uniprot, (Nov. 14, 2001), 2 pgs.

(56) References Cited

OTHER PUBLICATIONS

"Nucleotides Sequences of Influenza Virus Segments 1 and 3 Reveal Mosaic Structure of Small Viral RNA Segment", Database UniProt EBI / Accession No. NC_002023, (Jul. 10, 2008), 15 pgs.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Castrucci, M. R, et al., "Attenuation of Influenza A Virus by Insertion of a Foreign Epitope into the Neuraminidase", Journal of Virology, 66(8), (1992), 4647-4653.
Castrucci, M. R., et al., "Biologic Importance of Neuraminidase Stalk Length in Influenza A Virus", Journal of Virology, 67(2), (1993), 759-764.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.
Catchpole, A P, et al., "Alternative base pairs attenuate influenza A virus when introduced into the duplex region of the conserved viral RNA promoter of either the NS or the PA gene", Journal of General Virology, 84, (2003), 507-515.
Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.
Del Guidice, G., et al., "What are the limits of adjuvanticity?", (Abstract), Vaccine, 20(Suppl 1), S38-S41, (2001), 1 pg.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dollenmaier, G., et al., "Membrane-Associated Respiratory Syncytial Virus F Protein Expressed From A Human Rhinovirus Type 14 Vector Is Immunogenic", Virology, 281(2), (Mar. 15, 2001), 216-230.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2), Academic Press, Orlando, US, (Sep. 30, 2000), 278-285.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human H1N1 Influenza A Virus Infection by H3NB Equine Defective Interfering Virus: Comparison of Defective RNA Sequences Isolated from the DI Inoculum and Mouse Lung", Virology, 248(2), Academic Press, Orlando, US, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Durbin, A. P, et al., "Human Parainfluenza Virus Type 3 (PIV3) Expressing The Hemagglutinin Protein Of Measles Virus Provides A Potential Method For Immunization Against Measles Virus and PIV3 In Early Infancy", Journal of Virology, 74(15), (Aug. 2000), 6821-6831.
Essere, Boris, et al., "Critical role of segment-specific packaging signals in genetic reassortment of influenza A viruses", Proc. Natl. Acad. Sci. USA, 110(40), (2013), E3840-E3848.
Fields, S., et al., "Nucleotides Sequences of Influenza Virus Segments 1 and 3 Reveal Mosaic Structure of Small Viral RNA Segment", Cell, 28, (1982), 303-313.

Flandorfer, A., et al., "Chimeric Influenza A Viruses with a Functional Influenza B Virus Neuraminidase or Hemagglutinin", Journal of Virology, 77(17), (2003), 9116-9123.
Fuji, Y., et al., "Selective incorporation of influenza virus RNA segments into virions", Proc. Natl. Acad. Sci. USA, 100(4), (2003), 2002-2007.
Fujii, Y, et al., "The packaging of influenza viral genome", Virus, 52 (1), Uirusu (Japanese Journal Name), (Jun. 2002), 203-206.
Gao, Qinshan, et al., "A Seven-Segmented Influenza A Virus Expressing the Influenza C Virus Glycoprotein HEF", Journal of Virology, 82(13), (Jul. 2008), 6419-6426.
Garcia-Sastre, A., et al., "Introduction of Foreign Sequences into the Genome of Influenza A Virus", Dev. Biol. Stand. vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10), (Jun. 30, 1994), 6254-6261.
Ghate, Anita A, et al., "Influenza Type B Neuraminidase Can Replace the Function of Type A Neuraminidase", Virology, 264 (2), (Nov. 1999), 265-277.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.
Green, R. F., et al., "Glycosylation Does Not Determine Segregation of Viral Envelope Proteins in the Plasma Membrane of Epithelial Cells", J. Cell Biol., 89(2), (1981), 230-239.
Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.
Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).
Hiti, A. L., et al., "P03470—Neuraminidase", Entrez Protein Database, http://www.ncbi.nlm.nih.gov/entrez/viewer.fcgi?db=protein&val=84028231, (1982), 730-734.
Hossain, M. J., et al., "Establishment and Characterization of a Madin-Darby Canine Kidney Reporter Cell Line for Influenza A Virus Assays", J Clin Microbiol, 48(7), (2010), 2515-2523.
Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.
Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza A Viruses Lacking Sialidase Activity Can Undergo Multiple Cycles of Replication in Cell Culture, Eggs, or Mice", Journal of Virology, 74(11), (2000), 5206-212.
Hutchinson, Edward C., et al., "Genome packaging in influenza A virus", Journal of General Virology, 91(Pt 2), (2010), 313-328.
Hwang, Jung-Shan, et al., "Expression of Functional Influenza Virus RNA Polymerase in the Methylotrophic Yeast *Pichia pastoris*", Journal of Virology, 74(9), (2000), 4074-4084.

(56) References Cited

OTHER PUBLICATIONS

Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.

Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.

Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.

Kobayashi, H., et al., "A replication-incompetent influenza virus bearing the HN glycoprotein of human parainfluenza virus as a bivalent vaccine", Vaccine, 31(52), (2013), 6239-6246.

Latham, T, et al., "Formation of Wild-Type and Chimeric Influenza Virus-Like Particles following Simultaneous Expression of Only Four Structural Proteins", Journal of Virology 75 (13), (2001), 6154-6165.

Leal, et al., "New challenges in therapeutic vaccines against HIV infection", Expert Review of Vaccines, vol. 16, No. 6, (2017), 587-600.

Lee, D.-H., et al., "H9N2 avian influenza virus-like particle vaccine provides protective immunity and a strategy for the differentiation of infected from vaccinated animals", Vaccine, vol. 29, (2011), 4003-4007.

Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.

Li, S., et al., "Influenza A Virus Transfectants with Chimeric Hemagglutinins Containing Epitopes from Different Subtypes", Journal of Virology, 66(1), (1992), 399-404.

Li, S., et al., "Recombinant Influenza A Virus Vaccines for the Pathogenic Human A/Hong Kong/97 (H5N1) Viruses", J Infect Dis., 179(5), (1999), 1132-1138.

Liu, C., et al., "Influenza type A virus neuraminidase does not play a role in viral entry, replication, assembly, or budding.", Journal of Virology, 69(2), (1995), 1099-1106.

Liu, C., et al., "Selection and Characterization of a Neuraminidase-Minus Mutant of Influenza Virus and its Rescue by Cloned Neuraminidase Genes", Virology, 194(1), (1993), 403-407.

Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.

Luytjes, W., "Amplification, Expression, and Packaging of a Foreign Gene by Influenza Virus", Cell, 59(6), (1989), 1107-1113.

Manicassamy, Balaji, et al., "Analysis of in vivo dynamics of influenza virus infection in mice using a GFP reporter virus", Proc Natl Acad Sci. USA, 107(25), (2010), 11531-11536.

Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.

Martin, J., et al., "Studies of the Binding Properties of Influenza Hemagglutinin Receptor-Site Mutants", Virology, 241(1), (Feb. 1, 1998), 101-111.

Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.

Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.

Matta, M, et al., "Cell-surface sialoglycoconjugate structures in wild-type and mutant Crithidia fasciculata", Parasitol. Res., 85(4), (1999), 293-299.

Mishin, V. P, et al., "Protection afforded by intranasal immunization with the neuraminidase-lacking mutant of influenza A virus in a ferret model", Vaccine, 23(22), (Apr. 22, 2005), 2922-7.

Mitnaul, L. J., et al., "Balanced Hemagglutinin and Neuraminidase Activities are Critical for Efficient Replication of Influenza A Virus", Journal of Virology, 74 (13), (2000), 6015-6020.

Muramoto, Y., et al., "Hierarchy among Viral RNA (vRNA) Segments in Their Role in vRNA Incorporation into Influenza A Virions", J. Virol., 80(5), (2006), 2318-2325.

Muramoto, Yukiko, "Hierarchy among Viral RNA (vRNA) Segments in Their Role in vRNA Incorporation into Influenza A Virions", Journal of Virology, 80(5), (2006), 2318-2325.

Murphy, B. R, et al., "An influenza A live attenuated reassortant virus possessing three temperature-sensitive mutations in the PB2 polymerase gene rapidly loses temperature sensitivity following replication in hamsters", Vaccine, 15(12-13), (Aug.-Sep. 1997), 1372-8.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Neumann, G., et al., "Generation of influenza A viruses entirely from cloned cDNAs", Proc. Natl. Acad. Sci. USA., 96(16), (1999), 9345-9350.

Neumann, G., et al., "Influenza A virus NS2 protein mediates vRNP nuclear export through NES-independent interaction with hCRM1", The EMBO Journal, 19 (24), (2000), 6751-6758.

Neumann, G., et al., "Mutational analysis of influenza virus promoter elements in vivo", Journal of General Virology, 76, (1995), 1709-1717.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Neumann, G., et al., "Reverse genetics of influenza virus.", Virology, 287(2), (Sep. 1, 2001), 243-50.

Neumann, G., et al., "Reverse Genetics of Influenza Viruses—Applications in Research and Vaccine Design", Monographs in Virology, 27, (2008), 118-133.

Neumann, Gabriele, "Minireview Reverse Genetics of Influenza Virus", Virology, vol. 287, (2001), 243-250.

Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.

Ozawa, M., et al., "Replication-incompetent influenza A viruses that stably express a foreign gene", Journal of General Virology, 92(Part 12)., (2011), 2879-2888.

Pattnaik, A. K., et al., "The Termini of VSV DI Particle RNAs are Sufficient to Signal RNA Encapsidation, Replication, and Budding to Generate Infectious Particles", Virology, 206, (1995), 760-764.

Piatti, G., "Identification of immunodominant epitopes In the filamentous Hemagglutinin of Bordetella pertusis", FEMS Immunology and Medical Microbiology, 23(3), (1999), 235-241.

Portela, A., et al., "Replication of orthomyxoviruses", Advances in Virus Research, 54, (1999), 319-348.

Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.

Rayner, J., et al., "Alphavirus vectors and vaccination", Reviews in Medical Virology, 12, (2002), 279-296.

Restifo, N. P., et al., "Transfectant Influenza A Viruses are Effective Recombinant Immunogens in the Treatment of Experimental Cancer", Virology, 249(1), (1998), 89-97.

Rimmelzwaan, G. F., et al., "Use of GFP-expressing influenza viruses for the detection of influenza virus A/H5N1 neutralizing antibodies", Vaccine, 29(18), (2011), 3424-3430.

Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.

(56) References Cited

OTHER PUBLICATIONS

Schultz-Cherry, S., et al., "Influenza Virus NS1 Protein Induces Apoptosis in Cultured Cells", Journal of Virology, 75(17), (2001), 7875-7881.
Shengqiang, Li, et al., "Influenza A Virus Transfectants with Chimeric Hemagglutinins containing Epitopes from different subtypes", Journal of Virology, (1992), 399-404.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Stray, S. J., et al., "Influenza virus infection of desialylated cells", Glycobiology, 10(7), (2000), 649-658.
Strobel, I., et al., "Efficient Expression Of The Tumor-Associated Antigen MAGE-3 In Human Dendritic Cells, Using An Avian Influenza Virus Vector", Human Gene Therapy, 11(16), (2000), 2207-2218.
Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.
Terry, G., et al., "The Contruction of Defective Interfering Rubella Virus Particles", Archives of Virology, 145(3), (2000), 625-633.
Thompson, Christine M, et al., "Critical assessment of influenza VLP production in Sf9 and HEK293 expression systems", BMC Biotechnology, 15(1), (May 16, 2015), 12 pgs.
Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisonsin—Mad, (Feb. 1, 2012), 7.
Victor, Sylvia, et al., "A Replication-Incompetent PB2-Knockout Influenza A Virus Vaccine Vector", Journal of Virology, vol. 86, No. 8, (Apr. 2012), 4123-4128.
Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.
Watanabe, S., et al., "Influenza A Virus Lacking M2 Protein as a Live Attenuated Vaccine", Journal of Virology, 83(11), (2009), 5947-5950.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Yang, P., et al., "Hemagglutinin Specificity and Neuraminidase Coding Capacity of Meuraminidase-Deficient Influenza Viruses", Virology, 229(1), (1997), 155-165.
Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.
Zhao, Lili, et al., "New Insights into the Nonconserved Noncoding Region of the Subtype-Determinant Hemagglutinin and Neuraminidase Segments of Influenza A aViruses", Journal of Virology, 88(19), (Oct. 2014), 11493-11503.
Zhou, Yan, "Membrane-Anchored Incorporation of a Foreign Protein in Recombinant Influenza Virions", Virology 246(1), (1998), 83-94.
U.S. Appl. No. 10/366,630 U.S. Pat. No. 7,226,774, filed Feb. 12, 2003, Signal for Packaging of Influenza Virus Vectors.
U.S. Appl. No. 11/509,249 U.S. Pat. No. 7,585,657, filed Aug. 24, 2006, Signal for Packaging of Influenza Virus Vectors.
U.S. Appl. No. 12/470,287 U.S. Pat. No. 8,298,805, filed May 21, 2009, Signal for Packaging of Influenza Virus Vectors.
U.S. Appl. No. 12/113,690 U.S. Pat. No. 8,597,661, filed May 1, 2008, Neuraminidase-Deficient Live Influenza Vaccines.
U.S. Appl. No. 13/594,611 U.S. Pat. No. 9,101,653, filed Aug. 24, 2012, Influenza Viruses With Mutant PB2 Gene Segment as Live Attenuated Vaccines.
U.S. Appl. No. 14/699,213 U.S. Pat. No. 10,513,692, filed Apr. 29, 2015, Influenza Viruses With Mutant PB2 Segment as Live Attenuated Vaccines.
U.S. Appl. No. 16/694,748, filed Nov. 25, 2019, Influenza Viruses With Mutant PB2 Gene Segment as Live Attenuated Vaccines.
U.S. Appl. No. 15/247,006 U.S. Pat. No. 10,494,613, filed Aug. 25, 2016, Generation of Infectious Influenza Viruses From Virus-Like Particles.
U.S. Appl. No. 16/547,262 U.S. Pat. No. 11,180,737, filed Aug. 21, 2019, Generation of Infections Influenza Viruses From Virus-Like Particles.
"U.S. Appl. No. 17/212,836, Response filed Aug. 22, 2023 to Final Office Action mailed Jun. 22, 2023", 7 pgs.
"U.S. Appl. No. 17/212,836, Advisory Action mailed Aug. 29, 2023", 3 pgs.
"International Application Serial No. PCT US2023 063136, International Search Report mailed Sep. 8, 2023", 6 pgs.
"International Application Serial No. PCT US2023 063136, Written Opinion mailed Sep. 8, 2023", 7 pgs.
"U.S. Appl. No. 16/785,449, Corrected Notice of Allowability mailed Sep. 11, 2023", 10 pgs.
"International Application Serial No. PCT US2023 027622, International Search Report mailed Nov. 7, 2023", 5 pgs.
"International Application Serial No. PCT US2023 027622, Written Opinion mailed Nov. 7, 2023", 6 pgs.
"U.S. Appl. No. 16/785,449, Corrected Notice of Allowability mailed Nov. 8, 2023", 10 pgs.
"U.S. Appl. No. 16/785,449, Corrected Notice of Allowability mailed Nov. 17, 2023", 10 pgs.
Liu, Shufeng, "Stable Cell Clones Harboring Self-Replicating SARS-CoV-2 RNAs for Drug Screen", Journal of Virology, vol. 96, No. 6, [Online] Retrieved from the internet:https: www.ncbi.nlm.nih.gov pmc articles PMC8941906 pdf jvi.02216-21.pdf, (Mar. 23, 2022), 13 pgs.
Netland, Jason, "Immunization with an attenuated severe acute respiratory syndrome coronavirus deleted in E protein protects against lethal respiratory disease", Virolog, vol. 399, No. 1, (Jan. 27, 2010), 9 pgs.
Zhang, Xianwen, "A trans-complementation system for SARS-CoV-2 recapitulates authentic viral replication without virulence", Cell, Elsevier, Amsterdam NL, vol. 184, No. 8, (Feb. 23, 2021), 24 pgs.
"U.S. Appl. No. 17/004,583, Notice of Allowance mailed May 15, 2023", 7 pgs.
"U.S. Appl. No. 17/212,836, Response filed May 16, 2023 to Non Final Office Action mailed Feb. 16, 2023", 7 pgs.
"U.S. Appl. No. 16/785,449, Response filed May 22, 2023 to Final Office Action mailed Mar. 22, 2023", 9 pgs.
"U.S. Appl. No. 16/785,449, Advisory Action mailed Jun. 7, 2023", 17 pgs.
"U.S. Appl. No. 17/212,836, Final Office Action mailed Jun. 22, 2023", 15 pgs.
"U.S. Appl. No. 18/173,535, Preliminary Amendment filed Jun. 26, 2023", 16 pgs.
"U.S. Appl. No. 16/785,449, Response filed Jul. 13, 2023 to Advisory Action mailed Jun. 7, 2023", 12 pgs.
"U.S. Appl. No. 17/004,583, Notice of Allowability mailed Aug. 1, 2023", 2 pgs.
"U.S. Appl. No. 18/365,082, Preliminary Amendment filed Aug. 3, 2023", 4 pgs.
"U.S. Appl. No. 16/785,449, Notice of Allowance mailed Aug. 7, 2023", 14 pgs.
Abdoli, Mohsen, "Intranasal administration of cold-adapted live-attenuated SARS-CoV-2 candidate vaccine confers protection against SARS-CoV-2", Virus Research 319 198857, (2022), 10 pgs.

(56) References Cited

OTHER PUBLICATIONS

Faizuloev, Evgeny, "Cold-adapted SARS-CoV-2 variants with different sensitivity exhibit an attenuated phenotype and confer protective immunity", Science Direct Vaccine 41 892-902, (2023), 12 pgs.
Lu, Shan, "The SARS-CoV-2 nucleocapsid phosphoprotein forms mutually exclusive condensates with RNA and the membrane-associated M protein", nature communications 12:502, (2021), 15 pgs.
Plescia, Caroline B, "SARS-CoV-2 viral budding and entry can be modeled using BSL-2 level virus-like particles", JBC Research Article, (Nov. 19, 2020), 10 pgs.
Seo, Sang Heui, "Cold-Adapted Live Attenuated SARS-CoV-2 Vaccine Completely Protects Human ACE2 Transgenic Mice from SARS-Cov-2 Infection", Vaccines Aug. 2020, 584, (Oct. 3, 2020), 17 pgs.
Swann, Heather, "Minimal system for assembly of SARS CoV 2 virus like particles", Scientific Reports 10:21877 nature portfolio, (2020), 1-5.
Zhang, Zhikuan, "Structure of SARS-CoV-2 membrane protein essential for virus assembly", nature communications 13:4399, (Aug. 5, 2022), 12 pgs.
"U.S. Appl. No. 14/528,997, Preliminary Amendment filed Dec. 8, 2014", 3 pgs.
"U.S. Appl. No. 14/919,431, Restriction Requirement mailed Feb. 3, 2016", 18 pgs.
"Australian Application Serial No. 2004249133, Response filed Mar. 30, 2009 to First Examiner's Report mailed May 5, 2008", 30 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Response filed Jul. 4, 2016 to Subsequent Examiners Report mailed Feb. 1, 2016", 3 pgs.
"Australian Application Serial No. 2014202470, Response filed Jul. 20, 2016 to Subsequent Examiners Report mailed Jul. 19, 2016", 15 pgs.
"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb. 1, 2016", 2 pgs.
"Australian Application Serial No. 2014202470, Subsequent Examiners Report mailed Jul. 19, 2016", 3 pgs.
"Brazilian Application Serial No. PI0410702-0, Office Action mailed Feb. 23, 2012", w/ English Translation, 4 pgs.
"Brazilian Application Serial No. PI0410702-0, Response filed May 7, 2012 to Office Action mailed Feb. 23, 2012", w/ English Claims, 11 pgs.
"Canadian Application Serial No. 2,406,180, Office Action mailed Nov. 10, 2011", 3 pgs.
"Canadian Application Serial No. 2,406,180, Office Action mailed Nov. 23, 2009", 3 pgs.
"Canadian Application Serial No. 2,406,180, Office Action mailed Dec. 10, 2010", 2 Pgs.
"Canadian Application Serial No. 2,406,180, Response filed May 7, 2012 to Office Action mailed Nov. 10, 2011", 11 pgs.
"Canadian Application Serial No. 2,406,180, Response filed May 21, 2010 to Office action mailed Nov. 23, 2009", 13 pgs.
"Canadian Application Serial No. 2,406,180, Response filed Jun. 14, 2011 to Office Action mailed Dec. 10, 2010", 10 pgs.
"Canadian Application Serial No. 2,406,180, Response mailed Jun. 10, 2011 to Office Action mailed Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action mailed Jun. 6, 2011", 2 pgs.
"Canadian Application Serial No. 2,522,081, Office Action mailed Aug. 30, 2010", 2 pgs.
"Canadian Application Serial No. 2,522,081, Office Action mailed Oct. 8, 2009", 6 pgs.
"Canadian Application Serial No. 2,522,081, Response filed Feb. 28, 2011 to Office Action mailed Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action mailed Jun. 6, 2011", 11 pgs.
"Canadian Application Serial No. 2,525,953, Amendment and Response filed Feb. 1, 2017 to Office Action mailed Aug. 1, 2016", 28 pgs.
"Canadian Application Serial No. 2,525,953, Office Action mailed Jan. 21, 2016", 6 pgs.
"Canadian Application Serial No. 2,525,953, Office Action mailed Jul. 31, 2012", 4 pgs.
"Canadian Application Serial No. 2,525,953, Office Action mailed Aug. 1, 2016", 6 pgs.
"Canadian Application Serial No. 2,525,953, Office Action mailed Aug. 16, 2013", 3 pgs.
"Canadian Application Serial No. 2,525,953, Office Action mailed Nov. 6, 2014", 3 pgs.
"Canadian Application Serial No. 2,525,953, Office Action mailed Jun. 22, 2011", 4 pgs.
"Canadian Application Serial No. 2,525,953, Response filed Jan. 31, 2013 to Office Action mailed Jul. 31, 2012", 11 pgs.
"Canadian Application Serial No. 2,525,953, Response filed Feb. 1, 2017 to Office Action mailed Aug. 1, 2016", 28 pgs.
"Canadian Application Serial No. 2,525,953, Response filed Feb. 14, 2014 to Office Action mailed Aug. 2016, 13", 16 pgs.
"Canadian Application Serial No. 2,525,953, Response filed May 1, 2015 to Office Action mailed Nov. 6, 2014", 23 pgs.
"Canadian Application Serial No. 2,525,953, Response filed Jul. 11, 2016 to Office Action mailed Jan. 21, 2016", 21 pgs.
"Canadian Application Serial No. 2,525,953, Response filed Dec. 22, 2011 to Office Action mailed Jun. 22, 2011", 17 pgs.
"Canadian Application Serial No. 2,647,985 , Response filed Sep. 30, 2013 to Office Action mailed May 15, 2013", 20 pgs.
"Canadian Application Serial No. 2,647,985, Office Action mailed May 15, 2013", 3 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton mailed May 6, 2010", (w/ English Translation of Claims), 26 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Reexamination Decision mailed Mar. 25, 2013", (w/ English Translation), 17 pgs.

(56) References Cited

OTHER PUBLICATIONS

"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200580046922.5, Office Action mailed Jul. 24, 2009", 12 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.
"Chinese Application Serial No. 200780020095.1, Office Action mailed Apr. 26, 2016", (w/ English Summary), 4 pgs.
"Chinese Application Serial No. 200780020095.1, Office Action mailed May 3, 2012", (w/ English Translation), 10 pgs.
"Chinese Application Serial No. 200780020095.1, Office Action mailed Nov. 2, 2016", (w/ English Translation), 11 pgs.
"Chinese Application Serial No. 200780020095.1, Response filed Jan. 6, 2017 to Office Action mailed Nov. 2, 2016", (w/ English Translation of Claims), 15 pgs.
"Chinese Application Serial No. 200780020095.1, Response filed Jun. 9, 2013 to Office Action mailed Jan. 29, 2013", (w/ English Translation of Claims), 10 pgs.
"Chinese Application Serial No. 200780020095.1, Response filed Jun. 23, 2015 to Office Action mailed Mar. 5, 2015", (w/ English Translation of Claims), 16 pgs.
"Chinese Application Serial No. 200780020095.1, Response filed Jun. 30, 2016 to Office Action mailed Apr. 26, 2016", (w/ English Translation of Claims), 22 pgs.
"Chinese Application Serial No. 200780020095.1, Response filed Sep. 17, 2012 to Office Action mailed May 3, 2012", (w/ English Translation of Claims), 17 pgs.
"Chinese Application Serial No. 200780020095.1, Response filed Nov. 5, 2013 to to Decision on Rejection mailed Jul. 22, 2013", (w/ English Translation of Claims), 12 pgs.
"Chinese Application Serial No. 200780020095.1, Response filed Nov. 8, 2011 to Office Action mailed Jun. 24, 2011", (w/ English Translation of Amended Claims), 20 pgs.
"Chinese Application Serial No. 200480021259.9, Office Action mailed May 8, 2009", (w/ English Translation), 6 pgs.
"Eurasian Application No. 200501890, Notice of Allowance mailed Jun. 23, 2009", 1 pg.
"Eurasion Application Serial No. 200701097, Office Action mailed Jun. 16, 2009", 3 pgs.
"European Application Serial No. 01928486.8 Office Action mailed Oct. 1, 2009", 2 pgs.
"European Application Serial No. 01928486.8, Response filed Aug. 28, 2009 to Communication mailed Feb. 19, 2009", 5 pgs.
"European Application Serial No. 01928486.8, Response filed Dec. 9, 2009 to Office Action mailed Oct. 1, 2009", 11 pgs.
"European Application Serial No. 04750333.9, Response filed Nov. 17, 2009 to Communication mailed Jan. 22, 2009", 17 pgs.
"European Application Serial No. 04750333.9, Summons To Attend Oral Proceedings mailed Aug. 3, 2011", 13 pgs.
"European Application Serial No. 04776133.3, Examination Notification Art. 94(3) mailed Jul. 28, 2015", 4 pgs.
"European Application Serial No. 04776133.3, Examination Notification Art. 94(3) mailed Nov. 25, 2013", 5 pgs.
"European Application Serial No. 04776133.3, Office Action mailed Jan. 5, 2010", 4 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Jul. 15, 2010 to Office Action mailed Jan. 5, 2010", 9 pgs.
"European Application Serial No. 04776133.3, Response filed Sep. 18, 2015 to Examination Notification Art. 94(3) mailed Jul. 28, 2015", 47 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"European Application Serial No. 10777154.5, Examination Notification Art. 94(3) mailed Oct. 6, 2014", 7 pgs.
"European Application Serial No. 10777154.5, Office Action mailed May 2, 2016", 6 pgs.
"European Application Serial No. 10777154.5, Office Action mailed Jul. 4, 2012", 2 pgs.
"European Application Serial No. 10777154.5, Response filed Jan. 14, 2013 to Office Action mailed Jul. 4, 2012", 12 pgs.
"European Application Serial No. 10777154.5, Response filed Sep. 8, 2016 to Office Action mailed May 2, 2016", 69 pgs.
"European Application Serial No. 14745060.5, Office Action mailed Feb. 23, 2016", 2 pgs.
"European Application Serial No. 14745060.5, Response filed Dec. 22, 2016 to Communication pursuant to Rules 161(1) and 162 EPC mailed Feb. 23, 2016", 6 pgs.
"Evaluation of Medicines for human Use", EMEA/CPMP/BWP/2289/01, London The European Agency for the Evaluation of Medicinal Products, Committee for Proprietary Medicinal Products (CPMP), (Feb. 20, 2003), 14.
"Fluzone Influenza Virus Vaccine", Sanofi Aventis Pasteur, Swiftwater, (Jul. 2005), 12 pgs.
"Genbank", CY002484.1, (2005), 2 pgs.
"Genbank Accession # AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"Hemagglutinin [Influenza A virus (A/swine/France/WVL13/1995(H1N1)]", GenBank Accession# AC025026, (May 22, 2009), 1 pg.
"Hemagglutinin [Influenza B virus (B/Hong Kong/330/2001)]", GenBank ABL77178.1, (2006), 1 pg.
"Indian Application Serial No. 1026/KOLNP/2009, First Examiner Report mailed Mar. 13, 2014" 2 pgs.
"Indian Application Serial No. 2272/KOLNP/2005, Response filed Mar. 16, 2009 to Subsequent Examination Report mailed Mar. 6, 2009", 12 pgs.
"International Application Serial No. PCT/US2008/007582, International Preliminary Report on Patentability mailed Jan. 7, 2010", 9 pgs.
"International Application Serial No. PCT/US2009/000056, International Search Report mailed Feb. 9, 2010", 3 pgs.
"International Application Serial No. PCT/US2009/000056, Written Opinion mailed Feb. 9, 2010", 5 pgs.
"International Application Serial No. PCT/US2009/006019, International Preliminary Report on Patentability mailed May 19, 2011", 8 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 7 Pgs.

(56) References Cited

OTHER PUBLICATIONS

"International Application Serial No. PCT/US2009/006019, Written Opinion mailed Jun. 10, 2010", 6 pgs.
"International Application Serial No. PCT/US2010/054128, Preliminary Report on Patentability mailed May 10, 2012", 10 pgs.
"International Application Serial No. PCT/US2010/054128, Search Report mailed Feb. 23, 2011", 6 pgs.
"International Application Serial No. PCT/US2010/054128, Written Opinion mailed Feb. 23, 2011", 8 pgs.
"International Application Serial No. PCT/US2014/046731, International Preliminary Report on Patentability mailed Jan. 28, 2016", 12 pgs.
"International Application Serial No. PCT/US2014/046731, International Search Report mailed Nov. 25, 2014", 9 pgs.
"International Application Serial No. PCT/US2014/046731, Written Opinion mailed Nov. 25, 2014", 10 pgs.
"International Application Serial No. PCT/US2015/036803, International Preliminary Report on Patentability mailed Dec. 29, 2016", 10 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"Israeli Application Serial No. 171372, Office Action mailed Feb. 21, 2010", w/English Translation, 2 pgs.
"Israeli Application Serial No. 171372, Response filed Nov. 18, 2010 to Office Action mailed Feb. 21, 2010", w/English Translation, 19 pgs.
"Israeli Application Serial No. 171831, Office Action mailed Feb. 21, 2010", w/English Translation, 2 pgs.
"Israeli Application Serial No. 171831, Office Action mailed Apr. 18, 2012", (English Translation), 2 pgs.
"Israeli Application Serial No. 171831, Response filed Jan. 20, 2011 to Office Action mailed Feb. 21, 2010", w/English Translation, 18 pgs.
"Israeli Application Serial No. 171831, Response filed Jun. 24, 2009 to Notification of Defects mailed Nov. 10, 2008", w/English Claims, 10 pgs.
"Israeli Application Serial No. 171831, Response filed Nov. 6, 2012 to Office Action mailed Apr. 18, 2012", w/English Claims, 54 pgs.
"Israeli Application Serial No. 238584, Office Action mailed Apr. 14, 2016", (English Translation), 3 pgs.
"Israeli Application Serial No. 238584, Response filed Aug. 3, 2016 to Office Action mailed Apr. 14, 2016", (English Translation of Claims), 19 pgs.
"Israeli Application Serial No. 171372,Office Action mailed Feb. 20, 2011", (Translation), 2 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2001-576868, Office Action mailed Nov. 2, 2010", w/ English Translation), 10 pgs.
"Japanese Application Serial No. 2001-576868, Response filed Dec. 1, 2011 to Office Action mailed May 3, 2011", (w/ English Translation of Amended Claims), 37 pgs.
"Japanese Application Serial No. 2006-513125, Office Action mailed Mar. 9, 2010", (English Translation), 11 pgs.
"Japanese Application Serial No. 2006-513125, Response filed Aug. 30, 2010 to Office Action mailed Mar. 9, 2010", (w/ English Translation of Amended Claims), 60 pgs.
"Japanese Application Serial No. 2006-533439, Decision of Final Rejection mailed Aug. 14, 2012", (w/ English Translation), 5 pgs.
"Japanese Application Serial No. 2006-533439, Office Action mailed Mar. 9, 2010", (w/ English Translations), 20 pgs.
"Japanese Application Serial No. 2006-533439, Office Action mailed Mar. 27, 2012", w/ English Translation, 8 pgs.
"Japanese Application Serial No. 2006-533439, Response filed May 21, 2012 to Office Action mailed Mar. 27, 2012", (w/ English Translation of Amended Claims), 19 pgs.
"Japanese Application Serial No. 2006-533439, Response filed Aug. 3, 2011 to Office Action mailed Feb. 15, 2011", (w/ English Translation of Amended Claims), 18 pgs.
"Japanese Application Serial No. 2006-533439, Office Action mailed Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2009-502945, Examiners Decision of Final Refusal mailed Nov. 12, 2013", (w/ English Translation), 8 pgs.
"Japanese Application Serial No. 2009-502945, Office Action mailed Oct. 23, 2012", (w/ English Translation), 16 pgs.
"Japanese Application Serial No. 2009-502945, Response filed Apr. 10, 2013 to Office Action mailed Oct. 23, 2012", (w/ English Translation of Claims), 18 pgs.
"Japanese Application Serial No. 2011-111048, Office Action mailed Jun. 25, 2013", (w/ English Translation), 7 pgs.
"Japanese Application Serial No. 2011-111048, Office Action mailed Sep. 18, 2012", (w/ English Translation), 10 pga.
"Japanese Application Serial No. 2011-111048, Response filed Sep. 25, 2012 to Office Action mailed Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action mailed Jun. 10, 2014", (w/ English Translation), 7 pgs.
"Japanese Application Serial No. 2012-273898, Response filed Sep. 4, 2014 to Office Action mailed Jun. 10, 2014", W/ English Claims, 9 pgs.
"Japanese Application Serial No. 2012-536963, Amendment and Argument filed Jun. 26, 2015 to Office Action mailed Jan. 6, 2015", (w/ English Translation of Amended Claims), 12 pgs.
"Japanese Application Serial No. 2012-536963, Examiners Decision of Final Refusal mailed Nov. 17, 2015", (w/ English Translation), 8 pgs.
"Japanese Application Serial No. 2012-536963, Office Action mailed Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action mailed Jan. 6, 2015", (w/ English Translation), 9 pgs.
"Japanese Application Serial No. 2014-049025 Response filed Sep. 4, 2015 to Office Action mailed Jun. 16, 2015", (w/ Amended Claims), 12 pgs.
"Japanese Application Serial No. 2014-049025, Examiners Decision of Final Refusal mailed Feb. 2, 2016", W/ English Translation, 5 pgs.
"Japanese Application Serial No. 2014-049025, Office Action mailed Jun. 16, 2015", (w/ English Translation), 6 pgs.
"Japanese Application Serial No. 2006-513125,Final Office Action mailed Jan. 18, 2011", (English Translation), 4 pgs.
"Mexican Application No. PA/a/2005/012712 Office Action mailed Jul. 21, 2009", (w/ English Translation), 9 pgs.
"Mexican Application Serial No. MX/a/2009/006341, Office Action mailed Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action mailed May 19, 2015", (w/ English Translation of Claims), 21 pgs.
"Mexican Application Serial No. MX/a/2012/009249, Office Action mailed Feb. 5, 2016", W/ English Claims, 2 pgs.

(56) References Cited

OTHER PUBLICATIONS

"Mexican Application Serial No. MX/a/2012/009249, Office Action mailed May 19, 2015", (English Translation), 1 pg.
"Mexican Application Serial No. MX/a/2012/009249, Response filed Mar. 29, 2016 to Office Action mailed Feb. 5, 2016", (English Translation of Claims), 18 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", (w/ English Translation of Claims), 14 pgs.
"Mexican Application Serial No. PA/a/2005/012712 , Office Action Mailed Aug. 11, 2009", (English Translation), 5 pgs.
"Mexican Application Serial No. PA/a/2005/012712 , Response filed Sep. 28, 2009 to Office Action Mailed Jul. 21, 2009", (w/ English Translation of Claims), 24 pgs.
"Mexican Application Serial No. PA/a/2005/012712, Office Action mailed May 12, 2010", (w/ English Translation), 19 pgs.
"Mexican Application Serial No. PA/a/2005/012712, Office Action mailed Jun. 9, 2010", (w/ English Translation), 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Response filed Feb. 3, 2010 to Office Action mailed Nov. 30, 2009", (w/ English Translation of Amended Claims), 22 pgs.
"Mexican Application Serial No. PA/a/2005/012712, Response filed Sep. 27, 2010 to Office Action mailed May 12, 2010", (w/ English Translation of Claims), 19 pgs.
"Mexico Application Serial No. PA/a/2005/012712, Response filed Jun. 12, 2009 to Official Action mailed Mar. 5, 2009", (w/ English Translation of Claims), 11 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 555245, Subsequent Examiner Report mailed Jul. 3, 2009" 1 pg.
"Nonstructural protein 1 [influenza B virus (B/Hong Kong/330/2001)]", GenBank AAT69443.1, (2006), 1 pg.
"Norway Application Serial No. 20056074, Office Action mailed Jan. 17, 2017", (English Translation), 5 pgs.
"Norway Application Serial No. 20056074, Office Action mailed Apr. 25, 2017", (w English Translation), 3 pgs.
"Norway Application Serial No. 20056074, Office Action Response mailed 04-1817", W/ English Claims, 27 Pgs.
"Norweigan Application Serial No. 20056074, Office Action mailed Apr. 25, 2017", (Translation), 3 pgs.
"Polymerase acidic [influenza A virus (A/swine/Shizuoka/120/97(H3N2))]", GenBank AAO15329.1, (2003), 1 pg.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"The Influenza Virus: Structure and Replication", Rapid Reference to Influenza. Elsevier Ltd, [Online]. Retrieved from the Internet: http://www.rapidreferenceinfluenza.com/chapter/B978-0-7234-3433-7.50009-8/aim/influenza-virus-structure, (2006), 6 pgs.
"Ukrainese Application Serial No. 200512619, Response filed Jan. 21, 2010 to Office Action mailed Jun. 17, 2009", W/ English Claims, 14 pgs.
"Ukrainian Application Serial No. 200512619, Office Action mailed Jun. 17, 2009", (w/ English Translation), 4 pgs.
"Ukrainian Application Serial No. 200512619, Response filed Apr. 8, 2009 to Office Action mailed Feb. 27, 2009", (w/ English Translation of Claims), 9 pgs.

Abram, M. E, et al., "Nature, position, and frequency of mutations made in a single cycle of HIV-1 replication", J Virol., 84(19), (Oct. 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.
Akarsu, H., et al., "Crystal structure of the M1 protein-binding domain of the influenza A virus nuclear export protein (NEP/NS2).", EMBO J., 22(18), (Sep. 15, 2003), 4646-55.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for segment-nonspecific packaging of the influenza a virus genome", J Virol., 76(14), (Jul. 2002), 7133-9.
Bedford, M. T, et al., "FBP WW domains and the Abl SH3 domain bind to a specific class of proline-rich ligands", EMBO J., 16(9), (May 1, 1997), 2376-83.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(4948) 1306-1310, (1990), 5 pgs.
Brassard, D.L., et al., "Influenza B virus NB glycoprotein is a component of the virion", Virol., 220(2), No Document, (1996), 350-360.
Brooke, C B, "Biological activities of 'noninfectious' influenza A virus particles", Future Virol 9(1) 41-51, (Jan. 2014), 16 pgs.
Brown, E. G., et al., "Genetic analysis of mouse-adapted influenza A virus identifies roles for the NA, PB1, and PB2 genes in virulence", Virus Research, 61(1), (May 1999), 63-76.
Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.
Burmeister, W. P., et al., "The 2.2 A resolution crystal structure of influenza B neuraminidase and its complex with sialic acid", The EMBO Journal, 11(1), (1992), 49-56.
Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chang, M. W., et al., "Analysis of HIV Wild-Type and Mutant Structures via in Silico Docking against Diverse Ligand Libraries", J. Chem. Inf. Model., 47(3), (2007), 1258-1262.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.

(56) References Cited

OTHER PUBLICATIONS

Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.
Daddario-DiCaprio, K. M, et al., "Cross-protection against Marburg virus strains by using a live, attenuated recombinant vaccine", J Virol., 80(19), (Oct. 2006), 9659-66.
De Filette, Marina, et al., "An influenza A vaccine based on tetrameric ectodomain of matrix protein 2", J Biol Chem. 2008 ; 283 (17):, (Feb. 5, 2008), 11382-7.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Enterlein, S., et al., "Untersuchungen zur Replikation und Transkription von Marburgund Ebolavirus", [Online]. 2005, Philipps-Universitat Marburg, XP002563470, Retrieved from the Internet: <URL:http://deposit.ddb.de/cgi-bin/dokserv?>idn=977005607&dok_var=d1&dok_ext=pdf&filename=977005607.pdf> [retrieved on Jan. 15, 2010], (2005), p. 70-p. 84.
Fan, J, et al., "Preclinical study of influenza virus A M2 peptide conjugate vaccines in mice, ferrets, and rhesus monkeys", Vaccine, 22, (2004), 2993-3003.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fujii, Ken, et al., "Importance of both the Coding and the Segment-Speci?c Noncoding Regions of the In?uenza A Virus NS Segment for Its Ef?cient", Journal of Virology, 79(6). (Mar. 2005), 3766-3774.
Gao, Qinshan, et al., "A Nine-Segment In?uenza A Virus Carrying Subtype H1 and H3 Hemagglutinins", Journal of Virology, 84(16), (Aug. 2010), 8062-8071.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Genbank, "", ABD36884.1, (2007), 2 pgs.
Gotea, V, et al., "The functional relevance of somatic synonymous mutations in melanoma and other cancers", Pigment Cell & Melanoma Research, 28 issue 6, (Nov. 1, 2015), 673-686.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.

Hai, Rong, et al., "Influenza B Virus NS1-Truncated Mutants: Live-Attenuated Vaccine Approach", Journal of Virology, 82(21), (2008), 10580-10590.
Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.
Harvey, K. F, et al., "All three WW domains of murine Nedd4 are involved in the regulation of epithelial sodium channels by intracellular Na+,", J Biol Chem., 274(18), (Apr. 30, 1999), 12525-30.
Hickman, Danielle, et al., "An avian live attenuated master backbone for potential use in epidemic and pandemic influenza vaccines", Journal of General Virology, 89(Part 11), (2008), 2682-2690.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR .(Suppl 1), XP002574255 ISSN: 0022-1899 abstract, (Feb. 1999), 240-247.
Hurt, A. C, et al., "Identification of a human influenza type B strain with reduced sensitivity to neuraminidase inhibitor drugs", Virus Research, vol. (103), (2004), 205-211.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, et al., "Characterization of recombinant influenza B viruses with key neuraminidase inhibitor resistance mutations,", Journal of Antimicrobial Chemotherapy, vol. (55), (2005), 162-169.
Jang, S.-W., et al., "Deoxygedunin, a Natural Product with Potent Neurotrophic Activity in Mice", PLoS One 5(7): e11528, (2010). 1-15.
Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.
Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.
Kawaoka, Y, et al., "Sequence requirements for cleavage activation of influenza virus hemagglutinin expressed in mammalian cells", Proc Natl Acad Sci., 85(2), (1988), 324-328.
Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/girce/docs/2007/Kawaoka.pdf> [retrieved on Jan. 13, 2010] p. 10, under item C,—& Anonymous: "Index of GLRCE: documents from 2007" Great Lakes Regional Center of Excellence Index, [Online] 2007, XP002563469 Retrieved from the Internet: URL:http://www.rcebiodefense.org/glrce/docs/2007/> [retrieved on Jan. 14, 2010]—& Kawaoka Y.: , (2007), pp. 1-19.
Kawaoka, Y., "Prevention and Control of Ebola Virus Infection (Ongoing Research)", Great Lakes Regional Center of Excellence (GLRCE) Annual Meeting Schedule, (Abstract), [online] [retrieved on Jan. 14, 2010]. Retrieved from the Internet: <URL:http://www.rcebiodefense.org/glrce/annualmeeting/2007Agenda.pdf>, (Nov. 29, 2007), 4 pgs.

(56) References Cited

OTHER PUBLICATIONS

Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.

Kistner, Otfried, et al., "Cell culture (Vero) derived whole virus (H5N1) vaccine based on wild-type virus strain induces cross-protective immune responses", Vaccine, 25(32), (2007), 6028-6036.

Kittel, Christian, et al., "Generation of an Influenza A Virus Vector Expressing Biologically Active Human Interleukin-2 from the NS Gene Segment", Journal of Virology, 79(16), (Aug. 2005), 10672-10677.
Konduru, K., et al., "Ebola virus glycoprotein Fc fusion protein confers protection against lethal challenge in vaccinated mice", Vaccine, 29(16), (Apr. 5, 2011), 2968-77.
Kopecky, S. A, et al., "Matrix protein and another viral component contribute to induction of apoptosis in cells infected with vesicular stomatitis virus", J Virol., 75(24), (Dec. 2001), Abstract Only.
Kovacova, A., et al., "Sequence similarities and evolutionary relationships of influenza virus A hemagglutinins.", Virus Genes, 24(1), (2002), 57-63.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wu, Rui, et al., "A live bivalent influenza vaccine based on a H9N2 virus strain", Vaccine, 28, (2010), 673-680.
Xu, X., et al., "Reassortment and evolution of current human influenza A and B viruses", Virus Research, 103, (2004), 55-60.
Yagi, Y., et al., "In silico panning for a non-competitive peptide inhibitor", BMC Bioinformatics, 8(11), (2007), 11 pgs.
Yang, Z. Y, et al., "Identification of the Ebola virus glycoprotein as the main viral determinant of vascular cell cytotoxicity and injury", Nat Med., 6(8), (Aug. 2000), Abstract Only.
Yannarell, Dean A., et al., "Factors affecting the yield of cold-adapted influenza virus vaccine", Journal of Virological Methods, vol. 64, 161-169, (1997), 1 pg.
Yi, Pu Lin, et al., "Adaptation of Egg-Grown and Transfectant Influenza Viruses for Growth in Mammalian Cells: Selection of Hemagglutinin Mutants with Elevated pH of Membrane (Fusion", Virology, 233(2), (Jul. 7, 1997), 402-410.
Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.
Zhang, V. Q, et al., "Easy two-step method for randomizing and cloning gene fragments", Methods Mol Biol., 634, (2010), Abstract Only.
"U.S. Appl. No. 17/212,836, Non Final Office Action mailed Jun. 13, 2024", 14 pgs.
"U.S. Appl. No. 18/525,460, Preliminary Amendment filed Jun. 7, 2024", 6 pgs.
"International Application Serial No. PCT/US2024/020952, International Search Report mailed Jul. 30, 2024", 3 pgs.
"International Application Serial No. PCT/US2024/020952, Written Opinion mailed Jul. 30, 2024", 5 pgs.
Aria, Yasuha, et al., "PB2 mutations arising during H9N2 influenza evolution in the Middle East confer enhanced replication and growth in mammals", PLoS Pathogens 15(7): e1007919. https://doi.org/10.1371/journal.ppat.1007919, (Jul. 2, 2019), 25 pages.
Fan, Haitian, et al., "Structures of influenza A virus RNA polymerase offer insight into viral genome replication", Nature 573, 287-290 (2019). https://doi.org/10.1038/s41586-019-1530-7, (Sep. 4, 2019), 35 pages.
Kamiki, Haruhiko, et al., "Novel Biological System with Terminal Sialic Acid Knockout Cells", J Virol 96:e00416-22. https://doi.org/10.1128/jvi.00416-22, (Jul. 18, 2022), 15 pages.
Klimov, A.I., et al., "Correlation of amino acid residues in the M1 and M2 proteins of influenza virus with high yielding properties", Virus Research, vol. 19, Issue 1, 1991, pp. 105-114, ISSN 0168-1702, https://doi.org/10.1016/0168-1702(91)90098-G. (https://www.sciencedirect.com/science/article/pii/016817029190098G), (Mar. 1991), 10 pages.
Ma, Wenjun, et al., "The NS Segment of an H5N1 Highly Pathogenic Avian Influenza Virus (HPAIV) Is Sufficient To Alter Replication Efficiency, Cell Tropism, and Host Range of an H7N1 HPAIV", J Virol. Feb. 2010;84(4):2122-33. doi: 10.1128/JVI.01668-09. Epub Dec. 9, 2009. PMID: 20007264; PMCID: PMC2812369., (Feb. 2010), 12 pages.
Mahesutihan, Madina, et al., "CypA Regulates AIP4-Mediated M1 Ubiquitination of Influenza A Virus", Virologica Sinica 33 (2018): 440-448., (Oct. 16, 2018), 9 pages.
"U.S. Appl. No. 17/212,836, Notice of Allowability mailed Feb. 7, 2025", 5 pgs.
"U.S. Appl. No. 17/212,836, Notice of Allowance mailed Jan. 2, 2025", 8 pgs.
"U.S. Appl. No. 17/212,836, Response filed Nov. 26, 2024 to Non Final Office Action mailed Jun. 13, 2024", 9 pgs.
"U.S. Appl. No. 18/365,082, Notice of Allowance mailed Feb. 4, 2025", 10 pgs.
"U.S. Appl. No. 18/365,082, Notice of Allowance mailed Mar. 20, 2025", 8 pgs.
"U.S. Appl. No. 18/365,082, Restriction Requirement mailed Oct. 24, 2024", 12 pgs.
"U.S. Appl. No. 18/461,321, Advisory Action mailed Mar. 27, 2025", 2 pgs.
"U.S. Appl. No. 18/461,321, Final Office Action mailed Mar. 6, 2025", 8 pgs.
"U.S. Appl. No. 18/461,321, Non Final Office Action mailed Nov. 14, 2024", 6 pgs.
"U.S. Appl. No. 18/461,321, Response filed Jan. 7, 2025 to Non Final Office Action mailed Nov. 14, 2024", 6 pgs.
"U.S. Appl. No. 18/461,321, Response filed Mar. 19, 2025 to Final Office Action mailed Mar. 6, 2025", 6 pgs.
"U.S. Appl. No. 18/525,460, Corrected Notice of Allowability mailed Feb. 26, 2025", 7 pgs.
"U.S. Appl. No. 18/525,460, Notice of Allowance mailed Oct. 23, 2024", 11 pgs.
"International Application Serial No. PCT/US2023/027622, International Preliminary Report on Patentability mailed Jan. 23, 2025", 8 pgs.
"International Application Serial No. PCT/US2023/063136, International Preliminary Report on Patentability mailed Sep. 6, 2024", 9 pgs.
Chen, Xiaorui, et al., "Comparison of four adjuvants revealed the strongest protection against lethal pneumococcal challenge following immunization with PsaA-PspA fusion protein and AS02 as adjuvant", https://pubmed.ncbi.nlm.nih.gov/30707297/ (abstract), (2019), 1 pg.

| PB2 MUTANT vRNAs | 3' | 5' | NUMBER OF VLPs (/ml) | NUMBER OF VLPs POSSESSING GFP vRNA (/ml) | EFFICIENCY OF VIRION INCORPORATION |
|---|---|---|---|---|---|
| PB2(300)GFP(300) | 300 | 300 | 2,799,200 | 1,532,400 | 54.7% |
| PB2(120)GFP(120) | 120 | 120 | 1,080,800 | 753,600 | 69.7% |
| PB2(60)GFP(120) | 60 | 120 | 1,676,800 | 960,000 | 57.3% |
| PB2(30)GFP(120) | 30 | 120 | 1,807,200 | 839,200 | 46.4% |
| PB2(0)GFP(120) | ... | 120 | 1,093,600 | 322,400 | 29.5% |
| PB2(120)GFP(60) | 120 | 60 | 1,756,800 | 1,132,800 | 64.5% |
| PB2(120)GFP(30) | 120 | 30 | 1,068,000 | 549,600 | 51.5% |
| PB2(120)GFP(0) | 120 | ... | 56,000 | 42,400 | 75.7% |
| PB2(0)GFP(0) | ... | ... | 28,000 | 0 | 0.0% |
| PB2(-) | NONE | | 19,600 | — | — |

FIG. 1

SEQ ID NO: 1

```
agcgaaagca ggtactgatc caaaatggaa gattttgtgc gacaatgctt caatccgatg    60
attgtcgagc ttgcggaaaa acaatgaaa gagtatgggg aggacctgaa aatcgaaaca   120
aacaaatttg cagcaatatg cactcacttg gaagtatgct tcatgtattc agattttcac   180
ttcatcaatg agcaaggcga gtcaataatc gtagaacttg gtgatccaaa tgcacttttg   240
aagcacagat ttgaaataat cgagggaaga gatcgcacaa tggcctggac agtagtaaac   300
agtatttgca cactacagg ggctgagaaa ccaaagtttc taccagattt gtatgattac   360
aaggagaata gattcatcga aattggagta acaaggagag aagttcacat atactatctg   420
gaaaaggcca ataaaattaa atctgagaaa acacacatcc acatttctc gttcactggg   480
gaagaaatgg ccacaaaggc agactacact ctcgatgaag aaagcagggc taggatcaaa   540
accagactat tcaccataag acaagaaatg gccagcagag gcctctggga ttcctttcgt   600
cagtccgaga gaggagaaga gacaattgaa gaaaggtttg aaatcacagg aacaatgcgc   660
aagcttgccg accaaagtct cccgccgaac ttctccagcc ttgaaaattt tagagcctat   720
gtggatggat cgaaccgaa cggctacatt gagggcaagc tgtctcaaat gtccaaagaa   780
gtaaatgcta gaattgaacc ttttttgaaa acaacaccac gaccacttag acttccgaat   840
gggcctccct gttctcagcg gtccaaattc ctgctgatgg atgccttaaa attaagcatt   900
gaggacccaa gtcatgaagg agggaata ccgctatatg atgcaatcaa atgcatgaga   960
acattctttg gatggaagga acccaatgtt gttaaaccac acgaaaaggg aataaatcca  1020
aattatcttc tgtcatggaa gcaagtactg gcagaactgc aggacattga gaatgaggag  1080
aaaattccaa agactaaaaa tatgaagaaa acaagtcagc taaagtgggc acttggtgag  1140
aacatggcac cagaaaaggt agactttgac gactgtaaag atgtaggtga tttgaagcaa  1200
tatgatagtg atgaaccaga attgaggtcg cttgcaagtt ggattcagaa tgagttttaac  1260
aaggcatgcg aactgacaga ttcaagctgg atagagctcg atgagattgg agaagatgtg  1320
gctccaattg aacacattgc aagcatgaga aggaattatt tcacatcaga ggtgtctcac  1380
tgcagagcca cagaatacat aatgaaggga gtgtacatca atactgcctt gcttaatgca  1440
tcttgtgcag caatggatga tttccaatta attccaatga taagcaagtg tagaactaag  1500
gagggaaggc gaaagaccaa cctgtatggt ttcatcataa aaggaagatc ccacttaagg  1560
aatgacaccg acgtggtaaa ctttgtgagc atggagtttt ctctcactga cccaagactt  1620
gaaccacata aatgggagaa gtactgtgtt cttgagatag agatatgct tataagaagt  1680
gccataggcc aggtttcaag gcccatgttc ttgtatgtga gaacaaatgg aacctcaaaa  1740
attaaaatga atggggaat ggagatgagg cgttgcctcc tccagtcact tcaacaaatt  1800
gagagtatga ttgaagctga gtcctctgtc aaagagaaag acatgaccaa agagttcttt  1860
gagaacaaat cagaaacatg gccattgga gagtccccca aggagtggga ggaaagttcc  1920
attgggaagg tctgcaggac tttattagca aagtcggtat caacagctt gtatgcatct  1980
ccacaactag aaggattttc agctgaatca agaaaactgc ttctatcgt tcaggctctt  2040
agggacaacc tggaacctgg gacctttgat cttgggggc tatatgaagc aattgaggag  2100
tgcctgatta atgatcctg ggttttgctt aatgcttctt ggttcaactc cttccttaca  2160
catgcattga gttagttgtg gcagtgctac tatttgctat ccatactgtc caaaaagta  2220
ccttgtttct act                                                     2233
```

SEQ ID NO: 2

```
agcgaaagca ggcaaaccat ttgaatggat gtcaatccga ccttactttt cttaaaagtg    60
ccagcacaaa atgctataag cacaactttc ccttatactg gagaccctcc ttacagccat   120
gggacaggaa caggatacac catggatact gtcaacagga cacatcagta ctcagaaaag   180
ggaagatgga caacaaacac cgaaactgga gcaccgcaac tcaacccgat tgatgggcca   240
ctgccagaag acaatgaacc aagtggttat gcccaaacag attgtgtatt ggaggcgatg   300
gctttccttg aggaatccca tcctggtatt tttgaaaact cgtgtattga acgatggag   360
gttgttcagc aaacacgagt agacaagctg acacaaggcc gacagaccta tgactggact   420
ctaaatgaa accaacctgc tgcaacagca ttggccaaca aatagaagt gttcagatca   480
aatggcctca ggccaatga gtctggaagg ctcatagact ccttaagga tgtaatggag   540
tcaatgaaca aagaagaaat gggatcaca actcattc agagaaagag acgggtgaga   600
gacaatatga ctaagaaaat gataacacag agaacaatgg gtaaaagaa gcagagattg   660
aacaaaagga gttatctaat tagagcattg accctgaaca caatgaccaa agatgctgag   720
agagggaagc taaaacggag agcaattgca accccaggga tgcaaataag ggggtttgta   780
```

FIG. 2A

```
tactttgttg agacactggc aaggagtata tgtgagaaac ttgaacaatc agggttgcca     840
gttggaggca atgagaagaa agcaaagttg gcaaatgttg taaggaagat gatgaccaat     900
tctcaggaca ccgaactttc tttcaccatc actggagata caccaaatg  gaacgaaaat     960
cagaatcctc ggatgttttt ggccatgatc acatatatga ccagaaatca gcccgaatgg    1020
ttcagaaatg ttctaagtat tgctccaata atgttctcaa acaaaatggc gagactggga    1080
aaagggtata tgtttgagag caagagtatg aaacttagaa ctcaaatacc tgcagaaatg    1140
ctagcaagca tcgatttgaa atatttcaat gattcaacaa gaagaagat  tgaaaaaatc    1200
cgaccgctct aatagaggg  gactgcatca ttgagccctg gaatgatgat gggcatgttc    1260
aatatgttaa gcactgtatt aggcgtctcc atcctgaatc ttggacaaaa gagatacacc    1320
aagactactt actggtggga tggtcttcaa tcctctgacg attttgctct gattgtgaat    1380
gcacccaatc atgaaggat  tcaagccgga gtcgacaggt tttatcgaac ctgtaagcta    1440
cttgaatca  atatgagcaa gaaaaagtct tacataaaca gaacaggtac atttgaattc    1500
acaagttttt tctatcgtta tgggtttgtt gccaatttca gcatggagct tccagttt     1560
ggggtgtctg ggatcaacga gtcagcggac atgagtattg gagttactgt catcaaaaac    1620
aatatgataa acaatgatct tggtccagca acagctcaaa tggcccttca gttgttcatc    1680
aaagattaca ggtacacgta ccgatgccat ataggtgaca cacaaataca aacccgaaga    1740
tcatttgaaa taagaaaact gtgggagcaa acccgttcca agctggact  gctggtctcc    1800
gacggaggcc caaatttata caacattaga aatctccaca ttcctgaagt ctgcctaaaa    1860
tgggaattga tggatgagga ttaccagggg cgttatgca  acccactgaa cccatttgtc    1920
agccataaag aaattgaatc aatgaacaat gcagtgatga tgccagcaca tggtccagcc    1980
aaaaacatgg agtatgatgc tgttgcaaca acacactcct ggatcccaa  aagaaatcga    2040
tccatcttga atacaagtca aagaggagta cttgaggatg aacaaatgta ccaaaggtgc    2100
tgcaatttat ttgaaaaatt cttccccagc agttcataca gaagaccagt cgggatatcc    2160
agtatggtgg aggctatggt ttccagagcc cgaattgatg cacggattga tttcgaatct    2220
ggaaggataa agaaagaaga gttcactgag atcatgaaga tctgttccac cattgaagag    2280
ctcagacggc aaaaatagtg aatttagctt gtccttcatg aaaaaatgcc ttgtttctac    2340
t                                                                   2341

SEQ ID NO: 3
agcgaaagca ggtcaattat attcaatatg gaaagaataa aagaactacg aaatctaatg     60
tgcagtctc  gcacccgcga gatctcaca  aaaaccacg  tggaccatat ggccataatc    120
aagaagtaca catcaggaag acaggagaag acccagcac  ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca gtcaaaata  cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taccaaaga  gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctggaa  cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aataggggcga atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
```

FIG. 2B

```
gagatgtcaa tgagaggagt gagaatcagc aaaatgggtg tagatgagta ctccagcacg
gagagggtag tggtgagcat tgaccgtttt ttgagaatcc gggaccaacg aggaaatgta
ctactgtctc ccgaggaggt cagtgaaaca cagggaacag agaaactgac aataacttac
tcatcgtcaa tgatgtggga gattaatggt cctgaatcag tgttggtcaa tacctatcaa
tggatcatca gaaactggga aactgttaaa attcagtggt cccagaaccc tacaatgcta
tacaataaaa tggaatttga accatttcag tctttagtac ctaaggccat tagaggccaa
tacagtgggt ttgtaagaac tctgttccaa caaatgaggg atgtgcttgg gacatttgat
accgcacaga taataaaact tcttcccttc gcagccgctc caccaaagca agtagaatg
cagttctcct catttactgt gaatgtgagg ggatcaggaa tgagaatact tgtaaggggc
aattctcctg tattcaacta taacaaggcc acgaagagac tcacagttct cggaaaggat
gctggcactt taactgaaga cccagatgaa ggcacagctg gagtggagtc cgctgttctg
aggggattcc tcattctggg caaagaagac aagagatatg ggccagcact aagcatcaat
gaactgagca accttgcgaa aggagagaag gctaatgtgc taattgggca aggagacgtg
gtgttggtaa tgaaacggaa acgggactct agcatactta ctgacagcca gacagcgacc
aaagaattcc ggatggccat caattagtgt cgaatagttt aaaaacgacc ttgtttctac
t SEQ ID NO: 4
agcaaaagca gggtagataa tcactcactg agtgacatca aaatcatggc gtctcaaggc
accaaacgat cttacgaaca gatggagact gatggagaac gccagaatgc cactgaaatc
agagcatccg tcggaaaaat gattggtgga attggacgat ctacatcca aatgtgcacc
gaactcaaac tcagtgatta tgagggacgg ttgatccaaa acagcttaac aatagagaga
atggtgctct ctgcttttga cgaaggaga aatataacc ttgaagaaca tcccagtgcg
gggaaagatc ctaagaaac tggaggacct atatacagga gagtaaacgg aaagtggatg
agagaactca tcctttatga caaagaagaa ataaggcgaa tctgcgcgca agctaataat
ggtgacgatg caaccggctgg tctgactcac atgatgatct ggcattccaa tttgaatgat
gcaacttatc agaggacaag agctcttgtt cgcacggaa tggatccag gatgtgctct
ctgatgcaag gttcaactct ccctaggagg tctgagccg caggtgctgc agtcaaagga
gttggaacaa tggtgatgga attggtcaga atgatcaaac gtgggatcaa tgatcggaac
ttctggagggt gtgagaatgg acgaaaaaca agaattgctt atgaaagaat gtgcaacatt
ctcaaaggga aatttcaaac tgctgcacaa aaagcaatga tggatcaagt gagagagagc
cggaacccag ggaatgctga gttcgaagat ctcactttc tagcacggtc tgcactcata
ttgagagggt cggttgctca caagtcctgc ctgcctgcct gtgtgtatgg acctgccgta
gccagtgggt acgactttga aagggaggga tactctctag tggaataga cccttcaga
ctgcttcaaa acagccaagt gtacagccta atcagaccaa atgagaatcc agcacacaag
agtcaactgg tgtggatggc atgccattct gccgcatttg aagatctaag agtattaagc
ttcatcaaag ggacgaaggt gctcccaaga gggaagcttt ccactagagg agttcaaatt
gcttccaatg aaaatatgga gactatggaa tcaagtacac ttgaactgag aagcaggtac
tgggccataa ggaccagaag tggaggaaac accaatcaac agaggggcatc tgcgggccaa
atcagcatac aacctacgtt ctcagtacag agaaatctcc cttttgacag aacaaccatt
atggcagcat tcaatgggaa tacagagggg agaacatctg acatgaggac cgaaatcata
aggatgatgg aaagtgcaag accagaagat gtgtctttcc aggggcgggg agtcttcgag
ctctcggacg aaaaggcagc gagccgatc gtgccttcct ttgacatgag taatgaagga
tcttatttct tcggagacaa tgcagaggag tacgacaatt aaagaaaaat accttgttt
ctact SEQ ID NO: 5
agcaaaagca ggtagatatt gaaagatgag tcttctaacc gaggtcgaaa cgtacgtact
ctctatcatc ccgtcaggcc cctcaaagc cgagatcgca cagagacttg aagatgtctt
tgcagggaag aacaccgatc ttgaggttct catggaatgg ctaaagacaa gaccaatcct
gtcacctctg actaagggga tttaggatt tgtgttcacg ctcaccgtgc ccagtgagcg
aggactgcag cgtagacgct ttgtccaaaa tgcccttaat gggaacgggg atccaaataa
catggacaaa gcagttaaac tgtataggaa gctcaagagg gagataacat ccatggggc
caaagaaatc tcactcagtt attctgctgg tgcacttgcc agttgtatgg gcctcatata
caacaggatg gggctgtga ccactgaagt ggcatttgc ctggtatgtg caacctgtga
```

```
acagattgct gactcccagc atcggtctca taggcaaatg gtgacaacaa ccaatccact  540
aatcagacat gagaacagaa tggtttttagc cagcactaca gctaaggcta tggagcaaat  600
ggctggatcg agtgagcaag cagcagaggc catggaggtt gctagtcagg ctagacaaat  660
ggtgcaagcg atgagaacca ttgggactca tcctagctcc agtgctggtc tgaaaaatga  720
tcttcttgaa aatttgcagg cctatcagaa acgaatgggg gtgcagatgc aacggttcaa  780
gtgatcctct cactattgcc gcaaatatca ttgggatctt gcacttgaca ttgtggattc  840
ttgatcgtct tttttcaaa tgcatttacc gtcgctttaa atacggactg aaaggagggc  900
cttctacgga aggagtgcca aagtctatga gggaagaata cgaaaggaa cagcagagtg  960
ctgtggatgc tgacgatggt catttttgtca gcatagagct ggagtaaaaa actaccttgt 1020
ttctact                                                           1027

SEQ ID NO: 6
agcaaaagca gggtgacaaa aacataatgg atccaaacac tgtgtcaagc tttcaggtag   60
attgctttct ttggcatgtc cgcaaacgag ttgcagacca agaactaggc gatgccccat  120
tccttgatcg ggttcgccga gatcagaaat ccctaagagg aagggcagt actctcggtc  180
tggacatcaa gacagccaca cgtgctggaa agcagatagt ggagcggatt ctgaaagaag  240
aatccgatga ggcacttaaa atgaccatgg cctctgtacc tgcgtcgcgt tacctaactg  300
acatgactct tgaggaaatg tcaagggact ggtccatgct catacccaag cagaaagtgg  360
caggccctct ttgtatcaga atggaccagg cgatcatgga taagaacatc atactgaaag  420
cgaacttcag tgtgattttt gaccggctgg ttgactctaat attgctaagg gctttcaccg  480
aagagggagc aattgttggc gaaatttcac cattgccttc tcttccagga catactgcctg  540
aggatgtcaa aaatgcagtt ggagtcctca tcggaggact tgaatggaat gataacacag  600
ttcgagtctc tgaaactcta cagagattcg cttgggagaag cagtaatgag aatgggagac  660
ctccactcac tccaaaacag aaacgagaaa tggcgggaac aattaggtca gaagtttgaa  720
gaaataagat ggttgattga agaagtgaga cacaaactga gataacaga gaatagtttt  780
gagcaaataa catttatgca agccttacat ctattgcttg aagtggagca agagataaga  840
actttctcgt ttcagcttat ttagtactaa aaaacaccct tgtttctact             890

SEQ ID NO: 7
agcaaaagca ggggaaaata aaaacaacca aaatgaaggc aaacctactg gtcctgttat   60
gtgcacttgc agctgcagat gcagacacaa tatgtatagg ctaccatgcg aacaattcaa  120
ccgacactgt tgacacagta ctcgagaaga atgtgacagt gacacactct gttaacctgc  180
tcgaagacag ccacaacgga aaactatgta ttaaaagg aatagcccca ctacaattgg  240
ggaaatgtaa catcgccgga tggctcttgg gaaacccaga atgcgaccca ctgcttccag  300
tgagatcatg gtcctacatt gtagaaacac caaactctga atggataa tgttatccag  360
gagatttcat cgactatgag gagctgaggg agcaattgag ctcagtgtca tcattcgaaa  420
gattcgaaat attccccaaa gaaagctcat ggcccaacca acacaaaac ggagtaacgg  480
cagcatgctc ccatgagggg aaaagcagtt ttacagaaa tttgctatgg ctgacggaga  540
aggagggctc atacccaaag ctgaaaaatt cttatgtgaa caaaaaggg aagaagtcc  600
ttgtactgtg gggtattcat cacccgccta acagtaagga acaacagaat ctctatcaga  660
atgaaaatgc ttatgtctct gtagtgactt caaattataa caggagattt acccggaaa  720
tagcagaaag acccaaagta agagatcaag ctggaggat gaactattac tggaccttgc  780
taaaacccgg agacacaata atatttgagg caaatggaaa tctaatagca ccaatgtatg  840
ctttcgcact gagtagaggc tttgggtccg gcatcatcac ctcaaacgca tcaatgcatg  900
agtgtaacac gaagtgtcaa acaccctgg agctataaa cagcagtctc cttaccaga  960
atatacaccc agtcacaata ggagagtgcc caaaatacgt caggagtgcc aaattgagga 1020
tggttacagg actaaggaac attccgtcca ttcaatccag aggtctattt ggagccattg 1080
ccggttttat tgaaggggga tggactggaa tgatagatgg atggtatggt tatcatcatc 1140
agaatgaaca gggatcaggc tatgcagcgg atcaaaaag cacacaaaat gccattaacg 1200
ggattacaaa caaggtgaac actgttatcg agaaatgaa cattcaattc acagctgtgg 1260
gtaaagaatt caacaaatta gaaaaagga tggaaattt aataaaaaa gttgatgatg 1320
gatttctgga catttggaca tataatgcag aattgttagt tctactggaa atgaaagga 1380
ctctggattt ccatgactca aatgtgaaga atctgtatga gaaagtaaaa agccaattaa 1440
```

```
agaataatgc caaagaaatc ggaaatggat gttttgagtt ctaccacaag tgtgacaatg    1500
aatgcatgga aagtgtaaga aatgggactt atgattatcc caaatattca gaagagtcaa    1560
agttgaacag ggaaaaggta gatggagtga aattggaatc aatggggatc tatcagattc    1620
tggcgatcta ctcaactgtc gccagttcac tggtgctttt ggtctccctg ggggcaatca    1680
gttttctggat gtgttctaat ggatctttgc agtgcagaat atgcatctga gattagaatt    1740
tcagagatat gaggaaaaac accttgttt ctact                                1775
```

SEQ ID NO: 8
```
agcaaaagca ggggtttaaa atgaatccaa atcagaaaat aataaccatt ggatcaatct      60
gtctggtagt cggactaatt agcctaatat tgcaaatagg gaatataatc tcaatatgga     120
ttagccattc aattcaaact ggaagtcaaa accatactgg aatatgcaac caaacatca     180
ttacctataa aatagcacc tgggtaaagg acacaacttc agtgatatta ccggcaatt      240
catctctttg tccatccgt gggtgggcta tatacagcaa agacaatagc ataagaattg     300
gttccaaagg agacgttttt gtcataagag agcctttat tcatgttct cacttggaat      360
gcaggacctt ttttctgacc caaggtgcct tactgaatga caagcattca agtgggactg     420
ttaaggacag aagcccttat agggccttaa tgagctgccc tgtcggtgaa gctccgtccc     480
cgtacaattc aagatttgaa tcggttgctt ggtcagcaag tgcatgtcat gatggcatgg     540
gctggctaac aatcggaatt tcaggtccag ataatggagc agtggctgta ttaaaataca     600
acggcataat aactgaaacc ataaaaagtt ggaggaagaa atattgagg acacaagagt      660
ctgaatgtgc ctgtgtaaat ggttcatgtt ttactataat gactgatggc ccgagtgatg     720
ggctggcctc gtacaaaatt ttcaagatcg aaaaggggaa ggttactaaa tcaatagagt     780
tgaatgcacc taattctcac tatgaggaat gttcctgtta ccctgatacc ggcaaagtga     840
tgtgtgtgtg cagagacaat tggcatggtt cgaaccggcc atgggtgtct ttcgatcaaa     900
acctggatta tcaaatagga tacatctgca gtgggttttt cggtgacaac ccgcgtcccg     960
aagatggaac aggcagctgt ggtccagtgt atgttgatgg agcaaacgtg gtaaagggat    1020
tttcatatag gtatggtaat ggtgtttgga taggaaggac caaaagtcac agttccagac    1080
atgggtttga gatgatttgg gatcctaatg gatggacaga gactgatagt aagttctctg    1140
tgaggcaaga tgttgtggca atgactgatt ggtcagggta tagcggaagt ttcgttcaac    1200
atcctgagct gacagggcta gactgtatga ggccgtgctt ctgggttgaa ttaatcaggg    1260
gacgacctaa agaaaaaca atctggacta gtgcgagcag catttctttt tgtggcgtga    1320
atagtgatac tgtagattgg tcttggccag acggtgctga gttgccattc agcattgaca    1380
agtagtctgt tcaaaaaact ccttgtttct act                                 1413
```

SEQ ID NO: 10
```
agcgaaagca ggtcaattat attcaatatg gaaagaataa agaactaag aaatctaatg       60
tcgcagtctc gcacccgcga gatactcaca aaaccaccg tggaccatat ggccataatc      120
aagaagtaca catcaggaag acaggagaag aacccagcac ttaggatgaa atggatgatg     180
gcaatgaaat atccaattac agcagacaag aggataacgg aaatgattcc tgagagaaat     240
gagcaaggac aaactttatg gagtaaaatg aatgatgccg gatcagaccg agtgatggta     300
tcacctctgg ctgtgacatg gtggaatagg aatggaccaa tgacaaatac agttcattat     360
ccaaaaatct acaaaactta ttttgaaaga gtcgaaaggc taagcatgg aacctttggc      420
cctgtccatt ttagaaacca agtcaaaata cgtcggagag ttgacataaa tcctggtcat     480
gcagatctca gtgccaagga ggcacaggat gtaatcatgg aagttgtttt ccctaacgaa     540
gtgggagcca ggatactaac atcggaatcg caactaacga taccaaaga gaagaaagaa     600
gaactccagg attgcaaaat ttctcctttg atggttgcat acatgttgga gagagaactg     660
gtccgcaaaa cgagattcct cccagtggct ggtggaacaa gcagtgtgta cattgaagtg     720
ttgcatttga ctcaaggaac atgctggaaa cagatgtata ctccaggagg ggaagtgaag     780
aatgatgatg ttgatcaaag cttgattatt gctgctagga acatagtgag aagagctgca     840
gtatcagcag cccactagc atctttattg gagatgtgcc acagcacaca gattggtgga     900
attaggatgg tagacatcct taagcagaac ccaacagaag agcaagccgt ggatatatgc     960
aaggctgcaa tggactgag aattagctca tccttcagtt ttggtggatt cacatttaag    1020
agaacaagcg gatcatcagt caagagagag aagaggtgc ttacgggcaa tcttcaaaca    1080
ttgaagataa gagtgcatga gggatctgaa gagttcacaa tggttgggag aagagcaaca    1140
gccatactca gaaaagcaac caggagattg attcagctga tagtgagtgg gagagacgaa    1200
```

*FIG. 2E*

```
cagtcgattg ccgaagcaat aattgtggcc atggtatttt cacaagagga ttgtatgata  1260
aaagcagtta gaggtgatct gaatttcgtc aatagggcga atcagcgact gaatcctatg  1320
catcaacttt taagacattt tcagaaggat gcgaaagtgc tttttcaaaa ttggggagtt  1380
gaacctatcg acaatgtgat gggaatgatt gggatattgc ccgacatgac tccaagcatc  1440
gagatgtcaa tgagaggagt gagaatcagc aaaatgggtg tagatgagta ctccagcacg  1500
gagagggtag tggtgagcat tgaccggttc ttgagagtca gggaccaacg aggaaatgta  1560
ctactgtctc ccgaggaggt cagtgaaaca caggaacag agaaactgac aataacttac   1620
tcatcgtcaa tgatgtggga gattaatggt cctgaatcag tgttggtcaa tacctatcaa  1680
tggatcatca gaaactggga aactgttaaa attcagtggt cccagaaccc tacaatgcta  1740
tacaataaaa tggaatttga accatttcag tctttagtac ctaaggccat tagaggccaa  1800
tacagtgggt ttgtaagaac tctgttccaa caatgagggg atgtgcttgg acatttgat  1860
accgcacaga taataaaact tcttcccttc gcagccgctc caccaaagca agtagaatg  1920
cagttctcct catttactgt gaatgtgagg ggatcaggaa tgaatact tgtaaggggc  1980
aattctcctg tattcaacta caacaaggcc acgaagagac tcacgttct cggaaaggat  2040
gctggcactt taaccgaaga cccagatgaa ggcacagctg gagtggagtc cgctgttctg  2100
aggggattcc tcattctggg caaagaagac aggagatatg ggccagcatt aagcatcaat  2160
gaactgagca accttgcgaa aggagagaag gctaatgtgc taattgggca aggagacgtg  2220
gtgttggtaa tgaaacgaaa acgggactct agcatactta ctgacagcca gacagcgacc  2280
aaaagaattc ggatggccat caattagtgt cgaatagttt aaaaacgacc ttgtttctac  2340
t                                                                  2341

SEQ ID NO: 11
agcgaaagca ggcaaaccat ttgaatggat gtcaatccga ccttactttt cttaaaagtg    60
ccagcacaaa atgctataag cacaacttc ccttataccg gagaccctcc ttacagccat   120
gggacaggaa caggatacac catggatact gtcaacagga cacatcagta ctcagaaaag   180
ggaagatgga caacaaacac cgaaactgga gcaccgcaac tcaaccgat tgatgggcca   240
ctgccagaag acaatgaacc aagtggttat gcccaaacag attgtgtatt ggaagcaatg   300
gcttccttg aggaatccca tcctggtatt tttgaaaact cgtgtattga acgatggag    360
gttgttcagc aaacacgagt agacaagctg acacaaggcc gacagccta tgactggact   420
ttaaatagaa accagcctgc tgcaacagca ttggccaaca caataagagt gttcagatca    480
aatggcctca cggccaatga gtcaggaagg ctcatagact tccttaagga tgtaatggag   540
tcaatgaaaa aagaagaaat gggatcaca actcattttc agagaaagag acgggtgaga   600
gacaatatga ctaagaaaat gataacacag agaacaatag gtaaaaggaa acagagattg   660
aacaaagggg gttatctaat tagagcattg accctgaaca caatgaccaa agatgctgag   720
agagggaagc taaaacggag agcaattgca accccaggga catgcaataag gggtttgta   780
tactttgttg agacactggc aaggagtata tgtgagaaac ttgaacaatc agggtgtcca   840
gttgaggca atgagaagaa agcaaagttg gcaaatgttg taaggaagat gatgaccaat   900
tctcaggaca ccgaactttc tttcaccatc actggagata caccaaatg gaacgaaaat   960
cagaatcctc ggatgttttt ggccatgatc acatatatga ccagaaatca gccgaatgg  1020
ttcagaaatg tcctaagtat tgctccaata atgttctcaa acaaaatggc gagactggga  1080
aagggtata tgtttgagag caagagtatg aaacttagaa ctcaaatacc tgcagaaatg  1140
ctagcaagca ttgatttgaa atatttcaat gattcaacaa gaagaagat tgaaaaaatc  1200
cgaccgctct aatagaggg gactgcatca ttgagcctg aatgatgat gggcatgttc   1260
aatatgttaa gcactgtatt aggcgtctcc atcctgaatc ttggacaaaa gagatacacc  1320
aagactactt actggtggga tggtcttcaa tcctctgacg attttgctct gattgtgaat  1380
gcacccaatc atgaagggat tcaagccgga gtcgacaggt tttatcgaac ctgtaagcta  1440
cttggaatca atatgagcaa gaaaaagtct tacataaaca gaacaggtac atttgaattc  1500
acaagttttt tctatcgtta tgggtttgtt gccaatttca gcatggagct tcccagtttt  1560
ggggtgtctg gatcaacga gtcagcggac atgagtattg gagttactgt catcaaaaac  1620
aatatgataa acaatgatct tggtccagca acagctcaaa tggcccttca gttgttcatc  1680
aaagattaca ggtacacgta ccgatgccat agaggtgaca cacaaataca acccgaaga  1740
tcatttgaaa taagaaaact gtgggagcaa acccgttcca agctggact gctggtctcc  1800
gacggaggcc caaatttata caacattaga aatctccaca ttcctgaagt ctgcctaaaa  1860
tgggaattga tggatgagga ttaccagggg cgtttatgca acccactgaa cccatttgtc  1920
```

FIG. 2F

```
agccataaag aaattgaatc aatgaacaat gcagtgatga tgccagcaca tggtccagcc    1980
aaaaacatgg agtatgatgc tgttgcaaca acacactcct ggatcccaa aagaaatcga    2040
tccatcttga atacaagtca aagaggagta cttgaagatg aacaaatgta ccaaaggtgc    2100
tgcaatttat ttgaaaaatt cttccccagc agttcataca gaagaccagt cgggatatcc    2160
agtatggtgg aggctatggt ttccagagcc cgaattgatg cacggattga tttcgaatct    2220
ggaaggataa agaagaaga gttcactgag atcatgaaga tctgttccac cattgaagag    2280
ctcagacggc aaaaatagtg aatttagctt gtccttcatg aaaaaatgcc ttgtttctac    2340
t                                                                   2341

SEQ ID NO: 12
agcgaaagca ggtactgatt caaaatggaa gattttgtgc gacaatgctt caatccgatg     60
attgtcgagc ttgcggaaaa aacaatgaaa gagtatgggg aggacctgaa aatcgaaaca    120
aacaaatttg cagcaatatg cactcacttg gaagtatgct tcatgtattc agatttccac    180
ttcatcaatg agcaaggcga gtcaataatc gtagaacttg gtgatcctaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggaaaata gattcatcga aattggagta acaggagag aagttcacat atactatctg    420
gaaaaggcca ataaattaa atctgagaaa acacacatcc acattttctc gttcactggg    480
gaagaaatgg ccacaagggc cgactacact ctcgatgaag aaagcagggc taggatcaaa    540
accaggctat tcaccataag acaagaaatg gccagcagag gcctctggga ttcctttcgt    600
cagtccgaga gaggagaaga gacaattgaa gaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttgaaa acaacaccac gaccacttag acttccgaat    840
gggcctccct gttctcagcg gtccaaattc ctgctgatgg atgccttaaa attaagcatt    900
gaggacccaa gtcatgaagc gagggaata cgctatatg atgcaatcca atgcatgaga    960
acattctttg gatggaagga accaatgtt gttaaaccac acgaaaaggg aataaaatcca   1020
aattatcttc tgtcatggaa gcaagtactg cagaactgc aggacattga gaatgaggag   1080
aaaattccaa agactaaaaa tatgaaaaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagttcaac   1260
aaggcatgcg aactgacaga ttcaagctgg atagagcttg atgagattgg agaagatgtg   1320
gctccaattg aacacattgc aagcatgaga aggaattatt tcacatcaga ggtgtctcac   1380
tgcagagcca cagatacat aatgaagggg gtgtacatca atactgcctt acttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacaca atgggagaa gtactgtgtt cttgagatag gagatatgct tctaagaagt   1680
gccataggcc aggtttcaag gcccatgttc ttgtatgtga ggacaaatgg aacctcaaaa   1740
attaaaatga aatgggggaat ggagatgagg cgttgtctcc tccagtcact tcaacaaatt   1800
gagagtatga ttgaagctga gtcctctgtc aaagagaaag acatgaccaa agagttcttt   1860
gagaacaaat cagaaacatg gccattggaa gagtctccca aggagtggga ggaagttcc   1920
attgggaagg tctgcaggac tttattagca aagtcggtat taacagctt gtatgcatct   1980
ccacaactag aaggattttc agctgaatca agaaaactgc ttcttatcgt tcaggctctt   2040
agggacaatc tggaacctgg gaccttgat ctgggggc tatatgaagc aattgaggag   2100
tgcctaatta atgatcctg ggttttgctt aatgcttctt ggttcaactc cttccttaca   2160
catgcattga gttagttgtg gcagtgctac tatttgctat ccatactgtc caaaaagta   2220
ccttgttttct act                                                      2233

SEQ ID NO: 13
agcaaaagca gggtagataa tcactcactg agtgacatca aaatcatggc gtcccaaggc    50
accaaacggt cttacgaaca gatggagact gatggagaac gccagaatgc cactgaaatc    120
agagcatccg tcggaaaaat gattggtgga attgacgat tctacatcca aatgtgcaca    180
```

FIG. 2G

```
gaacttaaac tcagtgatta tgagggacgg ttgatccaaa acagcttaac aatagagaga      240
atggtgctct ctgcttttga cgaaaggaga aataaatacc tggaagaaca tcccagtgcg      300
gggaaagatc ctaagaaaac tggaggacct atatacagaa gagtaaacgg aaagtggatg      360
agagaactca tccttatga caaagaagaa ataaggcgaa tctggcgcca agctaataat       420
ggtgacgatg caacggctgg tctgactcac atgatgatct ggcattccaa tttgaatgat      480
gcaacttatc agaggacaag ggctcttgtt cgcaccggaa tggatcccag gatgtgctct      540
ctgatgcaag gttcaactct ccctaggagg tctggagccg caggtgctgc agtcaaagga      600
gttggaacaa tggtgatgga attggtcagg atgatcaaac gtgggatcaa tgatcggaac      660
ttctggaggg gtgagaatgg acgaaaaaca agaattgctt atgaaagaat gtgcaacatt      720
ctcaaaggga aatttcaaac tgctgcacaa aaagcaatga tggatcaagt gagagagagc      780
cggaacccag ggaatgctga gttcgaagat ctcacttttc tagcacggtc tgcactcata      840
ttgagagggt cggttgctca caagtcctgc ctgcctgcct gtgtgtatgg acctgccgta      900
gccagtgggt acgactttga agagaggga tactctctag tcggaataga cccttcaga       960
ctgcttcaaa acagccaagt gtacagccta atcagaccaa atgagaatcc agcacacaag    1020
agtcaactgg tgtggatggc atgccattct gccgcatttg aagatctaag agtattgagc    1080
ttcatcaaag ggacgaaggt ggtcccaaga gggaagcttt ccactagagg agttcaaatt    1140
gcttccaatg aaaatatgga gactatgaa tcaagtacac ttgaactgag aagcaggtac    1200
tgggccataa ggaccagaag tggaggaaac accaatcaac agagggcatc tgcggccaa    1260
atcagcatac aacctacgtt ctcagtacag agaaatctcc cttttgacag aacaacgtt    1320
atggcagcat tcactgggaa tacagagggg agaacatctg acatgaggac cgaaatcata   1380
aggatgatgg aaagtgcaag accagaagat gtgtctttcc aggggcgggg agtcttcgag   1440
ctctcggacg aaaaggcagc gagcccgatc gtgccttcct tgacatgag taatgaagga    1500
tcttatttct cggagacaa tgcagaggag tacgacaatt aaagaaaaat acccttgttt    1560
ctact                                                                1565

SEQ ID NO: 14
agcaaaagca ggtagatatt gaaagatgag tcttctaacc gaggtcgaaa cgtacgttct     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatgggc    360
caaagaaatc tcactcagtt attctgctgg tgcacttgcc agttgtatgg cctcatata     420
caacaggatg ggggctgtga ccactgaagt ggcatttggc ctggtatgtg caacctgtga    480
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cgctattgcc gcaaatatca ttgggatctt gcacttgata ttgtggattc    840
ttgatcgtct ttttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt cattttgtca gcatagagct ggagtaaaaa actaccttgt   1020
ttctact                                                              1027

SEQ ID NO: 15
agcaaaagca gggtgacaaa gacataatgg atccaaacac tgtgtcaagc tttcaggtag     60
attgctttct ttggcatgtc cgcaaacgag ttgcagacca gaactaggt gatgccccat     120
tccttgatcg gcttcgccga atcagaaatc cctaagagg aagggggcagc actcttggtc     180
tggacatcga gacagccaca cgtgctggaa gcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct tgtatcagaa atggaccagg cgatcatgga taaaaacatc atactgaaag    420
cgaacttcag tgtgattttt gaccggctgg agactctaat attgctaagg gctttcaccg    480
aagagggagc aattgttggc gaaatttcac cattgccttc tcttccagga catactgctg    540
```

```
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga aggtaacaga gaatagtttt    780
gagcaaataa catttatgca agccttacat ctattgcttg aagtggagca agagataaga    840
actttctcat ttcagcttat ttaataataa aaaacaccct tgtttctact              890
```

FIG. 21

FIG. 4

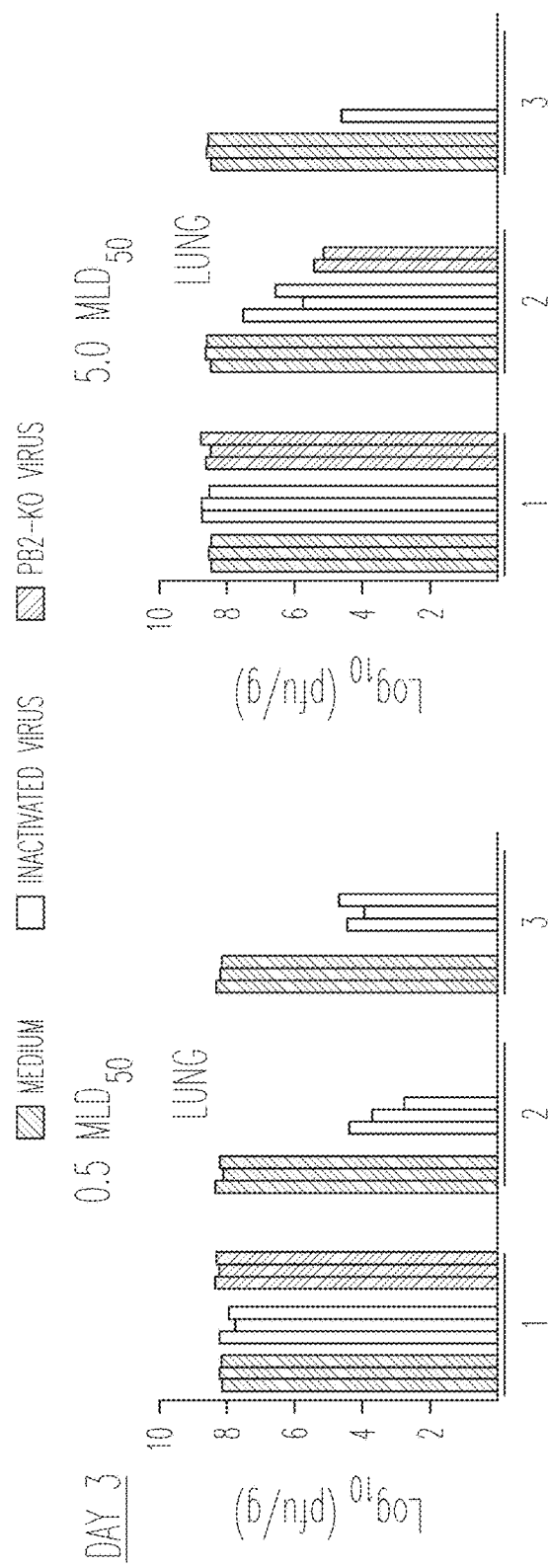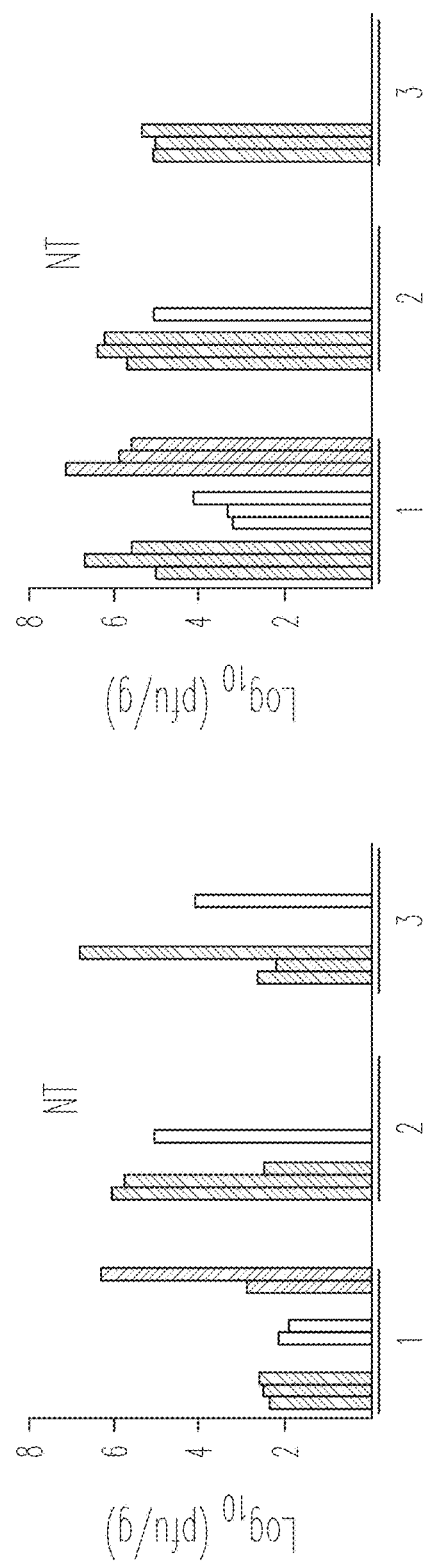
FIG. 9A, FIG. 9B, FIG. 9C, FIG. 9D

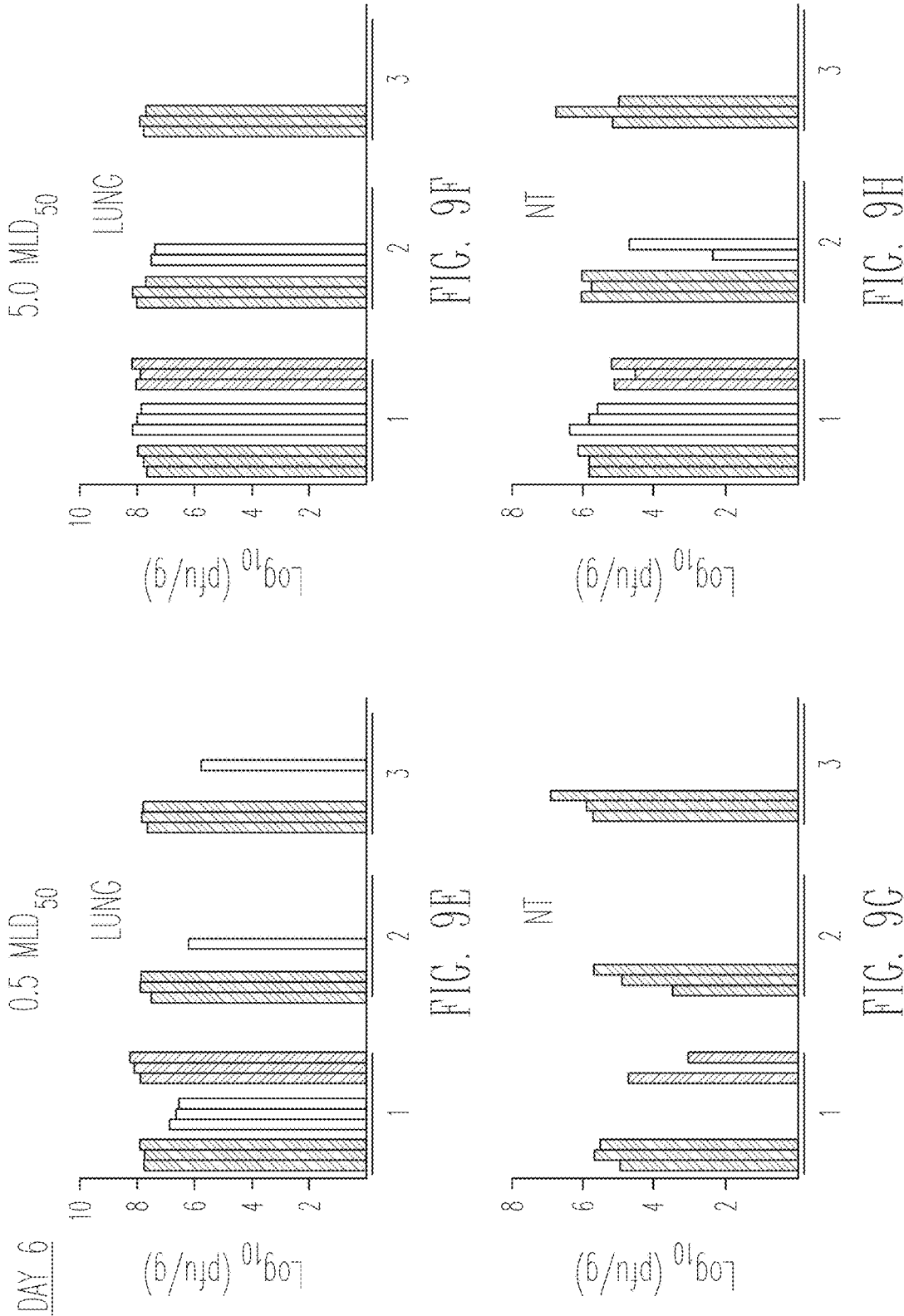

FIG. 11

PB2KO virus expressing pspA of pneumococcus

Anti-pspA

Anti-influenza virus

Growth kinetics of PB2KO-PspA virus

Normal cells

PB2-expressing cells

Hours post-infection (h)

PFU (Log$_{10}$ PFU/ml)

Survival post-challenge with pneumococcus

SEQUENCE LISTING

<160> NUMBER OF SEQ ID NOS: 16

<210> SEQ ID NO 1
<211> LENGTH: 2233
<212> TYPE: DNA
<213> ORGANISM: Artificial Sequence
<220> FEATURE:
<223> OTHER INFORMATION: A synthetic oligonucleotide

<400> SEQUENCE: 1

| | | | | | |
|---|---|---|---|---|---|
| agcgaaagca | ggtactgatc | caaaatggaa | gattttgtgc | gacaatgctt | caatccgatg | 60 |
| attgtcgagc | ttgcggaaaa | aacaatgaaa | gagtatgggg | aggacctgaa | aatcgaaaca | 120 |
| aacaaatttg | cagcaatatg | cactcacttg | gaagtatgct | tcatgtattc | agattttcac | 180 |
| ttcatcaatg | agcaaggcga | gtcaataatc | gtagaacttg | gtgatccaaa | tgcacttttg | 240 |
| aagcacagat | ttgaaataat | cgagggaaga | gatcgcacaa | tggcctggac | agtagtaaac | 300 |
| agtatttgca | acactacagg | ggctgagaaa | ccaaagtttc | taccagattt | gtatgattac | 360 |
| aaggagaata | gattcatcga | aattggagta | acaaggagag | aagttcacat | atactatctg | 420 |
| gaaaaggcca | ataaaattaa | atctgagaaa | acacacatcc | acattttctc | gttcactggg | 480 |
| gaagaaatgg | ccacaaaggc | agactacact | ctcgatgaag | aaagcagggc | taggatcaaa | 540 |
| accagactat | tcaccataag | acaagaaatg | gccagcagag | gcctctggga | ttcctttcgt | 600 |
| cagtccgaga | gaggagaaga | gacaattgaa | gaaaggtttg | aaatcacagg | aacaatgcgc | 660 |
| aagcttgccg | accaaagtct | cccgccgaac | ttctccagcc | ttgaaaattt | tagagcctat | 720 |
| gtggatggat | tcgaaccgaa | cggctacatt | gagggcaagc | tgtctcaaat | gtccaaagaa | 780 |
| gtaaatgcta | gaattgaacc | ttttttgaaa | acaacaccac | gaccacttag | acttccgaat | 840 |
| gggcctcct | gttctcagcg | gtccaaattc | ctgctgatgg | atgccttaaa | attaagcatt | 900 |
| gaggacccaa | gtcatgaagg | agagggaata | ccgctatatg | atgcaatcaa | atgcatgaga | 960 |
| acattctttg | gatggaagga | acccaatgtt | gttaaaccac | acgaaaaggg | aataaatcca | 1020 |
| aattatcttc | tgtcatggaa | gcaagtactg | gcagaactgc | aggacattga | gaatgaggag | 1080 |
| aaaattccaa | agactaaaaa | tatgaagaaa | acaagtcagc | taaagtgggc | acttggtgag | 1140 |
| aacatggcac | cagaaaaggt | agactttgac | gactgtaaag | atgtaggtga | tttgaagcaa | 1200 |
| tatgatagtg | atgaaccaga | attgaggtcg | cttgcaagtt | ggattcagaa | tgagtttaac | 1260 |
| aaggcatgcg | aactgacaga | ttcaagctgg | atagagctcg | atgagattgg | agaagatgtg | 1320 |
| gctccaattg | aacacattgc | aagcatgaga | aggaattatt | tcacatcaga | ggtgtctcac | 1380 |
| tgcagagcca | cagaatacat | aatgaaggga | gtgtacatca | atactgcctt | gcttaatgca | 1440 |
| tcttgtgcag | caatggatga | tttccaatta | attccaatga | taagcaagtg | tagaactaag | 1500 |
| gagggaaggc | gaaagaccaa | cttgtatggt | ttcatcataa | aaggaagatc | ccacttaagg | 1560 |
| aatgacaccg | acgtggtaaa | ctttgtgagc | atggagtttt | ctctcactga | cccaagactt | 1620 |
| gaaccacata | atgggagaa | gtactgtgtt | cttgagatag | gagatatgct | tataagaagt | 1680 |
| gccataggcc | aggtttcaag | gcccatgttc | ttgtatgtga | gaacaaatgg | aacctcaaaa | 1740 |
| attaaaatga | aatggggaat | ggagatgagg | cgttgcctcc | tccagtcact | tcaacaaatt | 1800 |
| gagagtatga | ttgaagctga | gtcctctgtc | aaagagaaag | acatgaccaa | agagttcttt | 1860 |
| gagaacaaat | cagaaacatg | gcccattgga | gagtccccca | aggagtggga | ggaaagttcc | 1920 |
| attgggaagt | tctgcaggac | tttattagca | aagtcggtat | tcaacagctt | gtatgcatct | 1980 |
| ccacaactag | aaggattttc | agctgaatca | agaaaactgc | ttcttatcgt | tcaggctctt | 2040 |

```
agggacaacc tggaacctgg gacctttgat cttgggggc tatatgaagc aattgaggag   2100
tgcctgatta atgatccctg ggttttgctt aatgcttctt ggttcaactc cttccttaca   2160
catgcattga gttagttgtg gcagtgctac tatttgctat ccatactgtc caaaaaagta   2220
ccttgtttct act                                                      2233

<210> SEQ ID NO 2
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 2
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
gttgttcagc aaaacgagt agacaagctg acacaaggcc gacagaccta tgactggact    420
ctaaatagaa accaacctgc tgcaacagca ttggccaaca caatagaagt gttcagatca    480
aatggcctca cggccaatga gtctggaagg ctcatagact ccttaagga tgtaatggag    540 tcaatgaaca aagaagaaat ggggatcaca actcattttc agagaaagag acgggtgaga    600
gacaatatga ctaagaaaat gataacacag agaacaatgg gtaaaagaa gcagagattg    660 aacaaaagga gttatctaat tagagcattg accctgaaca caatgaccaa agatgctgag    720
agagggaagc taaaacggag agcaattgca ccccaggga tgcaaataag ggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata caccaaatg gaacgaaaat    960 cagaatcctc ggatgttttt ggccatgatc acatatatga ccagaaatca gcccgaatgg   1020
ttcagaaatg ttctaagtat tgctccaata atgttctcaa acaaaatggc gagactggga   1080 aagggtata tgtttgagag caagagtatg aaacttagaa ctcaaatacc tgcagaaatg   1140
ctagcaagca tcgatttgaa atatttcaat gattcaacaa gaagaagat tgaaaaaatc   1200 cgaccgctct aatagaggg gactgcatca ttgagccctg aatgatgat gggcatgttc   1260 aatatgttaa gcactgtatt aggcgtctcc atcctgaatc ttggacaaaa gagatacacc   1320
aagactactt actggtggga tggtcttcaa tcctctgacg atttttgctct gattgtgaat   1380 gcacccaatc atgaagggat tcaagccgga gtcgacaggt tttatcgaac ctgtaagcta   1440
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aacccgaaga   1740
tcatttgaaa taagaaact gtgggagcaa acccgttcca aagctggact gctggtctcc   1800
```

| | |
|---|---|
| gacggaggcc caaatttata caacattaga aatctccaca ttcctgaagt ctgcctaaaa | 1860 |
| tgggaattga tggatgagga ttaccagggg cgtttatgca acccactgaa cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatcccccaa aagaaatcga | 2040 |
| tccatcttga atacaagtca aagaggagta cttgaggatg aacaaatgta ccaaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 3
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 3

| | |
|---|---|
| agcgaaagca ggtcaattat attcaatatg gaaagaataa aagaactacg aaatctaatg | 60 |
| tcgcagtctc gcacccgcga gatactcaca aaaaccaccg tggaccatat ggccataatc | 120 |
| aagaagtaca catcaggaag acaggagaag aacccagcac ttaggatgaa atggatgatg | 180 |
| gcaatgaaat atccaattac agcagacaag aggataacgg aaatgattcc tgagagaaat | 240 |
| gagcaaggac aaactttatg gagtaaaatg aatgatgccg gatcagaccg agtgatggta | 300 |
| tcacctctgg ctgtgacatg gtggaatagg aatggaccaa taacaaatac agttcattat | 360 |
| ccaaaaatct acaaaactta ttttgaaaga gtcgaaaggc taaagcatgg aacctttggc | 420 |
| cctgtccatt ttagaaacca agtcaaaata cgtcggagag ttgacataaa tcctggtcat | 480 |
| gcagatctca gtgccaagga ggcacaggat gtaatcatgg aagttgtttt ccctaacgaa | 540 |
| gtgggagcca ggatactaac atcggaatcg caactaacga taaccaaaga gaagaaagaa | 600 |
| gaactccagg attgcaaaat ttctcctttg atggttgcat acatgttgga gagagaactg | 660 |
| gtccgcaaaa cgagattcct cccagtggct ggtggaacaa gcagtgtgta cattgaagtg | 720 |
| ttgcatttga ctcaaggaac atgctgggaa cagatgtata ctccaggagg ggaagtgagg | 780 |
| aatgatgatg ttgatcaaag cttgattatt gctgctagga catagtgag aagagctgca | 840 |
| gtatcagcag atccactagc atctttattg gagatgtgcc acagcacaca gattggtgga | 900 |
| attaggatgg tagacatcct taggcagaac ccaacagaag agcaagccgt ggatatatgc | 960 |
| aaggctgcaa tgggactgag aattagctca tccttcagtt ttggtggatt cacattaag | 1020 |
| agaacaagcg gatcatcagt caagagagag gaagaggtgc ttacgggcaa tcttcaaaca | 1080 |
| ttgaagataa gagtgcatga gggatatgaa gagttcacaa tggttgggag aagagcaaca | 1140 |
| gccatactca gaaaagcaac caggagattg attcagctga tagtgagtgg gagagacgaa | 1200 |
| cagtcgattg ccgaagcaat aattgtggcc atggtatttt cacaagagga ttgtatgata | 1260 |
| aaagcagtca gaggtgatct gaatttcgtc aatagggcga atcaacgatt gaatcctatg | 1320 |
| catcaacttt taagacattt tcagaaggat gcgaaagtgc ttttttcaaaa ttggggagtt | 1380 |
| gaacctatcg acaatgtgat gggaatgatt gggatattgc cgacatgac tccaagcatc | 1440 |
| gagatgtcaa tgagaggagt gagaatcagc aaaatgggtg tagatgagta ctccagcacg | 1500 |

-continued

| | |
|---|---|
| gagagggtag tggtgagcat tgaccgtttt ttgagaatcc gggaccaacg aggaaatgta | 1560 |
| ctactgtctc ccgaggaggt cagtgaaaca cagggaacag agaaactgac aataacttac | 1620 |
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac ctaaggccat tagaggccaa | 1800 |
| tacagtgggt ttgtaagaac tctgttccaa caaatgaggg atgtgcttgg gacatttgat | 1860 |
| accgcacaga taataaaact tcttcccttc gcagccgctc caccaaagca agtagaatg | 1920 |
| cagttctcct catttactgt gaatgtgagg ggatcaggaa tgagaatact tgtaaggggc | 1980 |
| aattctcctg tattcaacta taacaaggcc acgaagagac tcacagttct cggaaaggat | 2040 |
| gctggcactt taactgaaga cccagatgaa ggcacagctg gagtggagtc cgctgttctg | 2100 |
| aggggattcc tcattctggg caaagaagac aagagatatg gccagcact aagcatcaat | 2160 |
| gaactgagca accttgcgaa aggagagaag gctaatgtgc taattgggca aggagacgtg | 2220 |
| gtgttggtaa tgaaacggaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 4
<211> LENGTH: 1565
<212> TYPE: DNA
<213> ORGANISM: Artificial Sequence
<220> FEATURE:
<223> OTHER INFORMATION: A synthetic oligonucleotide

<400> SEQUENCE: 4

| | |
|---|---|
| agcaaaagca gggtagataa tcactcactg agtgacatca aaatcatggc gtctcaaggc | 60 |
| accaaacgat cttacgaaca gatggagact gatggagaac gccagaatgc cactgaaatc | 120 |
| agagcatccg tcggaaaaat gattggtgga attggacgat tctacatcca aatgtgcacc | 180 |
| gaactcaaac tcagtgatta tgagggacgg ttgatccaaa acagcttaac aatagagaga | 240 |
| atggtgctct ctgcttttga cgaaggaga ataaatacc ttgaagaaca tcccagtgcg | 300 |
| gggaaagatc ctaagaaaac tggaggacct atatacagga gagtaaacgg aaagtggatg | 360 |
| agagaactca tcctttatga caaagaagaa ataaggcgaa tctggcgcca agctaataat | 420 |
| ggtgacgatg caacggctgg tctgactcac atgatgatct ggcattccaa tttgaatgat | 480 |
| gcaacttatc agaggacaag agctcttgtt cgcaccggaa tggatcccag gatgtgctct | 540 |
| ctgatgcaag gttcaactct ccctaggagg tctggagccg caggtgctgc agtcaaagga | 600 |
| gttggaacaa tggtgatgga attggtcaga atgatcaaac gtgggatcaa tgatcggaac | 660 |
| ttctggaggg gtgagaatgg acgaaaaaca agaattgctt atgaaagaat gtgcaacatt | 720 |
| ctcaaaggga aatttcaaac tgctgcacaa aaagcaatga tggatcaagt gagagagagc | 780 |
| cggaacccag ggaatgctga gttcgaagat ctcacttttc tagcacggtc tgcactcata | 840 |
| ttgagagggt cggttgctca caagtcctgc ctgcctgcct gtgtgtatgg acctgccgta | 900 |
| gccagtgggt acgactttga aagggaggga tactctctag tcggaataga cccttttcaga | 960 |
| ctgcttcaaa acagccaagt gtacagccta atcagaccaa atgagaatcc agcacacaag | 1020 |
| agtcaactgg tgtggatggc atgccattct gccgcatttg aagatctaag agtattaagc | 1080 |
| ttcatcaaag ggacgaaggt gctcccaaga gggaagcttt ccactagagg agttcaaatt | 1140 |

| | |
|---|---|
| gcttccaatg aaaatatgga gactatggaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccatt | 1320 |
| atggcagcat tcaatgggaa tacagagggg agaaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat accttgttt | 1560 |
| ctact | 1565 |

<210> SEQ ID NO 5
<211> LENGTH: 1027
<212> TYPE: DNA
<213> ORGANISM: Artificial Sequence
<220> FEATURE:
<223> OTHER INFORMATION: A synthetic oligonucleotide

<400> SEQUENCE: 5

| | |
|---|---|
| agcaaaagca ggtagatatt gaaagatgag tcttctaacc gaggtcgaaa cgtacgtact | 60 |
| ctctatcatc ccgtcaggcc ccctcaaagc cgagatcgca cagagacttg aagatgtctt | 120 |
| tgcaggaaag aacaccgatc ttgaggttct catggaatgg ctaaagacaa gaccaatcct | 180 |
| gtcacctctg actaagggga ttttaggatt tgtgttcacg ctcaccgtgc ccagtgagcg | 240 |
| aggactgcag cgtagacgct ttgtccaaaa tgcccttaat gggaacgggg atccaaataa | 300 |
| catggacaaa gcagttaaac tgtataggaa gctcaagagg gagataacat tccatggggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaatccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctagacaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cactattgcc gcaaatatca ttgggatctt gcacttgaca ttgtggattc | 840 |
| ttgatcgtct ttttttcaaa tgcatttacc gtcgctttaa atacggactg aaaggagggc | 900 |
| cttctacgga aggagtgcca aagtctatga gggaagaata tcgaaaggaa cagcagagtg | 960 |
| ctgtggatgc tgacgatggt cattttgtca gcatagagct ggagtaaaaa actaccttgt | 1020 |
| ttctact | 1027 |

<210> SEQ ID NO 6
<211> LENGTH: 890
<212> TYPE: DNA
<213> ORGANISM: Artificial Sequence
<220> FEATURE:
<223> OTHER INFORMATION: A synthetic oligonucleotide

<400> SEQUENCE: 6

| | |
|---|---|
| agcaaaagca gggtgacaaa aacataatgg atccaaacac tgtgtcaagc tttcaggtag | 60 |
| attgctttct ttggcatgtc cgcaaacgag ttgcagacca agaactaggc gatgccccat | 120 |
| tccttgatcg gcttcgccga gatcagaaat ccctaagagg aagggggcagt actctcggtc | 180 |
| tggacatcaa gacagccaca cgtgctggaa agcagatagt ggagcggatt ctgaaagaag | 240 |

| | |
|---|---|
| aatccgatga ggcacttaaa atgaccatgg cctctgtacc tgcgtcgcgt tacctaactg | 300 |
| acatgactct tgaggaaatg tcaagggact ggtccatgct catacccaag cagaaagtgg | 360 |
| caggccctct ttgtatcaga atggaccagg cgatcatgga taagaacatc atactgaaag | 420 |
| cgaacttcag tgtgattttt gaccggctgg agactctaat attgctaagg ctttcaccg | 480 |
| aagagggagc aattgttggc gaaatttcac cattgccttc tcttccagga catactgctg | 540 |
| aggatgtcaa aaatgcagtt ggagtcctca tcggaggact gaatggaat gataacacag | 600 |
| ttcgagtctc tgaaactcta cagagattcg cttggagaag cagtaatgag aatgggagac | 660 |
| ctccactcac tccaaaacag aaacgagaaa tggcgggaac aattaggtca gaagtttgaa | 720 |
| gaaataagat ggttgattga agaagtgaga cacaaactga agataacaga gaatagtttt | 780 |
| gagcaaataa catttatgca agccttacat ctattgcttg aagtggagca agagataaga | 840 |
| actttctcgt ttcagcttat ttagtactaa aaaacaccct tgtttctact | 890 |

<210> SEQ ID NO 7
<211> LENGTH: 1775
<212> TYPE: DNA
<213> ORGANISM: Artificial Sequence
<220> FEATURE:
<223> OTHER INFORMATION: A synthetic oligonucleotide

<400> SEQUENCE: 7

| | |
|---|---|
| agcaaaagca ggggaaaata aaacaacca aaatgaaggc aaacctactg gtcctgttat | 60 |
| gtgcacttgc agctgcagat gcagacacaa tatgtatagg ctaccatgcg aacaattcaa | 120 |
| ccgacactgt tgacacagta ctcgagaaga atgtgacagt gacacactct gttaacctgc | 180 |
| tcgaagacag ccacaacgga aaactatgta gattaaaagg aatagcccca ctacaattgg | 240 |
| ggaaatgtaa catcgccgga tggctcttgg gaaacccaga atgcgaccca ctgcttccag | 300 |
| tgagatcatg gtcctacatt gtagaaacac caaactctga gaatggaata tgttatccag | 360 |
| gagatttcat cgactatgag gagctgaggg agcaattgag ctcagtgtca tcattcgaaa | 420 |
| gattcgaaat atttcccaaa gaaagctcat ggcccaacca caacacaaac ggagtaacgg | 480 |
| cagcatgctc ccatgagggg aaaagcagtt tttacagaaa tttgctatgg ctgacggaga | 540 |
| aggagggctc atacccaaag ctgaaaaatt cttatgtgaa caaaaaaggg aaagaagtcc | 600 |
| ttgtactgtg gggtattcat cacccgccta acagtaagga caacagaat ctctatcaga | 660 |
| atgaaaatgc ttatgtctct gtagtgactt caaattataa caggagattt accccggaaa | 720 |
| tagcagaaag acccaaagta agagatcaag ctgggaggat gaactattac tggaccttgc | 780 |
| taaaacccgg agacacaata atatttgagg caaatggaaa tctaatagca ccaatgtatg | 840 |
| ctttcgcact gagtagaggc tttgggtccg gcatcatcac ctcaaacgca tcaatgcatg | 900 |
| agtgtaacac gaagtgtcaa acacccctgg gagctataaa cagcagtctc ccttaccaga | 960 |
| atatacaccc agtcacaata ggagagtgcc caaaatacgt caggagtgcc aaattgagga | 1020 |
| tggttacagg actaaggaac attccgtcca ttcaatccag aggtctattt ggagccattg | 1080 |
| ccggttttat tgaaggggga tggactggaa tgatagatgg atggtatggt tatcatcatc | 1140 |
| agaatgaaca gggatcaggc tatgcagcgg atcaaaaaag cacacaaaat gccattaacg | 1200 |
| ggattacaaa caaggtgaac actgttatcg agaaaatgaa cattcaattc acagctgtgg | 1260 |
| gtaaagaatt caacaaatta gaaaaaagga tggaaatttt aataaaaaaa gttgatgatg | 1320 |
| gatttctgga catttggaca tataatgcag aattgttagt tctactggaa aatgaaagga | 1380 |

```
ctctggattt ccatgactca aatgtgaaga atctgtatga gaaagtaaaa agccaattaa      1440
agaataatgc caaagaaatc ggaaatggat gttttgagtt ctaccacaag tgtgacaatg      1500
aatgcatgga aagtgtaaga aatgggactt atgattatcc caaatattca gaagagtcaa      1560
agttgaacag ggaaaaggta gatggagtga aattggaatc aatggggatc tatcagattc      1620
tggcgatcta ctcaactgtc gccagttcac tggtgctttt ggtctccctg ggggcaatca      1680
gtttctggat gtgttctaat ggatctttgc agtgcagaat atgcatctga gattagaatt      1740
tcagagatat gaggaaaaac accettgttt ctact                                1775
```

<210> SEQ ID NO 8
<211> LENGTH: 1413
<212> TYPE: DNA
<213> ORGANISM: Artificial Sequence
<220> FEATURE:
<223> OTHER INFORMATION: A synthetic oligonucleotide

<400> SEQUENCE: 8

```
agcaaaagca ggggtttaaa atgaatccaa atcagaaaat aataaccatt ggatcaatct        60
gtctggtagt cggactaatt agcctaatat tgcaaatagg gaatataatc tcaatatgga       120
ttagccattc aattcaaact ggaagtcaaa accatactgg aatatgcaac caaacatca        180 ttacctataa aaatagcacc tgggtaaagg acacaacttc agtgatatta accggcaatt       240
catctctttg tcccatccgt gggtgggcta tatacagcaa agacaatagc ataagaattg       300
gttccaaagg agacgttttt gtcataagag agccctttat ttcatgttct cacttggaat       360
gcaggacctt ttttctgacc caaggtgcct tactgaatga caagcattca gtgggactg        420 ttaaggacag aagcccttat agggccttaa tgagctgccc tgtcggtgaa gctccgtccc       480
cgtacaattc aagatttgaa tcggttgctt ggtcagcaag tgcatgtcat gatggcatgg       540
gctggctaac aatcggaatt tcaggtccag ataatggagc agtggctgta ttaaaataca       600
acggcataat aactgaaacc ataaaaagtt ggaggaagaa aatattgagg acacaagagt       660
ctgaatgtgc ctgtgtaaat ggttcatgtt ttactataat gactgatggc ccgagtgatg       720
ggctggcctc gtacaaaatt ttcaagatcg aaaaggggaa ggttactaaa tcaatagagt       780
tgaatgcacc taattctcac tatgaggaat gttcctgtta ccctgatacc ggcaaagtga       840
tgtgtgtgtg cagagacaat tggcatggtt cgaaccggcc atgggtgtct ttcgatcaaa       900
acctggatta tcaaatagga tacatctgca gtggggtttt cggtgacaac ccgcgtcccg       960
aagatggaac aggcagctgt ggtccagtgt atgttgatgg agcaaacgga gtaaagggat      1020
tttcatatag gtatggtaat ggtgtttgga taggaaggac caaaagtcac agttccagac      1080
atgggtttga gatgatttgg gatcctaatg gatggacaga gactgatagt aagttctctg      1140
tgaggcaaga tgttgtggca atgactgatt ggtcagggta tagcggaagt ttcgttcaac      1200
atcctgagct gacagggcta gactgtatga ggccgtgctt ctgggttgaa ttaatcaggg      1260
gacgacctaa agaaaaaaca atctggacta gtgcgagcag catttctttt tgtggcgtga      1320
atagtgatac tgtagattgg tcttggccag acggtgctga gttgccattc agcattgaca      1380
agtagtctgt tcaaaaaact ccttgtttct act                                  1413
```

<210> SEQ ID NO 9
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 9
atggaaagaa taaaagaact acga                                          24

<210> SEQ ID NO 10
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 10

| | | | | | |
|---|---|---|---|---|---|
| agcgaaagca | ggtcaattat | attcaatatg | gaaagaataa | agaactaag | aaatctaatg | 60 |
| tcgcagtctc | gcacccgcga | gatactcaca | aaaccaccg | tggaccatat | ggccataatc | 120 |
| aagaagtaca | catcaggaag | acaggagaag | aacccagcac | ttaggatgaa | atggatgatg | 180 |
| gcaatgaaat | atccaattac | agcagacaag | aggataacgg | aaatgattcc | tgagagaaat | 240 |
| gagcaaggac | aaactttatg | gagtaaaatg | aatgatgccg | gatcagaccg | agtgatggta | 300 |
| tcacctctgg | ctgtgacatg | gtggaatagg | aatggaccaa | tgacaaatac | agttcattat | 360 |
| ccaaaaatct | acaaaactta | ttttgaaaga | gtcgaaaggc | taaagcatgg | aacctttggc | 420 |
| cctgtccatt | ttagaaacca | agtcaaaata | cgtcggagag | ttgacataaa | tcctggtcat | 480 |
| gcagatctca | gtgccaagga | ggcacaggat | gtaatcatgg | aagttgtttt | ccctaacgaa | 540 |
| gtgggagcca | ggatactaac | atcggaatcg | caactaacga | taaccaaaga | gaagaaagaa | 600 |
| gaactccagg | attgcaaaat | ttctcctttg | atggttgcat | acatgttgga | gagagaactg | 660 |
| gtccgcaaaa | cgagattcct | cccagtggct | ggtggaacaa | gcagtgtgta | cattgaagtg | 720 |
| ttgcatttga | ctcaaggaac | atgctgggaa | cagatgtata | ctccaggagg | ggaagtgaag | 780 |
| aatgatgatg | ttgatcaaag | cttgattatt | gctgctagga | acatagtgag | aagagctgca | 840 |
| gtatcagcag | acccactagc | atctttattg | gagatgtgcc | acagcacaca | gattggtgga | 900 |
| attaggatgg | tagacatcct | taagcagaac | ccaacagaag | agcaagccgt | ggatatatgc | 960 |
| aaggctgcaa | tgggactgag | aattagctca | tccttcagtt | ttggtggatt | cacatttaag | 1020 |
| agaacaagcg | gatcatcagt | caagagagag | gaagaggtgc | ttacgggcaa | tcttcaaaca | 1080 |
| ttgaagataa | gagtgcatga | gggatctgaa | gagttcacaa | tggttgggag | aagagcaaca | 1140 |
| gccatactca | gaaaagcaac | caggagattg | attcagctga | tagtgagtgg | gagagacgaa | 1200 |
| cagtcgattg | ccgaagcaat | aattgtggcc | atggtatttt | cacaagagga | ttgtatgata | 1260 |
| aaagcagtta | gaggtgatct | gaatttcgtc | aataggcga | atcagcgact | gaatcctatg | 1320 |
| catcaacttt | taagacattt | tcagaaggat | gcgaaagtgc | tttttcaaaa | ttggggagtt | 1380 |
| gaacctatcg | acaatgtgat | gggaatgatt | gggatattgc | ccgacatgac | tccaagcatc | 1440 |
| gagatgtcaa | tgagaggagt | gagaatcagc | aaaatgggtg | tagatgagta | ctccagcacg | 1500 |
| gagagggtag | tggtgagcat | tgaccggttc | ttgagagtca | gggaccaacg | aggaaatgta | 1560 |
| ctactgtctc | ccgaggaggt | cagtgaaaca | cagggaacag | agaaactgac | aataacttac | 1620 |
| tcatcgtcaa | tgatgtggga | gattaatggt | cctgaatcag | tgttggtcaa | tacctatcaa | 1680 |
| tggatcatca | gaaactggga | aactgttaaa | attcagtggt | cccagaaccc | tacaatgcta | 1740 |
| tacaataaaa | tggaatttga | accatttcag | tctttagtac | ctaaggccat | tagaggccaa | 1800 |
| tacagtgggt | ttgtaagaac | tctgttccaa | caaatgaggg | atgtgcttgg | gacatttgat | 1860 |
| accgcacaga | taataaaact | tcttccccttc | gcagccgctc | caccaaagca | aagtagaatg | 1920 |

| | |
|---|---|
| cagttctcct catttactgt gaatgtgagg ggatcaggaa tgagaatact tgtaaggggc | 1980 |
| aattctcctg tattcaacta caacaaggcc acgaagagac tcacagttct cggaaaggat | 2040 |
| gctggcactt taaccgaaga cccagatgaa ggcacagctg gagtggagtc cgctgttctg | 2100 |
| agggggattcc tcattctggg caaagaagac aggagatatg gccagcatt aagcatcaat | 2160 |
| gaactgagca accttgcgaa aggagagaag gctaatgtgc taattgggca aggagacgtg | 2220 |
| gtgttggtaa tgaaacgaaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 11
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 11

| | |
|---|---|
| agcgaaagca ggcaaaccat ttgaatggat gtcaatccga ccttactttt cttaaaagtg | 60 |
| ccagcacaaa atgctataag cacaactttc ccttataccg agaccctcc ttacagccat | 120 |
| gggacaggaa caggatacac catggatact gtcaacagga cacatcagta ctcagaaaag | 180 |
| ggaagatgga caacaaacac cgaaactgga gcaccgcaac tcaacccgat tgatgggcca | 240 |
| ctgccagaag acaatgaacc aagtggttat gcccaaacag attgtgtatt ggaagcaatg | 300 |
| gctttccttg aggaatccca tcctggtatt tttgaaaact cgtgtattga acgatggag | 360 |
| gttgttcagc aaacacgagt agacaagctg acacaaggcc gacagaccta tgactggact | 420 |
| ttaaatagaa accagcctgc tgcaacagca ttggccaaca atagaagt gttcagatca | 480 |
| aatggcctca cggccaatga gtcaggaagg ctcatagact tccttaagga tgtaatggag | 540 |
| tcaatgaaaa aagaagaaat ggggatcaca actcattttc agagaaagag acgggtgaga | 600 |
| gacaatatga ctaagaaaat gataacacag agaacaatag gtaaaaggaa acagagattg | 660 |
| aacaaagggg gttatctaat tagagcattg accctgaaca caatgaccaa agatgctgag | 720 |
| agagggaagc taaaacggag agcaattgca accccaggga tgcaaataag ggggtttgta | 780 |
| tactttgttg agacactggc aaggagtata tgtgagaaac ttgaacaatc agggttgcca | 840 |
| gttggaggca atgagaagaa agcaaagttg gcaaatgttg taaggaagat gatgaccaat | 900 |
| tctcaggaca ccgaactttc tttcaccatc actggagata acaccaaatg gaacgaaaat | 960 |
| cagaatcctc ggatgttttt ggccatgatc acatatatga ccagaaatca gcccgaatgg | 1020 |
| ttcagaaatg ttctaagtat tgctccaata atgttctcaa acaaaatggc gagactggga | 1080 |
| aaggggtata tgtttgagag caagagtatg aaacttagaa ctcaaatacc tgcagaaatg | 1140 |
| ctagcaagca ttgatttgaa atatttcaat gattcaacaa gaagaagat tgaaaaaatc | 1200 |
| cgaccgctct aatagaggg gactgcatca ttgagccctg aatgatgat gggcatgttc | 1260 |
| aatatgttaa gcactgtatt aggcgtctcc atcctgaatc ttggacaaaa gagatacacc | 1320 |
| aagactactt actggtggga tggtcttcaa tcctctgacg attttgctct gattgtgaat | 1380 |
| gcacccaatc atgaagggat tcaagccgga gtcgacaggt tttatcgaac ctgtaagcta | 1440 |
| cttggaatca atatgagcaa gaaaaagtct tacataaaca gaacaggtac atttgaattc | 1500 |
| acaagttttt tctatcgtta tgggtttgtt gccaatttca gcatggagct tcccagtttt | 1560 |
| ggggtgtctg gatcaacga gtcagcggac atgagtattg gagttactgt catcaaaaac | 1620 |

| | | | | |
|---|---|---|---|---|
| aatatgataa | acaatgatct | tggtccagca | acagctcaaa | tggcccttca gttgttcatc | 1680 |
| aaagattaca | ggtacacgta | ccgatgccat | agaggtgaca | cacaaataca aacccgaaga | 1740 |
| tcatttgaaa | taaagaaact | gtgggagcaa | acccgttcca | aagctggact gctggtctcc | 1800 |
| gacggaggcc | caaatttata | caacattaga | aatctccaca | ttcctgaagt ctgcctaaaa | 1860 |
| tgggaattga | tggatgagga | ttaccagggg | cgtttatgca | acccactgaa cccatttgtc | 1920 |
| agccataaag | aaattgaatc | aatgaacaat | gcagtgatga | tgccagcaca tggtccagcc | 1980 |
| aaaaacatgg | agtatgatgc | tgttgcaaca | acacactcct | ggatccccaa agaaatcga | 2040 |
| tccatcttga | atacaagtca | aagaggagta | cttgaagatg | aacaaatgta ccaaaggtgc | 2100 |
| tgcaatttat | ttgaaaaatt | cttccccagc | agttcataca | gaagaccagt cgggatatcc | 2160 |
| agtatggtgg | aggctatggt | ttccagagcc | cgaattgatg | cacggattga tttcgaatct | 2220 |
| ggaaggataa | agaaagaaga | gttcactgag | atcatgaaga | tctgttccac cattgaagag | 2280 |
| ctcagacggc | aaaaatagtg | aatttagctt | gtccttcatg | aaaaaatgcc ttgtttctac | 2340 |
| t | | | | | 2341 |

<210> SEQ ID NO 12
<211> LENGTH: 2233
<212> TYPE: DNA
<213> ORGANISM: Artificial Sequence
<220> FEATURE:
<223> OTHER INFORMATION: A synthetic oligonucleotide

<400> SEQUENCE: 12

| | | | | | |
|---|---|---|---|---|---|
| agcgaaagca | ggtactgatt | caaaatggaa | gattttgtgc | gacaatgctt caatccgatg | 60 |
| attgtcgagc | ttgcggaaaa | aacaatgaaa | gagtatgggg | aggacctgaa atcgaaaca | 120 |
| aacaaatttg | cagcaatatg | cactcacttg | gaagtatgct | tcatgtattc agatttccac | 180 |
| ttcatcaatg | agcaaggcga | gtcaataatc | gtagaacttg | gtgatccaa tgcacttttg | 240 |
| aagcacagat | ttgaaataat | cgagggaaga | gatcgcacaa | tggcctggac agtagtaaac | 300 |
| agtatttgca | acactacagg | ggctgagaaa | ccaaagtttc | taccagattt gtatgattac | 360 |
| aaggaaaata | gattcatcga | aattggagta | acaaggagaa | aagttcacat atactatctg | 420 |
| gaaaaggcca | ataaaattaa | atctgagaaa | acacacatcc | acattttctc gttcactggg | 480 |
| gaagaaatgg | ccacaaggc | cgactacact | ctcgatgaag | aaagcagggc taggatcaaa | 540 |
| accaggctat | tcaccataag | acaagaaatg | gccagcagag | gcctctggga ttcctttcgt | 600 |
| cagtccgaga | gaggagaaga | gacaattgaa | gaaaggtttg | aaatcacagg aacaatgcgc | 660 |
| aagcttgccg | accaaagtct | cccgccgaac | ttctccagcc | ttgaaaattt tagagcctat | 720 |
| gtggatggat | tcgaaccgaa | cggctacatt | gagggcaagc | tgtctcaaat gtccaaagaa | 780 |
| gtaaatgcta | gaattgaacc | ttttttgaaa | acaacaccac | gaccacttag acttccgaat | 840 |
| gggcctccct | gttctcagcg | gtccaaattc | ctgctgatgg | atgccttaaa attaagcatt | 900 |
| gaggacccaa | gtcatgaagg | agagggaata | ccgctatatg | atgcaatcaa atgcatgaga | 960 |
| acattctttg | gatggaagga | acccaatgtt | gttaaaccac acgaaaaggg aataaatcca | 1020 |
| aattatcttc | tgtcatggaa | gcaagtactg | gcagaactgc | aggacattga gaatgaggag | 1080 |
| aaaattccaa | agactaaaaa | tatgaaaaaa | acaagtcagc | taaagtgggc acttggtgag | 1140 |
| aacatggcac | cagaaaaggt | agactttgac | gactgtaaag | atgtaggtga tttgaagcaa | 1200 |
| tatgatagtg | atgaaccaga | attgaggtcg | cttgcaagtt | ggattcagaa tgagttcaac | 1260 |

| | |
|---|---|
| aaggcatgcg aactgacaga ttcaagctgg atagagcttg atgagattgg agaagatgtg | 1320 |
| gctccaattg aacacattgc aagcatgaga aggaattatt tcacatcaga ggtgtctcac | 1380 |
| tgcagagcca cagaatacat aatgaagggg gtgtacatca atactgcctt acttaatgca | 1440 |
| tcttgtgcag caatggatga tttccaatta attccaatga taagcaagtg tagaactaag | 1500 |
| gagggaaggc gaaagaccaa cttgtatggt ttcatcataa aaggaagatc ccacttaagg | 1560 |
| aatgacaccg acgtggtaaa cttttgtgagc atggagtttt ctctcactga cccaagactt | 1620 |
| gaaccacaca aatgggagaa gtactgtgtt cttgagatag agatatgct tctaagaagt | 1680 |
| gccataggcc aggtttcaag gcccatgttc ttgtatgtga ggacaaatgg aacctcaaaa | 1740 |
| attaaaatga atggggaat ggagatgagg cgttgtctcc tccagtcact tcaacaaatt | 1800 |
| gagagtatga ttgaagctga gtcctctgtc aaagagaaag acatgaccaa agagttcttt | 1860 |
| gagaacaaat cagaaacatg gcccattgga gagtctccca aggagtggga ggaaagttcc | 1920 |
| attgggaagg tctgcaggac tttattagca aagtcggtat taacagctt gtatgcatct | 1980 |
| ccacaactag aaggattttc agctgaatca agaaaactgc ttcttatcgt tcaggctctt | 2040 |
| agggacaatc tggaacctgg gacctttgat cttgggggc tatatgaagc aattgaggag | 2100 |
| tgcctaatta atgatccctg ggttttgctt aatgcttctt ggttcaactc cttccttaca | 2160 |
| catgcattga gttagttgtg gcagtgctac tatttgctat ccatactgtc caaaaaagta | 2220 |
| ccttgtttct act | 2233 |

<210> SEQ ID NO 13
<211> LENGTH: 1565
<212> TYPE: DNA
<213> ORGANISM: Artificial Sequence
<220> FEATURE:
<223> OTHER INFORMATION: A synthetic oligonucleotide

<400> SEQUENCE: 13

| | |
|---|---|
| agcaaaagca gggtagataa tcactcactg agtgacatca aaatcatggc gtcccaaggc | 60 |
| accaaacggt cttacgaaca gatggagact gatggagaac gccagaatgc cactgaaatc | 120 |
| agagcatccg tcggaaaaat gattggtgga attggacgat tctacatcca aatgtgcaca | 180 |
| gaacttaaac tcagtgatta tgagggacgg ttgatccaaa acagcttaac aatagagaga | 240 |
| atggtgctct ctgcttttga cgaaggaga aataaatacc tggaagaaca tcccagtgcg | 300 |
| gggaaagatc ctaagaaaac tggaggacct atatacagaa gagtaaacgg aaagtggatg | 360 |
| agagaactca tcctttatga caagaagaa ataaggcgaa tctggcgcca agctaataat | 420 |
| ggtgacgatg caacggctgg tctgactcac atgatgatct ggcattccaa tttgaatgat | 480 |
| gcaacttatc agaggacaag ggctcttgtt cgcaccggaa tggatcccag gatgtgctct | 540 |
| ctgatgcaag gttcaactct ccctaggagg tctggagccg caggtgctgc agtcaaagga | 600 |
| gttgaacaa tggtgatgga attggtcagg atgatcaaac gtgggatcaa tgatcggaac | 660 |
| ttctggaggg gtgagaatgg acgaaaaaca agaattgctt atgaaagaat gtgcaacatt | 720 |
| ctcaaaggga aatttcaaac tgctgcacaa aaagcaatga tggatcaagt gagagagagc | 780 |
| cggaacccag gaatgctga gttcgaagat ctcactttc tagcacggtc tgcactcata | 840 |
| ttgagagggt cggttgctca caagtcctgc ctgcctgcct gtgtgtatgg acctgccgta | 900 |
| gccagtgggt acgactttga aagagggga tactctctag tcggaataga cccttttcaga | 960 |
| ctgcttcaaa acagccaagt gtacagccta atcagaccaa atgagaatcc agcacacaag | 1020 |
| agtcaactgg tgtggatggc atgccattct gccgcatttg aagatctaag agtattgagc | 1080 |

| | |
|---|---|
| ttcatcaaag ggacgaaggt ggtcccaaga gggaagcttt ccactagagg agttcaaatt | 1140 |
| gcttccaatg aaaatatgga gactatggaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccgtt | 1320 |
| atggcagcat tcactgggaa tacagagggg agaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat acccttgttt | 1560 |
| ctact | 1565 |

<210> SEQ ID NO 14
<211> LENGTH: 1027
<212> TYPE: DNA
<213> ORGANISM: Artificial Sequence
<220> FEATURE:
<223> OTHER INFORMATION: A synthetic oligonucleotide

<400> SEQUENCE: 14

| | |
|---|---|
| agcaaaagca ggtagatatt gaaagatgag tcttctaacc gaggtcgaaa cgtacgttct | 60 |
| ctctatcatc ccgtcaggcc ccctcaaagc cgagatcgca cagagacttg aagatgtctt | 120 |
| tgcagggaag aacaccgatc ttgaggttct catggaatgg ctaaagacaa gaccaatcct | 180 |
| gtcacctctg actaagggga ttttaggatt tgtgttcacg ctcaccgtgc ccagtgagcg | 240 |
| aggactgcag cgtagacgct ttgtccaaaa tgcccttaat gggaacgggg atccaaataa | 300 |
| catggacaaa gcagttaaac tgtataggaa gctcaagagg gagataacat tccatggggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaacccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctaggcaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cgctattgcc gcaaatatca ttgggatctt gcacttgata ttgtggattc | 840 |
| ttgatcgtct ttttttcaaa tgcatttacc gtcgctttaa atacgactg aaaggagggc | 900 |
| cttctacgga aggagtgcca aagtctatga gggaagaata tcgaaaggaa cagcagagtg | 960 |
| ctgtggatgc tgacgatggt catttgtca gcatagagct ggagtaaaaa actaccttgt | 1020 |
| ttctact | 1027 |

<210> SEQ ID NO 15
<211> LENGTH: 890
<212> TYPE: DNA
<213> ORGANISM: Artificial Sequence
<220> FEATURE:
<223> OTHER INFORMATION: A synthetic oligonucleotide

<400> SEQUENCE: 15

| | |
|---|---|
| agcaaaagca gggtgacaaa gacataatgg atccaaacac tgtgtcaagc tttcaggtag | 60 |
| attgctttct ttggcatgtc cgcaaacgag ttgcagacca agaactaggt gatgccccat | 120 |

```
tccttgatcg gcttcgccga gatcagaaat ccctaagagg aagggggcagc actcttggtc    180 tggacatcga gacagccaca cgtgctggaa agcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct ttgtatcaga atggaccagg cgatcatgga taaaaacatc atactgaaag    420
cgaacttcag tgtgattttt gaccggctgg agactctaat attgctaagg gctttcaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga aggtaacaga gaatagtttt    780
gagcaaataa catttatgca agccttacat ctattgcttg aagtggagca agagataaga    840
actttctcat ttcagcttat ttaataataa aaaacaccct tgtttctact                890

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16
gccacaatta ttgcttcggc                                                  20
```

INFLUENZA VIRUSES WITH MUTANT PB2 GENE SEGMENT AS LIVE ATTENUATED VACCINES

CROSS-REFERENCE TO RELATED APPLICATIONS

This application is a divisional of U.S. application Ser. No. 16/694,748, filed Nov. 25, 2019, which is a continuation of U.S. application Ser. No. 14/699,213, filed Apr. 29, 2015, which is a continuation of U.S. application Ser. No. 13/594,611, filed Aug. 24, 2012, which claims the benefit of the filing date of U.S. application Ser. No. 61/527,935, filed on Aug. 26, 2011, the disclosure of which are incorporated by reference herein.

STATEMENT OF GOVERNMENT RIGHTS

This invention was made with government support under AI047446 awarded by the National Institutes of Health. The government has certain rights in the invention.

BACKGROUND

Influenza viruses instigate annual global epidemics and sporadic pandemics. Influenza A viruses annually cause epidemics characterized by a contagious respiratory illness, mild to severe fever, and in some instances death (Palese & Shaw, 2007). Vaccine and curative antiviral research that focuses on the prevention and control of this potentially fatal virus is warranted to avoid considerable strains on health care systems and the global economy. Intensive research has led to the discovery of therapeutic interventions to combat influenza infections; however, due to the virus's error-prone polymerase, the hemagglutinin (HA) and neuraminidase (NA) influenza viral proteins are subject to point mutations, known as antigenic or genetic drift (Lin et al., 2004), that allow the virus to escape host immune responses or result in some types of drug resistance (Moss et al., 2010). Vaccination is one of the most effective means of preventing influenza-associated morbidity and mortality.

Currently available therapeutic and prophylactic interventions include two types of vaccines (i.e., inactivated and live vaccines) and two classes of antivirals (i.e., M2 ion channel blockers, such as amantadine and rimantadine, and neuraminidase (NA)-inhibitors, such as oseltamivir and zanamivir) (Davies et al., 1964; Hayden, 2001). Nonetheless, seasonal influenza is a contagious disease with one of the highest impacts on public health epidemiology. Further, during the 2009-2010 influenza season, a novel influenza A virus strain, the 2009 HiN1 pandemic virus, emerged and spread worldwide, causing the first influenza pandemic in 40 years with a considerable impact on global health and economics (http://www.cdc.gov/flu/about/disease/index-.htm). In the United States alone, an estimated 61 million H1N1 cases, including 274,000 hospitalizations and 12,470 deaths were reported (http://www.cdc.gov/flu/about/season/index.htm).

Due to an underdeveloped or impaired immune system, young, elderly or immunocompromised individuals are especially susceptible to infectious diseases such as influenza. Several studies conducted in Japan suggested that high rates of influenza vaccination among school age children provided protection, reduced community-wide effects, and reduced incidence and mortality of older persons from influenza infection; the 2001 study reported the prevention of approximately 37,000 to 49,000 deaths per year and the rise of excess mortality rates when vaccination of schoolchildren was discontinued (Reichert et al., 2001).

Currently available inactivated influenza vaccines are associated with short protection periods and limited efficacy, especially in young children and the elderly. Due to the inability to effectively elicit cell-mediated immunity, inactivated vaccines are generally less immunogenic, and hence less potent, than live attenuated vaccines, which are approved for use in a limited number of countries such as the Unites States. Intranasally administered live attenuated viruses are considered superior to inactivated vaccines for children because they elicit robust mucosal immunity and humoral and cellular immune responses coupled with long-lasting protective efficacy (Cox et al., 2004). However, live attenuated vaccines are currently licensed only for individuals aged 2 through 49 who lack chronic medical conditions and who are not pregnant or immunocompromised, even though licensed live attenuated influenza viruses are considered safe and stable with respect to the underlying risk of the emergence of revertant viruses.

Parenterally administered inactivated vaccines are also associated with adverse or anaphylactic reactions due to virus propagation in embryonated eggs, and the propensity of egg proteins in these vaccines to induce allergies by inducing hypersensitivity reactions in susceptible hosts. A prerequisite for successful egg-based vaccine propagation is the selection of variants adapted to embryonated chicken eggs; a criterion that may no longer match the antigenicity of circulating viruses. A further complication includes the possible depletion of chicken stocks in light of a looming zoonotic outbreak of avian influenza pandemic, which could compromise mass vaccine production.

Live attenuated influenza vaccine (LAIV) was originally derived by cold adaptation of an influenza type A strain (A/Ann Arbor/6/60 H2N2) and a type B strain (B/Ann Arbor/1/66) by serial passage at sequentially lower temperatures in specific pathogen-free primary chick kidney cells (Maassab et al., 1968). During this process, the viruses acquired multiple mutations in internal protein gene segments (i.e., genes encoding "internal" nonglycosylated proteins) that produced the cold-adapted (ca), temperature sensitive (ts), and attenuated (att) phenotype of the master donor viruses (MDVs). The MDVs represent the LAIV genetic backbone that is updated annually with hemagglutinin (HA) and neuraminidase (NA) genes from contemporary influenza viruses to produce the annual trivalent formulation. Thus, each of the three influenza virus strains is a 6:2 genetic reassortant virus, containing six internal gene segments from ca, is, and all MDVs and two gene segments (encoding the HA and NA proteins) from a wild-type influenza virus that is selected annually by the World Health Organization and the U.S. Public Health Service.

Because multiple loci in several genes control the ca, ts, and att phenotypes of LAIV vaccine viruses, it is highly improbable that LAIV would lose these phenotypes as a result of reversion (Kemble et al., 2003; Murphy et al., 2002). Given the error rate of $10^{-4}$ to $10^{-5}$ misincorporations per nucleotide position during influenza virus replication and the fact that at least five point mutations are responsible for the attenuated properties of each MDV (Murphy et al., 2002; Smith et al., 1987), the probability of a LAIV vaccine virus reverting to wild-type influenza, with mutations in the five attenuating loci, would be one in at least $10^{20}$ replication cycles. In one study of 135 vaccine strains recovered from young vaccinated children, no evidence of reversion was observed (Vesikari et al., 2006).

The first nasally administered LIAV was approved for use in the United States in 2003, marketed in the United States as FluMist® [Influenza Virus Vaccine Live, Intranasal]). Although LAIV vaccine viruses were originally generated using classical reassortment, in 2008 the process transitioned to reverse genetics technology. The genetic reassortant viruses therein are prepared using reverse genetics technology in cell culture, a technique whereby influenza viruses can be generated from DNA plasmids containing influenza genes. Three vaccine strains are formulated together to produce a trivalent LAIV vaccine in single-dose sprayers. The intranasal LAIV is currently approved in the United States for use in individuals 2-49 years of age.

Live attenuated viruses are considered superior to inactivated vaccines due to their ability to elicit both humoral and cellular immune responses and hence confer advanced protection in infants and young children. In particular, intranasally administered live attenuated vaccines elicit robust mucosal immunity and cellular responses coupled with longer lasting protective efficacies (Cox et al., 2004). Live attenuated influenza vaccine viruses replicate primarily in the ciliated epithelial cells of the nasopharyngeal mucosa to induce immune responses (via mucosal immunoglobulin IgA, serum IgG antibodies, and cellular immunity), but LAIV viruses do not replicate well at the warmer temperatures found in the lower airways and lung (Murphy et al., 2002; Gruber et al., 2002). In addition, there are several advantages of a cell-based (e.g., cells employed to amplify virus after virus generation using reverse genetics) alternative over the conventional egg-based vaccine propagation system. Cell-based vaccine studies have demonstrated significant advantages over egg-based vaccinology in that they are a more economically feasible, rapid, and less labor-intensive alternative whose manufacturing capacity can be readily scaled-up in proportion to demand in the context of a pandemic. Moreover, genetic engineering of viruses through recombinant DNA-based technologies allows the exploitation of a virus' genetic parasitism, while disarming its pathogenic power. Viruses can be rendered replication-incompetent and non-pathogenic or manipulated to introduce and express a foreign gene in a receptive host.

SUMMARY OF THE INVENTION

The invention provides a recombinant biologically contained influenza virus that is useful to generate a multivalent vaccine, and satisfies safety concerns regarding pathogenicity or reversion, which virus optionally may stably express a foreign gene and so can be effectively traced and have its replication easily assessed. As disclosed hereinbelow, a PB2-knock-out (PB2-KO) influenza virus was generated that harbors a reporter gene, e.g., a fluorescent protein gene such as a GFP gene or a luciferase gene, in the coding region of its PB2 viral RNA (vRNA), where the replication of the virus was restricted to a cell line that stably expressed the PB2 protein. The reporter gene-encoding PB2 vRNA was stably incorporated into progeny viruses during replication in PB2-expressing cells, and the reporter gene was expressed in virus infected cells with no evidence of recombination between the recombinant PB2 vRNA and the PB2 protein mRNA. Further, the HA and NA genes of different virus strains were readily accommodated by the PB2-KO virus. The PB2-KO virus was used to establish an improved assay to screen neutralizing antibodies against influenza viruses by using reporter gene expression as an indicator of virus infection rather than observing cytopathic effect. These results indicate that the PB2-KO virus have the potential to be a valuable tool for basic and applied influenza virology research, and that may be applicable to other polymerase gene knock-out viruses, e.g., PA-KO viruses or PB1-KO viruses.

In one embodiment, the invention provides isolated infectious, biologically contained influenza virus that has a viral gene segment that does not comprise contiguous nucleic acid sequences corresponding to those encoding PB2 (a mutant PB2 viral gene segment), a protein which is one of the viral RNA polymerase subunits and is essential for virus replication. To prepare such a virus in cell culture, a cell line is employed that expresses PB2 in trans in combination with vectors for influenza virus vRNA production, but not one for a wild-type PB2 viral gene segment, and in one embodiment vectors for influenza virus mRNA protein production. The resulting virus is not competent to express PB2 after infection of cells that do not express PB2 in trans or are not infected with helper virus, which provides for a "biologically contained" virus. However, virions produced from cells that express PB2 in trains contain PB2. Such an infectious, biologically contained influenza virus with a mutant PB2 viral gene segment was generated in multiple cell lines that express PB2 in trans, such as PB2-expressing 293 human embryonic kidney (293), human lung adenocarcinoma epithelial (A549), or 2,6-linked sialyltransferase-overexpressing Madin-Darby canine kidney (MDCK) cells (AX4 cells), resulting in high virus titers of at least $10^4$, $10^5$, $10^6$, $10^7$ or $10^8$ PFU/mL, or more.

Vaccination is the primary means for prophylaxis against influenza infection. As disclosed herein, the PB2-KO virus replicated to high titers (>$10^8$ PFU/mL) in PB2-expressing but not in normal uninfected cells (cells that do not express PB2 in trans), accommodated HA and NA genes of a heterologous influenza virus), stably incorporated a reporter gene into progeny PB2-KO virions that was retained through sequential passages, and was attenuated in mice, suggesting its potential as a vaccine. Its ability to express antigens and its vaccine candidacy was tested in a murine model. Significantly higher levels of IgG and IgA antibodies were induced in sera, nasal washes and broncho-alveolar lavage samples from mice immunized with only one dose of PB2-KO (GFP) virus compared to inactivated influenza vaccine. All PB2-KO virus-treated mice survived challenge with various lethal doses of PR8. Limited replication of that virus occurs in vivo as the virus produced in cells that express PB2 in trans carries along a small amount of PB2 protein into the host cell which is subsequently infected (such as a host cell which does not itself express or comprise PB2 or comprise wild-type PB2 vRNA), thereby allowing for a limited amount (e.g., a round or so) of replication to occur but without a significant infectious process (for instance, amplification of virus titers of over about 1000). The limited replication of the KO virus in vivo allows for an immune response that provides for a more robust immune response than induced by conventional inactivated influenza vaccines. It is noteworthy that the immunized mice produce antibodies against the reporter, as determined by an immunofluorescence assay, suggesting that PB2-KO virus has the potency of a multivalent vaccine. The PB2-KO exhibited similar or better safety and efficacy profiles when compared to controls, and so holds promise for combating influenza virus infection.

In one embodiment, the invention provides an isolated infectious, biologically contained recombinant influenza virus comprising 8 gene segments including a PA viral gene segment, a PB1 viral gene segment, a mutant PB2 viral gene segment, a HA viral gene segment, a NA viral gene segment, a NP viral gene segment, a M (M1 and M2) viral gene segment, and a NS (NS1 and NS2) viral gene segment. In another embodiment, the invention provides an isolated infectious, biologically contained recombinant influenza virus comprising 8 gene segments including a PA viral gene segment, a PB1 viral gene segment, a mutant PB2 viral gene segment, a HA viral gene segment, a NA (NA and NB) viral gene segment, a NP viral gene segment, a M (M1 and BM2) viral gene segment, and a NS (NS1 and NS2) viral gene segment. In one embodiment, the infectious, biologically contained recombinant influenza virus has a M viral gene segment for M1 and M2. In one embodiment, the infectious, biologically contained recombinant influenza virus has a NA viral gene segment for NB and NA. In one embodiment, the infectious, biologically contained recombinant influenza virus has a HEF gene segment.

In yet another embodiment, the invention provides an isolated infectious, biologically contained recombinant influenza virus comprising gene segments including a PA viral gene segment, a PB1 viral gene segment, a mutant PB2 viral gene segment, a NP viral gene segment, a M viral gene segment, a NS viral gene segment (for NS1 and NS2), and a HEF viral gene segment. In one embodiment, the mutant PB2 viral gene segment includes 5' and/or 3' PB2 viral non-coding and coding incorporation sequences, optionally flanking a heterologous nucleotide sequence, and does not include contiguous sequences corresponding to sequences encoding a functional PB2. The PB2 open reading frame in the mutant PB2 viral gene segment may be replaced with or disrupted by a heterologous nucleotide sequence, such as one that is readily detectable after transfection or infection, e.g., a reporter gene such as a GFP gene or a luciferase gene, e.g., a *Renilla* luciferase gene, or a gene encoding an antigen from a pathogen. In one embodiment, the PB2 coding region in the mutant PB2 viral gene segment may include mutations such as insertions or deletions of one or more nucleotides or those that result in one or more amino acid substitutions or a stop codon, or any combination thereof, that yields a non-functional PB2 coding sequence. In one embodiment, the heterologous nucleotide sequence is about 30 to about 5,000, e.g., about 100 to about 4,500 or about 500 to about 4,000, nucleotides in length.

The infectious, biologically contained viruses of the invention may thus be used as influenza vaccines to induce an immunogenic response in a host, without the risk of symptoms associated with an infection or genetic reversion from an attenuated to a fully infectious form. The infectious, biologically contained viruses of the invention may elicit a better immune response than chemically inactivated viruses because they are live viruses, yet because they are biologically contained, the viruses of the invention likely do not cause symptoms of the disease, which is often an issue with live attenuated vaccines. And in contrast to the use of virus-like particles (VLPs), which are non-replicative, the KO viruses of the invention contain RNA, which is an adjuvant that enhances the host's immune response against the virus. The properties of a PB2-KO influenza virus of the invention were surprising given that a similar virus, a M2 deficient virus that lacks the transmembrane and cytoplasmic domains of M2 (see, Watanabe et al., *J. Virol.*, 83:5944 (2009)) grew to low titers, e.g., $10^2$-$10^3$ PFU/mL, in the absence of M2 supplied in trans, and so was replication-defective but not biologically contained.

In one embodiment, the invention provides an isolated recombinant infectious, biologically contained influenza virus comprising 7 gene segments including a PA viral gene segment, a PB1 viral gene segment, a HA viral gene segment, a NA viral gene segment, a NP viral gene segment, a M viral gene segment, and a NS1 and NS2 viral gene segment, i.e., the virus lacks a PB2 viral gene segment.

In one embodiment, for the 8 segment PB2-KO influenza virus having a mutant PB2 viral gene segment, the mutant PB2 viral gene segment has a deletion of PB2 coding sequences, a deletion of PB2 coding sequences and an insertion of heterologous nucleotide sequences, or an insertion of heterologous nucleotide sequences which disrupts PB2 coding sequences. That virus replicates in vitro when PB2 is supplied in trans to titers that are substantially the same or at most 10, 100 or 1,000 fold less than a corresponding wild-type influenza virus, but is attenuated in vivo or in vitro in the absence of PB2 supplied in trans. In one embodiment, the deletion of PB2 coding sequences includes 1 or more contiguous or noncontiguous nucleotides of PB2 and may include a deletion of the entire coding region, e.g., a region encoding 759 amino acids. In one embodiment, the deletion includes at least 10%, 30%, 40%, 50%, 70%, 80%, 85%, 90%, 93%, 95% and up to 99%, or a percent numerical value that is any integer between 10 and 99, but not all, of the PB2 coding region. In one embodiment, the deletion of PB2 coding sequences does not include the deletion of 5' or 3' coding sequences that enhance incorporation of the resulting viral gene segment into virions, e.g., sequences that are contiguous to 3' or 5' non-coding PB2 sequences, relative to a recombinant viral gene segment with only non-coding PB2 incorporation sequences.

In one embodiment, the mutant PB2 gene segment may comprise an insertion of one or more nucleotides, e.g., those that result in a frame-shift, so that functional PB2 cannot be expressed. In one embodiment, the insertion does not include the alteration of 5' or 3' coding sequences that enhance incorporation of the gene segment into virions relative to a recombinant gene segment with only non-coding PB2 incorporation sequences.

In one embodiment, the mutant PB2 viral gene segment may comprise at least one mutation that results in at least one amino acid substitution relative to a corresponding wild-type PB2 protein, e.g., a mutation that removes or replaces the initiator codon, or that introduces one or more stop codons into the coding region, so that functional PB2 cannot be expressed from that viral gene segment after infection. In one embodiment, the substitution, removal or replacement of the initiator codon, or introduction of the one or more stop codons in the reading frame for PB2, does not include the alteration of 5' or 3' coding sequences that enhance incorporation of the gene segment into virions relative to a recombinant gene segment with only non-coding PB2 incorporation sequences.

In one embodiment of the invention, the heterologous nucleotide sequence may encode a heterologous protein (a non-influenza viral protein such as a glycoprotein or a cytosolic, nuclear or mitochondrial specific protein, or any antigenic protein such as an antigen from a microbial pathogen), which may confer a detectable phenotype. In one embodiment, the heterologous nucleotide sequence may be fused to truncated portions of PB2 coding sequences, e.g., those corresponding to 5' or 3' PB2 coding incorporation sequences, optionally forming a chimeric protein. In one embodiment, the heterologous nucleotide sequence replaces or is introduced to sequences in the viral gene segment corresponding to the coding region for that segment, so as not to disrupt the incorporation sequences in the coding region of the gene segment. For instance, the heterologous nucleotide sequence may be flanked by about 3 to about 400 nucleotides of the 5' and/or 3' PB2 coding region adjacent to non-coding sequence. In one embodiment, the 3' PB2 incorporation sequences correspond to nucleotides 3 to 400, nucleotides 3 to 300, nucleotides 3 to 100, nucleotides 3 to 50, or any integer between 3 and 400, of the N-terminal and/or C-terminal PB2 coding region. In one embodiment, after infection of a host cell with the biologically contained PB2-KO virus, a heterologous protein is produced which is a fusion with the N-terminus and/or C-terminus of the remaining residues of the deleted PB2 protein.

A vector for vRNA production of the mutant PB2 gene segment is introduced into a cell along with a vector or vectors for vRNA production for PA vRNA, PB1 vRNA, NP vRNA, HA vRNA, NA vRNA, M vRNA, and NS (NS1 and/or NS2) vRNA, and vectors for mRNA (protein) production for one or more of PA, PB1, PB2, and NP, or vectors for mRNA production of up to three of PA, PB1, PB2, and NP, where the cell stably expresses the remaining viral protein(s), and optionally expresses HA, NA, M, e.g., M1 and M2, NS1 and/or NS2. The vRNA for the mutant PB2 gene segment may be incorporated into virions at an efficiency that is at least 1%, 5%, 10%, or 30%, or at least 50%, that of a corresponding wild-type PB2 vRNA.

In one embodiment, the influenza virus of the invention elicits both systemic and mucosal immunity at the primary portal of infection. Thus, the invention provides a live, attenuated vaccine or immunogenic composition comprising the recombinant biologically contained virus of the invention, and a method of using the vaccine or immunogenic composition to immunize a vertebrate, e.g., an avian or a mammal, such as a human, or induce an immune response in a vertebrate, respectively. In one embodiment, the composition or vaccine is formulated for intranasal administration. In one embodiment, the recombinant biologically contained virus in a vaccine comprises a HA gene segment for influenza A virus HA, e.g., H1, H2, H3, H5, H7, or H9 HA. In one embodiment, the HA in the recombinant biologically contained virus in a vaccine is modified at the HA cleavage site. In one embodiment, the vaccine comprises at least one influenza virus strain that is different than the recombinant biologically contained virus of the invention, for instance, the vaccine comprises two or three different influenza viruses.

The invention provides a plurality of vectors to prepare an infectious, biologically contained 8 segment influenza A virus having one or more vectors which include transcription cassettes for vRNA production and transcription cassettes for mRNA production. The transcription cassettes for vRNA production are a transcription cassette comprising a promoter for vRNA production, e.g., a PolI promoter, operably linked to an influenza virus PA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus PB1 DNA in an orientation for genomic viral RNA production linked to a transcription termination sequence that results in influenza virus-like vRNA termini, for instance, PolI transcription termination sequence, a transcription cassette comprising a promoter for vRNA production, e.g., a PolI promoter, operably linked to a mutant influenza virus PB2 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus HA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NP DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus M DNA in an orientation for genomic viral RNA production linked to a transcription termination sequence that results in influenza virus-like vRNA termini, for instance, a PolI transcription termination sequence, and a transcription cassette comprising a promoter for vRNA production, e.g., a PolI promoter, operably linked to an influenza virus NS (NS1 and NS2) DNA in an orientation for genomic viral RNA production linked to a transcription termination sequence that results in influenza virus-like vRNA termini, for instance, a PolI transcription termination sequence. The mutant PB2 DNA includes 5 and 3' incorporation sequences flanking a heterologous nucleotide sequence and does not include contiguous sequences corresponding to sequences that encode a functional PB2. The transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, and a transcription cassette comprising a PolII promoter operably linked to a DNA coding region for influenza virus NP linked to a PolII transcription termination sequence, and optionally a transcription cassette comprising a PolII promoter operably linked to a DNA coding region for influenza virus one or more of PB2, HA, NA, NS1, NS2, M1 and/or M2 linked to a PolII transcription termination sequence. Further provided is a composition having the vectors, and a method which employs the vectors.

The invention also provides a plurality of vectors to prepare an infectious, biologically contained 8 segment influenza B virus having one or more vectors which include transcription cassettes for vRNA production and transcription cassettes for mRNA production. The transcription cassettes for vRNA production are a transcription cassette comprising a promoter for vRNA production, e.g., a PolI promoter, operably linked to an influenza virus PA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus PB1 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to a mutant influenza virus PB2 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus HA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NA and NB DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NP DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus M DNA in an orientation for genomic viral RNA production linked to a transcription termination sequence that results in influenza virus-like vRNA termini, for instance, a PolI transcription termination sequence, and a transcription cassette comprising a PolI promoter operably linked to an influenza virus NS (NS1 and NS2) DNA in an orientation for genomic viral RNA production linked to a PolI transcription termination sequence, The mutant PB2 DNA is includes 5' and 3' incorporation sequences, optionally flanking a heterologous nucleotide sequence, and does not include contiguous sequences corresponding to sequences that encode a functional PB2. The transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, and a transcription cassette comprising a PolII promoter operably linked to a DNA coding region for influenza virus NP linked to a PolII transcription termination sequence, and optionally a transcription cassette comprising a PolII promoter operably linked to a DNA coding region for influenza virus one or more of PB2, HA, NA, NS1, NS2, M1 and/or BM2 linked to a PolII transcription termination sequence. Further provided is a composition having the vectors and a method which employs the vectors.

In one embodiment, the promoter in a vRNA vector includes but is not limited to a RNA polymerase I (PolI) promoter, e.g., a human RNA PolI promoter, a RNA polymerase II (PolII) promoter, a RNA polymerase III promoter, a SP6 promoter, a T7 promoter, or a T3 promoter. In one embodiment, one or more vRNA vectors include a PolII promoter and ribozyme sequences 5' to influenza virus sequences and the same or different ribozyme sequences 3' to the influenza virus sequences. In one embodiment, the mutant PB2 gene segment is in a vector and is operably linked to a promoter including, but not limited to, a RNA PolI promoter, e.g., a human RNA PolI promoter, a RNA PolII promoter, a RNA polymerase III promoter, a SP6 promoter, a T7 promoter, or a T3 promoter. In one embodiment, the vRNA vectors include a transcription termination sequence including, but not limited to, a PolI transcription termination sequence, a PolII transcription termination sequence, or a PolIII transcription termination sequence, or one or more ribozymes.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid. In one embodiment, one or more vectors for vRNA production are on the same plasmid (see, e.g., U.S. published application No. 20060166321, the disclosure of which is incorporated by reference herein). In one embodiment, one or more vectors for mRNA production are on the same plasmid (see, e.g., U.S. published application No. 2006/0166321). In one embodiment, the vRNA vectors employed in the method are on one plasmid or on two or three different plasmids. In one embodiment, the mRNA vectors for PA, PB1, and NP, and optionally PB2, employed in the method are on one plasmid or on two or three different plasmids.

Also provided is a host cell comprising a vector expressing PB2, e.g., PB2 from PR8 or other master vaccine strain. In one embodiment, the PB2 has at least 90%, 95%, 98%, 99% or 100% identity to PB2 encoded by SEQ ID NO:3. In one embodiment, the host cell is transduced with a viral vector, e.g., a vector which is stably maintained in the cell as an episome or integrated into a chromosome, such as a lentiviral or retroviral vector. In one embodiment, the host cell further includes one or more vectors which include transcription cassettes for transient vRNA production and transcription cassettes for transient mRNA production. The transcription cassettes for vRNA production are a transcription cassette comprising a promoter for vRNA production, e.g., a PolI promoter, operably linked to an influenza virus PA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter operably linked to an influenza virus PB1 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to a mutant influenza virus PB2 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus HA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NP DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus M DNA in an orientation for genomic viral RNA production linked to a transcription termination sequence that results in influenza virus-like vRNA termini, for instance, a PolI transcription termination sequence, and a transcription cassette comprising a promoter for vRNA production, e.g., a PolI promoter, operably linked to an influenza virus NS (NS1 and NS2) DNA in an orientation for genomic viral RNA production linked to a transcription termination sequence that results in influenza virus-like vRNA termini, for instance, a PolI transcription termination sequence. The mutant PB2 DNA includes 5' and 3' incorporation sequences, optionally flanking a heterologous nucleotide sequence, and does not include contiguous sequences corresponding to sequences that encode a functional PB2. The transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, and a transcription cassette comprising a PolII promoter operably linked to a DNA coding region for influenza virus NP linked to a PolII transcription termination sequence. The host cell does not include sequences corresponding to PB2 coding sequences for vRNA production of a wild-type PB2 viral gene segment.

The invention also provides a method to prepare influenza virus, e.g., using a host cell of the invention. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with virus of the invention. In another embodiment, the invention includes contacting the cell with one or more vectors, either vRNA or protein production vectors, prior to other vectors, either vRNA or protein production vectors.

In one embodiment, the invention provides a method of preparing a recombinant influenza virus comprising a mutant PB2 viral gene segment. The method comprises contacting a host cell with a plurality of influenza vectors, including a vector comprising the mutant PB2 gene segment sequence, so as to yield recombinant virus. For example, the host cell is contacted with vectors for vRNA production including a vector comprising a promoter for vRNA production operably linked to an influenza virus PA DNA linked to a transcription termination sequence, a vector comprising a promoter for vRNA production operably linked to an influenza virus PB1 DNA linked to a transcription termination sequence, a vector comprising a promoter for vRNA production operably linked to a mutant influenza virus PB2 DNA linked to a transcription termination sequence, a vector comprising a promoter for vRNA production operably linked to an influenza virus HA DNA linked to a transcription termination sequence, a vector comprising a promoter for vRNA production operably linked to an influenza virus NP DNA linked to a transcription termination sequence, a vector comprising a promoter for vRNA production operably linked to an influenza virus NA DNA linked to a transcription termination sequence, a vector comprising a promoter for vRNA production operably linked to an influenza virus M DNA linked to a transcription termination sequence, and a vector comprising a promoter for vRNA production operably linked to an influenza virus NS (NS1 and NS2) DNA linked to a transcription termination sequence, wherein the mutant PB2 DNA is in an orientation for genomic vRNA production and includes 5' and 3' incorporation sequences, optionally flanking a heterologous nucleotide sequence, and does not include contiguous sequences corresponding to those for a functional PB2, and vectors for mRNA production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus NP, wherein the cell is not contacted with sequences corresponding to PB2 coding sequences for vRNA production. Optionally, the host cell is contacted with a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding a M2 protein, e.g., a mutant M2 protein, and a vector comprising a promoter operably linked to a DNA segment encoding influenza virus NS1 and/or NS2. In one embodiment, separate vectors for M1 and M2 mRNA, and/or for NS1 and NS2 mRNA are provided and employed.

In one embodiment of a method of preparing a recombinant biologically contained influenza virus of the invention, each transcription cassette is on a plasmid vector. In one embodiment of a method of preparing a biologically contained influenza virus of the invention, one or more transcription cassettes are on one or more plasmid vectors, e.g., one plasmid vector has transcription cassettes for vRNA production of PA, PB1, HA, NP, NA, M1, NS1 and/or NS2, and the mutant PB2 cDNAs. In one embodiment of a method of preparing a biologically contained influenza virus of the invention, one plasmid vector has one of the transcription cassette for mRNA production and another plasmid vector has the other transcription cassettes for mRNA production. In one embodiment of a method of preparing a biologically contained influenza virus of the invention, three plasmid vectors for mRNA production are employed, each with one of the transcription cassettes for mRNA production. In one embodiment of a method of preparing a biologically contained influenza virus of the invention, one plasmid vector has six of the transcription cassettes for vRNA production and another plasmid vector has the other transcription cassette for vRNA production, e.g., one plasmid vector has one of the transcription cassettes for mRNA production and another plasmid vector has the other transcription cassettes for mRNA production. In one embodiment of a method of preparing a biologically contained influenza virus of the invention, three plasmid vectors for mRNA production are employed. In one embodiment of a method of preparing a biologically contained influenza virus of the invention, one plasmid has the three transcription cassettes for mRNA production. In one embodiment of a method of preparing a biologically contained influenza virus of the invention, the HA cDNA encodes an avirulent cleavage site. In one embodiment of a method of preparing a biologically contained influenza virus of the invention, the HA and NA are from the same virus isolate. In one embodiment of a method of preparing a biologically contained influenza virus of the invention, the HA is a type B HA.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host. In one embodiment, the PolI promoter for each PolI containing vector is the same. In one embodiment, the PolI promoter is a human PolI promoter. In one embodiment, the PolII promoter for each PolII containing vector is the same. In one embodiment, the PolII promoter for two or more, but not all, of the PolII containing vectors, is the same. In one embodiment, the PolII promoter for each PolII containing vector is different.

In another embodiment, the method includes contacting a host cell with a vector having a PolII promoter linked to a PolI transcription termination sequence linked to an influenza virus PA DNA linked to a PolI promoter linked to a PolII transcription termination sequence (a bidirectional cassette), a vector having a PolII promoter linked to a PolI transcription termination sequence linked to an influenza virus PB1 DNA linked to a PolI promoter linked to a PolII transcription termination sequence, a vector having a PolII promoter linked to a PolI transcription termination sequence linked to a mutant influenza virus PB2 DNA linked to a PolI promoter linked to a PolII transcription terminator sequence, a vector having a PolII promoter linked to a PolI transcription termination sequence linked to an influenza virus HA DNA linked to a PolI promoter linked to a PolII transcription termination sequence, a vector having a PolII promoter linked to a PolI transcription termination sequence linked to an influenza virus NP DNA linked to a PolI promoter linked to a PolII transcription termination sequence, a vector having a PolII promoter linked to a PolI transcription termination sequence linked to an influenza virus NA DNA linked to a PolI promoter linked to a PolII transcription termination sequence, a vector having a PolII promoter linked to a PolI transcription termination sequence linked to an influenza virus M DNA linked to a PolI promoter linked to PolII transcription termination sequence, and a vector having a PolII promoter linked to a PolI transcription termination sequence linked to an influenza virus NS1 and/or NS2 DNA linked to a PolI promoter linked to PolII transcription termination sequence. The host cell comprises PB2 DNA expressing a PB2 protein, e.g., from a chicken beta-actin promoter. No sources of vRNA for wild-type PB2 are present so that replication-incompetent virus is provided.

In one embodiment, the promoter for vRNA production in a bidirectional cassette includes but is not limited to a RNA polymerase I (PolI) promoter, e.g., a human RNA PolI promoter, a RNA polymerase II (PolII) promoter, a RNA polymerase III promoter, a SP6 promoter, a T7 promoter, or a T3 promoter. In one embodiment, one or more vRNA vectors include a PolII promoter and ribozyme sequences 5' to influenza virus sequences and the same or different ribozyme sequences 3' to the influenza virus sequences. In one embodiment, the mutant PB2 gene segment is in a vector and is operably linked to a promoter including, but not limited to, a RNA PolI promoter, e.g., a human RNA PolI promoter, a RNA PolII promoter, a RNA polymerase III promoter, a SP6 promoter, a T7 promoter, or a T3 promoter. In one embodiment, the vRNA vectors include a transcription termination sequence including, but not limited to, a PolI transcription termination sequence, a PolII transcription termination sequence, or a PolIII transcription termination sequence, or one or more ribozymes. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

The plurality of vectors, compositions and host cells of the invention may also include another vector for vRNA production or protein production that includes heterologous sequences, e.g., for a therapeutic or prophylactic gene of interest e.g., an immunogen for a cancer associated antigen or for a pathogen such as a bacteria, a noninfluenza virus, fungus, or other pathogen. For example, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

In one embodiment, the recombinant virus of the invention includes one or more genes from influenza A virus. In another embodiment, the recombinant virus of the invention may include one or more genes from influenza B virus, e.g., an influenza B HA gene. In yet another embodiment, the recombinant virus of the invention may include one or more genes from influenza C virus. The DNA for vRNA production of NA may be from any NA, e.g., any of N1-N9, a chimeric NA sequence or any non-native NA sequence, and the DNA for vRNA production of HA may be from any HA, e.g., H1-H16, a chimeric HA sequence or any non-native HA sequence. In one embodiment, the DNAs for vRNA production may be for an influenza B or C virus. In one embodiment, other attenuating mutations may be introduced to the vectors, e.g., a mutation in a HA cleavage site that results in a site that is not cleaved. The DNAs for vRNA production of NA and HA may be from different strains or isolates relative to those for the (6:1:1 reassortants) or from the same strain or isolate (6:2 reassortants), the NA may be from the same strain or isolate as that for the internal genes (7:1 reassortant), or one of the internal genes, NA and HA may be from the same strain or isolate (5:3 reassortant).

Viruses that may provide the internal genes for reassortants within the scope of the invention include viruses that have high titers in Vero cells, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, 109 $EID_{50}$/mL or $10^{10}$ $EID_{50}$/mL; high titers in MDCK, e.g., AX5, cells, e.g., titers of at least about $10^7$ PFU/mL, e.g., at least $10^8$ PFU/mL, or high titers in two of more of those host cells. In one embodiment, the DNAs for vRNA production of PB1 vRNA, mutant PB2 vRNA, PA vRNA, NP vRNA, M vRNA (for M1 and/or M2 or M1 and/or BM2), and/or NS vRNA (for NS1 and/or NS2), may have sequences from an influenza virus that replicates to high titers in cultured mammalian cells such as AX4 cells, Vero cells or PER.C6® cells and also optionally embryonated eggs, and/or from a vaccine virus, e.g., one that does not cause significant disease in humans.

For example, reassortants with internal genes from other PR8 isolates or vaccine viruses may be employed in recombinant reassortant viruses of the invention. In particular, 5:1:2 reassortants having PR8(UW) PB1, PB2, PA, NP, and M ("5") and PR8(Cam) NS ("1"); 6:1:1 reassortants having PR8(UW) NA, PB1, PB2, PA, NP, and M ("6") and PR8 (Cam) NS ("1") gene segments; and 7:1 reassortants having PR8(UW) PB1, PB2, PA, NP, M, NA, and NS ("7") gene segments may be employed.

In one embodiment, the DNAs for the internal genes for PB1, PB2, PA, NP, M, and NS encode proteins with substantially the same activity as a corresponding polypeptide encoded by one of SEQ ID NOs:1-6 or 10-15. As used herein, "substantially the same activity" includes an activity that is about 0.1%, 1%, 10%, 30%, 50%, 90%, e.g., up to 100% or more, or detectable protein level that is about 80%, 90,% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:1-6 or 10-15. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 or 33-38 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs:1-6 or 10-15. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:1-6 or 10-15. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:1-6 or 10-15.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The methods include administering to a host organism, e.g., a mammal, an effective amount of the influenza virus of the invention, e.g., a live or inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. In one embodiment, two to three doses are administered. The vaccine may be multivalent as a result of the heterologous nucleotide sequence introduced into a viral gene segment in the influenza virus of the invention. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

In one embodiment, the influenza viruses of the invention may be vaccine vectors for influenza virus and for at least one other pathogen, such as a viral or bacterial pathogen, or for a pathogen other than influenza virus, pathogens including but not limited to, lentiviruses such as HIV, hepatitis B virus, hepatitis C virus, herpes viruses such as CMV or HSV, Foot and Mouth Disease Virus, Measles virus, Rubella virus, Mumps virus, human Rhinovirus, Parainfluenza viruses, such as respiratory syncytial virus and human parainfluenza virus type 1, Coronavirus, Nipah virus, Hantavirus, Japanese encephalitis virus, Rotavirus, Dengue virus, West Nile virus, *Streptococcus pneumoniae, Mycobacterium tuberculosis, Bordetella pertussis*, or *Haemophilus* influenza. For example, the biologically contained influenza virus of the invention may include sequences for H protein of Measles virus, viral envelope protein E1 of Rubella virus, HN protein of Mumps virus, RV capsid protein VP1 of human Rhinovirus, G protein of Respiratory syncytial virus, S protein of Coronavirus, G or F protein of Nipah virus, G protein of Hantavirus, E protein of Japanese encephalitis virus, VP6 of Rotavirus, E protein of Dengue virus, E protein of West Nile virus, PspA of *Streptococcus pneumonia*, HSP65 from *Mycobacterium tuberculosis*, IRP1-3 of *Bordetella pertussis*, or the heme utilization protein, protective surface antigen D15, heme binding protein A, or outer membrane protein P1, P2, P5 or P6 of *Haemophilus influenza*.

Further provided is a method to detect neutralizing antibodies for a selected influenza virus strain in a physiological sample of a vertebrate. The method includes contacting the sample, a recombinant virus of the invention which expresses HA and/or NA of the selected strain, and cells susceptible to influenza virus infection. The presence or amount of the reporter or the antigen in the cells is detected, wherein the absence of the reporter or antigen or a reduced amount of the reporter or antigen in the sample relative to a control sample, is indicative of a vertebrate that has been infected with the influenza virus strain.

BRIEF DESCRIPTION OF FIGURES

FIG. 1. Schematic diagram of mutant PB2 vRNAs and their efficiencies in virion formation and virion incorporation. The numbers of VLPs and the virion incorporation efficiencies of mutant PB2 vRNAs were determined by using the numbers of WSN HA- and GFP-expressing cells as a denominator. All mutants are shown in the negative-sense orientation. Each mutant contains the GFP reading frame (green bar); 27 and 34 nucleotides of the 3' and 5' noncoding regions, respectively (gray bars); and coding regions of various lengths (black bars). The dotted lines represent deleted sequences of the PB2 coding region. PB2(−) indicates the omission of this vRNA (i.e., VLPs were generated using only seven vRNA segments).

FIG. 2A-I. Exemplary vaccine virus internal gene sequences (SEQ ID NOs:1-8 and 10-15).

FIG. 3A-3D. Characterization of PR8/PB2-GFP virus. A) Schematic diagram of wild-type PB2 and PB2(120)GFP(120) vRNAs. PB2(120)GFP(120) vRNA possesses the 3' noncoding region, 120 nucleotides of the coding sequence of PB2 vRNA, the GFP gene, and 120 nucleotides of the 3' coding and the 5' noncoding regions of PB2 vRNA. The noncoding region and coding regions of PB2 vRNA are represented by gray and red bars, respectively. The GFP gene is represented by the green bar. B) PB2 gene expression in AX4/PB2 cells (AX4 cells are derived from MDCK cells). RNA was extracted from both wild-type AX4 and AX4/PB2 cells. RT-PCR was performed by using an oligo(dT) primer followed by cDNA synthesis and PCR with PB2− (upper panel) or canine beta-actin- (lower panel) specific primers. C) PB2 protein expression in AX4/PB2 cells. Cells were reacted with an anti-PB2 antibody 18/1 (Hatta et al., 2000) (left panels) and Hoechst 33342 (right panels). Scale bar, 50 μm. D) Growth kinetics of PR8/PB2-GFP monitored over 72 hours. Wild-type AX4 (upper panel) and AX4/PB2 (lower panel) cells were infected with wild-type PR8 (red) or PR8/PB2-GFP (green) viruses at an MOI of 0.001. Supernatants collected at the indicated time points were assayed for infectious virus in plaque assays in AX4/PB2 cells.

FIG. 4. Accommodation of various HA genes in PB2-KO virus. HA expression in PB2-KO virus-infected cells. AX4/PB2 cells were infected with PR8/PB2-GFP, WSN/PB2-GFP, CA04/PB2-GFP, or VN1203/PB2-GFP. At 16 hours post-infection, the cells were stained with monoclonal antibodies specific for WSN, CA04, or VN1203 HA protein. The expression of HA and GFP were examined by using fluorescence microscopy.

FIG. 5A-5B. Accommodation of various reporter genes in PB2-456 KO virus. A) Luciferase activity in PB2-KO virus-infected cells. Wild-type AX4 and AX4/PB2 cells were infected with PR8/PB2-Fluc (upper graph) and PR8/PB2-Rluc (lower graph) at the indicated MOIs. At 8 hours post-infection, Fluc and Rluc activities in cells were measured by using a dual-luciferase reporter assay system. Results from virus-infected cells were compared with those from uninfected cells (indicated by ‘0’) and P values were calculated by using the Student’s t test. Asterisk, $P<0.05$. RLU, relative light unit. B) GFP intensity in PB2-KO virus-infected cells. AX4/PB2 cells were infected with PR8/PB2-GFP at the indicated MOI. At 8 hours post-infection, GFP intensity was measured with the Infinite M1000 microplate reader. Results from virus-infected cells were compared with those from uninfected cells (indicated by ‘0’) and P values were calculated by using the Student’s t test. Asterisk, $P<0.05$. RFU, relative fluorescent unit.

FIG. 6. PB2-KO virus-based microneutralization assay. AX4/PB2 cells were infected with 100 PFU of CA04/PB2-Rluc that were pre-mixed with serially diluted ferret sera in triplicate wells. Rluc activity in cells was measured by using a *Renilla* luciferase assay system at 24 hours post-infection. Results from virus-infected cells were compared with those from cells that were infected with serum-untreated virus (indicated by ‘Serum (−)’). P values were calculated by using the Student’s t test. Asterisk, $P<0.05$. RLU, relative light unit.

FIG. 7A-F. Body weight change after challenge in mice. Mice immunized with the indicated agents once (A), twice (B), or three times (C) were challenged with 0.5 (i) or 5 (ii) $MLD_{50}$ of PR8 virus. Values are expressed as mean changes in body weight±SD (n=3).

FIG. 8A-C. Virus-specific antibody responses in immunized mice. Purified PR8 virus was used as an antigen to analyze IgG and IgA antibody titers in the sera, nasal washes, and BAL fluids (top, middle, and bottom, respectively) of mice mock immunized with medium or immunized with the formalin-inactivated virus or with the PB2-KO virus. Sera (top panels) were obtained at different time points, i.e., prevaccination (bars A), before the second vaccination (bars B), before the third vaccination (bars C), and before challenge (bars D). Nasal washes and BAL fluids (middle and bottom panels, respectively) were obtained 1 day before challenge from mice given 1 vaccination (bars 1), 2 vaccinations (bars 2), or 3 vaccinations (bars 3). Values are expressed as the mean absorbance±standard deviation (SD) (n=3). Statistical significance between samples obtained from mice immunized with inactivated virus and PB2-KO virus is indicated.

FIG. 9A-9H. Virus titers in the lungs and nasal turbinates (NT) of immunized mice after challenge. The numbers on the x axis indicate the number of vaccinations. Three BALB/c mice per group were intranasally infected with the indicated doses of PR8 virus (50 μL per mouse) and sacrificed on days 3 and 6 postinfection for virus titration. Bars indicate the virus titer in each organ of each mouse. The absence of bars indicates that virus titers were below the detection limit of 5 PFU/mL/organ.

FIG. 10A-10D. Detection of antibodies against GFP in the sera of mice immunized with the PB2-KO virus. Confluent 293 cells that transiently express GFP were treated with sera (1/20 dilution) obtained from mice inoculated with medium (A), the formalin-inactivated virus (B), or the PB2-KO virus (C) or were treated with a commercial anti-GFP antibody (D). DNA (first column) was stained with Hoechst 33342. GFP (second column) represents cells transfected with a plasmid for the expression of GFP. GFP antibody (third column) represents the presence of the GFP antibody in the samples. These three images were merged (fourth column). Scale bars, 20 μm.

FIG. 11. Detection of heterologous antigen expression after infection of cells with PB2-KO virus having sequences for pspA of pneumococcus (*S. pneumoniae*). Anti-influenza virus antibodies and anti-PspA antibodies were used to detect expression of influenza virus and PspA proteins in cells with PB2-KO-GFP or PB2-KO-PspA.

FIG. 12. Growth kinetics of PB2-KO-PspA in cells that do not express PB2 and cells that stably express PB2.

Figure 13:
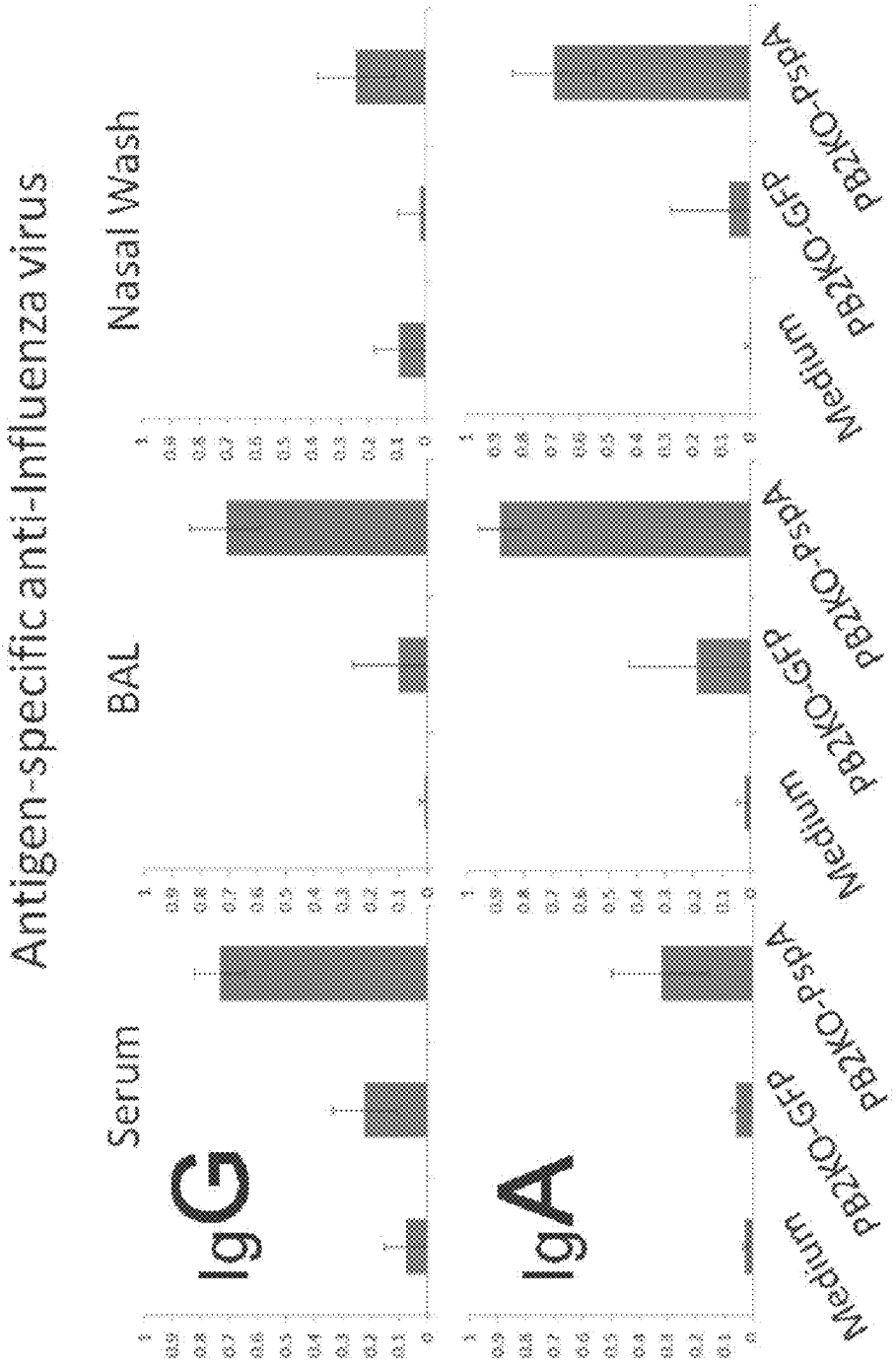

FIG. 13. Influenza antigen specific IgG and IgA in serum, BAL and nasal washes from mice immunized three times with PB2-KO-PspA or PB2-KO-GFP.

Figure 14:
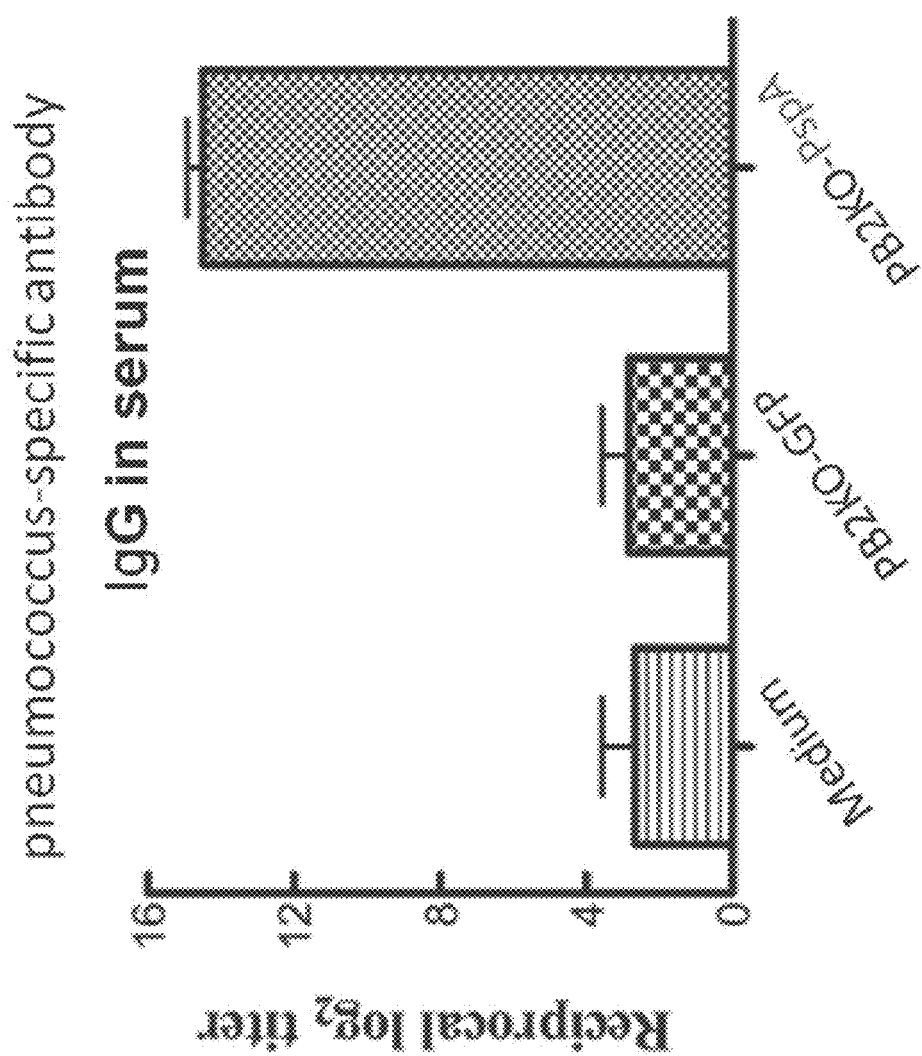

FIG. 14. PspA specific IgG in serum from mice immunized three times with PB2-KO-PspA.

Figure 15:
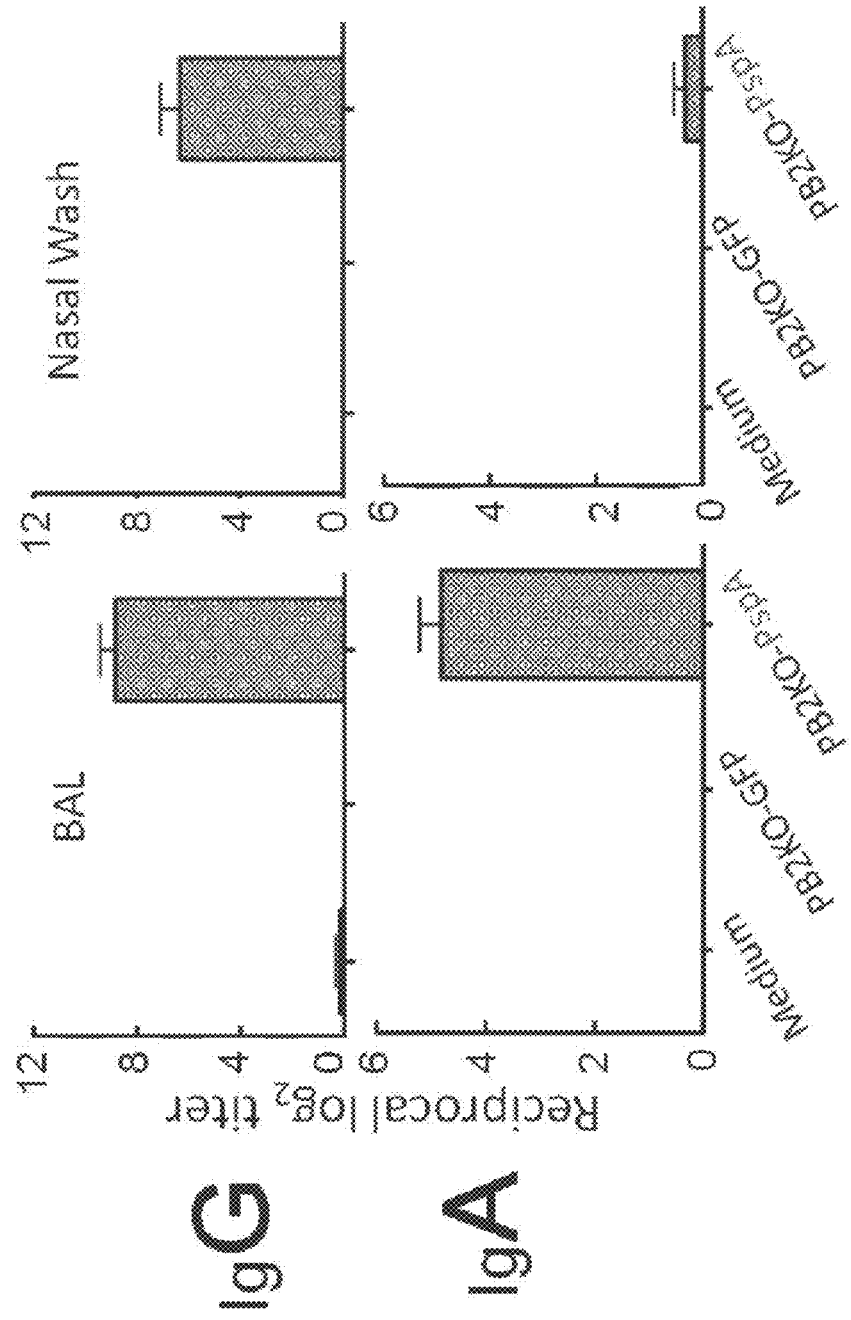

FIG. 15. PspA specific IgG and IgA in BAL and nasal washes from mice immunized three times with PB2-KO-PspA.

Figure 16:
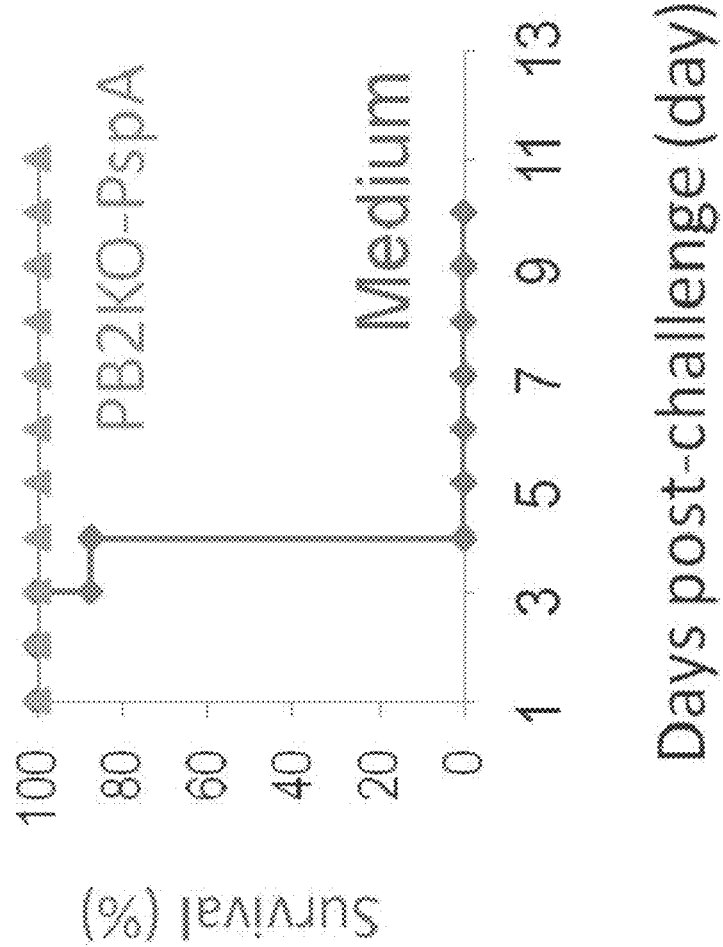

FIG. 16. Survival post-challenge of mice immunized three times with PB2-KO-PspA and challenged with 10 $LD_{50}$ or 100 $LD_{50}$ of influenza virus.

Figure 17:
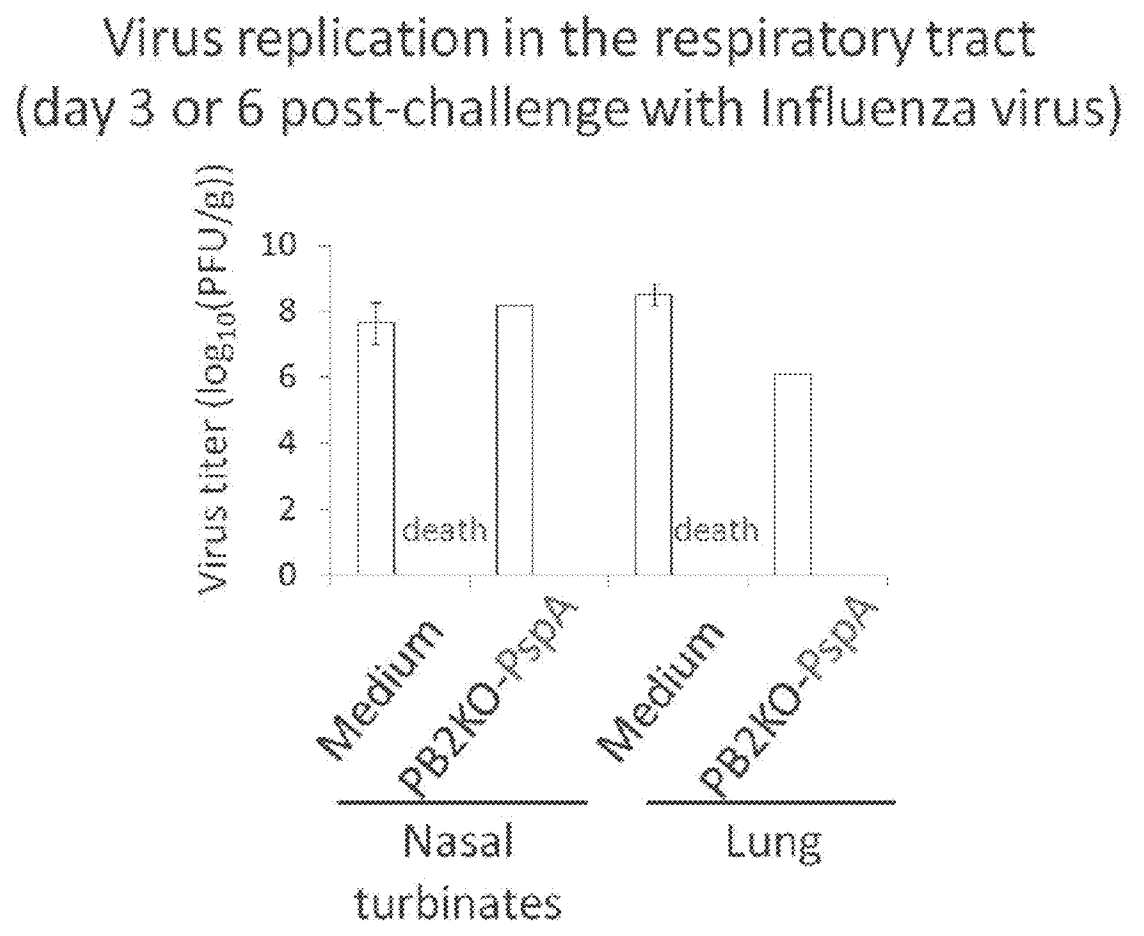

FIG. 17. Virus replication in the respiratory tract at day 3 post-challenge in mice immunized three times with PB2-KO-PspA and challenged with 10 $LD_{50}$ or 100 $LD_{50}$ of influenza virus.

Figure 18:
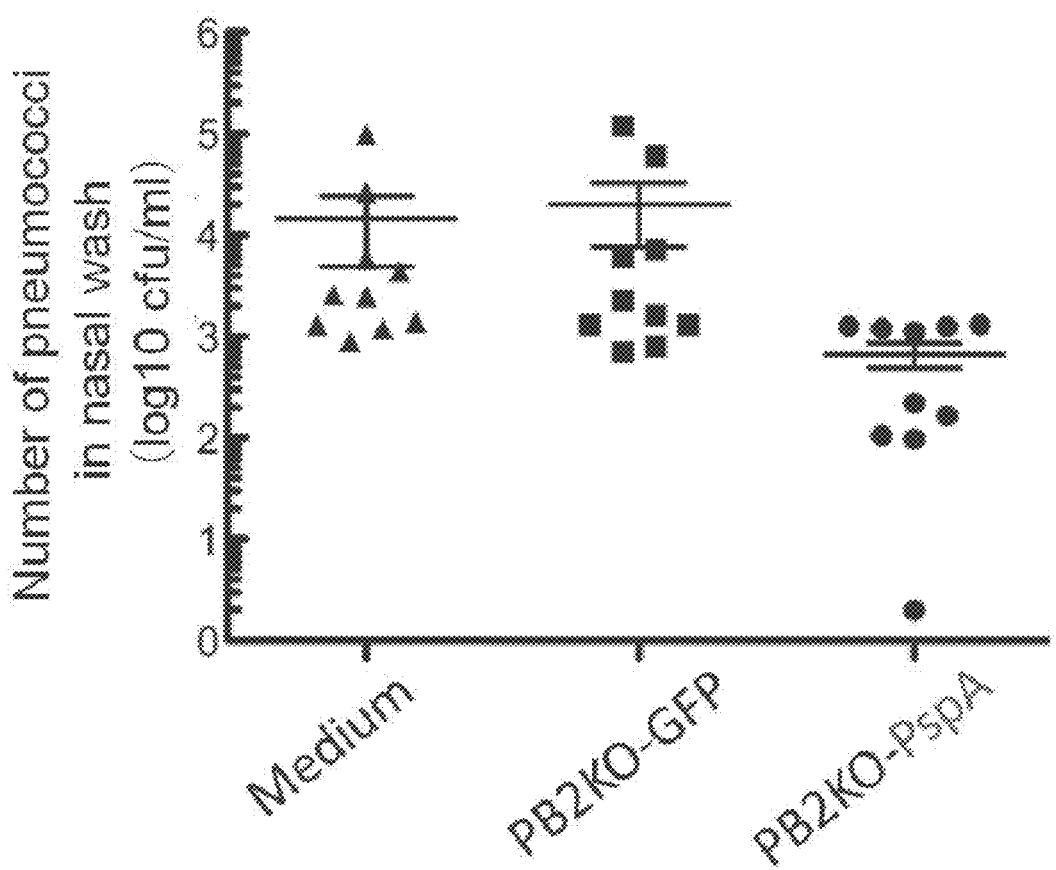

FIG. 18. Number of pneumococci in nasal washes from mice immunized three times with PB2-KO-PspA or PB2-KO-GFP and challenged with $10^2$ CFU *S. pneumoniae* (EF3030)/mouse.

Figure 19:
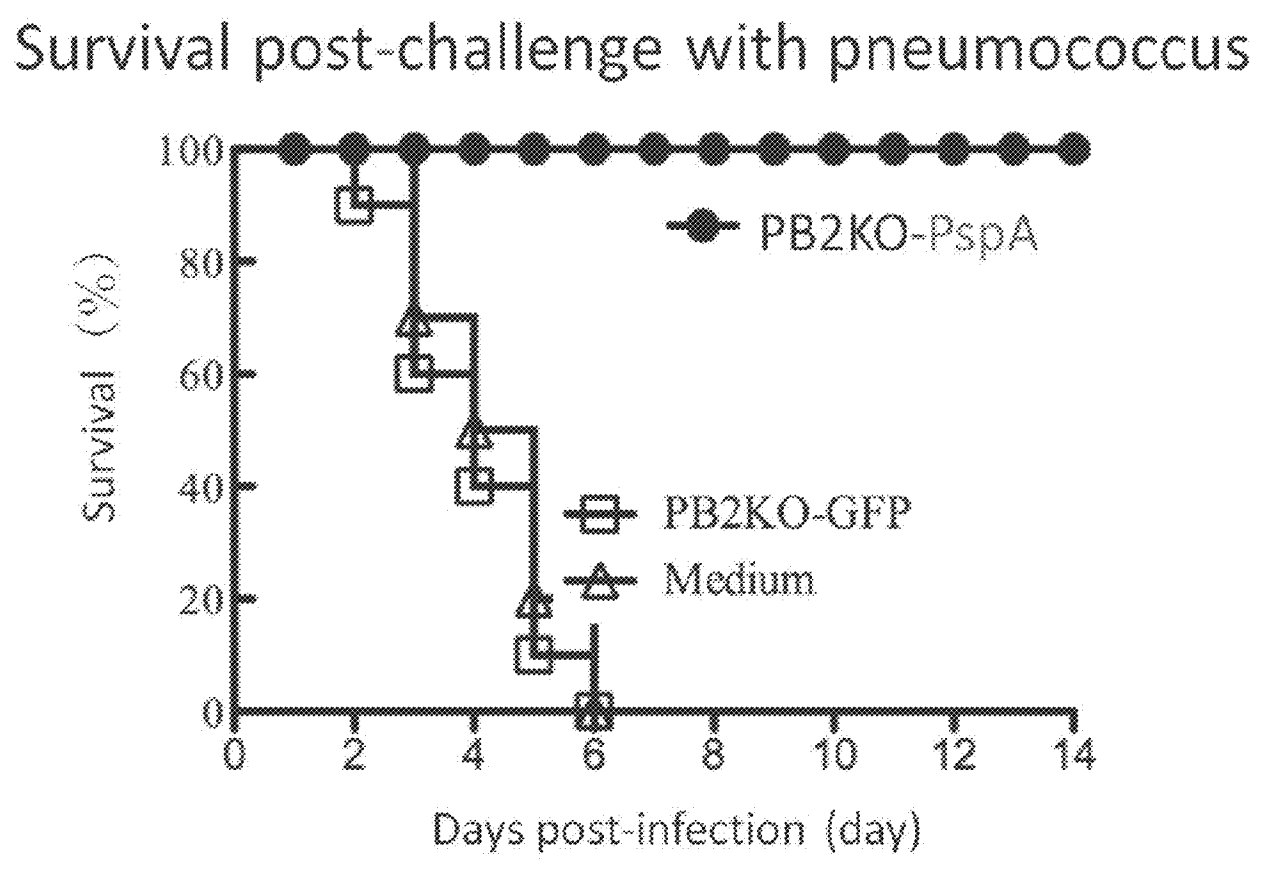

FIG. 19. Survival post-challenge of mice immunized three times with PB2-KO-PspA and challenged with 2×10, CFU pneumococcus WU2 (a lethal strain)/mouse.

DETAILED DESCRIPTION

Definitions

As used herein, an "infectious, biologically contained" virus means that the virus is incapable of producing progeny in normal cells or incapable of significant replication in vitro or in vivo, e.g., titers of less than about $10^2$ to $10^3$ PFU/mL, in the absence of helper virus or a viral protein stably supplied in trans.

A used herein, "replication-deficient" virus means that the virus can replicate to a limited extent in vitro or in vivo, e.g., titers of at least about $10^2$ to $10^3$ PFU/mL, in the absence of helper virus or a viral protein supplied in trans.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro so that its sequence is not naturally occurring or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" nucleotide sequence is from a source other than a parent influenza virus, e.g., a reporter gene or a gene from another virus or organism, e.g., a bacterium, or is from an influenza virus source but is in a context that does not mimic a native influenza virus genome, e.g., it is a subset of a full length influenza virus gene segment and is in a non-native context, e.g., fused to truncated PB2 coding sequences.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus

The life cycle of viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell (reviewed by Roizman and Palese, 1996). Different viral proteins play a role in each of these steps.

The influenza A virus is an enveloped negative-strand virus with eight RNA segments encapsidated with nucleoprotein (NP) (reviewed by Lamb and Krug, 1996). The eight single-stranded negative-sense viral RNAs (vRNAs) encode a total of ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M1 protein; the product of the unspliced mRNA is proteolytically cleaved to yield the CM2 protein. In addition, influenza C virus encodes a HA-esterase (HEF) rather than individual HA and NA proteins.

Spanning the viral membrane for influenza A virus are three proteins: hemagglutinin (HA), neuraminidase (NA), and M2. The extracellular domains (ectodomains) of HA and NA are quite variable, while the ectodomain domain of M2 is essentially invariant among influenza A viruses. The M2 protein which possesses ion channel activity (Pinto et al., 1992), is thought to function at an early state in the viral life cycle between host cell penetration and uncoating of viral RNA (Martin and Helenius, 1991; reviewed by Helenius, 1992; Sugrue et al., 1990). Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm (reviewed by Helenius, 1992). In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment (Hay et al., 1985; Ohuchi et al., 1994; Takeuchi and Lamb, 1994).

Cell Lines that can be Used in the Present Invention

Any cell, e.g., any avian or mammalian cell, such as a human, e.g., 293T or PER.C6® cells, or canine, bovine, equine, feline, swine, ovine, rodent, for instance mink, e.g., MvLu1 cells, or hamster, e.g., CHO cells, non-human primate, e.g., Vero cells, or non-primate higher vertebrate cells, e.g., MDCK cells, including mutant cells such as AX4 cells, which support efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the M2 gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates.

This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition, and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicadbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 10 to 100 µg, such as about 15 µg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 µg or any range or value therein, such as about 15 µg, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 µg or any range or value therein, or the amount recommended by the U.S. Public Health Service (PHS), which is usually 15 µg, per component for older children □3 years of age, and 7.5 µg per component for older children<3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

The invention will be described by the following nonlimiting examples.

Example I

PB2 Incorporation Sequences

Most defective RNA segments of influenza A viruses retain 150 to 300 nucleotides corresponding to the 5' and 3' ends of the respective gene segment (Duhaut et al., 1998; Jennings et al., 1983; Noble et al., 1995; and Odagiri et al., 1990), indicating that these 300 to 600 nucleotides may possess the structural features required for efficient genome packaging. To identify the regions in the PB2, PB1, and PA vRNAs that are critical for vRNA virion incorporation and virion formation, plasmids were generated in which the GFP gene is flanked by the noncoding regions and portions of the coding regions derived from both termini [PB2(300)GFP (300), PB1(300)GFP(300), and PA(120)GFP(120)]. Transfection of such a plasmid into 293T cells, together with expression plasmids for the PB2, PB1, PA, and NP proteins (minimal components for transcription and replication of vRNAs), resulted in the expression of GFP in cells, indicating that the chimeric vRNAs were synthesized by the cellular RNA polymerase I and transcribed into mRNA by the viral proteins produced by the expression plasmids.

To calculate the vRNA virion incorporation efficiencies, the number of virions containing a test vRNA must be compared with the total number of VLPs. The total number of VLPs could be determined by inoculating cells with VLPs and then counting the number of cells expressing a given influenza virus protection. To ensure that the number of infectious VLPs determined by this method was not drastically affected by the viral gene product selected as a marker, we determined the number of cells expressing either HA or NP. Because we were testing the incorporation efficiencies of the PB2, PB1, and PA vRNAs, helper virus was needed to provide functional polymerase proteins. To distinguish between the HA and NP proteins expressed from out test VLPs (derived from WSN virus) and those expressed from the helper PR8 virus, we used antibiotics that recognize the WSN HA and NP proteins, but not their PR8 virus counterparts.

To establish a system that allowed the assessment of the number of VLPs generated, 293T cells were transfected with a plasmid for the transcription of a test vRNA (derived from the PB2, PB1, or PA segment), 7 plasmids for the production of the remaining vRNAs, and 10 expression plasmids for the expression of the viral proteins (i.e., PB2, PB1, PA, HA, NP, NA, M1, M2, NS1, and NS2). Forty-eight hours later, VLP-containing supernatants derived from transfected cells were mixed with PR8 helper virus and used to infect MDCK cells. Twelve hours postinfection, the number of cells that expressed either HA or NP protein were determined. For all three vRNAs, the numbers of HA- or NP-expressing cells differed by less than a factor of 3; for example, using the PB2(300)GFP(300) test vRNA, 240,800 HA-expressing cells versus 353,200 NP-expressing cells were detected. Therefore, for the subsequent experiments, the number of HA-expressing cells was employed as an indicator of the efficiency of infectious virion formation. The incorporation efficiencies of test vRNAs were thus calculated by dividing the number of GFP-expressing cells (as a marker for the test vRNA) by the sum of the number of HA-expressing cells (as a marker for the number of virions) plus the number of GFP-expressing cells.

Sequences in the coding region of the PB2 vRNA affect infectious virion formation and vRNA virion incorporation. To delineate the sequences in the PB2 vRNA that are critical for virion formation and/or vRNA virion incorporation, a series of plasmids was generated for the production of PB2 vRNAs that express GFP and contain portions of the PB2 coding region derived from both termini (FIG. 1), in addition to the noncoding regions of the PB2 vRNA (FIG. 1). The numbers of VLPs and the incorporation efficiencies of the test vRNAs were determined as described above.

With PB2(300)GFP(300), which contains 300 nucleotides corresponding to the 5' and 3' coding regions of the PB2 vRNA, about $2.8\times10^6$ VLPs per mL were detected. Stepwise deletion of the coding sequences at the 3' end of the vRNA (referred to as the 3' coding region) had only moderate effects on the efficiency of VLP production; PB2(0)GFP (120), which lacks the entire coding region of the 3' end, yielded about $1\times10^6$ VLPs/mL. Deletion of the coding sequences at the 5' end of the vRNA (referred to as the 5' coding region) [PB2(120)GFP(0)], however, reduced VLP production by 98% of that of PB2(300)GFP(300) and yielded a number of VLPs comparable to that obtained in the absence of the PB2 vRNA [PB2(−)]. This result suggests that sequences in the 5' coding region of the PB2 vRNA are critical for the efficient generation of infectious virions. Further analysis revealed that 30 nucleotides of the 5' coding region are critical for this effect [compare the numbers of VLPs for PB2(120)GFP(0) and PB2(120)GFP(30)].

With regard to the efficiencies of vRNA virion incorporation. PB2(300)GFP(300), 54.7% of the VLPs contained the PB2(300)GFP(300) test vRNA, indicating that the 300 terminal nucleotides at both ends are sufficient for virion incorporation. To achieve the incorporation efficiencies observed for wild-type segments, internal PB2 coding sequences would likely be required. Stepwise deletion of nucleotides in the 3' coding region of the PB2 vRNA had only moderate effects provided 30 or more nucleotides were retrained; the deletion of these remaining 30 nucleotides, however, reduced the virion incorporation efficiency to 29.5% for PB2(0)GFP(120), demonstrating that this region is important for the efficient incorporation of the PB2 vRNA into virions. For PB2 vRNAs that lack a functional packaging sequence in the 3' coding region, sequences in the 5' coding region do contribute to viron incorporation, as exemplified by the inability of the PB2(0)GFP(0) test vRNA to be incorporated.

Deletions in the 5' coding region only, by contrast, had no effect on incorporation efficiencies, as demonstrated by a 75.7% incorporation rate for PB2(120)GFP(0). Thus while the use of this test vRNA produced a very low number of infectious VLPs, the test vRNA was efficiently incorporated into these particles. This finding suggests that sequences in the PB2 vRNA are involved in two biologically distinct processes: efficient infectious virion formation (a function residing in the 5' coding region) and efficient vRNA incorporation into particles (a function primarily residing in the 3' coding region).

The difference in packaging efficiencies could reflect differences in transcription levels of the test vRNAs in 293T cells. To exclude this possibility, the levels of PB2(0)GFP(0) and PB2(120)GFP(120) in plasmid-transfected 293T cells were examined using real-time PCR. The amount of PB2 (0)GFP(0) vRNA was 52% of that of PB2(120)GFP(120); however, this difference is unlikely to explain the 99% reduction in VLP generation and the abrogation of vRNA virion incorporation.

PB2 vRNA is more critical for efficient infectious virion generation than the PB1 or PA vRNA. Thus, a hierarchy may exist in which the PB2 vRNA is critical for the efficient virion incorporation of other vRNAs, while the omission of other segments is tolerable to some extent.

Omission of the PB2 vRNA resulted in an about 30-fold reduction in VLP production, whereas omission of the other vRNA segments resulted in 1.4- to 5.1-fold reductions. These results provided further proof of a hierarchy among the vRNA segments with respect to the importance of the individual vRNAs for the incorporation of the other vRNA segments.

Example II

The stable expression of a foreign gene in a replication-incompetent influenza virus allows for the effective tracking of the manipulated virus. In pursuit of a biologically contained foreign gene-expressing virus with extensive applications in the field of virology, the PB2 protein, an influenza viral polymerase subunit that forms part of the trimeric viral RNA-dependent RNA polymerase that is essential for virus replication was selected. The partial coding sequences of the 3' and 5' ends of the PB2 viral RNA (vRNA) confer its more critical role in efficient infectious virion generation relative to the other vRNAs in the vRNA hierarchy (Example I and Muramoto et al., 2006). This finding suggests that a PB2-knock out (PB2-KO) influenza virus harboring a reporter gene flanked by the coding and non-coding sequences of the PB2 vRNA would replicate only in PB2-expressing cells while stably expressing the reporter gene.

A cell line that stably expresses PB2 protein was established and used to characterize a PB2-KO virus that possesses the GFP gene. The potential for various virus strain-derived HA and NA genes, as well as other reporter genes, to be accommodated by the PB2-KO virus, was also investigated. Further, the PB2-KO virus was employed as a platform to screen neutralizing antibodies against 2009 pandemic viruses.

Methods

Cells. 293T human embryonic kidney cells (a derivative of the 293 line into which the gene for simian virus 40 T antigen was inserted (DuBridge et al., 1987)) were maintained in Dulbecco's modified Eagle medium (Lonza)

supplemented with 10% fetal calf serum (Invitrogen). Madin-Darby canine kidney (MDCK) cells were maintained in minimum essential medium (MEM; Invitrogen) supplemented with 5% newborn calf serum (NCS; Sigma, St. Louis, MO). AX4 cells, derived from MDCK cells and transfected with the cDNA of human 2,6-sialyltransferase (Hatakeyama et al., 2005), were maintained in 5% NCS/MEM+puromycin (2 µg/mL). AX4/PB2 cells (AX4 cells stably expressing the PB2 protein derived from A/Puerto Rico/8/34 (H1N1, PR8), established by transduction with a retroviral vector, see the Results section) were maintained in 5% NCS/MEM+puromycin (2 µg/mL)+blasticidin (10 µg/mL). All cells were maintained at 37° C. in 5% $CO_2$.

Reverse genetics and virus propagation. Reverse genetics was performed with plasmids that contained the cDNAs of the PR8 viral genes between the human RNA polymerase 1 promoter and the mouse RNA polymerase 1 terminator (referred to as PolI plasmids) and eukaryotic protein expression plasmids (NP, PA, PB1, and PB2) under the control of the chicken β-actin promoter (Niwa et al., 1991), as described in Neumann et al. (1999). Briefly, the wild-type PR8 virus was engineered by using the eight previously produced wild-type constructs derived from PR8 (Horimoto et al., 2007); whereas the PB2-KO mutant was comprised of pPolIPB2(120)GFP(120) (FIG. 3A) (Muramoto et al., 2006) and the remaining seven segmental PolI plasmids. The pPolIPB2(120)GFP(120) plasmid contains the A/WSN/33 (H1N1, WSN)-derived 3' PB2 non-coding region, 120 nucleotides that correspond to the PB2 coding sequence at the 3' end of the vRNA followed by the GFP coding sequence, 120 nucleotides that correspond to the PB2 coding sequence at the 5' end of the vRNA, and finally the 5' PB2 non-coding region (Muramoto et al., 2006). Likewise, pPolIPB2(120)Fluc(120) and pPolIPB2(120)Rluc(120) were constructed to generate PB2-KO viruses possessing the firefly luciferase (Fluc) or *Renilla* luciferase (Rluc) genes, respectively. The eight PolI plasmids and protein expression plasmids were mixed with the transfection reagent TransIT-293 (Mirus), incubated at room temperature for 15 minutes, and added to $10^6$ 293T cells cultured in Opti-MEM 1 (Invitrogen). Forty-eight hours post-transfection, the supernatant containing wild-type PR8 or PB2-KO virus was harvested and propagated in 10-day-old embryonated chicken eggs or AX4/PB2 cells, respectively. Wild-type CA04 was also generated by using reverse genetics, as described in Yamada et al. (2010), and propagated in MDCK cells. The propagated viruses were titrated by using plaque assays in MDCK cells to determine plaque-forming units (PFU) of virus.

Immunofluorescence staining of the PB2 protein. Confluent AX4 and AX4/PB2 cells seeded in 35 mm glass bottom dishes (Asahi Techno Glass) were fixed in phosphate buffered saline (PBS) containing 4% paraformaldehyde (Wako Pure Chemical Industries Ltd) and permeabilized with 0.1% Triton X-100. Cells were incubated with an anti-PB2 antibody clone 18/1 (Hatta et al., 2000) and further incubated with an Alexa Fluor 594-labeled anti-mouse secondary antibody (Invitrogen) in Hoescht 33342 (Invitrogen). Samples were observed under a confocal laser microscope (LSM510META; Carl Zeiss).

Reverse transcription-PCR (RT-PCR). To detect PB2 mRNA in AX4/PB2 cells, total RNA was extracted by using an RNeasy RNA extraction kit (Qiagen Sciences). Viral RNAs were isolated from virions by using a QIAmp viral RNA mini kit (Qiagen Sciences). Reverse transcription and cDNA synthesis were performed by using oligo(dT) primer and SuperScript III reverse transcriptase (Invitrogen). RT-minus samples were prepared as negative controls. The synthesized cDNA was amplified by use of PCR with Phusion PCR polymerase (Finnzymes) and PB2-specific primers. Primer sequences are as follows: forward primer, ATGGAAAGAATAAAAGAACTACGA (SEQ ID NO:9), and reverse primer GCCACAATTATTGCTTCGGC (SEQ ID NO:16).

Growth kinetics and virus titration. To determine virus growth rates, triplicate wells of confluent AX4 or AX4/PB2 cells were infected at a multiplicity of infection (MOI) of 0.001. After 1 hour of virus adsorption, cells were washed in MEM containing 0.3% BSA, overlaid with MEM containing L-(tosylamido-2-phenyl) ethyl chloromethyl ketone (TPCK)-treated trypsin (0.5 µg/mL). Supernatants were collected every 12 hours for three days and assayed for infectious virus in plaque assays in AX4/PB2 cells.

Immunostaining. To assess the stability of the GFP reporter gene incorporation in the PB2-KO virus, AX4/PB2 cells were infected with various PB2-KO virus dilutions (undiluted to $10^{-10}$). The supernatant from the second to last well in which a cytopathic effect (CPE) was observed, was harvested and diluted for subsequent infections. Supernatants from five rounds of virus passaging were subjected to standard virus plaque assays. Once the number of plaques formed was counted, the agar was removed and wells containing plaques were fixed with 100% methanol for 30 minutes. Wells were then washed with PBS and incubated with a monoclonal anti-GFP antibody (clone GFP-20; Sigma-Aldrich) at room temperature for 1 hour. Immunohistochemical staining was performed by using a biotinylated anti-mouse antibody according to the Vectastain Elite ABC kit instructions (Vector Laboratories). GFP-positive plaques were visualized by using Sigma Fast 3,3'-Diaminobenzidine tablets (Sigma), and the number of GFP-positive plaques was calculated as a percentage of the total number of plaques that formed in the respective wells.

Immunofluorescent staining for HA protein. GFP-encoding PB2-KO virus possessing HA and NA vRNAs derived from PR8, WSN, A/California/04/09 (CA04), or A/Vietnam/1203/04 (VN1203) were generated by using reverse genetics, as described above, and propagated in AX4/PB2 cells. The multiple basic amino acid residues in the VN1203 HA cleavage site were replaced with a non-virulent type cleavage sequence. Confluent AX4/PB2 cells were infected with these viruses at an MOI of 0.2-1. At 16 hours post-infection, cells were fixed with 4% paraformaldehyde in PBS and permeabilized with 0.1% Triton X-100. Cells were then incubated with an anti-WSN HA antibody (WS 3-54), an anti-CA04 HA antibody (IT-096; eENZYME), and an anti-H5 HA antibody (VN04-10; Rockland Immunochemicals Inc.) and then further incubated with an Alexa Fluor 594-labeled anti-mouse secondary antibody. Samples were observed under a fluorescence microscope.

Luciferase assay. Cells infected with PB2-KO virus encoding Fluc or Rluc gene were subjected to a luciferase assay by using a dual-luciferase reporter assay system (Promega) at 8 hours post-infection according to the manufacturer's instructions. Fluc and Rluc activities were measured with a microplate reader Infinite M1000 (Tecan).

Microneutralization assay. Sera were collected from two ferrets infected with $10^6$ PFU of wild-type CA04 three weeks post-infection and from two uninfected ferrets. Two-fold serial dilutions of receptor-destroying enzyme (DENKA SEIKEN CO., LTD)-treated ferret sera were mixed with 100 PFU of wild-type CA04 or Rluc-encoding PB2-KO virus possessing CA04-derived HA and NA vRNAs (CA04/PB2-Rluc). After incubation at 37° C. for 1 hour, wild-type AX4 or AX4/PB2 cells were inoculated with the wild-type virus- or PB2-KO virus-serum mixtures, respectively, in triplicate wells and incubated for three days or 24 hours for the wild-type virus or PB2-KO virus, respectively. The neutralization activity of the ferret sera was determined on the basis of the CPE observed under the microscope or the Rluc activity as measured by using the Renilla luciferase assay system (Promega) for the wild-type virus or PB2-KO virus, respectively.

Results

Figure 3B:
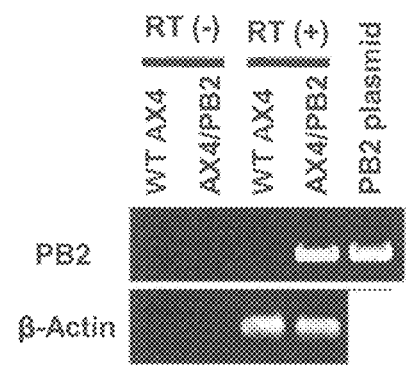
Figure 3C:
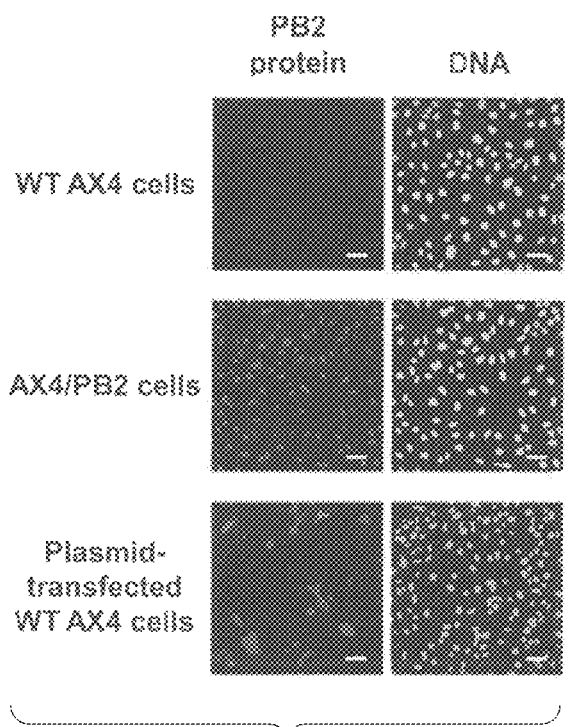

Characterization of the PR8/PB2-GFP virus. To establish a cell line that stably expresses PB2 protein, AX4 cells, which are human 2,6-sialyltransferase overexpressing Madin-Darby canine kidney (MDCK) cells that allow better replication of clinical influenza isolates compared with wild-type MDCK cells (Hatakeyama et al., 2005) were transduced, with a retroviral vector that possessed the cDNA of the A/Puerto Rico/8/34 (H1N1, PR8) PB2 protein followed by an internal ribosome entry site sequence derived from the encephalomyocarditis virus and the blasticidin resistance gene. A blasticidin-resistant cell clone was designated as AX4/PB2. To confirm the expression of mRNA for the PB2 protein in AX4/PB2 cells, total RNAs were extracted from AX4/PB2 and wild-type AX4 cells and subjected to RT-PCR with PB2-specific primers. PB2 mRNA was detected in AX4/PB2 cells but not in wild-type AX4 cells (FIG. 3B). To further validate the expression of the PB2 protein in AX4/PB2 cells, immunofluorescence staining of AX4/PB2 cells was performed by using a PB2-specific monoclonal antibody. Fluorescent signals were detected in AX4/PB2 cells and in some of the PB2 protein expression plasmid-transfected AX4 cells (which served as a positive control), whereas no signal was detected in wild-type AX4 cells (FIG. 3C). These results indicate that AX4/PB2 cells stably express the PB2 protein.

Figure 3D:
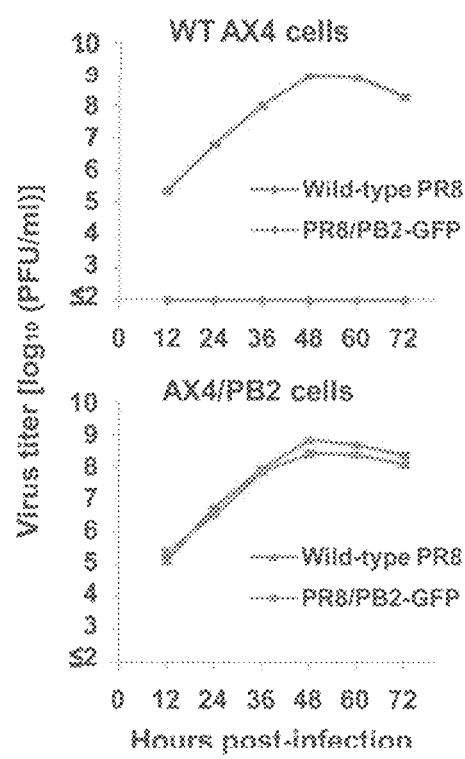

To investigate whether PB2-expressing cells support PB2-KO virus replication, a PR8-based PB2-KO virus possessing PB2(120)GFP(120) vRNA (FIG. 3A), designated as PR8/PB2-GFP (Table 1), was generated by and used to infect AX4/PB2 and wild-type AX4 cells (FIG. 3D). Although no infectious virus was detected in wild-type AX4 cells, replication of PR8/PB2-GFP virus in AX4/PB2 cells was comparable to that of wild-type PR8 (FIG. 3D). These results indicate that the replication of PB2-KO virus is restricted to PB2-expressing cells.

TABLE 1

| | Origin of: | | | |
|---|---|---|---|---|
| Virus | HA gene | NA gene | PB2 gene | Remaining genes |
| Wild-type PR8 | PR8* | PR8 | PR8 | |
| PR8/PB2-GFP | PR8 | PR8 | PB2(120)GFP(120)[ǁ] | |
| PR8ΔPB2 | PR8 | PR8 | —[¶] | |
| WSN/PB2-GFP | WSN[†] | WSN | PB2(120)GFP(120) | |
| CA04/PB2-GFP | CA04[‡] | CA04 | PB2(120)GFP(120) | PR8 |
| VN1203/PB2-GFP | VN1203[§] | VN1203 | PB2(120)GFP(120) | |
| PR8/PB2-Rluc | PR8 | PR8 | PB2(120)Rluc(120)[ǁ] | |
| PR8/PB2-Fluc | PR8 | PR8 | PB2(120)Fluc(120)[ǁ] | |
| CA04/PB2-Rluc | CA04 | CA04 | PB2(120)Rluc(120) | |

*PR8, A/Puerto Rico/8/34 (H1N1).
[†]WSN, A/WSN/33 (H1N1).
[‡]CA04, A/California/04/09 (H1N1).
[§]VN1203, A/Vietnam/1203/04 (H5N1). The multiple basic amino acid residues in the HA cleavage site (RERRRKKR↓G) were replaced with a non-virulent type cleavage sequence (RETR↓G).
[ǁ]PB2(120)GFP(120), PB2(120)Rluc(120), and PB2(120)Fluc(120). GFP, firefly luciferase, and Renilla luciferase genes, respectively, flanked by the 3' and 5' non-coding sequences and 120 bases of the 3' and 5' coding sequences of the PB2 gene.
[¶], not applicable.

The stability of the reporter gene in PB2-KO virus was ascertained by serial passaging of PR8/PB2-GFP virus in AX4/PB2 cells. GFP-expressing plaques versus total plaques formed were calculated to determine the percentage of plaque-forming viruses expressing the GFP reporter gene (Table 2); after five serial passages, 80%-90% of the plaque-forming viruses expressed GFP. PB2-KO virus failed to form plaques in wild-type cells even after five serial passages in AX4/PB2 cells, indicating that reversion of PB2-KO virus to a replication-competent genotype by recombination between the PB2-GFP vRNA and the cell-expressed PB2 mRNA is unlikely. An attempt was made to rescue a PB2 gene-deficient virus possessing seven vRNA segments (PR8ΔPB2, Table 1); however, neither cytopathic effect (CPE) nor NP protein expression were observed in AX4/PB2 or wild-type AX4 cells inoculated with the transfectant supernatant for PR8ΔPB2 (data not shown). These results highlight the importance of the PB2 vRNA for efficient generation of infectious virions (Muramoto et al., 2006).

TABLE 2

Genetic stability of PB2-KO virus.

| | Ratio of GFP-positive plaques* from viruses in: | | | | |
|---|---|---|---|---|---|
| | Passage 1 | Passage 2 | Passage 3 | Passage 4 | Passage 5 |
| Exp. 1 | 100% | 90% | 90% | 100% | 80% |
| Exp. 2 | 100% | 100% | 90% | 100% | 90% |
| Exp. 3 | 100% | 90% | 90% | 100% | 90% |

*The respective viral supernatants were subjected to standard virus plaque assays in confluent AX4/PB2 cells. Ten plaques were marked per well, which were then subjected to the immunodetection assay by using an anti-GFP antibody to detect GFP-expressing viral plaques.
The percentage of plaques that stained brown among all plaques is presented. The results of three independent experiments (Exp.) are shown.

Figure 4:
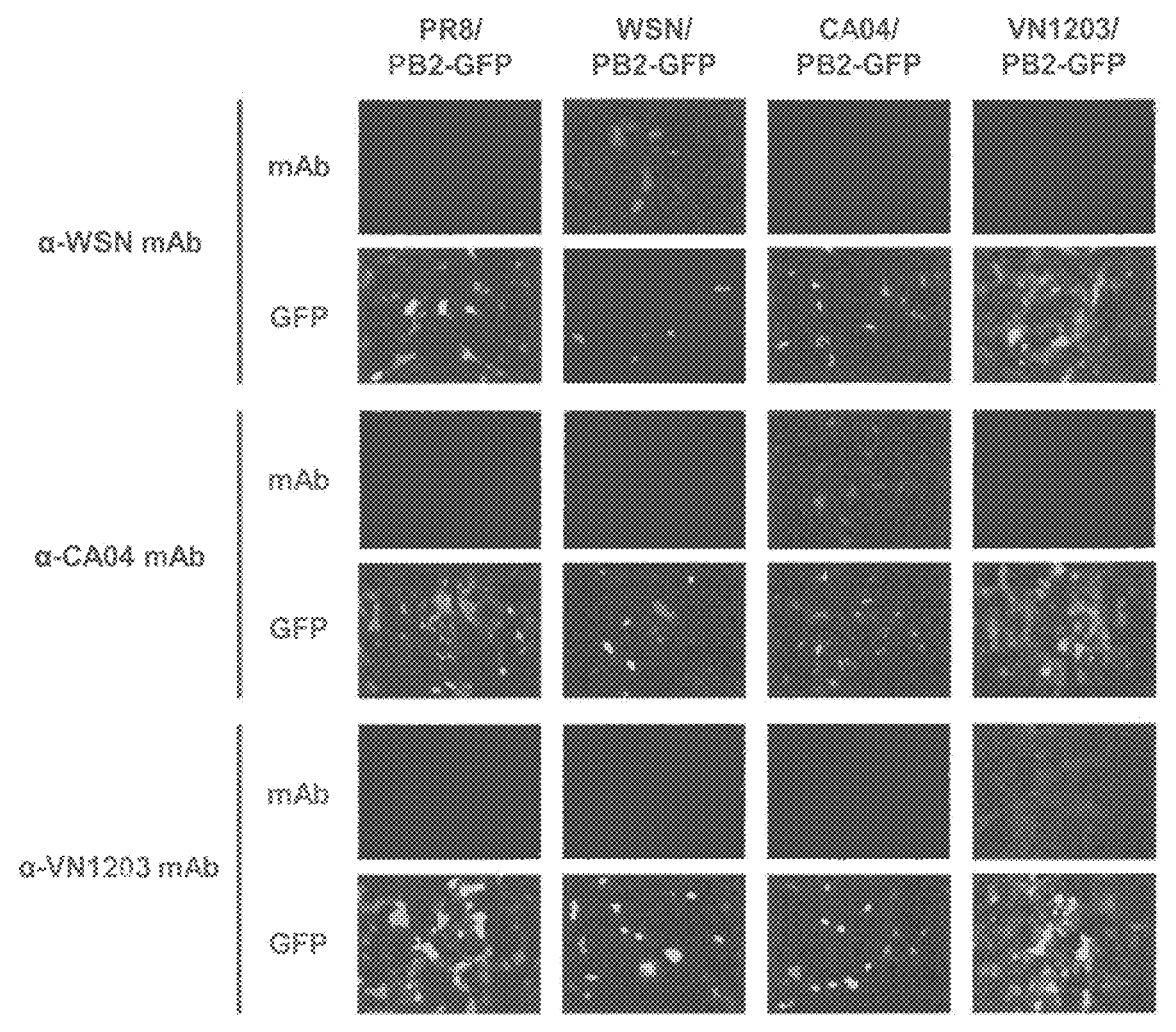

Functional expression of different HA and NA genes in PB2-KO virus. Two surface glycoproteins on influenza A virions, hemagglutinin (HA) and neuraminidase (NA), are the main protective antigens (Wright et al., 2007). In particular, HA mediates cell attachment; therefore, an antibody against HA is crucial for virus neutralization. It was tested whether the relevant glycoproteins of a PR8 virus-based PB2-KO virus could be replaced with those of other virus strains. To this end, GFP-encoding PB2-KO viruses were generated by substituting PR8 HA and NA vRNAs with those derived from a laboratory H1N1 strain A/WSN/33 (WSN/PB2-GFP), a 2009 pandemic (H1N1) strain A/California/04/2009 (CA04/PB2-GFP), or a highly pathogenic H5N1 strain A/Vietnam/1203/2004 (VN1203/PB2-GFP) (Table 1). AX4/PB2 cells were infected with these viruses and subjected to an immunofluorescence assay with various anti-HA monoclonal antibodies. In the GFP-positive virus-infected cells, virus strain-specific HA expression was detected (FIG. 4). It was confirmed by sequencing that the corresponding NA vRNAs were incorporated into virions (data not shown). These results indicate that the HA and NA genes of other influenza viruses can also be accommodated in the PB2-KO virus and hence be expressed in virus-infected cells.

Figure 5A:
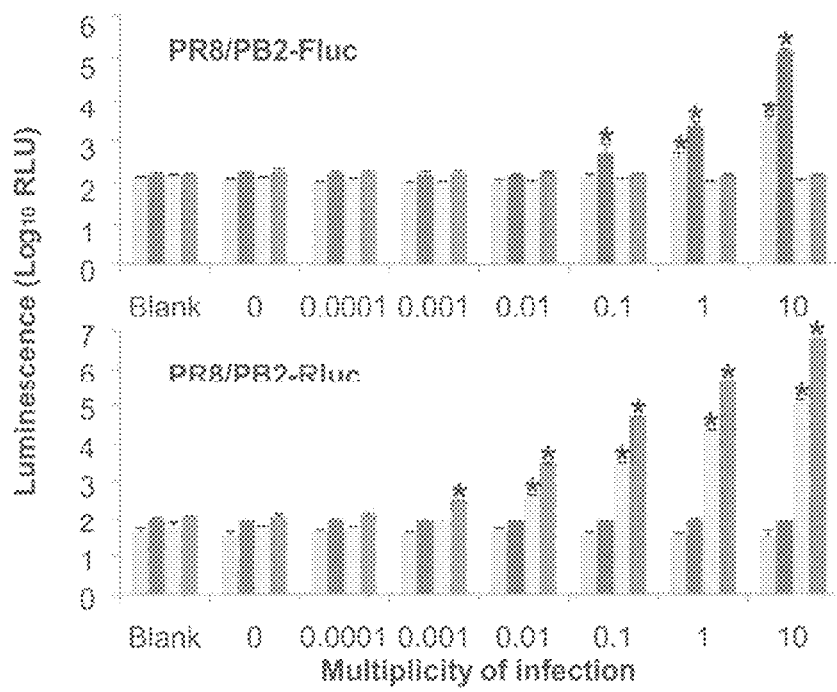
Figure 5B:
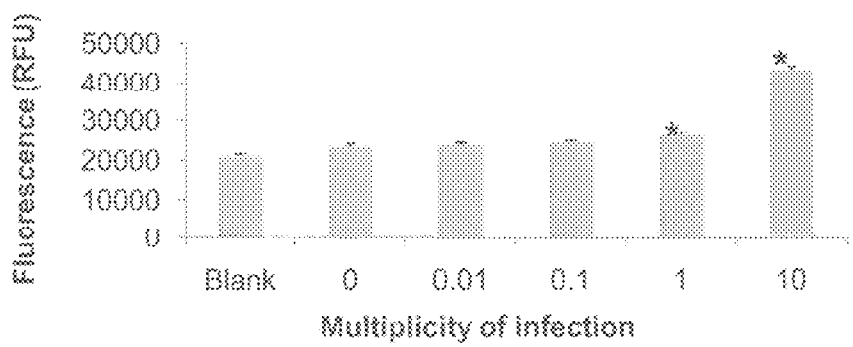

Expression of alternative reporter genes in PB2-KO virus. The activity of the luciferase reporter gene is readily quantifiable and, therefore, its incorporation into PB2-KO virus should allow one to measure virus replication based on luciferase activity. To test this possibility, PB2-KO viruses were generated that possessed either the firefly (PR8/PB2-Fluc) or Renilla (PR8/PB2-Rluc) luciferase gene in the PB2 vRNA (Table 1). AX4/PB2 and wild-type AX4 cells were infected with these viruses at various multiplicities of infection (MOIs) and subjected to a luciferase assay at 8 hours post-infection. In virus-infected AX4/PB2 cells, Fluc and Rluc activities were detected in a dose-dependent manner; viruses infected at an MOI of 0.1 and 0.001 were adequate for detecting significant Fluc and Rluc activities, respectively (FIG. 5A). By contrast, to detect significant GFP intensity in virus-infected cells, we needed to infect PR8/PB2-GFP at an MOI of 1 or higher (FIG. 5B). These results indicate that the Fluc and Rluc genes can be accommodated in PB2-KO virus and represent a more quantitative indicator for virus replication than does the GFP gene. Wild-type AX4 cells infected with PR8/PB2-Fluc and PR8/PB2-Rluc also exhibited detectable Fluc and Rluc activities, respectively, at an MOI of more than 1 for PR8/PB2-Fluc or 0.01 for PR8/PB2-Rluc, although the activity of both reporter genes was more than 10-fold lower than that detected in AX4/PB2 cells (FIG. 5A). Since the PB2 protein was not provided in trans to the wild-type AX4 cells, the expression of these reporter genes suggests that viral ribonucleoproteins (i.e., PB2, PB1, PA, and NP) derived from incoming viruses mediate the transcription of the PB2 vRNA of PB2-KO virus at a significantly high level in wild-type AX4 cells.

Figure 6:
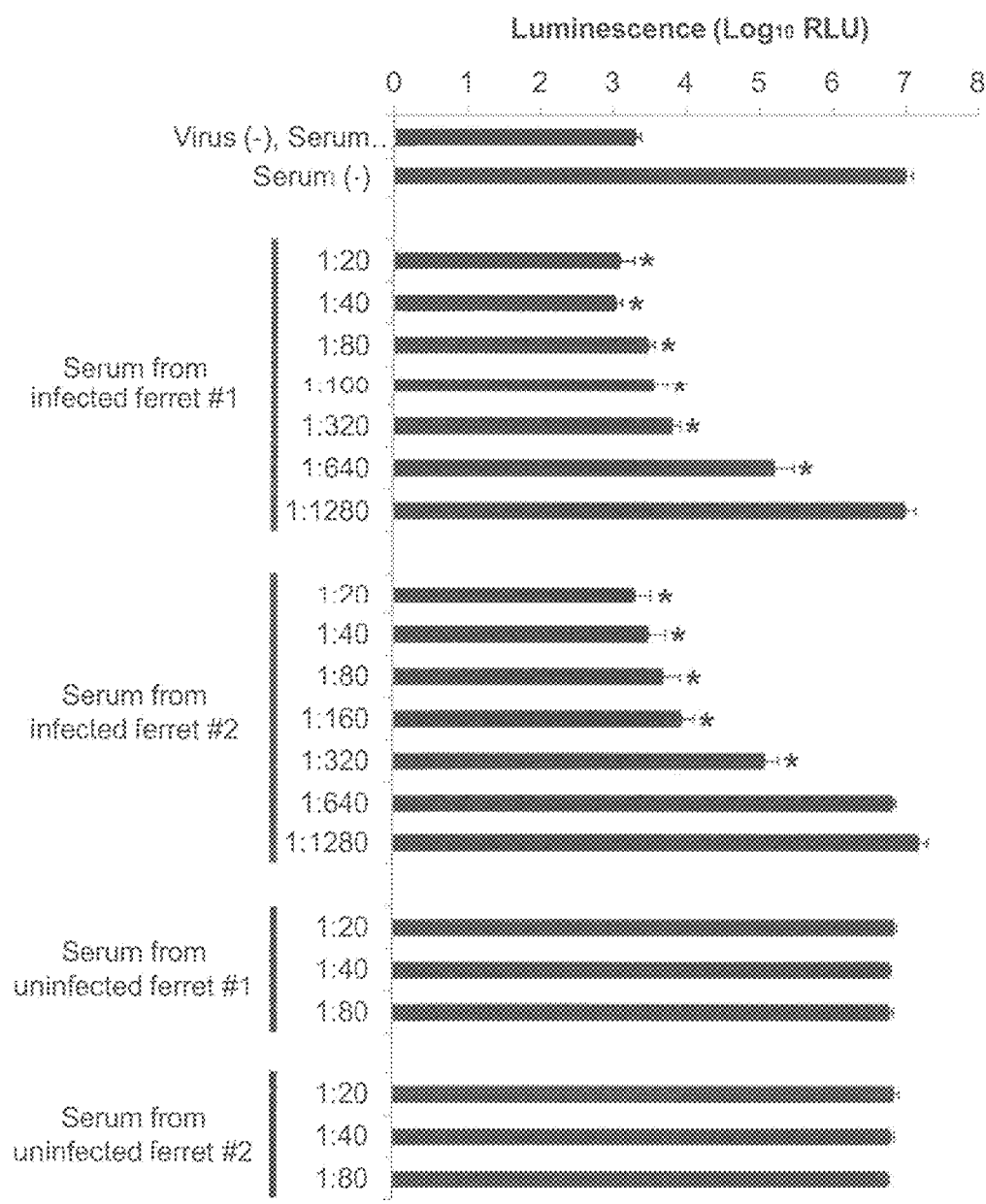

PB2-KO virus-based microneutralization. Biologically contained, reporter gene-expressing influenza viruses have the potential to supersede conventional virus replication evaluation systems in part because of the ability to quantitate growth via platereader assays. The neutralization activity of antisera is typically determined by using conventional microneutralization assays (Itoh et al., 2009; Kobasa et al., 2004), which allow the detection of neutralizing antibodies based on the presence or absence of virus infection-induced CPE or of virus antigens, as detected by using an enzyme-linked immunosorbent assay. To use PB2-KO virus to detect neutralizing antibodies against 2009 pandemic viruses, a PB2-KO virus was generated that possessed the Rluc gene-encoding PB2 vRNA and A/California/04/2009-derived HA and NA vRNAs (CA04/PB2-Rluc). CA04/PB2-Rluc (100 PFU) was mixed with serially diluted antisera collected from CA04-infected ferrets and incubated at 37° C. for 1 hour. Sera from uninfected ferrets served as negative control. The virus-sera mixtures were used to inoculate AX4/PB2 cells. At 24 hours post-infection, Rluc activity in cells was measured by using the Renilla luciferase assay system (Promega). To compare the detection sensitivity, the same antisera were also tested for neutralization activity by using a CPE-based conventional microneutralization assay with wild-type CA04 and wild-type AX4 cells. In the PB2-KO virus-based assay, 1:1280- and 1:640-diluted ferret sera induced a significant decrease in Rluc activity in virus-infected cells (FIG. 6). By contrast, the neutralizing titers of the same ferret sera as determined in the conventional microneutralization assay were 160 and 80 (data not shown). These results indicate that the PB2-KO virus coupled with PB2-expressing cells offer a neutralizing antibody detection method that is more sensitive than the conventional microneutralization assay.

Discussion

Here, it is demonstrated that PB2-KO influenza viruses are replication-incompetent in wild-type cells, but undergo multiple replication cycles in PB2 protein-expressing cells (FIG. 3D). In addition, reporter genes flanked by the PB2 vRNA packaging signals were stably maintained in progeny viruses (Table 1) and expressed in virus-infected cells (FIGS. 4 and 5). It was also confirmed that different virus strain-derived HA and NA genes were accommodated by PB2-KO viruses (FIG. 4). These results indicate that PB2-KO viruses have broad potential use throughout the field of influenza virology.

As a practical application, a PB2-KO virus-based microneutralization assay was developed and used to detect neutralizing antibodies against the 2009 pandemic virus (FIG. 6). This PB2-KO virus-based assay proved to be more sensitive than the conventional microneutralization assay in terms of neutralizing antibody detection. The use of replication-incompetent PB2-KO viruses as a screening platform (FIGS. 3C and 3D) may enable the detection of neutralizing antibodies against highly pathogenic viruses such as H5N1 and 1918 strains, which normally must be handled in BSL3 facilities and under biosafety level 2 containment, although an additional layer of biosafety (e.g., modification of the amino acid sequence of the HA cleavage site) would be required. Kong et al. (2006) previously developed a neutralizing antibody screening system based on influenza HA-pseudotyped lentiviruses, which also allows the detection of neutralizing antibodies against the biosafety level 3 agents. However, these lentiviruses do not express influenza viral neuraminidase, which, along with HA, has the potential to induce neutralizing antibodies (Nayak et al., 2010); therefore, the PB2-KO virus-based assay should more accurately reflect the neutralizing antibody titers. Although cells that stably express reporter gene-encoding influenza vRNA have also been shown to allow the sensitive detection of neutralizing antibodies (Hossain et al., 2010; Li et al., 2009), infectious viruses are required for these recombinant cell-based assays.

Another potential application of the PB2-KO virus is its use as a novel influenza vaccine, which we believe is feasible for the following reasons. First, PB2-KO virus generates high titers ($>10^8$ PFU/mL) in the AX4/PB2 cell line (FIG. 3D); second, the fact that HA and NA proteins can be expressed (FIG. 4) demonstrates that PB2-KO virus is customizable to encode desired antigens; third, the vRNA transcription that occurs in PB2-KO virus-infected cells (FIG. 5A) may stimulate cellular innate immunity by producing double-stranded RNA; and fourth, the stable maintenance of a foreign gene inserted in the PB2 vRNA (Table 2) could serve as a carrier of an additional antigen, enabling the engineering of PB2-KO as a safe multi-valent vaccine.

To date, several recombinant influenza viruses that lack a particular viral protein have been shown to replicate comparably to wild-type virus in cell culture when the missing protein is provided in trans. M2-lacking influenza virus efficiently replicates in M2-expressing cells and has demonstrated potential as a live attenuated vaccine (Watanabe et al., 2009). A distinct advantage of the PB2-KO virus over its M2 counterpart is that the former is replication-incompetent in normal cells and, thus, safer. Further, it remains unknown whether a foreign gene encoded in the M2 protein-coding region can be incorporated into progeny viruses and expressed in virus-infected cells.

Martinez-Sobrido et al. (2010) developed an improved screening assay for the rapid detection of neutralizing antibodies by using influenza virus possessing the GFP gene flanked by the HA vRNA packaging signals. Although this HA-KO virus underwent multiple replication cycles only in cells that expressed the HA protein, the stability of reporter genes in this HA-KO virus was not tested in the study. In fact, an HA vRNA-deficient virus possessing seven vRNA segments underwent multiple rounds of replication in HA-expressing MDCK cells (data not shown) in contrast to the PB2 vRNA-deficient PR8ΔPB2 virus (see above), suggesting that the reporter gene-encoding HA vRNA in HA-KO virus could be easily dropped during replication in HA-expressing cells. A replication-competent virus that possesses the GFP gene in its NA vRNA has also been used to detect neutralizing antibodies (Rimmelzwaan et al., 2011). An in trans bacterial sialidase improved the restricted replication of this NA-KO virus and allowed reasonable virus titer recovery; however, the reporter gene stability of the NA-KO virus remains uncertain.

More recently, GFP gene-possessing replication-competent influenza viruses have been generated by using recombinant NS (Manicassamy et al., 2010) or NA (Li et al., 2010) genes. Although these viruses have potential as research tools, their replicability raises biosafety issues, which are not a concern with the PB2-KO virus. Overall, the fact that the PB2-KO virus produced in this study stably expresses a foreign gene and is replication-incompetent makes it ideal in terms of reliability and biosafety.

In conclusion, a biologically contained foreign gene-expressing influenza virus was generated by replacing the viral PB2 gene with reporter genes. The replication of the virus was restricted to cells that expressed the PB2 protein in trans. The reporter gene was stably inherited in progeny viruses during replication in PB2-expressing cells. Various HA, NA, and reporter genes were accommodated in the PB2-KO virus. This virus, therefore, shows promise in terms of its numerous applications for basic and applied studies of influenza virus.

Example III

The PB2 protein of influenza viruses is an essential component of the trimeric viral RNA-dependent RNA polymerase subunit. PB2 is implicated in the regulation of host antiviral immune pathways and hence virulence and plays a major role in the incorporation of other individual vRNA segments (Muramoto et al., 2006). Example II described as PB2-knock-out (PB2-KO) influenza virus that harbors reporter genes, such as the green fluorescent protein (GFP) in the coding region of its PB2 viral RNA (vRNA). The replication of the PB2-KO virus was restricted to only a cell line stably expressing the PB2 protein, yielding a high titre of >10$^8$ PFU/mL. Moreover, during replication PB2 vRNA encoding the reporter gene was stably incorporated into progeny virions and retained through sequential passages. Also, HA and NA vRNA of any influenza virus could be accommodated in the PB2-KO virus and be expressed in virus-infected cells. Therefore, the PB2-KO virus can be tailored to encode desired combinations of HA and NA that are the main influenza antigens, suggesting that the PB2-KO virus can be used as a multivalent vaccine platform. Here, we tested the vaccine potential of the PB2-KO virus by immunizing mice, examining antibody response and protective efficacy in mice.

Materials and Methods

Cells. 293 and 293T (a derivative of the 293 line into which the gene for simian virus 40 T antigen was inserted (DuBridge et al., 1987) human embryonic kidney cells were maintained in Dulbecco's modified Eagle medium (Lonza, Basel, Switzerland) supplemented with 10% fetal calf serum (Invitrogen, Carlsbad, CA). Madin-Darby canine kidney (MDCK) cells were maintained in minimum essential medium (MEM) (Invitrogen) supplemented with 5% newborn calf serum (NCS) (Sigma, St. Louis, MO). AX4 cells, which are an MDCK-derived cell line with enhanced expression of human-type receptors for influenza virus and were produced by stable transfection of a plasmid expressing the human α-2,6-sialyltransferase (Hatakeyama et al., 2005), were maintained in 5% NCS-MEM supplemented with puromycin (2 µg/mL). AX4/PB2 cells (AX4 cells stably expressing the PB2 protein derived from A/Puerto Rico/8/34 [H1N1, PR8], established by transduction with a retroviral vector (Ozawa et al., 2011) were maintained in 5% NCS-MEM supplemented with puromycin (2 µg/mL) and blasticidin (10 µg/mL). All cells were maintained in a humidified incubator at 37° C. in 5% $CO_2$.

Plasmid-driven reverse genetics. The wild-type PR8 and PB2-KO viruses used in this study were engineered by using reverse genetics, as previously described (Neumann et al., 1999). For expression of viral RNA (vRNA), plasmids contained the cloned cDNAs of PR8 genes between the human RNA polymerase I promoter and the mouse RNA polymerase I terminator (referred to as PolI plasmids). A plasmid [pPolIPB2(120)GFP(120)] was constructed to replace the PolI plasmid encoding the PB2 segment and contained the A/WSN/33(H1N1)-derived 3' PB2 noncoding region, 120 nucleotides that correspond to the PB2-coding sequence at the 3' end of the vRNA followed by the GFP-coding sequence, 120 nucleotides that correspond to the PB2-coding sequence at the 5' end of the vRNA, and finally the 5' PB2 noncoding region (Muramoto et al., 2006). To generate the PB2-KO virus, pPolIPB2(120)GFP(120) and the remaining 7 PolI plasmids were cotransfected into 293T cells along with eukaryotic protein expression plasmids for PB2, PB1, PA, and NP derived from A/WSN/33 by use of the TransIT 293 transfection reagent (Mirus, Madison, WI), following the manufacturer's instructions. At 48 hours post-transfection, the supernatants containing the PR8 or PB2-KO virus were harvested and inoculated into 10-day-old embryonated chicken eggs or AX4/PB2 cells, respectively. Both viruses were titrated by use of plaque assay with AX4/PB2 cells.

Preparation of formalin-inactivated virus. Egg-propagated PR8 viruses were concentrated and purified by ultracentrifugation of the infected allantoic fluid through a 10% to 50% sucrose density gradient and resuspended in phosphate-buffered saline (PBS). Formalin (final concentration, 0.1%) was added to inactivate the purified PR8 virus at 4° C. for 1 week. Inactivation of the virus was confirmed by passaging viruses twice in MDCK cells and examining the cytopathic effect or lack thereof.

Experimental infection of mice with PB2-KO virus. To test the safety of the PB2-KO virus in mice, six 4-week-old female BALB/c mice were intranasally inoculated with 10$^6$ PFU/mouse of the virus. The body weight and survival of the infected mice were monitored daily for 14 days postinoculation. Also, on days 1, 3, and 6 postinoculation, lungs and nasal turbinates from the inoculated mice were harvested, homogenized, and subjected to plaque assays to detect the presence of virus.

Immunization and protection test. Eight-, six-, or four-week-old female BALB/c mice (3 mice per group) were anesthetized with isoflurane and intranasally inoculated with 50 µl of medium (MEM-containing 0.3% bovine serum albumin fraction V), formalin-inactivated PR8 (64 hemagglutination units, which is equivalent to 10$^6$ PFU of the PB2-KO virus), or PB2-KO virus (10$^6$ PFU) once, twice, or three times at 2-week intervals, respectively. Three weeks after the final inoculation, mice were intranasally challenged with 0.5 or 5 50% mouse lethal doses ($MLD_{50}$) of PR8 virus. On days 3 and 6 postinfection, lungs and nasal turbinates of mice (3 mice per group) were collected, homogenized in 1 ml of PBS by using TissueLyser II (Qiagen, Valencia, CA), and clarified by low-speed centrifugation (5,000 rpm for 10 minutes at 4° C.). Virus titers in homogenates were determined by using plaque assays with AX4/PB2 cells. The body weight and survival of the remaining challenged mice (3 mice per group) were monitored daily for 14 days.

Detection of virus-specific antibodies. Sera from mice (3 mice per group) were obtained via mandibular vein bleeding prior to each immunization and via the femoral artery 1 day before challenge. Nasal wash and bronchoalveolar lavage (BAL) fluid samples (3 mice per group) were also obtained 1 day before challenge from mice sacrificed by cervical dislocation. Incisions were made to insert a cannula into the trachea. The lungs were then perfused with 1 ml of PBS by using a syringe. The lavage fluid was recovered and stored in microtubes on ice. Nasal wash was collected by passing 400 μl of PBS through the nasal cavity. IgG and IgA antibodies in the sera, nasal washes, and BAL fluid samples were detected by using an enzyme-linked immunosorbent assay (ELISA) as previously described (Kida et al., 1982). Each well was coated with purified PR8 disrupted with 0.05 M Tris-HCl (pH 7.8) containing 0.5% Triton X-100 and 0.6 M KCl. After incubation of the virus-coated plates with the test samples, IgA and IgG antibodies in the samples were detected by use of goat anti-mouse IgA or IgG antibodies conjugated to horseradish peroxidase (Kirkegaard & Perry Laboratories, Inc., Gaithersburg, MD). Neutralizing antibody titers in sera of immunized mice were also evaluated as previously described (Iwatsuki-Horimoto et al., 2011). Briefly, virus (100 50% tissue culture infectious doses [$TCID_{50}$]) was incubated with 2-fold serial dilutions of receptor-destroying enzyme-treated sera for 30 minutes at 33° C., and the mixtures were added to confluent MDCK cells on 96-well microplates to determine the neutralizing activity.

IFA for detection of antibodies against GFP. 293 cells grown in 35-mm glass-bottom dishes (Asahi Techno Glass) were transfected with a plasmid expressing GFP and incubated for 48 hours prior to the immunofluorescence assay (IFA). Cells were fixed in PBS containing 4% paraformaldehyde (Wako Pure Chemical Industries Ltd.) for 15 min and permeabilized with 0.1% Triton X-100 for 5 minutes. They were incubated for 1 hour with 20-fold-diluted serum collected from mice mock immunized with medium or immunized with formalin-inactivated PR8 or with the PB2-KO virus. Anti-GFP antibody (clone GFP-20; Sigma-Aldrich)-treated cells served as a positive control. All cells were then further incubated for 1 hour with an Alexa Fluor 594-labeled goat anti-mouse secondary antibody (Invitrogen) and Hoechst 33342 (Invitrogen) for the detection of GFP antibody and nuclear staining, respectively. Samples were observed under a confocal laser microscope (LSM510META; Carl Zeiss, Jena, Germany).

Results

Figure 7A:
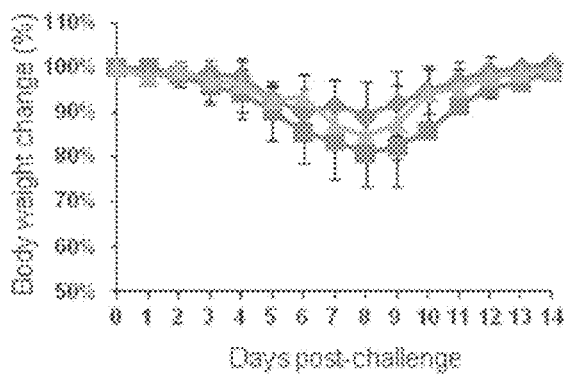
Figure 7B:
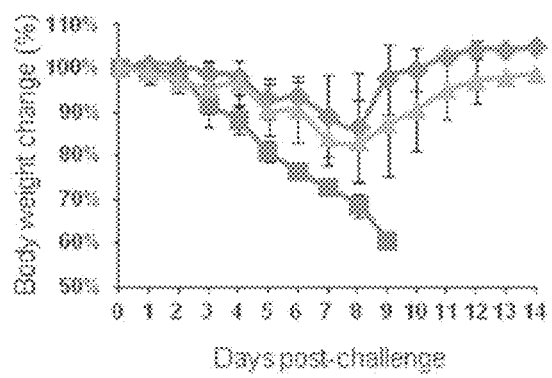
Figure 7C:
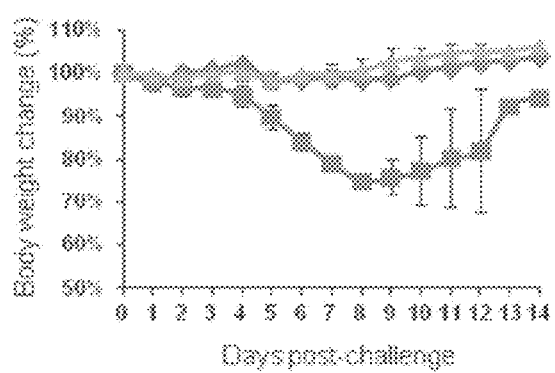
Figure 7D:
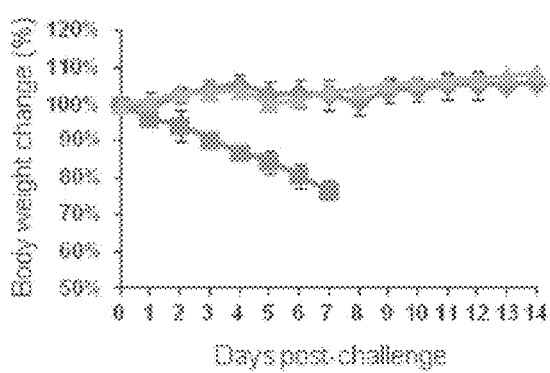
Figure 7E:
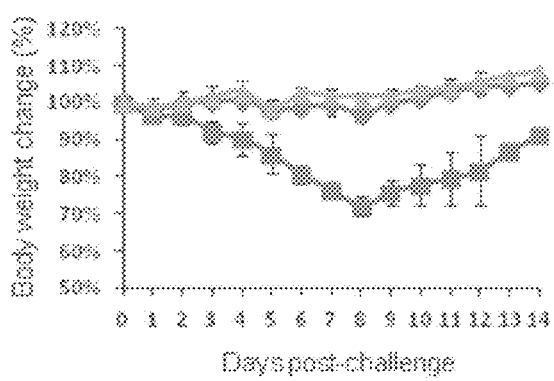
Figure 7F:
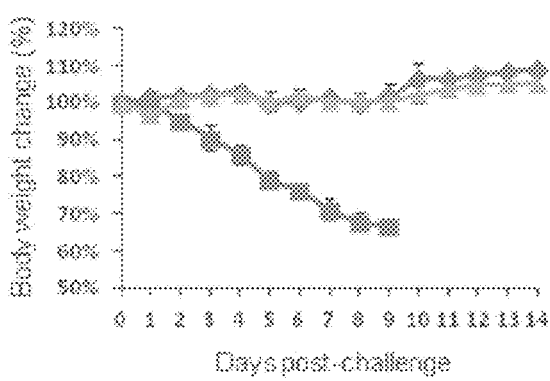

Characterization of the PB2-KOvirus in mice. The PB2-KO virus was replication incompetent in AX4 cells but yielded high titers similar to those of PR8 in AX4/PB2 cells. To determine whether the PB2-KO virus could serve as an influenza vaccine, its safety profile was assessed in mice by intranasally inoculating each mouse with the PB2-KO virus ($10^6$ PFU in 50 μL) and monitoring body weight for 2 weeks. Mice steadily achieved stable growth increments and appeared unperturbed by PB2-KO virus infection (data not shown). Lungs and nasal turbinates obtained on days 1, 3, and 6 postinoculation were homogenized and subjected to plaque assays in AX4/PB2 cells to assess the growth of the PB2-KO virus in mice. No plaques were detected from organs of mice infected with the PB2-KO virus, whereas a high virus titer ($10^8$ PFU/g) was found in lung tissue of mice infected with $10^6$ PFU of PR8 virus. These results indicate that the PB2-KO virus did not grow in mice and that reversion to a replication-competent virus did not occur.

Virus-specific antibody responses in mice inoculated with the PB2-KO virus. The level of antibody responses elicited by the PB2-KO virus was examined in mice that were intranasally inoculated with the PB2-KO virus once, twice, or three times at 2-week intervals. For comparison, mice were also mock immunized with medium or immunized with formalin-inactivated PR8 virus at a dose equivalent to $10^6$ PFU of the PB2-KO virus. Sera were collected at various time points to determine the presence of different levels of antibodies over time. Also, at 3 weeks after the final inoculation, the levels of IgG and IgA antibodies against PR8 in the sera, nasal washes, and BAL fluid samples were examined by using an ELISA (FIG. 8). Neither the IgG nor the IgA response in any sample was appreciable in mice inoculated with medium. In contrast, mice immunized with the formalin-inactivated PR8 and PB2-KO viruses exhibited a time-dependent increase in serum IgG and IgA levels. After three immunizations, similar antibody levels were detected in both inactivated virus- and PB2-KO virus-immunized mice. Interestingly, when mice were immunized once or twice, significantly higher serum IgG or IgA titers, respectively, were observed in PB2-KO virus-immunized mice than in mice immunized with the formalin-inactivated virus (FIG. 8, top panel). In nasal washes of mice inoculated with PB2-KO virus twice and in BAL fluids of mice inoculated once and twice, IgG and IgA levels were significantly higher than those in mice inoculated with the formalin-inactivated virus (FIG. 8, middle and bottom panels, respectively). Thus, PB2-KO virus efficiently induced IgG and IgA antibody responses in this murine model. Sera obtained from mice mock immunized with medium had no neutralizing antibodies, whereas those from PB2-KO-treated mice had neutralizing antibody titers of 1:16, which was approximately 2-fold higher than that in mice treated with inactivated virus (data not shown). Neutralizing activities were not detected in any nasal wash sample or BAL fluid (data not shown).

Vaccine efficacy of the PB2-KO virus. To assess the vaccine efficacy of the PB2-KO virus, mice were challenged with 0.5 or 5 $MLD_{50}$ of PR8 virus. The former challenge dose was tested to mimic natural infections, in which individuals are usually infected with a relatively low virus dose (certainly not a lethal dose).

(i) Body weight changes and survival of immunized mice after challenge. To assess the vaccine efficacy of the PB2-KO virus, body weight changes and survival of mice immunized with the PB2-KO virus were examined after they were challenged with the PR8 virus. Mice mock immunized with medium and challenged with 0.5 $MLD_{50}$ of PR8 experienced substantial body weight loss, which they subsequently recovered (FIG. 7, left panels). On the other hand, all mice mock immunized with medium and challenged with 5 $MLD_{50}$ of PR8 showed substantial body weight loss and died at approximately 1 week postinfection (FIGS. 2, right panels). Mice immunized once with the formalin-inactivated or PB2-KO virus experienced weight loss (15%) after each challenge dose (FIG. 7A). It is noteworthy that 100% of mice immunized once with the PB2-KO virus survived, whereas one out of three mice immunized once with the formalin-inactivated virus died on day 8 postinfection after being challenged with 5 $MLD_{50}$ of the PR8 virus (data not shown). All mice immunized twice and three times with the inactivated and PB2-KO viruses survived without any appreciable body weight loss (FIGS. 7B and C).

(ii) Virus replication in lungs and nasal turbinates. To evaluate virus replication in the lungs and nasal turbinates of mice immunized with the PB2-KO virus, both organs were collected on days 3 and 6 post-challenge with the PR8 virus. FIG. 9A-9H shows the extent of virus replication in these organs. The PR8 virus replicated to a high titer in the lungs and nasal turbinates of all mock-immunized mice. Although the potency of the PB2-KO vaccine was similar to that of the formalin-inactivated vaccine in mice immunized once, in mice that received two or three vaccinations, the PB2-KO vaccine was more efficacious than the formalin-inactivated vaccine, with virus titers in both organs being considerably lower in mice immunized with the former than in those immunized with the latter. Taken together, these results indicate that the PB2-KO virus has better potency as an influenza vaccine than the formalin-inactivated virus.

Detection of antibodies against GFP in mice inoculated with the PB2-KO virus. Finally, it was determined whether the PB2-KO virus could induce antibodies against GFP, because the PB2-KO virus used here possesses the GFP gene in its PB2-coding region and GFP was expressed in PB2-KO virus-infected culture cells (data not shown). The detection of an anti-GFP antibody in the sera of mice inoculated with the PB2-KO virus would suggest the potential for this system as a platform for the development of an influenza virus-based multivalent vaccine. Therefore, sera was collected from mice on day 3 post challenge and tested them in an IFA. GFP was not detected with sera from mock-immunized mice or from those immunized with the inactivated vaccine (FIG. 10A-10D); however, sera from mice immunized with the PB2-KO virus, as well as a commercial anti-GFP antibody (which served as a positive control), detected GFP expression. These results indicate that an antibody against GFP was induced in mice immunized with the PB2-KO virus, suggesting the potential application of the PB2-KO virus as a multivalent vaccine.

Discussion

Here, it was demonstrated that a replication-incompetent PB2-KO virus elicits virus-specific protective antibody responses and that this virus also induces antibodies against the reporter protein encoded in the coding region of its PB2 segment. In particular, the PB2-KO vaccine protected mice from lethal challenge with H1N1 PR8 virus, suggesting the potential of this vaccine against influenza A infection. The ability to detect antibody against GFP in sera of mice inoculated with PB2-KO virus suggested that if the reporter gene, or GFP in this case, were to be replaced with the antigenic region of another pathogen, mice inoculated with the recombinant virus will express antibodies against this secondary pathogen; in turn suggesting its potential as a multivalent vaccine. Therefore, replication-incompetent PB2-KO virus can serve as a platform for an influenza vaccine as well as for a multivalent vaccine if the PB2-coding region is replaced with the antigenic portion of another pathogen.

Inactivated and live-attenuated vaccines including gene knock-out viruses have been reported to successfully immunize mice against lethal influenza infections. The M2-KO virus lacking transmembrane and cytoplasmic tail domains efficiently replicates in M2-expression cells and demonstrates potential as a live attenuated vaccine (Watanabe et al., 2009). The HA-KO was also shown to undergo multiple replication cycles in cells that constitutively express the HA protein (Martinez-Sobrido et al., 2010); however, large quantities of viruses yielding sufficient HA protein in high titers seem to be required for protective efficacy. The stable incorporation and maintenance of the reporter gene has not been studied in the M2-KO or HA-KO systems. Previously, it was demonstrated that replication-incompetent virus-like particles (VLPs) efficiently elicit mucosal and systemic immune responses in a murine model. VLPs that lack NS2 protect mice against various lethal doses of influenza viruses (Watanabe et al., 2002). However, the absence of a cell line that constitutively expresses NS2 precludes the efficient production of sufficient VLPs to elicit protective efficacy.

In contrast to the M2-KO, HA-KO and/or VLPs described above, PB2-KO virus could be prepared in a cell line that expressed PB2, yielded high titers, and stably incorporated and maintained a GFP gene during virus replication (Ozawa et al., 2011). These data clearly establish the feasibility of using this system for efficient vaccine production Safety is of utmost importance when the potential use of viruses as vaccines is concerned. Both live attenuated and most inactivated influenza vaccines are currently propagated in embryonated chicken eggs, although cell-based vaccines have been licensed in Europe. Since a prerequisite for successful egg-based vaccine propagation is the selection of variants adapted to embryonated chicken eggs at the time of implementation, the virus in the vaccine may be slightly different from the circulating viruses in terms of antigenicity (Fulvini et al., 2011; Hardy et al., 1995; Robertson, 1993). Because of the propensity of egg proteins in these vaccines to induce allergies, parenterally administered inactivated vaccines produced in eggs are associated with adverse or anaphylactic reactions in some individuals (Halperin et al., 2002). An added complication is the possible depletion of chicken stocks in the event of an outbreak of a highly pathogenic avian influenza pandemic, which could compromise mass vaccine production (Hampson, 2008).

In contrast, cell-based alternatives offer several advantages over conventional egg-based vaccine propagation. Manufacturing capacity can be readily scaled up in proportion to demand. In addition, unlike for viruses grown in eggs, the antigenicity of viruses grown in cells matches that in animals and humans (Katz et al., 1990; Robertson et al., 1991).

A cell line was established that stably expresses PB2 and PB2-KO virus efficiently replicated in this cell line (i.e., at a level comparable to that for wild-type virus) (Ozawa et al., 2011). In cells that do not express PB2 in trans, replication-incompetent PB2-KO virus only undergoes a single cycle of replication and will not result in the formation of infectious particles; thus PB2-KO virus induces a protective antibody response without allowing the replication of infectious virus. Therefore, a cell-based PB2-KO vaccine eliminates various obstacles to vaccine preparation and delivery.

Furthermore, knocking out the PB2 gene renders the PR8 influenza virus replication incompetent with no evidence of recombination between the recombinant PB2 vRNA and the PB2 protein mRNA even upon multiple replication cycles.

Figure 8A:
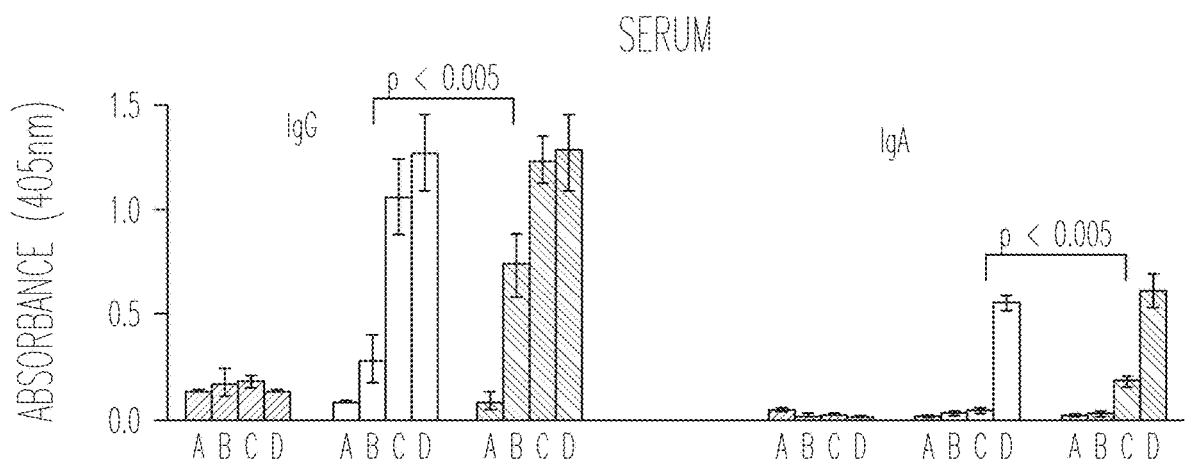
Figure 8B:
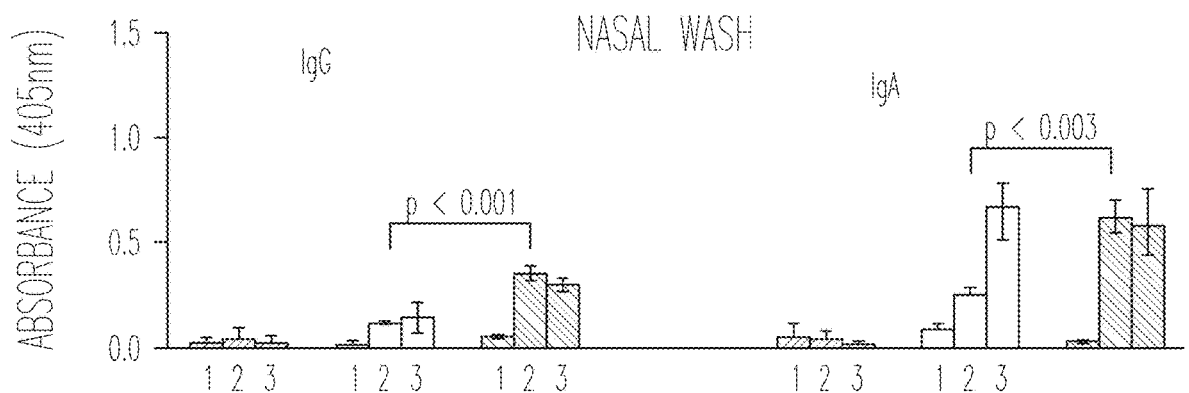
Figure 8C:
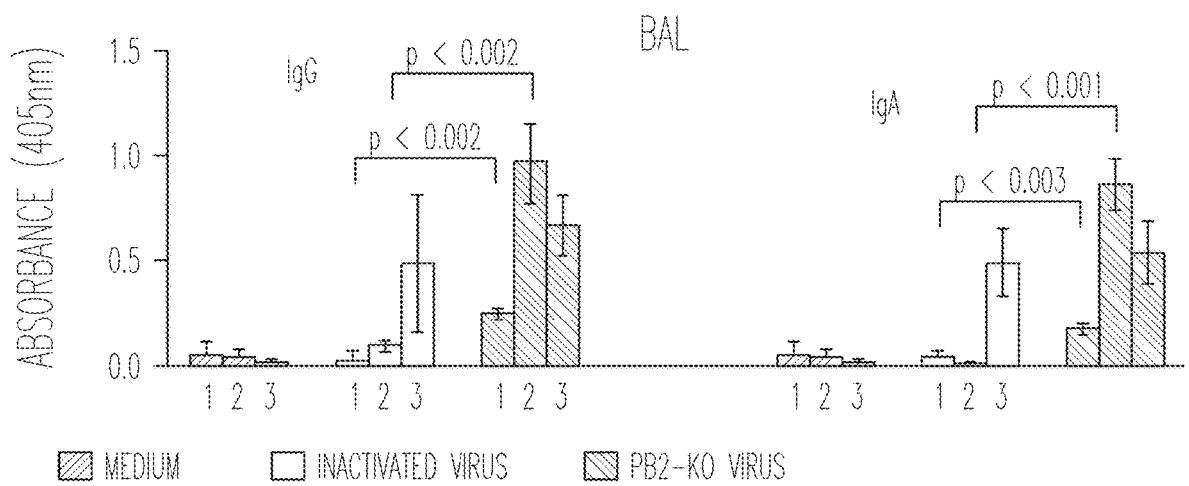
Figure 10A:
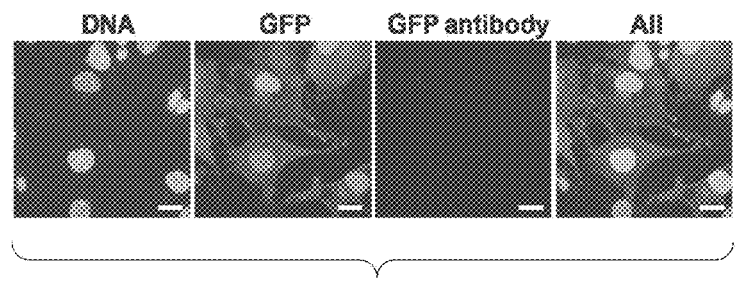
Figure 10B:
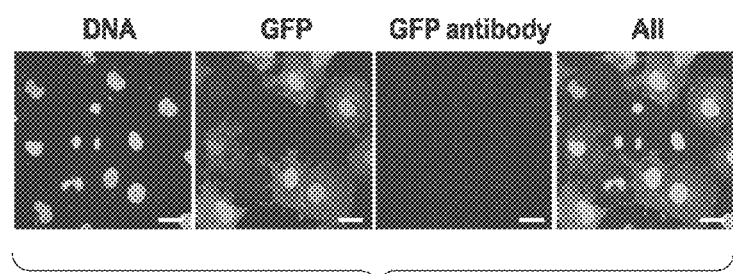
Figure 10C:
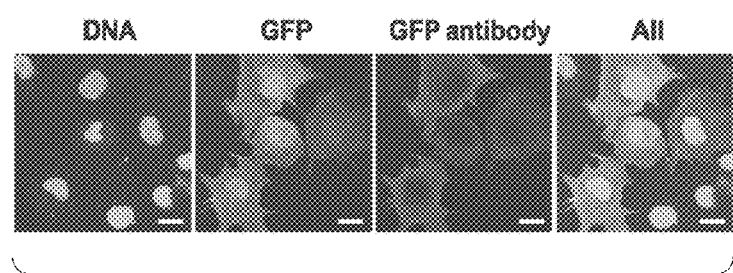
Figure 10D:
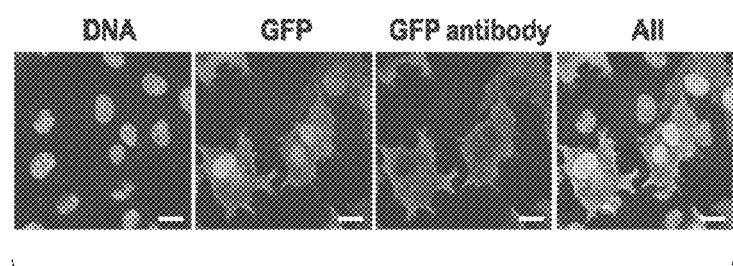

A formalin-inactivated vaccine efficiently protected mice from challenges with lethal doses of the PR8 virus by eliciting immune responses (FIGS. 7-9). However, even though the outcomes in terms of survival and body weight loss were similar for mice immunized with the formalin-inactivated vaccine and those immunized with the PB2-KO vaccine (FIG. 7), the virus titers in the lungs and nasal turbinates of the mice immunized with the former vaccine were higher than in those in mice immunized with the latter (FIG. 9). This finding likely reflects differences in the levels of immune responses (FIG. 8). It is also plausible that cytotoxic T lymphocyte (CTL) responses were activated by the PB2-KO virus but not by the formalin-inactivated virus, since inactivated antigens are thought not to induce CTL responses, although CTL responses were not examined in this study.

By definition, a multi-valent or poly-valent vaccine refers to a vaccine designed to elicit an immune response to more than one infectious agent or to several different antigenic determinants of a single agent. Based on the fact that other reporter genes and the HA and NA genes of different virus strains can be accommodated by the PB2-KO virus, the design and manufacturing of a multi-valent vaccine is made feasible. As a result, it is conceivable that the PB2-KO vaccine may confer protection against several different antigenic strains of influenza, or subtypes of influenza and/or other pathogens. An added advantage includes the possibility of mucosal delivery of vaccine precluding the use of needles for subcutaneous injection of vaccine and so forth.

In conclusion, given that the PB2-KO virus elicited effective immune responses, induced antibodies against the product of a reporter gene encoded in its PB2 segment, is easily propagated, and can be safely administered as a vaccine, the PB2-KO virus represents a credible, safe, and efficacious vaccine candidate.

Example IV

*Streptococcus pneumoniae* is a respiratory pathogen that causes secondary bacterial infection following influenza virus infection, which is associated with elevated mortality in the elderly. Parainfluenza viruses, such as respiratory syncytial virus and human parainfluenza virus type 1, are respiratory pathogens that cause severe manifestations in infants. No vaccines are currently available for parainfluenza virus. The PB2-KO virus could be used as a multivalent vaccine because an antibody against the reporter gene product (GFP in this case) encoded in the coding region of the PB2 segment was induced in place of authentic PB2 (FIG. 10A-10D). If major antigens of pathogens are similarly encoded in the coding region of the PB2 segment, the PB2-KO virus could induce immune responses against those antigens as well as against influenza viral proteins, thereby protecting infants and the elderly from these serious respiratory diseases.

FIG. 11 shows expression of PspA of *Streptococcus pneumonia* and influenza virus antigen in cells having PB2-KO-PspA, and expression of influenza virus antigen in cells having PB2-KO-GFP. PB2-KO-PspA has growth kinetics similar to wild-type influenza virus in cells that express PB2 in trans but is unable to expand in cells that do not express PB2 in trans (FIG. 12).

Mice infected with PB2-KO-PspA or PB2-KO-GFP have influenza specific IgG and IgA in sera, BAL and nasal washes (FIG. 13), and mice infected with PB2-KO-PspA, but not PB2-KO-GFP, have pneumococcal specific IgG in sera (FIG. 14), and BAL and nasal washes (FIG. 15).

Mice immunized three times with PB2-KO-PspA survived challenge with influenza virus (FIG. 16) and *Streptococcus pneumonia* (FIG. 19). Influenza virus in the control and immunized mice could be detected in nasal turbinates and lung at day 3 post-challenge (FIG. 17). Post-challenge, bacterial load was reduced in PB2-KO-PspA, but not PB2-KO-GFP, immunized mice (FIG. 18).

REFERENCES

Cox et al., *Scand. J. Immunol.*, 59:1 (2004).
Davies et al., *Science*, 144:862 (1964).
DuBridge et al., *Mol. Cell Biol.*, 7:379 (1987).
Duhaut et al., *Virology*, 248:241 (1998).
Gruber, *Vaccine*, 20:566 (2002).
Fiore et al., *MMWR Recommend. Rep.*, 9:1 (2010).
Fulvini et al., *PLoS One*, 6:e20823 (2011)
Halperin et al., *Vaccine*, 20:1240 (2002).
Hampson, *Ann. Acad. Med. Singapore*, 37:510 (2008).
Hardy et al., *Virology*, 211:302 (1995).
Hatakeyuma et al., *J. Clin. Microbiol.*, 43:4139 (2005).
Hatta et al., *Arch. Virol.*, 14:1947 (2000).
Hayden, *Trans. R. Soc. Lond. B. Biol. Sci.*, 356:1877 (2001).
Hoffmann et al., *J. Virol.*, 79:11014 (2005).
Horimoto et al., *Virology*, 366:23 (2007).
Hossain et al., *J. Clin. Microbiol.*, 48:2515 (2010).
Itoh et al., *Nature*, 460:1021 (2009).
Iwatsuki-Horimoto et al., *Clin. Vaccine Immunol.* 18:860 (2011).
Jennings et al., *Cell*, 34:619 (1983).
Katz et al., *J. Virol.*, 64:1808 (1990).
Kemble et al., *Vaccine*, 21:1789 (2003).
Kida et al., *Virology* 122:38 (1982).
Kobasa et al., *Nature*, 431:703 (2004).
Kong et al., *Proc. Natl. Acad. Sci. USA*, 103:15987 (2006).
Li et al., *J. Virol.*, 84:12075 (2010).
Li et al., *Viruses*, 3:241 (2009).
Lin et al., *Virus Res.*, 103:47 (2004).
Maassab, *Nature*, 219:645 (1968).
Manicassamy et al., *Proc. Natl. Acad. Sci. USA*, 107:11531 (2010).
Martinez-Sobrido et al., *J. Virol.*, 4:2157 (2010).
Moss et al., *J. Antimicrob. Chemother.*, 65:1086 (2010).
Muramoto et al., *J. Virol.*, 80:2318 (2006).
Murphy et al., *Viral. Immunol.*, 15:295 (2002).
Nayak et al., *J. Virol.*, 84:2408 (2010).
Neumann et al., *Proc. Natl. Acad. Sci. USA*, 96:9345 (1999).
Niwa et al., *Gene*, 108:193 (1991).
Noble et al., *Virology*. 210:9 (1995).
Odagiri et al., *Proc. Natl. Acad. Sci. USA*, 87:5988 (1990).
Ozawa et al., *J. Gen. Virol.*, 92:2879 (2011).
Palese et al., *J. Clin. Invest.*, 110:9 (2002).
Palese et al., In *Fields virology*, 5th edn, pp. 1647-1689 (2007), Edited by D. M. Knipe & P. M. Howley, Philadelphia, Pa.: Lippincott-Raven Publishers.
Reichert et al, *N. Engl. J. Mol.*, 344:889 (2001).
Rimmelzwaan et al., *Vaccine*, 29:3424 (2011).
Robertson, *Rev. Med. Virol.*, 3:97 (1993).
Robertson et al., *J. Gen. Virol.*, 72:2671 (1991).
Smith et al., *J. Gen. Virol.*, 68:2729 (1987).
Vesikari et al., *Pediatr. Infect. Dis. J.*, 25:590 (2006).
Watanabe et al., *J. Virol.*, 76:767 (2002).
Watanabe et al., *J. Virol.*, 83-5947 (2009).
Wright et al., In *Fields virology*, 5th edn, pp. 1691-1740 (2007). Edited by D. M.
Knipe & P. M. Howley, Philadelphia, Pa.: Lippincott-Raven Publishers.
Yamada et al., *PLoS Pathog.*, 6:e1001034 (2010).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A vaccine comprising an effective amount of a biologically contained influenza A virus comprising: 8 different viral segments including a PA viral segment, a PB1 viral segment, a mutant PB2 viral segment, a HA viral segment, a NA viral segment, a NP viral segment, a M (M1 and M2) viral segment, and a NS (NS1 and NS2) viral segment, wherein the mutant PB2 viral segment includes 5' and 3' incorporation sequences including 3' or 5' coding and non-coding incorporation sequences flanking a heterologous nucleotide sequence comprising a therapeutic or prophylactic gene and does not include contiguous sequences corresponding to sequences encoding a functional PB2, and wherein the HA viral segment encodes one of subtypes H1 to H16.

2. The vaccine of claim 1 wherein the heterologous nucleotide sequence encodes a gene product that induces a prophylactic or therapeutic immune response to a pathogen.

3. The vaccine of claim 1 wherein the heterologous nucleotide sequence encodes a heterologous protein that with the influenza virus HA encoded by the HA viral segment provides for multivalency.

4. The vaccine of claim 1 wherein the heterologous nucleotide sequence encodes a glycoprotein.

5. The vaccine of claim 1 which comprises H1, H3, H5, H7, or H9 HA.

6. The vaccine of claim 1 wherein the viral segments for HA and NA are from a different isolate than the PA, PB1, PB2, NP, NS, and M viral segments.

7. The vaccine of claim 1 wherein the heterologous nucleotide sequence encodes a protein of a bacterium, yeast, fungus, or a virus that is not an influenza virus.

8. The vaccine of claim 1 wherein the heterologous nucleotide sequence encodes a cancer associated antigen.

9. The vaccine of claim 1 wherein the heterologous nucleotide sequence is flanked by about 3 to about 400 nucleotides of the 5' and/or 3' PB2 coding region adjacent to non-coding sequence.

10. A method to immunize a vertebrate, comprising: contacting the vertebrate with the vaccine of claim 1.

11. The method of claim 10 wherein the vertebrate is a mammal.

12. The method of claim 11 wherein the mammal is a human.

13. The method of claim 10 wherein the contacting is by injection.

14. The method of claim 10 wherein the contacting is by intranasal administration.

* * * * *